United States Patent
Knopf et al.

(10) Patent No.: US 10,501,547 B2
(45) Date of Patent: Dec. 10, 2019

(54) ALK7 BINDING PROTEINS AND USES THEREOF

(71) Applicants: Acceleron Pharma Inc., Cambridge, MA (US); Adimab, LLC, Lebanon, NH (US)

(72) Inventors: John Knopf, Cambridge, MA (US); Jonathan Belk, Lebanon, NH (US); Nathan J. Sharkey, Lebanon, NH (US); Ravindra Kumar, Cambridge, MA (US); Asya Grinberg, Cambridge, MA (US); Dianne Sako, Cambridge, MA (US); Roselyne Castonguay, Cambridge, MA (US); Yossi Dagon, Cambridge, MA (US)

(73) Assignees: Acceleron Pharma Inc., Cambridge, MA (US); Adimab, LLC, Lebanon, NH (US)

( * ) Notice: Subject to any disclaimer, the term of this patent is extended or adjusted under 35 U.S.C. 154(b) by 71 days.

(21) Appl. No.: 15/494,081

(22) Filed: Apr. 21, 2017

(65) Prior Publication Data

US 2017/0306028 A1    Oct. 26, 2017

Related U.S. Application Data

(60) Provisional application No. 62/326,313, filed on Apr. 22, 2016.

(51) Int. Cl.
| | | |
|---|---|---|
| *C07K 16/28* | (2006.01) | |
| *A61K 39/00* | (2006.01) | |
| *A61P 3/04* | (2006.01) | |

(52) U.S. Cl.
CPC ............ *C07K 16/2863* (2013.01); *A61P 3/04* (2018.01); *A61K 2039/505* (2013.01); *C07K 2317/56* (2013.01); *C07K 2317/565* (2013.01); *C07K 2317/76* (2013.01); *C07K 2317/92* (2013.01)

(58) Field of Classification Search
CPC .......... C07K 16/2863; C07K 2317/565; C07K 2317/56; A61K 2039/505
See application file for complete search history.

(56) References Cited

U.S. PATENT DOCUMENTS

| | | |
|---|---|---|
| 5,811,245 A | 9/1998 | Ibanez et al. |
| 2004/0202659 A1 | 10/2004 | Berchtold et al. |
| 2009/0252733 A1 | 10/2009 | Tesar |
| 2012/0014954 A1 | 1/2012 | Trieu |
| 2015/0266975 A1 | 9/2015 | Lee et al. |

FOREIGN PATENT DOCUMENTS

| | | |
|---|---|---|
| WO | WO-9612805 A1 | 5/1996 |
| WO | WO-2015/091935 A2 | 6/2015 |
| WO | WO-2017177013 A1 | 10/2017 |
| WO | WO-2017185037 A1 | 10/2017 |

OTHER PUBLICATIONS

International Search Report and Written Opinion for International Application No. PCT/US17/28952 dated Sep. 22, 2017.
UniProtKB-I7ZP16 (I7ZP16_ASPO3), Oct. 3, 2012[http://www.uniprot.org/uniprot/I7ZP16].
Yogosawa et al., "Activin Receptor-Like Kinase 7 Suppresses Lipolysis to Accumulate Fat in Obesity Through Downregulation of Peroxisome Proliferator-Activated Receptor Gamma and C/EBPalpha," Diabetes, 62(1): 115-123 (2013).
Guo et al., "Adipocyte ALK7 links nutrient overload to catecholamine resistance in obesity," Elife, 3:e03245 (2014).
International Preliminary Report on Patentability for International Application No. PCT/US2017/028952 dated Oct. 23, 2018.
International Search Report and Written Opinion for International Application No. PCT/US2018/057482 dated Jan. 8, 2019.
Kogame et al., "ALK7 is a novel marker for adipocyte differentiation," The Journal of Medical Investigation, 4:238-245 (2006).

*Primary Examiner* — Ruixiang Li
(74) *Attorney, Agent, or Firm* — Foley Hoag LLP

(57) ABSTRACT

This disclosure provides ALK7-binding proteins such as anti-ALK7 antibodies, and compositions and methods for making the ALK7-binding proteins. In certain embodiments the ALK7-binding proteins inhibit, or antagonize ALK7 activity. In addition, the disclosure provides compositions and methods for diagnosing and treating overweight, obesity, diabetes, overweight, obesity, type 2 diabetes, and their associated conditions; metabolic disorders, and other diseases or conditions that can be treated, prevented or ameliorated by targeting ALK7.

7 Claims, 2 Drawing Sheets

Figure 1:
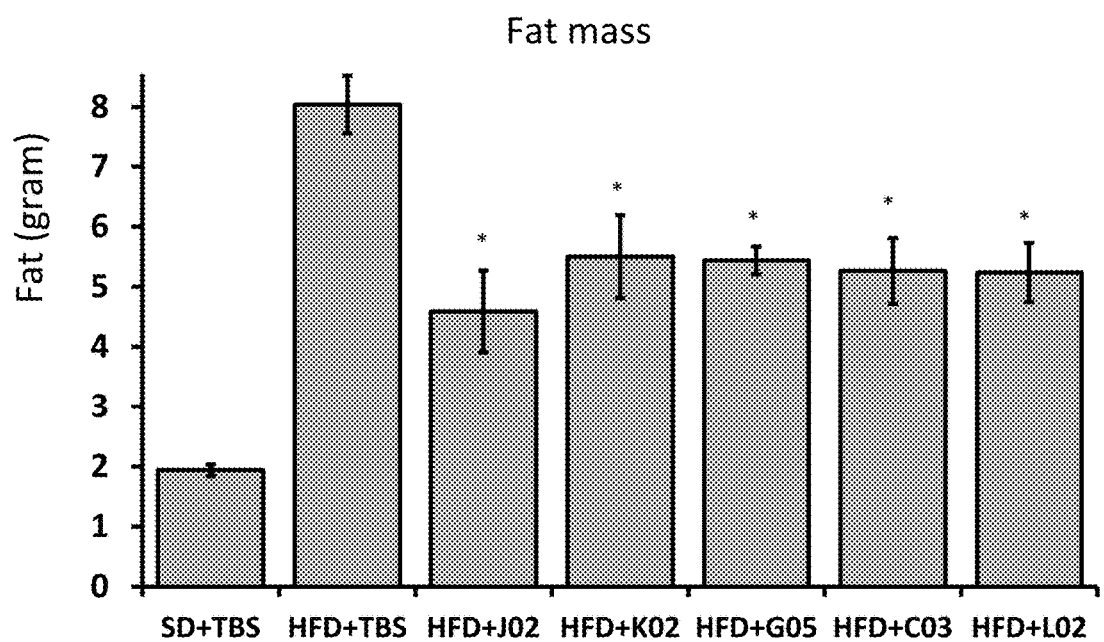

Specification includes a Sequence Listing.

ALK7 BINDING PROTEINS AND USES THEREOF

CROSS-REFERENCE TO RELATED APPLICATION

This application claims the benefit of U.S. Provisional Appl. No. 62/326,313, filed Apr. 22, 2016, which is incorporated herein by reference.

REFERENCE TO SEQUENCE LISTING SUBMITTED ELECTRONICALLY

The content of the electronically submitted sequence listing in ASCII text file 3174.004PC01_SeqList.ST25txt (Size: 72,898 bytes; and Date of Creation: Apr. 21, 2017) filed with the application is herein incorporated by reference in its entirety.

BACKGROUND

Overweight and obesity have reached epidemic proportion in the United States and a number of countries throughout the world, increasing among all age, race and ethnic groups and in both men and women. Overweight and obesity are also associated with other diseases or conditions that disrupt life activities and lifestyles. Obesity is recognized as a serious risk factor for other diseases and conditions such as type 2 diabetes, inflammation, and cardiovascular, pulmonary, fatty liver disease, neurologic, and hepatic, and renal disease.

Type 2 diabetes is a chronic, progressive disease that has likewise reached epidemic proportion. There is no established cure for type II diabetes, but there are numerous recognized treatments that attempt to delay or mitigate the inevitable consequences of the disease. Type 2 diabetes is initially treated by adjustments in diet and exercise, and by weight loss, most especially in obese subjects. The amount of weight loss which improves the clinical picture is sometimes modest (e.g., 4.4 to 11 lbs.); this is likely due to poorly understood aspects of fat tissue activity, for instance chemical signaling (especially in visceral fat tissue in and around abdominal organs).

In view of the foregoing, there is a need for new treatments for controlling and treating the overweight, obesity and type 2 diabetes epidemics. It is an object of this disclosure to provide ALK7-binding proteins and uses of the same in the diagnosis and treatment, prevention and/or amelioration of overweight, obesity, type 2 diabetes, and their associated conditions; metabolic disorders, and other diseases or conditions that can be treated, prevented or ameliorated by targeting ALK7.

BRIEF SUMMARY

The disclosure provides ALK7-binding proteins and methods of using the ALK7-binding proteins. In particular embodiments, the ALK7-binding proteins are capable of inhibiting or blocking the binding of ALK7 to one or more cognate ALK7 ligands and/or one or more cognate ActRI receptors. In some embodiments, the ALK7-binding proteins are capable of inhibiting or blocking the multimerization of ALK7, and ActRII receptor (ActRIIA or ActRIIB) and GDF1, GDF3, GDF8, activin B, activin A/B, or Nodal. The disclosure also provides methods of using ALK7-binding proteins for the diagnosis, or treatment, prevention and/or amelioration of a disease or condition associated with ALK7 expression and/or elevated ALK7-mediated signaling. Such diseases or conditions include but are not limited to, overweight, obesity (e.g., abdominal obesity); insulin resistance; metabolic syndrome and other metabolic diseases or conditions; a lipid disorder such as, low HDL levels, high LDL levels, hyperlipidemia, hypertriglyceridemia or dyslipidemia; lipoprotein aberrations; decreased triglycerides; inflammation (e.g., liver inflammation and/or inflammation of adipose tissue), fatty liver disease; non-alcoholic fatty liver disease; hyperglycemia; impaired glucose tolerance (IGT); hyperinsulinemia; high cholesterol (e.g., high LDL levels and hypercholesterolemia); cardiovascular disease such as, heart disease including coronary heart disease, congestive heart failure, stroke, peripheral vascular disease, disordered fibrinolysis, atherosclerosis; arteriosclerosis, and hypertension; Syndrome X; vascular restenosis; neuropathy; retinopathy; neurodegenerative disease; endothelial dysfunction, respiratory dysfunction, renal disease (e.g., nephropathy); pancreatitis; polycystic ovarian syndrome; elevated uric acid levels; haemochromatosis (iron overload); acanthosis nigricans (dark patches on the skin); and cancer (e.g., myeloma (e.g., multiple myeloma, plasmacytoma, localized myeloma, or extramedullary myeloma), or an ovarian, breast, colon, endometrial, liver, kidney, pancreatic, gastric, uterine or colon cancer); and other disorders/conditions associated with one or more of the above diseases or conditions, or with excessive body weight (e.g., body mass index (BMI)≥25 kg/m$^2$), or too much body fat. The disclosure also provides without limitation, methods for reducing body weight (e.g., promoting weight loss), and methods for reducing weight gain (e.g., preventing weight gain), using antagonist ALK7-binding proteins, such as antibodies.

In some embodiments, the ALK7-binding protein specifically binds ALK7. In further embodiments, the provided ALK7-binding protein specifically binds ALK7 and has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with ActRIIA or ActRIIB) for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics. In further embodiments, the ALK7-binding protein cross-blocks or competes for binding to ALK7 with an antibody having an ALK7-binding VH and VL pair disclosed herein. In further embodiments, the ALK7-binding protein is an anti-ALK7 antibody or an ALK7-binding antibody fragment.

In some embodiments, the ALK7-binding protein comprises a set of complementary determining regions (CDRs): heavy chain variable region (VH)-CDR1, VH-CDR2, VH-CDR3, light chain variable region (VL)-CDR1, VL-CDR2 and VL-CDR3, wherein the CDRs are present in a heavy chain variable region (VH) and a light chain variable region (VL) pair disclosed in Table 1A. In some embodiments, the ALK7-binding protein comprises a set of CDRs present in a VH and a VL pair selected from the group consisting of: (a) a VH sequence of SEQ ID NO:4, and a VL sequence of SEQ ID NO:13; (b) a VH sequence of SEQ ID NO:22, and a VL sequence of SEQ ID NO:31; (c) a VH sequence of SEQ ID NO:40, and a VL sequence of SEQ ID NO:49; and (d) a VH sequence of SEQ ID NO:58 and a VL sequence of SEQ ID NO:67.

In some embodiments, the ALK7-binding protein comprises a set of complementary determining regions (CDRs): heavy chain variable region (VH)-CDR1, VH-CDR2, VH-CDR3, light chain variable region (VL)-CDR1, VL-CDR2 and VL-CDR3, wherein the CDRs are present in a heavy chain variable region (VH) and a light chain variable region (VL) pair disclosed in Table 1B or Table 3. In some embodiments, the ALK7-binding protein comprises a set of CDRs present in a VH and a VL pair selected from the group consisting of: (a) a VH sequence of SEQ ID NO:152, and a VL sequence of SEQ ID NO:98; (b) a VH sequence of SEQ ID NO:159, and a VL sequence of SEQ ID NO:110; and (c) a VH sequence of SEQ ID NO:165, and a VL sequence of SEQ ID NO:171. In some embodiments, the ALK7-binding protein comprises a set of CDRs present in a VH and a VL pair selected from the group consisting of: (a) a VH sequence of SEQ ID NO:91, and a VL sequence of SEQ ID NO:98; (b) a VH sequence of SEQ ID NO:105, and a VL sequence of SEQ ID NO:110; (c) a VH sequence of SEQ ID NO:117, and a VL sequence of SEQ ID NO:124; (d) a VH sequence of SEQ ID NO:128 and a VL sequence of SEQ ID NO:135; and (e) a VH sequence of SEQ ID NO:140 and a VL sequence of SEQ ID NO:148.

In additional embodiments, the ALK7-binding protein specifically binds ALK7 and comprises a set of CDRs: VH-CDR1, VH-CDR2, VH-CDR3, VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (a)(i) VH-CDR1 comprises the amino acid sequence of SEQ ID NO:1; (ii) VH-CDR2 comprises the amino acid sequence of SEQ ID NO:2; (iii) VH-CDR3 comprises the amino acid sequence of SEQ ID NO:3; (iv) VL-CDR1 comprises the amino acid sequence of SEQ ID NO:10; (v) VL-CDR2 comprises the amino acid sequence of SEQ ID NO:11; and (vi) VL-CDR3 comprises the amino acid sequence of SEQ ID NO:12; (b)(i) VH-CDR1 comprises the amino acid sequence of SEQ ID NO:19; (ii) VH-CDR2 comprises the amino acid sequence of SEQ ID NO:20; (iii) VH-CDR3 comprises the amino acid sequence of SEQ ID NO:21; (iv) VL-CDR1 comprises the amino acid sequence of SEQ ID NO:28; (v) VL-CDR2 comprises the amino acid sequence of SEQ ID NO:29; and (vi) VL-CDR3 comprises the amino acid sequence of SEQ ID NO:30; (c)(i) VH-CDR1 comprises the amino acid sequence of SEQ ID NO:37; (ii) VH-CDR2 comprises the amino acid sequence of SEQ ID NO:38; (iii) VH-CDR3 comprises the amino acid sequence of SEQ ID NO:39; (iv) VL-CDR1 comprises the amino acid sequence of SEQ ID NO:46; (v) VL-CDR2 comprises the amino acid sequence of SEQ ID NO:47; and (vi) VL-CDR3 comprises the amino acid sequence of SEQ ID NO:48; or (d)(i) VH-CDR1 comprises the amino acid sequence of SEQ ID NO:55; (ii) VH-CDR2 comprises the amino acid sequence of SEQ ID NO:56; (iii) VH-CDR3 comprises the amino acid sequence of SEQ ID NO:57; (iv) VL-CDR1 comprises the amino acid sequence of SEQ ID NO:64; (v) VL-CDR2 comprises the amino acid sequence of SEQ ID NO:65; and (vi) VL-CDR3 comprises the amino acid sequence of SEQ ID NO:66; and wherein the protein binds ALK7.

In additional embodiments, the ALK7-binding protein specifically binds ALK7 and comprises a set of CDRs: VH-CDR1, VH-CDR2, VH-CDR3, VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (a)(i) VH-CDR1 comprises the amino acid sequence of SEQ ID NO:88; (ii) VH-CDR2 comprises the amino acid sequence of SEQ ID NO:89; (iii) VH-CDR3 comprises the amino acid sequence of SEQ ID NO:90; (iv) VL-CDR1 comprises the amino acid sequence of SEQ ID NO:95; (v) VL-CDR2 comprises the amino acid sequence of SEQ ID NO:96; and (vi) VL-CDR3 comprises the amino acid sequence of SEQ ID NO:97; (b)(i) VH-CDR1 comprises the amino acid sequence of SEQ ID NO:102; (ii) VH-CDR2 comprises the amino acid sequence of SEQ ID NO:103; (iii) VH-CDR3 comprises the amino acid sequence of SEQ ID NO:104; (iv) VL-CDR1 comprises the amino acid sequence of SEQ ID NO:107; (v) VL-CDR2 comprises the amino acid sequence of SEQ ID NO:108; and (vi) VL-CDR3 comprises the amino acid sequence of SEQ ID NO:109; (c)(i) VH-CDR1 comprises the amino acid sequence of SEQ ID NO:114; (ii) VH-CDR2 comprises the amino acid sequence of SEQ ID NO:115; (iii) VH-CDR3 comprises the amino acid sequence of SEQ ID NO:116; (iv) VL-CDR1 comprises the amino acid sequence of SEQ ID NO:121; (v) VL-CDR2 comprises the amino acid sequence of SEQ ID NO:122; and (vi) VL-CDR3 comprises the amino acid sequence of SEQ ID NO:123; (d)(i) VH-CDR1 comprises the amino acid sequence of SEQ ID NO:125; (ii) VH-CDR2 comprises the amino acid sequence of SEQ ID NO:126; (iii) VH-CDR3 comprises the amino acid sequence of SEQ ID NO:127; (iv) VL-CDR1 comprises the amino acid sequence of SEQ ID NO:132; (v) VL-CDR2 comprises the amino acid sequence of SEQ ID NO:133; and (vi) VL-CDR3 comprises the amino acid sequence of SEQ ID NO:134; or (e)(i) VH-CDR1 comprises the amino acid sequence of SEQ ID NO:137; (ii) VH-CDR2 comprises the amino acid sequence of SEQ ID NO:138; (iii) VH-CDR3 comprises the amino acid sequence of SEQ ID NO:139; (iv) VL-CDR1 comprises the amino acid sequence of SEQ ID NO:145; (v) VL-CDR2 comprises the amino acid sequence of SEQ ID NO:146; and (vi)

VL-CDR3 comprises the amino acid sequence of SEQ ID NO:147; and wherein the protein binds ALK7.

In some embodiments, the ALK7-binding protein specifically binds ALK7 and comprises a set of CDRs in which: (a)(i) VH-CDR1 comprises the amino acid sequence of SEQ ID NO:1; (ii) VH-CDR2 comprises the amino acid sequence of SEQ ID NO:2; (iii) VH-CDR3 comprises the amino acid sequence of SEQ ID NO:3; (iv) VL-CDR1 comprises the amino acid sequence of SEQ ID NO:10; (v) VL-CDR2 comprises the amino acid sequence of SEQ ID NO:11; and (vi) VL-CDR3 comprises the amino acid sequence of SEQ ID NO:12; (b)(i) VH-CDR1 comprises the amino acid sequence of SEQ ID NO:19; (ii) VH-CDR2 comprises the amino acid sequence of SEQ ID NO:20; (iii) VH-CDR3 comprises the amino acid sequence of SEQ ID NO:21; (iv) VL-CDR1 comprises the amino acid sequence of SEQ ID NO:28; (v) VL-CDR2 comprises the amino acid sequence of SEQ ID NO:29; and (vi) VL-CDR3 comprises the amino acid sequence of SEQ ID NO:30; (c)(i) VH-CDR1 comprises the amino acid sequence of SEQ ID NO:37; (ii) VH-CDR2 comprises the amino acid sequence of SEQ ID NO:38; (iii) VH-CDR3 comprises the amino acid sequence of SEQ ID NO:39; (iv) VL-CDR1 comprises the amino acid sequence of SEQ ID NO:46; (v) VL-CDR2 comprises the amino acid sequence of SEQ ID NO:47; and (vi) VL-CDR3 comprises the amino acid sequence of SEQ ID NO:48; or (d)(i) VH-CDR1 comprises the amino acid sequence of SEQ ID NO:55; (ii) VH-CDR2 comprises the amino acid sequence of SEQ ID NO:56; (iii) VH-CDR3 comprises the amino acid sequence of SEQ ID NO:57; (iv) VL-CDR1 comprises the amino acid sequence of SEQ ID NO:64; (v) VL-CDR2 comprises the amino acid sequence of SEQ ID NO:65; and (vi) VL-CDR3 comprises the amino acid sequence of SEQ ID NO:66; and wherein the protein binds ALK7.

In some embodiments, the ALK7-binding protein specifically binds ALK7 and comprises a set of CDRs in which: (a)(i) VH-CDR1 comprises the amino acid sequence of SEQ ID NO:88; (ii) VH-CDR2 comprises the amino acid sequence of SEQ ID NO:89; (iii) VH-CDR3 comprises the amino acid sequence of SEQ ID NO:90; (iv) VL-CDR1 comprises the amino acid sequence of SEQ ID NO:95; (v) VL-CDR2 comprises the amino acid sequence of SEQ ID NO:96; and (vi) VL-CDR3 comprises the amino acid sequence of SEQ ID NO:97; (b)(i) VH-CDR1 comprises the amino acid sequence of SEQ ID NO:102; (ii) VH-CDR2 comprises the amino acid sequence of SEQ ID NO:103; (iii) VH-CDR3 comprises the amino acid sequence of SEQ ID NO:104; (iv) VL-CDR1 comprises the amino acid sequence of SEQ ID NO:107; (v) VL-CDR2 comprises the amino acid sequence of SEQ ID NO:108; and (vi) VL-CDR3 comprises the amino acid sequence of SEQ ID NO:109; (c)(i) VH-CDR1 comprises the amino acid sequence of SEQ ID NO:114; (ii) VH-CDR2 comprises the amino acid sequence of SEQ ID NO:115; (iii) VH-CDR3 comprises the amino acid sequence of SEQ ID NO:116; (iv) VL-CDR1 comprises the amino acid sequence of SEQ ID NO:121; (v) VL-CDR2 comprises the amino acid sequence of SEQ ID NO:122; and (vi) VL-CDR3 comprises the amino acid sequence of SEQ ID NO:123; (d)(i) VH-CDR1 comprises the amino acid sequence of SEQ ID NO:125; (ii) VH-CDR2 comprises the amino acid sequence of SEQ ID NO:126; (iii) VH-CDR3 comprises the amino acid sequence of SEQ ID NO:127; (iv) VL-CDR1 comprises the amino acid sequence of SEQ ID NO:132; (v) VL-CDR2 comprises the amino acid sequence of SEQ ID NO:133; and (vi) VL-CDR3 comprises the amino acid sequence of SEQ ID NO:134; or (e)(i) VH-CDR1 comprises the amino acid sequence of SEQ ID NO:137; (ii) VH-CDR2 comprises the amino acid sequence of SEQ ID NO:138; (iii) VH-CDR3 comprises the amino acid sequence of SEQ ID NO:139; (iv) VL-CDR1 comprises the amino acid sequence of SEQ ID NO:145; (v) VL-CDR2 comprises the amino acid sequence of SEQ ID NO:146; and (vi) VL-CDR3 comprises the amino acid sequence of SEQ ID NO:147; and wherein the protein binds ALK7.

In some embodiments, the ALK7-binding protein specifically binds ALK7 and comprises a VH and a VL pair selected from the group consisting of: (a)(i) a VH having at least 90%, 95%, 96%, 97%, 98%, 99%, or 100% sequence identity to SEQ ID NO:4, and (ii) a VL having at least 90%, 95%, 96%, 97%, 98%, 99%, or 100% sequence identity to SEQ ID NO:13; (b)(i) a VH having at least 90%, 95%, 96%, 97%, 98%, 99%, or 100% sequence identity to SEQ ID NO:22, or 132, and (ii) a VL having at least 90%, 95%, 96%, 97%, 98%, 99%, or 100% sequence identity to SEQ ID NO:31; (c)(i) a VH having at least 90%, 95%, 96%, 97%, 98%, 99%, or 100% sequence identity to SEQ ID NO:40, and (ii) a VL having at least 90%, 95%, 96%, 97%, 98%, 99%, or 100% sequence identity to SEQ ID NO:49; and (d)(i) a VH having at least 90%, 95%, 96%, 97%, 98%, 99%, or 100% sequence identity to SEQ ID NO:58, and (ii) a VL having at least 90%, 95%, 96%, 97%, 98%, 99%, or 100% sequence identity to SEQ ID NO:67; and wherein the protein binds ALK7.

In some embodiments, the ALK7-binding protein specifically binds ALK7 and comprises a VH and a VL pair selected from the group consisting of: (a)(i) a VH having at least 90%, 95%, 96%, 97%, 98%, 99%, or 100% sequence identity to SEQ ID NO:91, and (ii) a VL having at least 90%, 95%, 96%, 97%, 98%, 99%, or 100% sequence identity to SEQ ID NO:98; (b)(i) a VH having at least 90%, 95%, 96%, 97%, 98%, 99%, or 100% sequence identity to SEQ ID NO:105, or 132, and (ii) a VL having at least 90%, 95%, 96%, 97%, 98%, 99%, or 100% sequence identity to SEQ ID NO:110; (c)(i) a VH having at least 90%, 95%, 96%, 97%, 98%, 99%, or 100% sequence identity to SEQ ID NO:117, and (ii) a VL having at least 90%, 95%, 96%, 97%, 98%, 99%, or 100% sequence identity to SEQ ID NO:124; (d)(i) a VH having at least 90%, 95%, 96%, 97%, 98%, 99%, or 100% sequence identity to SEQ ID NO:128, and (ii) a VL having at least 90%, 95%, 96%, 97%, 98%, 99%, or 100% sequence identity to SEQ ID NO:135; and (e)(i) a VH having at least 90%, 95%, 96%, 97%, 98%, 99%, or 100% sequence identity to SEQ ID NO:140, and (ii) a VL having at least 90%, 95%, 96%, 97%, 98%, 99%, or 100% sequence identity to SEQ ID NO:148; and wherein the protein binds ALK7.

In one embodiment, the ALK7-binding protein comprises a VH and a VL containing a VH sequence of SEQ ID NO:40 or 58, and a VL sequence of SEQ ID NO:49 or 67; and the protein binds ALK7. In a further embodiment, the ALK7-binding protein comprises a VH sequence of SEQ ID NO:40 and a VL sequence of SEQ ID NO:49, and the protein binds ALK7. In a further embodiment, the ALK7-binding protein comprises a VH sequence of SEQ ID NO:58 and a VL sequence of SEQ ID NO:67, and the protein binds ALK7.

In one embodiment, the ALK7-binding protein comprises a VH and a VL pair comprising a VH sequence of SEQ ID NO:4 and a VL sequence of SEQ ID NO:13, and the protein binds ALK7.

In one embodiment, the ALK7-binding protein comprises a VH and a VL pair comprising a VH sequence of SEQ ID NO:22 and a VL sequence of SEQ ID NO:31, and the protein binds ALK7.

In one embodiment, the ALK7-binding protein comprises a VH and a VL pair comprising a VH sequence of SEQ ID NO:40 and a VL sequence of SEQ ID NO:49, and the protein binds ALK7.

In one embodiment, the ALK7-binding protein comprises a VH and a VL pair comprising a VH sequence of SEQ ID NO:58 and a VL sequence of SEQ ID NO:67, and the protein binds ALK7.

In one embodiment, the ALK7-binding protein comprises a VH and a VL pair comprising a VH sequence of SEQ ID NO:91 and a VL sequence of SEQ ID NO:98, and the protein binds ALK7.

In one embodiment, the ALK7-binding protein comprises a VH and a VL pair comprising a VH sequence of SEQ ID NO:105 and a VL sequence of SEQ ID NO:110, and the protein binds ALK7.

In one embodiment, the ALK7-binding protein comprises a VH and a VL pair comprising a VH sequence of SEQ ID NO:117 and a VL sequence of SEQ ID NO:124, and the protein binds ALK7.

In one embodiment, the ALK7-binding protein comprises a VH and a VL pair comprising a VH sequence of SEQ ID NO:128 and a VL sequence of SEQ ID NO:135, and the protein binds ALK7.

In one embodiment, the ALK7-binding protein comprises a VH and a VL pair comprising a VH sequence of SEQ ID NO:140 and a VL sequence of SEQ ID NO:148, and the protein binds ALK7.

In some embodiments, the ALK7-binding protein comprises a VH and a VL pair selected from the group consisting of: (a)(i) a VH sequence having a total of one, two, three, four, five, six, seven, eight, nine, ten, fewer than fifteen, or zero, amino acid substitutions, deletions, and/or insertions from a reference VH sequence selected from the group consisting of SEQ ID NO:4, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:13; (b)(i) a VH sequence having a total of one, two, three, four, five, six, seven, eight, nine, ten, fewer than fifteen, or zero, amino acid substitutions, deletions, and/or insertions from a reference VH sequence of SEQ ID NO:22, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:31; (c)(i) a VH sequence having a total of one, two, three, four, five, six, seven, eight, nine, ten, fewer than fifteen, or zero, amino acid substitutions, deletions, and/or insertions from a reference VH sequence of SEQ ID NO:40, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:49; and (d)(i) a VH sequence having a total of one, two, three, four, five, six, seven, eight, nine, ten, fewer than fifteen, or zero, amino acid substitutions, deletions, and/or insertions from a reference VH sequence of SEQ ID NO:58, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:67; and wherein the protein binds ALK7.

In some embodiments, the ALK7-binding protein comprises a VH and a VL pair selected from the group consisting of: (a)(i) a VH sequence having a total of one, two, three, four, five, six, seven, eight, nine, ten, fewer than fifteen, or zero, amino acid substitutions, deletions, and/or insertions from a reference VH sequence selected from the group consisting of SEQ ID NO:91, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:98; (b)(i) a VH sequence having a total of one, two, three, four, five, six, seven, eight, nine, ten, fewer than fifteen, or zero, amino acid substitutions, deletions, and/or insertions from a reference VH sequence of SEQ ID NO:105, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:110; (c)(i) a VH sequence having a total of one, two, three, four, five, six, seven, eight, nine, ten, fewer than fifteen, or zero, amino acid substitutions, deletions, and/or insertions from a reference VH sequence of SEQ ID NO:117, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:124; (d)(i) a VH sequence having a total of one, two, three, four, five, six, seven, eight, nine, ten, fewer than fifteen, or zero, amino acid substitutions, deletions, and/or insertions from a reference VH sequence of SEQ ID NO:128, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:135; and (e)(i) a VH sequence having a total of one, two, three, four, five, six, seven, eight, nine, ten, fewer than fifteen, or zero, amino acid substitutions, deletions, and/or insertions from a reference VH sequence of SEQ ID NO:140, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:148; and wherein the protein binds ALK7.

In some embodiments, the ALK7-binding protein is an antibody that specifically binds ALK7. In additional embodiments, the antibody is a monoclonal antibody, a recombinant antibody, a human antibody, a humanized antibody, a chimeric antibody, a bi-specific antibody, or a multi-specific antibody. In some embodiments, the ALK7-binding protein is an ALK7-binding antibody fragment. In some embodiments the antibody is an antibody fragment selected from the group consisting of a Fab, Fab', F(ab')$_2$, Fv, diabody, DART, and a single chain antibody molecule (e.g., a BiTE).

In some embodiments, the ALK7-binding protein specifically binds to ALK7 between amino acids 20-113 of SEQ ID NO:85. In some embodiments, the ALK7-binding protein specifically binds to ALK7 between amino acids 20-113 of SEQ ID NO:85 and inhibits one or more ALK ligands (e.g., GDF1, GDF3, GDF8, activin B, activin A/B, and/or Nodal) from binding to ALK7. In some embodiments, the ALK7-binding protein specifically binds to ALK7 between amino acids 20-113 of SEQ ID NO: 85 and contacts one or more amino acids selected from the group consisting of: (a) a Glu at position 21 of SEQ ID NO:85; (b) a Leu at position 22 of SEQ ID NO:85; (c) a Ser at position 23 of SEQ ID NO:85; (d) a Pro at position 24 of SEQ ID NO:85; (e) a Gly at position 25 of SEQ ID NO:85; (f) a Leu at position 26 of SEQ ID NO:85; (g) a Lys at position 27 of SEQ ID NO:85; (h) a Cys at position 28 of SEQ ID NO:85; (i) a Val at position 29 of SEQ ID NO:85; (j) a Cys at position 30 of SEQ ID NO:85; (k) a Leu at position 31 of SEQ ID NO:85; (l) a Leu at position 32 of SEQ ID NO:85; (m) a Cys at position 33 of SEQ ID NO:85; (n) a Asp at position 34 of SEQ ID NO:85; (o) a Ser at position 35 of SEQ ID NO:85; (p) a Ser at position 36 of SEQ ID NO:85; (q) a Asn at position 37 of SEQ ID NO:85; (r) a Phe at position 38 of SEQ ID NO:85; (s) a Thr at position 39 of SEQ ID NO:85; (t) a Cys at position 40 of SEQ ID NO:85; (u) a Gln at position 41 of SEQ ID NO:85; (v) a Thr at position 42 of SEQ ID NO:85; (w) a Glu at position 43 of SEQ ID NO:85; (x) a Gly at position 44 of SEQ ID NO:85; (y) a Ala at position 45 of SEQ ID NO:85; (z) a Cys at position 46 of SEQ ID NO:85; (aa) a Trp at position 47 of SEQ ID NO:85; (ab) a Ala at position 48 of SEQ ID NO:85; (ac) a Ser at position 49 of SEQ ID NO:85; (ad) a Val at position 50 of SEQ ID NO:85; (ae) a Met at position 51 of SEQ ID NO:85; (af) a Leu at position 52 of SEQ ID NO:85; (ag) a Thr at position 53 of SEQ ID NO:85; (ah) a Asn at position 54 of SEQ ID NO:85; (ai) a Gly at position 55 of SEQ ID NO:85; (aj) a Lys at position 56 of SEQ ID NO:85; (ak) a Glu at position 57 of SEQ ID NO:85; (al) a Gln at position 58 of SEQ ID NO:85; (am) a Val at position 59 of SEQ ID NO:85; (an) a Ile at position 60 of SEQ ID NO:85; (ao) a Lys at position 61 of SEQ ID NO:85; (ap) a Ser at position 62 of SEQ ID NO:85; (aq) a Cys at position 63 of SEQ ID NO:85; (ar) a Val at position 64 of SEQ ID NO:85; (as) a Ser at position 65 of SEQ ID NO:85; (at) a Leu at position 66 of SEQ ID NO:85; (au) a Pro at position 67 of SEQ ID NO:85; (av) a Glu at position 68 of SEQ ID NO:85; (aw) a Leu at position 69 of SEQ ID NO:85; (ax) a Asn at position 70 of SEQ ID NO:85; (ay) a Ala at position 71 of SEQ ID NO:85; (az) a Gln at position 72 of SEQ ID NO:85; (ba) a Val at position 73 of SEQ ID NO:85; (bb) a Phe at position 74 of SEQ ID NO:85; (bc) a Cys at position 75 of SEQ ID NO:85; (bd) a His at position 76 of SEQ ID NO:85; (be) a Ser at position 77 of SEQ ID NO:85; (bf) a Ser at position 78 of SEQ ID NO:85; (bg) a Asn at position 79 of SEQ ID NO:85; (bh) a Asn at position 80 of SEQ ID NO:85; (bi) a Val at position 81 of SEQ ID NO:85; (bj) a Thr at position 82 of SEQ ID NO:85; (bk) a Lys at position 83 of SEQ ID NO:85; (bl) a Thr at position 84 of SEQ ID NO:85; (bm) a Glu at position 85 of SEQ ID NO:85; (bn) a Cys at position 86 of SEQ ID NO:85; (bo) a Cys at position 87 of SEQ ID NO:85; (bp) a Phe at position 88 of SEQ ID NO:85; (bq) a Thr at position 89 of SEQ ID NO:85; (br) a Asp at position 90 of SEQ ID NO:85; (bs) a Phe at position 91 of SEQ ID NO:85; (bt) a Cys at position 92 of SEQ ID NO:85; (bu) a Asn at position 93 of SEQ ID NO:85; (bv) a Asn at position 94 of SEQ ID NO:85; (bw) a Ile at position 95 of SEQ ID NO:85; (bx) a Thr at position 96 of SEQ ID NO:85; (by) a Leu at position 97 of SEQ ID NO:85; (bz) a His at position 98 of SEQ ID NO:85; (ca) a Leu at position 99 of SEQ ID NO:85; (cb) a Pro at position 100 of SEQ ID NO:85; (cc) a Thr at position 101 of SEQ ID NO:85; (cd) a Ala at position 102 of SEQ ID NO:85; (ce) a Ser at position 103 of SEQ ID NO:85; (cf) a Pro at position 104 of SEQ ID NO:85; (cg) a Asn at position 105 of SEQ ID NO:85; (ch) a Ala at position 106 of SEQ ID NO:85; (ci) a Pro at position 107 of SEQ ID NO:85; (cj) a Lys at position 108 of SEQ ID NO:85; (ck) a Leu at position 109 of SEQ ID NO:85; (cl) a Gly at position 110 of SEQ ID NO:85; (cm) a Pro at position 111 of SEQ ID NO:85; (cn) a Met at position 112 of SEQ ID NO:85; and (co) a Glu at position 113 of SEQ ID NO:85. In some embodiments, the ALK7-binding protein specifically binds to ALK7 between amino acids 20-113 of SEQ ID NO: 85 and contacts one or more amino acids selected from the group consisting of: (a) a Glu at position 21 of SEQ ID NO:85; (b) a Leu at position 22 of SEQ ID NO:85; (c) a Ser at position 23 of SEQ ID NO:85; (d) a Pro at position 24 of SEQ ID NO:85; (e) a Gly at position 25 of SEQ ID NO:85; (f) a Leu at position 26 of SEQ ID NO:85; (g) a Lys at position 27 of SEQ ID NO:85; (h) a Cys at position 28 of SEQ ID NO:85; (i) a Val at position 29 of SEQ ID NO:85; (j) a Cys at position 30 of SEQ ID NO:85; (k) a Leu at position 31 of SEQ ID NO:85; (l) a Leu at position 32 of SEQ ID NO:85; (m) a Cys at position 33 of SEQ ID NO:85; (n) a Asp at position 34 of SEQ ID NO:85; (o) a Ser at position 35 of SEQ ID NO:85; (p) a Ser at position 36 of SEQ ID NO:85; (q) a Asn at position 37 of SEQ ID NO:85; (r) a Phe at position 38 of SEQ ID NO:85; (s) a Thr at position 39 of SEQ ID NO:85; (t) a Cys at position 40 of SEQ ID NO:85; (u) a Gln at position 41 of SEQ ID NO:85; (v) a Thr at position 42 of SEQ ID NO:85; (w) a Glu at position 43 of SEQ ID NO:85; (x) a Gly at position 44 of SEQ ID NO:85; (y) a Ala at position 45 of SEQ ID NO:85; (z) a Cys at position 46 of SEQ ID NO:85; (aa) a Trp at position 47 of SEQ ID NO:85; (ab) a Ala at position 48 of SEQ ID NO:85; (ac) a Ser at position 49 of SEQ ID NO:85; (ad) a Val at position 50 of SEQ ID NO:85; (ae) a Met at position 51 of SEQ ID NO:85; (af) a Leu at position 52 of SEQ ID NO:85; (ag) a Thr at position 53 of SEQ ID NO:85; (ah) a Asn at position 54 of SEQ ID NO:85; (ai) a Gly at position 55 of SEQ ID NO:85; (aj) a Lys at position 56 of SEQ ID NO:85; (ak) a Glu at position 57 of SEQ ID NO:85; (al) a Gln at position 58 of SEQ ID NO:85; (am) a Val at position 59 of SEQ ID NO:85; (an) a Ile at position 60 of SEQ ID NO:85; (ao) a Lys at position 61 of SEQ ID NO:85; (ap) a Ser at position 62 of SEQ ID NO:85; (aq) a Cys at position 63 of SEQ ID NO:85; (ar) a Val at position 64 of SEQ ID NO:85; (as) a Ser at position 65 of SEQ ID NO:85; (at) a Leu at position 66 of SEQ ID NO:85; (au) a Pro at position 67 of SEQ ID NO:85; (av) a Glu at position 68 of SEQ ID NO:85; (aw) a Leu at position 69 of SEQ ID NO:85; (ax) a Asn at position 70 of SEQ ID NO:85; (ay) a Ala at position 71 of SEQ ID NO:85; (az) a Gln at position 72 of SEQ ID NO:85; (ba) a Val at position 73 of SEQ ID NO:85; (bb) a Phe at position 74 of SEQ ID NO:85; (bc) a Cys at position 75 of SEQ ID NO:85; (bd) a His at position 76 of SEQ ID NO:85; (be) a Ser at position 77 of SEQ ID NO:85; (bf) a Ser at position 78 of SEQ ID NO:85; (bg) a Asn at position 79 of SEQ ID NO:85; (bh) a Asn at position 80 of SEQ ID NO:85; (bi) a Val at position 81 of SEQ ID NO:85; (bj) a Thr at position 82 of SEQ ID NO:85; (bk) a Lys at position 83 of SEQ ID NO:85; (bl) a Thr at position 84 of SEQ ID NO:85; (bm) a Glu at position 85 of SEQ ID NO:85; (bn) a Cys at position 86 of SEQ ID NO:85; (bo) a Cys at position 87 of SEQ ID NO:85; (bp) a Phe at position 88 of SEQ ID NO:85; (bq) a Thr at position 89 of SEQ ID NO:85; (br) a Asp at position 90 of SEQ ID NO:85; (bs) a Phe at position 91 of SEQ ID NO:85; (bt) a Cys at position 92 of SEQ ID NO:85; (bu) a Asn at position 93 of SEQ ID NO:85; (bv) a Asn at position 94 of SEQ ID NO:85; (bw) a Ile at position 95 of SEQ ID NO:85; (bx) a Thr at position 96 of SEQ ID NO:85; (by) a Leu at position 97 of SEQ ID NO:85; (bz) a His at position 98 of SEQ ID NO:85; (ca) a Leu at position 99 of SEQ ID NO:85; (cb) a Pro at position 100 of SEQ ID NO:85; (cc) a Thr at position 101 of SEQ ID NO:85; (cd) a Ala at position 102 of SEQ ID NO:85; (ce) a Ser at position 103 of SEQ ID NO:85; (cf) a Pro at position 104 of SEQ ID NO:85; (cg) a Asn at position 105 of SEQ ID NO:85; (ch) a Ala at position 106 of SEQ ID NO:85; (ci) a Pro at position 107 of SEQ ID NO:85; (cj) a Lys at position 108 of SEQ ID NO:85; (ck) a Leu at position 109 of SEQ ID NO:85; (cl) a Gly at position 110 of SEQ ID NO:85; (cm) a Pro at position 111 of SEQ ID NO:85; (cn) a Met at position 112 of SEQ ID NO:85; and (co) a Glu at position 113 of SEQ ID NO:85; and inhibits one or more ALK7 ligands (e.g., GDF1, GDF3, GDF8, activin B, activin A/B, and/or Nodal) from binding to ALK7. In some embodiments, the ALK7-binding protein specifically binds to ALK7 between amino acids 20-113 of SEQ ID NO:85 and increases lipolysis (e.g., lipolysis of white adipocytes and/or brown adipocytes). In some embodiments, the ALK7-binding protein specifically binds to ALK7 between amino acids 20-113 of SEQ ID NO: 85 and contacts one or more amino acids selected from the group consisting of: (a) a Glu at position 21 of SEQ ID NO:85; (b) a Leu at position 22 of SEQ ID NO:85; (c) a Ser at position 23 of SEQ ID NO:85; (d) a Pro at position 24 of SEQ ID NO:85; (e) a Gly at position 25 of SEQ ID NO:85; (f) a Leu at position 26 of SEQ ID NO:85; (g) a Lys at position 27 of SEQ ID NO:85; (h) a Cys at position 28 of SEQ ID NO:85; (i) a Val at position 29 of SEQ ID NO:85; (j) a Cys at position 30 of SEQ ID NO:85; (k) a Leu at position 31 of SEQ ID NO:85; (l) a Leu at position 32 of SEQ ID NO:85; (m) a Cys at position 33 of SEQ ID NO:85; (n) a Asp at position 34 of SEQ ID NO:85; (o) a Ser at position 35 of SEQ ID NO:85; (p) a Ser at position 36 of SEQ ID NO:85; (q) a Asn at position 37 of SEQ ID NO:85; (r) a Phe at position 38 of SEQ ID NO:85; (s) a Thr at position 39 of SEQ ID NO:85; (t) a Cys at position 40 of SEQ ID NO:85; (u) a Gln at position 41 of SEQ ID NO:85; (v) a Thr at position 42 of SEQ ID NO:85; (w) a Glu at position 43 of SEQ ID NO:85; (x) a Gly at position 44 of SEQ ID NO:85; (y) a Ala at position 45 of SEQ ID NO:85; (z) a Cys at position 46 of SEQ ID NO:85; (aa) a Trp at position 47 of SEQ ID NO:85; (ab) a Ala at position 48 of SEQ ID NO:85; (ac) a Ser at position 49 of SEQ ID NO:85; (ad) a Val at position 50 of SEQ ID NO:85; (ae) a Met at position 51 of SEQ ID NO:85; (af) a Leu at position 52 of SEQ ID NO:85; (ag) a Thr at position 53 of SEQ ID NO:85; (ah) a Asn at position 54 of SEQ ID NO:85; (ai) a Gly at position 55 of SEQ ID NO:85; (aj) a Lys at position 56 of SEQ ID NO:85; (ak) a Glu at position 57 of SEQ ID NO:85; (al) a Gln at position 58 of SEQ ID NO:85; (am) a Val at position 59 of SEQ ID NO:85; (an) a Ile at position 60 of SEQ ID NO:85; (ao) a Lys at position 61 of SEQ ID NO:85; (ap) a Ser at position 62 of SEQ ID NO:85; (aq) a Cys at position 63 of SEQ ID NO:85; (ar) a Val at position 64 of SEQ ID NO:85; (as) a Ser at position 65 of SEQ ID NO:85; (at) a Leu at position 66 of SEQ ID NO:85; (au) a Pro at position 67 of SEQ ID NO:85; (av) a Glu at position 68 of SEQ ID NO:85; (aw) a Leu at position 69 of SEQ ID NO:85; (ax) a Asn at position 70 of SEQ ID NO:85; (ay) a Ala at position 71 of SEQ ID NO:85; (az) a Gln at position 72 of SEQ ID NO:85; (ba) a Val at position 73 of SEQ ID NO:85; (bb) a Phe at position 74 of SEQ ID NO:85; (bc) a Cys at position 75 of SEQ ID NO:85; (bd) a His at position 76 of SEQ ID NO:85; (be) a Ser at position 77 of SEQ ID NO:85; (bf) a Ser at position 78 of SEQ ID NO:85; (bg) a Asn at position 79 of SEQ ID NO:85; (bh) a Asn at position 80 of SEQ ID NO:85; (bi) a Val at position 81 of SEQ ID NO:85; (bj) a Thr at position 82 of SEQ ID NO:85; (bk) a Lys at position 83 of SEQ ID NO:85; (bl) a Thr at position 84 of SEQ ID NO:85; (bm) a Glu at position 85 of SEQ ID NO:85; (bn) a Cys at position 86 of SEQ ID NO:85; (bo) a Cys at position 87 of SEQ ID NO:85; (bp) a Phe at position 88 of SEQ ID NO:85; (bq) a Thr at position 89 of SEQ ID NO:85; (br) a Asp at position 90 of SEQ ID NO:85; (bs) a Phe at position 91 of SEQ ID NO:85; (bt) a Cys at position 92 of SEQ ID NO:85; (bu) a Asn at position 93 of SEQ ID NO:85; (by) a Asn at position 94 of SEQ ID NO:85; (bw) a Ile at position 95 of SEQ ID NO:85; (bx) a Thr at position 96 of SEQ ID NO:85; (by) a Leu at position 97 of SEQ ID NO:85; (bz) a His at position 98 of SEQ ID NO:85; (ca) a Leu at position 99 of SEQ ID NO:85; (cb) a Pro at position 100 of SEQ ID NO:85; (cc) a Thr at position 101 of SEQ ID NO:85; (cd) a Ala at position 102 of SEQ ID NO:85; (ce) a Ser at position 103 of SEQ ID NO:85; (cf) a Pro at position 104 of SEQ ID NO:85; (cg) a Asn at position 105 of SEQ ID NO:85; (ch) a Ala at position 106 of SEQ ID NO:85; (ci) a Pro at position 107 of SEQ ID NO:85; (cj) a Lys at position 108 of SEQ ID NO:85; (ck) a Leu at position 109 of SEQ ID NO:85; (cl) a Gly at position 110 of SEQ ID NO:85; (cm) a Pro at position 111 of SEQ ID NO:85; (cn) a Met at position 112 of SEQ ID NO:85; and (co) a Glu at position 113 of SEQ ID NO:85; and increases lipolysis (e.g., lipolysis of white adipocytes and/or brown adipocytes).

In some embodiments, the ALK7-binding protein specifically binds to ALK7 between amino acids 28-92 of SEQ ID NO:85. In some embodiments, the ALK7-binding protein specifically binds to ALK7 between amino acids 28-92 of SEQ ID NO:85 and inhibits one or more ALK7 ligands (e.g., GDF1, GDF3, GDF8, activin B, activin A/B, and/or Nodal) from binding to ALK7. In some embodiments, the ALK7-binding protein specifically binds to ALK7 between amino acids 28-92 of SEQ ID NO:85 and contacts one or more amino acids selected from the group consisting of: (a) a Cys at position 28 of SEQ ID NO:85; (b) a Val at position 29 of SEQ ID NO:85; (c) a Cys at position 30 of SEQ ID NO:85; (d) a Leu at position 31 of SEQ ID NO:85; (e) a Leu at position 32 of SEQ ID NO:85; (f) a Cys at position 33 of SEQ ID NO:85; (g) a Asp at position 34 of SEQ ID NO:85; (h) a Ser at position 35 of SEQ ID NO:85; (i) a Ser at position 36 of SEQ ID NO:85; (j) a Asn at position 37 of SEQ ID NO:85; (k) a Phe at position 38 of SEQ ID NO:85; (l) a Thr at position 39 of SEQ ID NO:85; (m) a Cys at position 40 of SEQ ID NO:85; (n) a Gln at position 41 of SEQ ID NO:85; (o) a Thr at position 42 of SEQ ID NO:85; (p) a Glu at position 43 of SEQ ID NO:85; (q) a Gly at position 44 of SEQ ID NO:85; (r) a Ala at position 45 of SEQ ID NO:85; (s) a Cys at position 46 of SEQ ID NO:85; (t) a Trp at position 47 of SEQ ID NO:85; (u) a Ala at position 48 of SEQ ID NO:85; (v) a Ser at position 49 of SEQ ID NO:85; (w) a Val at position 50 of SEQ ID NO:85; (x) a Met at position 51 of SEQ ID NO:85; (y) a Leu at position 52 of SEQ ID NO:85; (z) a Thr at position 53 of SEQ ID NO:85; (aa) a Asn at position 54 of SEQ ID NO:85; (ab) a Gly at position 55 of SEQ ID NO:85; (ac) a Lys at position 56 of SEQ ID NO:85; (ad) a Glu at position 57 of SEQ ID NO:85; (ae) a Gln at position 58 of SEQ ID NO:85; (af) a Val at position 59 of SEQ ID NO:85; (ag) a Ile at position 60 of SEQ ID NO:85; (ah) a Lys at position 61 of SEQ ID NO:85; (ai) a Ser at position 62 of SEQ ID NO:85; (aj) a Cys at position 63 of SEQ ID NO:85; (ak) a Val at position 64 of SEQ ID NO:85; (al) a Ser at position 65 of SEQ ID NO:85; (am) a Leu at position 66 of SEQ ID NO:85; (an) a Pro at position 67 of SEQ ID NO:85; (ao) a Glu at position 68 of SEQ ID NO:85; (ap) a Leu at position 69 of SEQ ID NO:85; (aq) a Asn at position 70 of SEQ ID NO:85; (ar) a Ala at position 71 of SEQ ID NO:85; (as) a Gln at position 72 of SEQ ID NO:85; (at) a Val at position 73 of SEQ ID NO:85; (au) a Phe at position 74 of SEQ ID NO:85; (av) a Cys at position 75 of SEQ ID NO:85; (aw) a His at position 76 of SEQ ID NO:85; (ax) a Ser at position 77 of SEQ ID NO:85; (ay) a Ser at position 78 of SEQ ID NO:85; (az) a Asn at position 79 of SEQ ID NO:85; (ba) a Asn at position 80 of SEQ ID NO:85; (bb) a Val at position 81 of SEQ ID NO:85; (bc) a Thr at position 82 of SEQ ID NO:85; (bd) a Lys at position 83 of SEQ ID NO:85; (be) a Thr at position 84 of SEQ ID NO:85; (bf) a Glu at position 85 of SEQ ID NO:85; (bg) a Cys at position 86 of SEQ ID NO:85; (bh) a Cys at position 87 of SEQ ID NO:85; (bi) a Phe at position 88 of SEQ ID NO:85; (bj) a Thr at position 89 of SEQ ID NO:85; (bk) a Asp at position 90 of SEQ ID NO:85; (bl) a Phe at position 91 of SEQ ID NO:85; and (bm) a Cys at position 92 of SEQ ID NO:85. In some embodiments, the ALK7-binding protein specifically binds to ALK7 between amino acids 28-92 of SEQ ID NO: 85 and contacts one or more amino acids selected from the group consisting of: (a) a Cys at position 28 of SEQ ID NO:85; (b) a Val at position 29 of SEQ ID NO:85; (c) a Cys at position 30 of SEQ ID NO:85; (d) a Leu at position 31 of SEQ ID NO:85; (e) a Leu at position 32 of SEQ ID NO:85; (f) a Cys at position 33 of SEQ ID NO:85; (g) a Asp at position 34 of SEQ ID NO:85; (h) a Ser at position 35 of SEQ ID NO:85; (i) a Ser at position 36 of SEQ ID NO:85; (j) a Asn at position 37 of SEQ ID NO:85; (k) a Phe at position 38 of SEQ ID NO:85; (l) a Thr at position 39 of SEQ ID NO:85; (m) a Cys at position 40 of SEQ ID NO:85; (n) a Gln at position 41 of SEQ ID NO:85; (o) a Thr at position 42 of SEQ ID NO:85; (p) a Glu at position 43 of SEQ ID NO:85; (q) a Gly at position 44 of SEQ ID NO:85; (r) a Ala at position 45 of SEQ ID NO:85; (s) a Cys at position 46 of SEQ ID NO:85; (t) a Trp at position 47 of SEQ ID NO:85; (u) a Ala at position 48 of SEQ ID NO:85; (v) a Ser at position 49 of SEQ ID NO:85; (w) a Val at position 50 of SEQ ID NO:85; (x) a Met at position 51 of SEQ ID NO:85; (y) a Leu at position 52 of SEQ ID NO:85; (z) a Thr at position 53 of SEQ ID NO:85; (aa) a Asn at position 54 of SEQ ID NO:85; (ab) a Gly at position 55 of SEQ ID NO:85; (ac) a Lys at position 56 of SEQ ID NO:85; (ad) a Glu at position 57 of SEQ ID NO:85; (ae) a Gln at position 58 of SEQ ID NO:85; (af) a Val at position 59 of SEQ ID NO:85; (ag) a Ile at position 60 of SEQ ID NO:85; (ah) a Lys at position 61 of SEQ ID NO:85; (ai) a Ser at position 62 of SEQ ID NO:85; (aj) a Cys at position 63 of SEQ ID NO:85; (ak) a Val at position 64 of SEQ ID NO:85; (al) a Ser at position 65 of SEQ ID NO:85; (am) a Leu at position 66 of SEQ ID NO:85; (an) a Pro at position 67 of SEQ ID NO:85; (ao) a Glu at position 68 of SEQ ID NO:85; (ap) a Leu at position 69 of SEQ ID NO:85; (aq) a Asn at position 70 of SEQ ID NO:85; (ar) a Ala at position 71 of SEQ ID NO:85; (as) a Gln at position 72 of SEQ ID NO:85; (at) a Val at position 73 of SEQ ID NO:85; (au) a Phe at position 74 of SEQ ID NO:85; (av) a Cys at position 75 of SEQ ID NO:85; (aw) a His at position 76 of SEQ ID NO:85; (ax) a Ser at position 77 of SEQ ID NO:85; (ay) a Ser at position 78 of SEQ ID NO:85; (az) a Asn at position 79 of SEQ ID NO:85; (ba) a Asn at position 80 of SEQ ID NO:85; (bb) a Val at position 81 of SEQ ID NO:85; (bc) a Thr at position 82 of SEQ ID NO:85; (bd) a Lys at position 83 of SEQ ID NO:85; (be) a Thr at position 84 of SEQ ID NO:85; (bf) a Glu at position 85 of SEQ ID NO:85; (bg) a Cys at position 86 of SEQ ID NO:85; (bh) a Cys at position 87 of SEQ ID NO:85; (bi) a Phe at position 88 of SEQ ID NO:85; (bj) a Thr at position 89 of SEQ ID NO:85; (bk) a Asp at position 90 of SEQ ID NO:85; (bl) a Phe at position 91 of SEQ ID NO:85; and (bm) a Cys at position 92 of SEQ ID NO:85; and inhibits one or more ALK7 ligands (e.g., GDF1, GDF3, GDF8, activin B, activin A/B, and/or Nodal) from binding to ALK7. In some embodiments, the ALK7-binding protein specifically binds to ALK7 between amino acids 28-92 of SEQ ID NO:85 and increases lipolysis (e.g., lipolysis of white adipocytes and/or brown adipocytes). In some embodiments, the ALK7-binding protein specifically binds to ALK7 between amino acids 28-92 of SEQ ID NO:85 and contacts one or more amino acids selected from the group consisting of: (a) a Cys at position 28 of SEQ ID NO:85; (b) a Val at position 29 of SEQ ID NO:85; (c) a Cys at position 30 of SEQ ID NO:85; (d) a Leu at position 31 of SEQ ID NO:85; (e) a Leu at position 32 of SEQ ID NO:85; (f) a Cys at position 33 of SEQ ID NO:85; (g) a Asp at position 34 of SEQ ID NO:85; (h) a Ser at position 35 of SEQ ID NO:85; (i) a Ser at position 36 of SEQ ID NO:85; (j) a Asn at position 37 of SEQ ID NO:85; (k) a Phe at position 38 of SEQ ID NO:85; (l) a Thr at position 39 of SEQ ID NO:85; (m) a Cys at position 40 of SEQ ID NO:85; (n) a Gln at position 41 of SEQ ID NO:85; (o) a Thr at position 42 of SEQ ID NO:85; (p) a Glu at position 43 of SEQ ID NO:85; (q) a Gly at position 44 of SEQ ID NO:85; (r) a Ala at position 45 of SEQ ID NO:85; (s) a Cys at position 46 of SEQ ID NO:85; (t) a Trp at position 47 of SEQ ID NO:85; (u) a Ala at position 48 of SEQ ID NO:85; (v) a Ser at position 49 of SEQ ID NO:85; (w) a Val at position 50 of SEQ ID NO:85; (x) a Met at position 51 of SEQ ID NO:85; (y) a Leu at position 52 of SEQ ID NO:85; (z) a Thr at position 53 of SEQ ID NO:85; (aa) a Asn at position 54 of SEQ ID NO:85; (ab) a Gly at position 55 of SEQ ID NO:85; (ac) a Lys at position 56 of SEQ ID NO:85; (ad) a Glu at position 57 of SEQ ID NO:85; (ae) a Gln at position 58 of SEQ ID NO:85; (af) a Val at position 59 of SEQ ID NO:85; (ag) a Ile at position 60 of SEQ ID NO:85; (ah) a Lys at position 61 of SEQ ID NO:85; (ai) a Ser at position 62 of SEQ ID NO:85; (aj) a Cys at position 63 of SEQ ID NO:85; (ak) a Val at position 64 of SEQ ID NO:85; (al) a Ser at position 65 of SEQ ID NO:85; (am) a Leu at position 66 of SEQ ID NO:85; (an) a Pro at position 67 of SEQ ID NO:85; (ao) a Glu at position 68 of SEQ ID NO:85; (ap) a Leu at position 69 of SEQ ID NO:85; (aq) a Asn at position 70 of SEQ ID NO:85; (ar) a Ala at position 71 of SEQ ID NO:85; (as) a Gln at position 72 of SEQ ID NO:85; (at) a Val at position 73 of SEQ ID NO:85; (au) a Phe at position 74 of SEQ ID NO:85; (av) a Cys at position 75 of SEQ ID NO:85; (aw) a His at position 76 of SEQ ID NO:85; (ax) a Ser at position 77 of SEQ ID NO:85; (ay) a Ser at position 78 of SEQ ID NO:85; (az) a Asn at position 79 of SEQ ID NO:85; (ba) a Asn at position 80 of SEQ ID NO:85; (bb) a Val at position 81 of SEQ ID NO:85; (bc) a Thr at position 82 of SEQ ID NO:85; (bd) a Lys at position 83 of SEQ ID NO:85; (be) a Thr at position 84 of SEQ ID NO:85; (bf) a Glu at position 85 of SEQ ID NO:85; (bg) a Cys at position 86 of SEQ ID NO:85; (bh) a Cys at position 87 of SEQ ID NO:85; (bi) a Phe at position 88 of SEQ ID NO:85; (bj) a Thr at position 89 of SEQ ID NO:85; (bk) a Asp at position 90 of SEQ ID NO:85; (bl) a Phe at position 91 of SEQ ID NO:85; and (bm) a Cys at position 92 of SEQ ID NO:85; and increases lipolysis (e.g., lipolysis of white adipocytes and/or brown adipocytes).

Nucleic acids and sets of nucleic acids encoding ALK7-binding proteins are also provided. Vectors and sets of vectors containing the nucleic acids and sets of nucleic acids, and host cells transformed with the nucleic acids and vectors are further provided. In some embodiments, the host cell is a hybridoma or mammalian host cell such as, a NS0 murine myeloma cell, a PER.C6® human cell, or a Chinese hamster ovary (CHO) cell. Host cells including mammalian host cells and hybridomas that produce ALK7-binding proteins are also provided.

Methods for making an ALK7-binding protein are also provided. In some embodiments, the method comprises culturing a host cell capable of expressing the ALK7-binding protein under suitable conditions for expressing the protein and optionally isolating the expressed ALK7-binding protein. ALK7-binding proteins prepared and/or isolated using methods disclosed herein or otherwise known in the art are also provided.

Pharmaceutical compositions comprising an ALK7-binding protein and a pharmaceutically acceptable carrier are further provided. In some embodiments, the disclosure provides methods for treating and/or ameliorating a condition in a subject associated with elevated ALK7 expression or ALK7-mediated signaling, or that can be treated and/or ameliorated by decreased ALK7 signaling. In some embodiments, the methods decrease ALK7-mediated signaling in the subject.

Conditions that may be treated and/or ameliorated in a subject using the provided methods include, but are not limited to: obesity (e.g., abdominal obesity); overweight; insulin resistance; metabolic syndrome and other metabolic diseases or conditions; a lipid disorder such as, low HDL levels, high LDL levels, hyperlipidemia, hypertriglyceridemia or dyslipidemia; lipoprotein aberrations; decreased triglycerides; inflammation (e.g., liver inflammation and/or inflammation of adipose tissue), fatty liver disease; non-alcoholic fatty liver disease; hyperglycemia; impaired glucose tolerance (IGT); hyperinsulinemia; high cholesterol (e.g., high LDL levels and hypercholesterolemia); cardiovascular disease such as, heart disease including coronary heart disease, congestive heart failure, stroke, peripheral vascular disease, disordered fibrinolysis, atherosclerosis; arteriosclerosis, and hypertension; Syndrome X; vascular restenosis; neuropathy; retinopathy; neurodegenerative disease; endothelial dysfunction, respiratory dysfunction, renal disease (e.g., nephropathy); pancreatitis; polycystic ovarian syndrome; elevated uric acid levels; haemochromatosis (iron overload); acanthosis nigricans (dark patches on the skin); and cancer (e.g., myeloma (multiple myeloma, plasmacytoma, localized myeloma, or extramedullary myeloma), or an ovarian, breast, colon, endometrial, liver, kidney, pancreatic, gastric, uterine and/or colon cancer); and other disorders/conditions associated with one or more of the above diseases or conditions, or with overweight (e.g., BMI≥25 kg/m$^2$), or too much body fat.

In some embodiments, the disclosed methods include administering a pharmaceutical composition comprising an effective amount of an ALK7-binding protein (e.g., an antagonist ALK7 binding protein such as an antagonist anti-ALK7 antibody) to a subject in need thereof. In some embodiments, the ALK7-binding protein is administered alone. In other embodiments, the ALK7-binding protein is administered as a combination therapy. In further embodiments, the ALK7-binding protein is administered as a combination therapy to the standard of care treatment/therapy.

Methods of blocking or reducing ALK7 activity (e.g., ligand binding and/or signaling) are also provided. In some embodiments the method comprises contacting an ALK7-binding protein and a cell that expresses ALK7, (e.g., a differentiated white or brown adipocyte). In some instances the method comprises contacting an ALK7-binding protein and a cell that expresses ALK7, in the presence of GDF1, GDF3, GDF8, activin B, activin A/B, and/or Nodal. In some embodiments, the method is performed in vivo. In other embodiments, the method is performed in vitro. In some embodiments the blocked or reduced ALK7 activity is the phosphorylation of ALK7. In additional embodiments the blocked or reduced ALK7 activity is the phosphorylation of Smads (e.g., Smad2 and/or Smad3). In some embodiments, the disclosure provides a method of blocking or reducing ALK7 activity in a subject that comprises administering an effective amount of an ALK7-binding protein to a subject in need thereof.

Also provided is a method of blocking or reducing ALK7 activity in a pathological condition associated with ALK7 expression and/or ALK7 signaling, or in a pathological condition that can be treated and/or ameliorated by reducing or inhibiting the activity of an ALK7-ligand. In some instances, the method comprises administering an ALK7-binding protein to a subject having increased expression of ALK7 or an ALK7-ligand. In some embodiments, the pathological condition is obesity, diabetes, metabolic disease, dyslipidemia; cardiovascular disease, type 2 diabetes, inflammation, or a pulmonary, fatty liver disease, neurologic, and hepatic, or renal disease.

In one embodiment, the disclosure provides a method of treating or ameliorating overweight or a condition associated with being overweight, comprising administering to an overweight subject an effective amount of an ALK7-binding protein (e.g., an antagonist ALK7 binding protein such as an antagonist anti-ALK7 antibody). In one embodiment, the he treated or ameliorated condition is obesity. In another embodiment, the treated or ameliorated condition is a member selected from the group consisting of dyslipidemia, hyperlipidemia, hypercholesterolemia, low HDL serum level, high LDL serum level (e.g., LDL-C≥100 mg/dL, ≥130 mg/dL, ≥160 mg/dL), and hypertriglyceridemia (e.g., TG≥150 mg/dL, ≥160 mg/dL, ≥170 mg/dL). In another embodiment, the treated or ameliorated condition is hypertension. In another embodiment, the treated or ameliorated condition is diabetes. In one embodiment, the administered ALK7-binding protein is an ALK7 antagonist. In one embodiment, the administered antagonist ALK7-binding protein is an anti-ALK7 antibody or an ALK7-binding antibody fragment. In another embodiment the administered antagonist ALK7-binding protein is an anti-ALK7 antibody or an ALK7-binding antibody fragment disclosed herein. In one embodiment, the administered ALK7-binding protein comprises a VH and VL pair disclosed in Table 1A. In another embodiment, the administered ALK7-binding protein cross-blocks or competes for binding to ALK7 with an antibody comprising a VH and a VL sequence pair disclosed in Table 1A. In one embodiment, the administered ALK7-binding protein comprises a VH and VL pair disclosed in Table 1B or Table 3. In another embodiment, the administered ALK7-binding protein cross-blocks or competes for binding to ALK7 with an antibody comprising a VH and a VL sequence pair disclosed in Table 1B or Table 3. In one embodiment, the administered ALK7-binding protein comprises a VH and VL pair disclosed in Table 1A, Table 1B, or Table 3. In another embodiment, the administered ALK7-binding protein cross-blocks or competes for binding to ALK7 with an antibody comprising a VH and a VL sequence pair disclosed in Table 1A, Table 1B, or Table 3.

In one embodiment, the disclosure provides a method of treating or ameliorating obesity or a condition associated with obesity, comprising administering to an obese subject an effective amount of an ALK7-binding protein (e.g., an antagonist ALK7 binding protein such as an antagonist anti-ALK7 antibody). In one embodiment the treated or ameliorated condition is hypertension, dyslipidemia (for example, high total cholesterol or high levels of triglycerides), type 2 diabetes, coronary heart disease, stroke, gallbladder disease, osteoarthritis, sleep disorders, respiratory problems, cancer (e.g., myeloma (multiple myeloma, plasmacytoma, localized myeloma, or extramedullary myeloma), or an ovarian, breast, colon, endometrial, liver, kidney, pancreatic, gastric, uterine and/or colon cancer), obesity linked gallbladder disease, obesity linked inflammation, obesity induced sleep apnea, steatosis (fatty liver), glucagonomas, arteriosclerosis or heart failure. In some embodiments the subject to which the ALK7 binding protein is administered is at risk of developing hypertension, dyslipidemia (for example, high total cholesterol or high levels of triglycerides), type 2 diabetes, coronary heart disease, stroke, gallbladder disease, osteoarthritis, sleep disorders, respiratory problems, cancer (e.g., a myeloma (multiple myeloma, plasmacytoma, localized myeloma, or extramedullary myeloma), or an ovarian, breast, colon, endometrial, liver, kidney, pancreatic, gastric, uterine or colon cancer), obesity linked gallbladder disease, obesity linked inflammation, obesity induced sleep apnea, steatosis, glucagonomas, arteriosclerosis or heart failure. In one embodiment, the administered ALK7-binding protein is an ALK7 antagonist. In one embodiment, the administered antagonist ALK7-binding protein is an anti-ALK7 antibody or an ALK7-binding antibody fragment. In another embodiment the administered antagonist ALK7-binding protein is an anti-ALK7 antibody or an ALK7-binding antibody fragment disclosed herein. In one embodiment, the administered ALK7-binding protein comprises a VH and VL pair disclosed in Table 1A. In another embodiment, the administered ALK7-binding protein cross-blocks or competes for binding to ALK7 with an antibody comprising a VH and a VL sequence pair disclosed in Table 1A. In one embodiment, the administered ALK7-binding protein comprises a VH and VL pair disclosed in Table 3. In another embodiment, the administered ALK7-binding protein cross-blocks or competes for binding to ALK7 with an antibody comprising a VH and a VL sequence pair disclosed in Table 3. In one embodiment, the administered ALK7-binding protein comprises a VH and VL pair disclosed in Table 1A, Table 1B, or Table 3. In another embodiment, the administered ALK7-binding protein cross-blocks or competes for binding to ALK7 with an antibody comprising a VH and a VL sequence pair disclosed in Table 1A, Table 1B, or Table 3.

In one embodiment, the disclosure provides a method of treating or ameliorating type II diabetes or a condition associated with type II diabetes, comprising administering to a diabetic subject an effective amount of an ALK7-binding protein (e.g., an antagonist ALK7 binding protein such as an antagonist anti-ALK7 antibody). In one embodiment, the disclosure provides a method of treating or ameliorating a condition associated with type II diabetes. In a further embodiment, the condition is a member selected from: an eye condition (e.g., glaucoma, cataracts, and retinopathy), cardiovascular disease (e.g., hypertension, atherosclerosis, myocardial infarction, and stroke), hyperglycemia, peripheral neuropathy, and kidney disease (e.g., nephropathy). In an additional embodiment, the subject is at risk of developing type II diabetes or a condition associated with type II diabetes. In another embodiment, the subject is at risk of developing an eye condition (e.g., glaucoma, cataracts, and retinopathy), cardiovascular disease (e.g., hypertension, atherosclerosis, myocardial infarction, disordered fibrinolysis, and stroke), hyperglycemia, peripheral neuropathy, or kidney disease (e.g., nephropathy). In one embodiment, the administered ALK7-binding protein is an ALK7 antagonist. In one embodiment, the administered antagonist ALK7-binding protein is an anti-ALK7 antibody or an ALK7-binding antibody fragment. In another embodiment the administered antagonist ALK7-binding protein is an anti-ALK7 antibody or an ALK7-binding antibody fragment disclosed herein. In one embodiment, the administered ALK7-binding protein comprises a VH and VL pair disclosed in Table 1A. In another embodiment, the administered ALK7-binding protein comprises a VH and VL pair disclosed in Table 3. In another embodiment, the administered ALK7-binding protein cross-blocks or competes for binding to ALK7 with an antibody comprising a VH and a VL sequence pair disclosed in Table 3.

In one embodiment, the disclosure provides a method of treating or ameliorating a metabolic disease or disorder or a condition associated with a metabolic disease or disorder, comprising administering to an effective amount of an ALK7-binding protein (e.g., an antagonist ALK7 binding protein such as an antagonist anti-ALK7 antibody) to a subject in need thereof. In one embodiment the treated or ameliorated condition is an alteration of lipid, lipoprotein or apolipoprotein metabolism. In another embodiment the embodiment, the metabolic condition is high plasma triglyceride levels, hypertension, dyslipidemia high fasting blood sugar, low HDL cholesterol levels. In another embodiment, the treated or ameliorated condition is atherosclerosis, arteriosclerosis, or endothelial dysfunction. In one embodiment the treated or ameliorated condition is chronic inflammation. In another embodiment the treated or ameliorated condition is non-alcoholic fatty liver disease (e.g., fatty liver and/or NASH). In one embodiment, the administered ALK7-binding protein is an ALK7 antagonist. In one embodiment, the administered antagonist ALK7-binding protein is an anti-ALK7 antibody or an ALK7-binding antibody fragment. In another embodiment the administered antagonist ALK7-binding protein is an anti-ALK7 antibody or an ALK7-binding antibody fragment disclosed herein. In one embodiment, the administered ALK7-binding protein comprises a VH and VL pair disclosed in Table 1A. In another embodiment, the administered ALK7-binding protein cross-blocks or competes for binding to ALK7 with an antibody comprising a VH and a VL sequence pair disclosed in Table 1A. In one embodiment, the administered ALK7-binding protein comprises a VH and VL pair disclosed in Table 1B or Table 3. In another embodiment, the administered ALK7-binding protein cross-blocks or competes for binding to ALK7 with an antibody comprising a VH and a VL sequence pair disclosed in Table 1B or Table 3.

In one embodiment, the disclosure provides a method of treating or ameliorating insulin resistance or a condition associated with insulin resistance, comprising administering an effective amount of an ALK7-binding protein (e.g., an antagonist ALK7 binding protein such as an antagonist anti-ALK7 antibody) to a subject in need thereof. In a further embodiment, the he treated or ameliorated condition is associated with impaired glucose tolerance or hyperglycemia. In another embodiment, the treated or ameliorated condition is associated with hypertension or atherosclerosis. In another embodiment, the treated or ameliorated condition is a member selected from the group consisting of: dyslipidemia, hyperlipidemia, hypercholesterolemia, low HDL serum level, high LDL serum level (e.g., LDL-C≥100 mg/dL, ≥130 mg/dL, ≥160 mg/dL), and hypertriglyceridemia (e.g., TG≥150 mg/dL, ≥160 mg/dL, ≥170 mg/dL). In one embodiment, the administered ALK7-binding protein is an ALK7 antagonist. In one embodiment, the administered antagonist ALK7-binding protein is an anti-ALK7 antibody or an ALK7-binding antibody fragment. In another embodiment the administered antagonist ALK7-binding protein is an anti-ALK7 antibody or an ALK7-binding antibody fragment disclosed herein. In one embodiment, the administered ALK7-binding protein comprises a VH and VL pair disclosed in Table 1A. In another embodiment, the administered ALK7-binding protein cross-blocks or competes for binding to ALK7 with an antibody comprising a VH and a VL sequence pair disclosed in Table 1A. In one embodiment, the administered ALK7-binding protein comprises a VH and VL pair disclosed in Table 1B or Table 3. In another embodiment, the administered ALK7-binding protein cross-blocks or competes for binding to ALK7 with an antibody comprising a VH and a VL sequence pair disclosed in Table 1B or Table 3.

In one embodiment, the disclosure provides a method of treating or ameliorating a disease or disorder of the eyes, nervous system, kidney, lungs, and/or liver, or associated condition, comprising administering to an effective amount of an ALK7-binding protein (e.g., an antagonist ALK7 binding protein such as an antagonist anti-ALK7 antibody) to a subject in need thereof. In one embodiment, the treated or ameliorated condition is inflammation. In one embodiment, the treated or ameliorated condition is nephropathy (e.g., diabetic nephropathy), arteriosclerosis of the renal artery), or kidney failure. In a further embodiment, the treated or ameliorated condition is chronic inflammation. In a further embodiment the treated or ameliorated condition inflammation of adipose tissue. In another embodiment, the treated or ameliorated condition is inflammation of the liver. In another embodiment the treated or ameliorated condition is NAFLD (e.g., fatty liver and/or NASH). In some embodiments, the subject to which the ALK7 binding protein is administered is at risk of developing a disease or disorder of the kidney, lungs, or liver. In some embodiments, the subject to which the ALK7 binding protein is administered is at risk of developing nephropathy. In some embodiments, the subject to which the ALK7 binding protein is administered is at risk of developing nephropathy. In one embodiment, the subject is at risk of developing chronic inflammation. In one embodiment, the subject is at risk of developing inflammation of adipose tissue. In an additional embodiment, the subject is at risk of developing inflammation of the liver. In one embodiment, the administered ALK7-binding protein is an ALK7 antagonist. In one embodiment, the administered antagonist ALK7-binding protein is an anti-ALK7 antibody or an ALK7-binding antibody fragment. In another embodiment the administered antagonist ALK7-binding protein is an anti-ALK7 antibody or an ALK7-binding antibody fragment disclosed herein. In one embodiment, the administered ALK7-binding protein comprises a VH and VL pair disclosed in Table 1A. In another embodiment, the administered ALK7-binding protein cross-blocks or competes for binding to ALK7 with an antibody comprising a VH and a VL sequence pair disclosed in Table 1A. In one embodiment, the administered ALK7-binding protein comprises a VH and VL pair disclosed in Table 1B or Table 3. In another embodiment, the administered ALK7-binding protein cross-blocks or competes for binding to ALK7 with an antibody comprising a VH and a VL sequence pair disclosed in Table 1B or Table 3.

In one embodiment, the disclosure provides a method of treating or ameliorating a cardiovascular disease or disorder or a condition associated with a cardiovascular disease or disorder, comprising administering to an effective amount of an ALK7-binding protein (e.g., an antagonist ALK7 binding protein such as an antagonist anti-ALK7 antibody) to a subject in need thereof. In one embodiment, the treated or ameliorated condition is coronary heart disease, congestive heart failure, vascular restenosis, stroke, peripheral vascular disease, microvascular disease, disordered fibrinolysis, or arteriosclerosis. In one embodiment, the subject to which the ALK7 binding protein is administered is at risk of developing coronary heart disease, congestive heart failure, vascular restenosis, stroke, peripheral vascular disease, microvascular disease, or arteriosclerosis. In one embodiment, the treated or ameliorated condition is hypertension (e.g., blood pressure >130/80 mmHg in a resting state). In one embodiment, the subject to which the ALK7 binding protein is administered is at risk of developing hypertension. In one embodiment, the treated or ameliorated condition is atherosclerosis. In one embodiment, the subject to which the ALK7 binding protein is administered is at risk of developing atherosclerosis. In one embodiment, the administered ALK7-binding protein is an ALK7 antagonist. In one embodiment, the administered antagonist ALK7-binding protein is an anti-ALK7 antibody or an ALK7-binding antibody fragment. In another embodiment the administered antagonist ALK7-binding protein is an anti-ALK7 antibody or an ALK7-binding antibody fragment disclosed herein. In one embodiment, the administered ALK7-binding protein comprises a VH and VL pair disclosed in Table 1A. In another embodiment, the administered ALK7-binding protein cross-blocks or competes for binding to ALK7 with an antibody comprising a VH and a VL sequence pair disclosed in Table 1A. In one embodiment, the administered ALK7-binding protein comprises a VH and VL pair disclosed in Table 1B. In another embodiment, the administered ALK7-binding protein cross-blocks or competes for binding to ALK7 with an antibody comprising a VH and a VL sequence pair disclosed in Table 1B. In one embodiment, the administered ALK7-binding protein comprises a VH and VL pair disclosed in Table 3. In another embodiment, the administered ALK7-binding protein cross-blocks or competes for binding to ALK7 with an antibody comprising a VH and a VL sequence pair disclosed in Table 3.

BRIEF DESCRIPTION OF THE DRAWINGS/FIGURES

FIG. 1 shows the amount of adipose change in TBS and ALK7 mAb treated high-fat diet (HFD) mice. Changes in the amount of adipose are relative to baseline prior to ALK7 Ab or TBS treatment. Treatment with ALK7 mAbs (i.e., J02, K02, G05, C03, and L02) significantly reduced fat mass in HFD mice. * designates p>0.001 vs. HFD+TBS.

Figure 2:
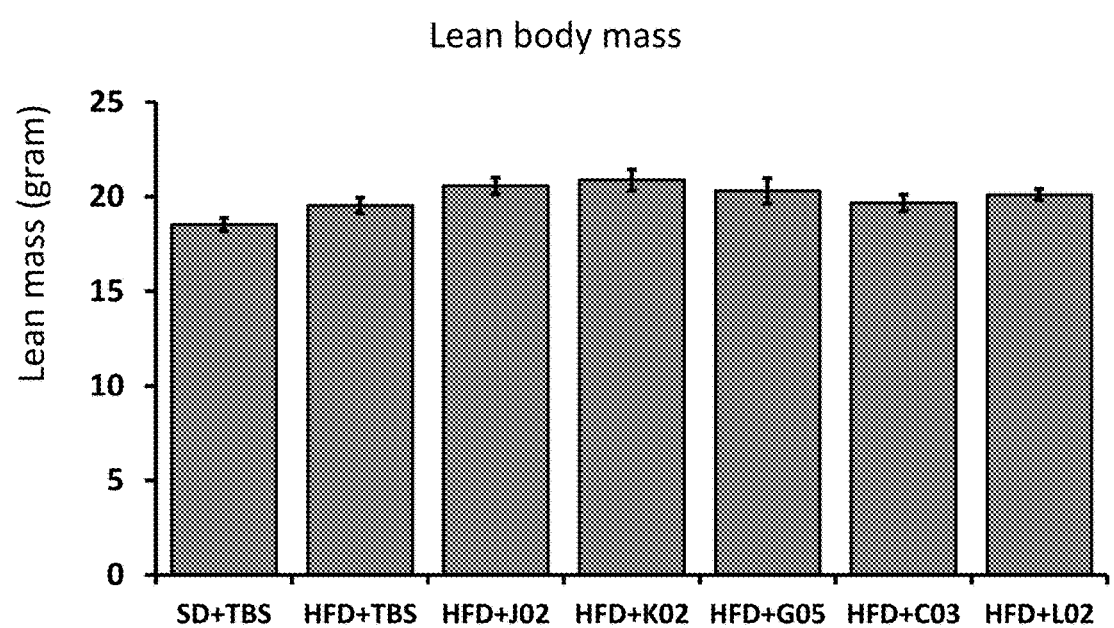

FIG. 2 shows the amount of lean body mass change in TBS and ALK7 mAb treated high-fat diet (HFD) mice. Changes in the amount of lean mass are relative to baseline prior to ALK7 Ab or TBS treatment. Treatment with ALK7 mAbs (i.e., J02, K02, G05, C03, and L02) did not change lean body mass in HFD mice.

DETAILED DESCRIPTION

The disclosure provides isolated and/or recombinant ALK7-binding proteins. In certain embodiments the ALK7-binding proteins specifically bind ALK7. In further embodiments, the ALK7-binding proteins are anti-ALK7 antibodies. Nucleic acids encoding the ALK7-binding proteins, vectors and host cells containing the nucleic acids, and methods of making and using the ALK7-binding proteins are also provided. The provided ALK7-binding proteins have uses in diagnosing, treating, and/or ameliorating diseases and conditions associated with increased ALK7 expression and/or signaling. Such uses include but are not limited to, preventing, and/or ameliorating obesity (e.g., abdominal obesity); overweight; insulin resistance; metabolic syndrome and other metabolic diseases or conditions; a lipid disorder such as, low HDL levels, high LDL levels, hyperlipidemia, hypertriglyceridemia or dyslipidemia; lipoprotein aberrations; decreased triglycerides; inflammation (e.g., liver inflammation and/or inflammation of adipose tissue), fatty liver disease; non-alcoholic fatty liver disease; hyperglycemia; impaired glucose tolerance (IGT); hyperinsulinemia; high cholesterol (e.g., high LDL levels and hypercholesterolemia); cardiovascular disease such as, heart disease including coronary heart disease, congestive heart failure, stroke, peripheral vascular disease, atherosclerosis; arteriosclerosis, and hypertension; Syndrome X; vascular restenosis; neuropathy; retinopathy; neurodegenerative disease; endothelial dysfunction, respiratory dysfunction, renal disease (e.g., nephropathy); pancreatitis; polycystic ovarian syndrome; elevated uric acid levels; haemochromatosis (iron overload); acanthosis nigricans (dark patches on the skin); and cancer (e.g., a myeloma (multiple myeloma, plasmacytoma, localized myeloma, or extramedullary myeloma), or an ovarian, breast, colon, endometrial, liver, kidney, pancreatic, gastric, uterine and/or colon cancer); and other disorders/conditions associated with one or more of the above diseases or conditions, or with overweight (e.g., BMI of 25 kg/m$^2$), or too much body fat.

Definitions

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure. The headings provided herein are not limitations of the various embodiments which can be had by reference to the specification as a whole. Moreover, the terms defined immediately below are more fully defined by reference to the specification in its entirety.

The terms "a," "an" and "the" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "comprise" is generally used in the sense of include, that is to say permitting the presence of one or more features or components. Wherever embodiments are described herein with the language "comprising," otherwise analogous embodiments described in terms of "consisting of," and/or "consisting essentially of" are also provided.

The terms "about" and "approximately" as used in connection with a numerical value throughout the specification and the claims denotes an interval of accuracy, familiar and acceptable to a person skilled in the art. In general, such interval of accuracy is ±10%. Alternatively, and particularly in biological systems, the terms "about" and "approximately" may mean values that are within an order of magnitude, preferably ≤5-fold and more preferably ≤2-fold of a given value.

Numeric ranges are inclusive of the numbers defining the range.

An ALK7-binding protein refers to a protein that specifically binds to ALK7, preferably binding to the extracellular domain of ALK7.

The terms "ALK7" and "ALK7 receptor" are used interchangeably and refer to ALK7 (also referred to as ACVRLK7, Activin A Receptor, Type IC, ACVR-1C, Activin Receptor-Like kinase 7, and EC 2.7.11 in the literature). Reference sequence for human ALK7 is provided in NCBI Reference Sequences NP_001104501.1. The provided ALK7-binding proteins bind the extracellular domain of human ALK7 corresponding to the amino acid sequence of SEQ ID NO:86. Reference sequence for rat ALK7 is provided in NCBI Reference Sequences P70539. In some embodiments, the provided ALK7-binding proteins bind the extracellular domain of rat ALK7 corresponding to the amino acid sequence of SEQ ID NO:87.

The term "compete" or "competes" when used in the context of ALK7-binding proteins (e.g., neutralizing antibodies) means competition between antigen binding proteins as determined by an assay in which the antigen binding protein (e.g., an anti-ALK7 antibody or an ALK7-binding fragment thereof) under test prevents or inhibits specific binding of a reference antigen binding protein (e.g., a ligand, or a reference antibody) to a common antigen (e.g., an ALK7 extracellular domain or a fragment thereof). Numerous types of competitive binding assays can be used, for example: solid phase direct or indirect radioimmunoassay (RIA) (see, e.g., Moldenhauer et al., *Scand. J. Immunol.* 32:77-82 (1990) and Morel et al., *Molec. Immunol.* 25:7-15 (1988)), solid phase direct or indirect enzyme immunoassay (EIA), solid phase direct biotin-avidin EIA (see, e.g., Cheung, et al., *Virology* 176:546-552 (1990) and Kirkland et al., *J. Immunol.* 137:3614-3619 (1986)) and a sandwich competition assay (see, e.g., Stahli et al., *Methods in Enzymology* 92:242-253 (1983)). Typically, such an assay involves the use of purified antigen bound to a solid surface or cells bearing either of these, an unlabeled test antigen binding protein and a labeled reference antigen binding protein. Competitive inhibition can be measured by determining the amount of label bound to the solid surface or cells in the presence of the test antigen binding protein. Usually the test antigen binding protein is present in excess. Antigen binding proteins identified by competition assay (competing antigen binding proteins) include ALK7-binding proteins that bind to the same epitope as the reference ALK7-binding protein as well as ALK7-binding proteins that bind to an adjacent epitope sufficiently proximal to the epitope bound by the reference ALK7-binding protein for steric hindrance to occur. Usually, when a competing ALK7 binding protein is present in excess, it will inhibit specific binding of a reference ALK7-binding protein to ALK7 by at least 40%, 45%, 50%, 55%, 60%, 65%, 70% or 75%. In some instance, a competing antigen binding protein inhibits specific binding of a reference ALK7-binding protein by at least 80%, 85%, 90%, 91%, 92%, 93%, 94%, 95%, 96%, 97% 98%, or 99%.

The term "epitope" when used in context of an ALK7 protein refers to an ALK7 (e.g., human ALK7 or murine ALK7) protein determinant capable of binding to an ALK7-binding protein (e.g., an antibody) of the disclosure. Epitopes usually consist of chemically active surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents. The ALK7 epitope bound by an ALK7-binding protein can readily be determined using techniques known in the art.

Antigen binding proteins such as the anti-ALK7-binding antibodies and ALK7-binding fragments, variants, or derivatives thereof disclosed herein, can be described or specified in terms of the epitope(s) or portion(s) of an antigen, e.g., a target polypeptide that they recognize or specifically bind. For example, the portion of ALK7 that specifically interacts with the antigen binding domain of an ALK7-binding protein disclosed herein is an "epitope." Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. Epitope determinants may include chemically active surface groupings of molecules such as amino acids, sugar side chains, phosphoryl or sulfonyl groups, and may have specific three dimensional structural characteristics, and/or specific charge characteristics. An epitope typically includes at least 3, 4, 5, 6, 3, 4, 5, 6, 7, 8, 9, 10, 11, 12, 13, 14, 15, 16, 17, 18, 19, 20, 25, 30, 35 amino acids in a unique spatial conformation. Epitopes can routinely be determined using methods known in the art.

The terms "inhibit," "block," "reduce," "decrease," "suppress," "antagonize," and "neutralize" are used interchangeably and refer to any statistically significant decrease in activity (e.g., ALK7 ligand binding and/or ALK7 signaling), including full blocking of the activity. For example, "inhibition," "suppression," or "antagonize" can refer to a decrease of about 10%, 20%, 30%, 40%, 50%, 60%, 70%, 80%, 90% or 100% in activity compared to a control.

In some embodiments, the term "decrease," "inhibit," or "antagonize" may refer to the ability of an ALK7-binding protein such as an antibody or ALK7-binding fragment thereof, to statistically significantly (e.g., with a p value less than or equal to 0.05) decrease the phosphorylation of one or more Smads (e.g., Smad2 and/or Smad3) induced by contacting a cell expressing ALK7 and ActrIIA/B with an ALK7 ligand such as, GDF1, GDF3, GDF8, activin B, activin A/B, and/or Nodal, relative to the extent of Smad phosphorylation in the cell when not contacted with the ALK7-binding protein. The cell which expresses ALK7 can be a naturally occurring cell or a cell line, or can be recombinantly produced by introducing a nucleic acid encoding ALK7 into a host cell. In one embodiment, the ALK7-binding protein, e.g., an ALK7 antibody or ALK7-binding fragment thereof, antagonizes (decreases) ALK7 ligand mediated phosphorylation of one or more Smads (e.g., Smad2 and/or Smad3) by at least 10%, 20%, 30%, 40%, 50%, 60%, 70%, 80%, 90%, or 95%, or by about 100%, as determined, for example, by Western blotting followed by probing with an anti-phosphotyrosine antibody or by ELISA (e.g., P-Smad ELISA) or a Smad dependent reporter gene assay using techniques described herein or otherwise known in the art. In one embodiment, the ALK7-binding protein, antagonizes (decreases) ALK7-mediated inhibition of lipolysis in adipose cells. In one embodiment, an ALK7-binding protein is an ALK7 antagonist and antagonizes ALK7-mediated inhibition of lipolysis in white adipose cell by 5% to 100%, 10% to 95%, 10 to 90%, 10 to 85%, 10 to 80%, 10 to 75%, 10 to 70%, 10 to 75%, 10 to 70%, 10 to 60%, 10 to 55%, 10 to 50%, or 10 to 45%, as determined in a lipolysis assay. In another embodiment, an ALK7-binding protein reduces or decreases ALK7-mediated inhibition of lipolysis in white adipose cells by at least 5%, 10%, 20%, 30%, 40%, 50%, 60%, 70%, 80%, 90%, or 95%, or by about 100%, as determined in a lipolysis assay. In some embodiments the lipolysis assay is performed in the presence of one or more ALK7 ligands. In further embodiments, the lipolysis assay is performed in the presence of one or more ALK7 ligands selected from the group consisting of GDF1, GDF3, GDF8, activin B, activin A/B, and Nodal).

In one embodiment, an ALK7-binding protein is an ALK7 antagonist and antagonizes ALK7-mediated inhibition of lipolysis in white and/or brown adipose cells by 5% to 100%, 10% to 95%, 10 to 90%, 10 to 85%, 10 to 80%, 10 to 75%, 10 to 70%, 10 to 75%, 10 to 70%, 10 to 60%, 10 to 55%, 10 to 50%, or 10 to 45%, as determined in a lipolysis assay. In another embodiment, an ALK7-binding protein reduces or decreases ALK7-mediated inhibition of lipolysis in white and/or brown adipose cells by at least 5%, 10%, 20%, 30%, 40%, 50%, 60%, 70%, 80%, 90%, or 95%, or by about 100%, as determined in a lipolysis assay. In some embodiments the lipolysis assay is performed in the presence of one or more ALK7 ligands. In further embodiments, the lipolysis assay is performed in the presence of one or more ALK7 ligands selected from the group consisting of GDF1, GDF3, GDF8, activin B, activin A/B, and Nodal).

The terms "increase," "promote" and "agonist" are used interchangeably and refer to any statistically significant increase in activity (e.g., ALK7 ligand binding and/or ALK7 signaling). For example, "increase" or "promote" can refer to an increase of about 10%, 20%, 30%, 40%, 50%, 60%, 70%, 80%, 90% or 100% in activity compared to a control.

In some embodiments, the ALK7-binding protein increases lipolysis in cells. In some embodiments, the ALK7-binding protein increases lipolysis in cells by at least 5% to 100%, 10% to 95%, 10 to 90%, 10 to 85%, 10 to 80%, 10 to 75%, 10 to 70%, 10 to 75%, 10 to 70%, 10 to 60%, 10 to 55%, 10 to 50%, or 10 to 45%, as determined in a lipolysis assay. In some embodiments, the ALK7-binding protein increases lipolysis in adipose cells. In some embodiments, the ALK7-binding protein increases lipolysis in adipose cells by at least 5% to 100%, 10% to 95%, 10 to 90%, 10 to 85%, 10 to 80%, 10 to 75%, 10 to 70%, 10 to 75%, 10 to 70%, 10 to 60%, 10 to 55%, 10 to 50%, or 10 to 45%, as determined in a lipolysis assay. In some embodiments the lipolysis assay is performed in the presence of one or more ALK7 ligands. In further embodiments, the lipolysis assay is performed in the presence of one or more ALK7 ligands selected from the group consisting of GDF1, GDF3, GDF8, activin B, activin A/B, and Nodal. In some embodiments, the ALK7-binding protein increases lipolysis in white adipose cells or brown adipose cells.

In some embodiments, the ALK7-binding protein increases lipolysis in white adipose cells. In some embodiments, the ALK7-binding protein increases lipolysis in white adipose cells by at least 5% to 100%, 10% to 95%, 10 to 90%, 10 to 85%, 10 to 80%, 10 to 75%, 10 to 70%, 10 to 75%, 10 to 70%, 10 to 60%, 10 to 55%, 10 to 50%, or 10 to 45%, as determined in a lipolysis assay. In some embodiments the lipolysis assay is performed in the presence of one or more ALK7 ligands. In further embodiments, the lipolysis assay is performed in the presence of one or more ALK7 ligands selected from the group consisting of GDF1, GDF3, GDF8, activin B, activin A/B, and Nodal.

In some embodiments, the ALK7-binding protein increases lipolysis in brown adipose cells. In some embodiments, the ALK7-binding protein increases lipolysis in brown adipose cells by at least 5% to 100%, 10% to 95%, 10 to 90%, 10 to 85%, 10 to 80%, 10 to 75%, 10 to 70%, 10 to 75%, 10 to 70%, 10 to 60%, 10 to 55%, 10 to 50%, or 10 to 45%, as determined in a lipolysis assay. In some embodiments the lipolysis assay is performed in the presence of one or more ALK7 ligands. In further embodiments, the lipolysis assay is performed in the presence of one or more ALK7 ligands selected from the group consisting of GDF1, GDF3, GDF8, activin B, activin A/B, and Nodal.

In some embodiments, the ALK7-binding protein increases lipolysis in white and brown adipose cells. In some embodiments, the ALK7-binding protein increases lipolysis in white and brown adipose cells by at least 5% to 100%, 10% to 95%, 10 to 90%, 10 to 85%, 10 to 80%, 10 to 75%, 10 to 70%, 10 to 75%, 10 to 70%, 10 to 60%, 10 to 55%, 10 to 50%, or 10 to 45%, as determined in a lipolysis assay. In some embodiments the lipolysis assay is performed in the presence of one or more ALK7 ligands. In further embodiments, the lipolysis assay is performed in the presence of one or more ALK7 ligands selected from the group consisting of GDF1, GDF3, GDF8, activin B, activin A/B, and Nodal.

In an additional embodiment, an ALK7-binding protein increases lipolysis in white adipose cells by at least 5% to 100%, 10% to 95%, 10 to 90%, 10 to 85%, 10 to 80%, 10 to 75%, 10 to 70%, 10 to 75%, 10 to 70%, 10 to 60%, 10 to 55%, 10 to 50%, or 10 to 45%, as determined using standard techniques and conditions in a lipolysis assay performed in the presence of activin B (50 ng/ml) (e.g., as described in the examples herein). In another embodiment, an ALK7-binding protein reduces or decreases ALK7-mediated inhibition of lipolysis in white adipose cells by at least 5%, 10%, 20%, 30%, 40%, 50%, 60%, 70%, 80%, 90%, or 95%, or by about 100%, as determined, using standard techniques and conditions in a lipolysis inhibition assay. the lipolysis assay is performed in the presence of activin B (50 ng/ml) (e.g., as described in the examples herein).

In an additional embodiment, an ALK7-binding protein increases lipolysis in white and/or brown adipose cells by at least 5% to 100%, 10% to 95%, 10 to 90%, 10 to 85%, 10 to 80%, 10 to 75%, 10 to 70%, 10 to 75%, 10 to 70%, 10 to 60%, 10 to 55%, 10 to 50%, or 10 to 45%, as determined using standard techniques and conditions in a lipolysis assay performed in the presence of activin B (50 ng/ml) (e.g., as described in the examples herein). In another embodiment, an ALK7-binding protein reduces or decreases ALK7-mediated inhibition of lipolysis in white adipose cells by at least 5%, 10%, 20%, 30%, 40%, 50%, 60%, 70%, 80%, 90%, or 95%, or by about 100%, as determined, using standard techniques and conditions in a lipolysis inhibition assay. the lipolysis assay is performed in the presence of activin B (50 ng/ml) (e.g., as described in the examples herein).

In some embodiments, the ALK7-binding protein increases glycerol production in adipose cells. In some embodiments, the ALK7-binding protein increases glycerol production in adipose cells by at least 5% to 100%, 10% to 95%, 10 to 90%, 10 to 85%, 10 to 80%, 10 to 75%, 10 to 70%, 10 to 75%, 10 to 70%, 10 to 60%, 10 to 55%, 10 to 50%, or 10 to 45%, as determined in a lipolysis assay. In some embodiments the lipolysis assay is performed in the presence of one or more ALK7 ligands. In some embodiments, the lipolysis assay is performed in the presence of one or more ALK7 ligands selected from the group consisting of GDF1, GDF3, GDF8, activin B, activin A/B, and Nodal. In some embodiments, the ALK7-binding protein increases glycerol production in white adipose cells or brown adipose cells.

The terms "antibody" and "immunoglobulin," are used interchangeably herein, and include whole (full-length) antibodies and antigen binding fragment or single chains thereof. A typical antibody comprises at least two heavy (H) chains and two light (L) chains interconnected by disulfide bonds. Each heavy chain is comprised of a heavy chain variable region (abbreviated herein as VH) and a heavy chain constant region. The heavy chain constant region is comprised of three domains, CHI, CH2, and CH3. Each light chain is comprised of a light chain variable region (abbreviated herein as VL) and a light chain constant region. The light chain constant region is comprised of one domain, CL. The VH and VL regions can be further subdivided into regions of hypervariability, termed Complementarity Determining Regions (CDR), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. Exemplary antibodies include typical antibodies, scFvs, and combinations thereof where, for example, an scFv is covalently linked (for example, via peptidic bonds or via a chemical linker) to the N or C-terminus of either the heavy chain and/or the light chain of a typical antibody, or intercalated in the heavy chain and/or the light chain of a typical antibody.

The terms "antibody" and "immunoglobulin," encompass intact polyclonal antibodies, intact monoclonal antibodies, antibody fragments (such as Fab, Fab', F(ab')2, and Fv fragments), single chain Fv (scFv) derivatives and mutants, multispecific antibodies such as bispecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired binding activity. An antibody can be of any the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc. The term "IgG" refers to a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, and IgG3.

The terms "ALK7 antibody," "an antibody that binds to ALK7," or "anti-ALK7 antibody" refer to an antibody that is capable of binding ALK7 with sufficient affinity such that the antibody is useful as a therapeutic agent or diagnostic reagent in targeting ALK7, respectively.

By "specifically binds" when used in the context of ALK7 proteins, it is generally meant the ability of a binding protein such as an antibody, to bind to ALK7 (e.g., human ALK7, preferably an extracellular domain of ALK7), with greater affinity than the binding protein binds to an unrelated control protein. In some embodiments, the control protein is hen egg white lysozyme. Preferably the binding protein binds ALK7 with an affinity that is at least, 100, 500, or 1000 times greater than the affinity for a control protein. Preferably, the binding protein has a binding affinity for human ALK7 of $\leq 1\times 10^{-7}$ M or $\leq 1\times 10^{-8}$ as measured using a binding assay known in the art. In some embodiments, the binding affinity is measured using a radioimmunoassay (RIA) or BIA-CORE® (e.g., using ALK7 as the analyte and ALK7-binding protein as the ligand, or vice versa).

In some embodiments, the extent of binding of an ALK7-binding protein (e.g., an anti-ALK7 antibody) to an unrelated, non-ALK7 protein is less than about 10% of the binding of the ALK7-binding protein to ALK7 as measured, for example, by a radioimmunoassay (RIA), BIACORE® (using recombinant ALK7 as the analyte and ALK7-binding protein as the ligand, or vice versa), kinetic exclusion assay (KINEXA®), or other binding assays known in the art. In certain embodiments, the ALK7-binding protein is a full-length antibody or an ALK7-binding antibody fragment that has a dissociation constant ($K_D$) of $\leq 1$ µM, $\leq 100$ nM, $\leq 10$ nM, $\leq 1$ nM, $\leq 0.1$ nM, $\leq 10$ pM, $\leq 1$ pM, or $\leq 0.1$ pM.

The term "antigen binding antibody fragment" (e.g., "ALK7-binding antibody fragment") refers to a fragment containing all or a portion of an antigen binding variable region (e.g., CDR3) of an intact antibody. It is known that the antigen binding function of an antibody can be performed by fragments of a full-length antibody. Examples of antibody fragments include, but are not limited to Fab, Fab', F(ab')2, and Fv fragments, linear antibodies, single chain antibodies, and multispecific antibodies formed from one or more antibody fragments. In some embodiments the disclosure provides ALK7-binding antibody fragments wherein the antibody fragment is a Fab fragment, a Fab' fragment, a F(ab')$_2$ fragment, a Fv fragment, a diabody, or a single chain antibody molecule.

The Fc region includes polypeptides comprising the constant region of an antibody excluding the first constant region immunoglobulin domain. Thus, Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cγ2 and Cγ3 and the hinge between Cγ1 and Cγ2. Although the boundaries of the Fc region may vary, the human IgG heavy chain Fc region is usually defined to comprise residues C226 or P230 to its carboxyl-terminus, wherein the numbering is according to the EU index as set forth in Kabat (Kabat et al., Sequences of Proteins of Immunological Interest, 5th Ed. Public Health Service, NIH, Bethesda, Md. (1991)). Fc may refer to this region in isolation, or this region in the context of a whole antibody, antibody fragment, or Fc fusion protein. Polymorphisms have been observed at a number of different Fc positions, including but not limited to positions 270, 272, 312, 315, 356, and 358 as numbered by the EU index, and thus slight differences between the presented sequence and sequences in the prior art may exist.

A "monoclonal antibody" refers to a homogeneous antibody population involved in the highly specific recognition and binding of a single antigenic determinant or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, and Fv), single chain (scFv) mutants, and fusion proteins) comprising an antibody portion, and any other modified immunoglobulin molecule comprising an antigen recognition site. A monoclonal antibody may be made in any number of ways including, but not limited to, by hybridoma, phage selection, recombinant expression, and transgenic animals.

The term "chimeric antibody" refers to an antibody wherein the amino acid sequence of the immunoglobulin molecule is derived from two or more species. Typically, the variable region of both light and heavy chains corresponds to the variable region of antibodies derived from one species of mammal (e.g., mouse, rat, rabbit, etc.) with the desired antigen-binding specificity, affinity, and/or capability while the constant regions are homologous to the sequences in antibodies derived from another species (usually human) to avoid eliciting an immune response in that species.

The term "humanized antibody" refers to an antibody derived from a non-human (e.g., murine) immunoglobulin, which has been engineered to contain fewer preferably minimal non-human (e.g., murine) sequences. Typically, humanized antibodies are human immunoglobulins in which residues from the CDR are replaced by residues from the CDR of a non-human species (e.g., mouse, rat, rabbit, or hamster) that have the desired antigen-binding specificity, affinity, and/or capability (Jones, Nature 321:522-525 (1986); Riechmann, Nature 332:323-327 (1988); Verhoeyen, Science 239:1534-1536 (1988)). In some instances, the Fv framework region (FW) residues of a human immunoglobulin are replaced with the corresponding residues in an antibody from a non-human species that has the desired antigen-binding specificity, affinity, and/or capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. Nos. 5,225,539 and 5,639,641.

The term "human antibody" refers to an antibody produced by a human or an antibody having an amino acid sequence corresponding to an antibody produced by a human made using any technique known in the art. The term "human antibody" includes intact (full-length) antibodies, fragments thereof, and/or antibodies comprising at least one human heavy and/or light chain polypeptide such as, an antibody comprising murine light chain and human heavy chain polypeptides.

An "antagonist," "blocking," or "neutralizing" binding protein is one that inhibits or reduces activity of the antigen it binds, such as ALK7. In some embodiments, the antagonist ALK7-binding protein reduces or inhibits the multimerization of ALK7, and ActRII receptor (e.g., ActRIIA or ActRIIB) an GDF1, GDF3, GDF8, activin B, activin A/B, and/or Nodal. In certain embodiments the antagonist ALK7-binding protein substantially or completely inhibits the activity of the ALK7. In some embodiments, the ALK7 activity is reduced by 10%, 20%, 30%, 50%, 70%, 80%, 90%, 95%, or 100%. In certain embodiments the antagonist ALK7-binding protein is an anti-ALK7 antibody, such as a full-length antibody or an ALK7-binding antibody fragment. In further embodiments, the antagonist anti-ALK7 antibody inhibits or reduces the activity of ALK7 by at least 10%, 20%, 30%, 50%, 70%, 80%, 90%, 95%, or even 100%.

"Binding affinity" generally refers to the strength of the sum total of non-covalent interactions between a single binding site of a molecule (e.g., an antibody) and its binding partner (e.g., an antigen). Unless indicated otherwise, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein and can be used for the purposes of the present disclosure.

"Potency" is a measure of pharmacological activity of a compound expressed in terms of the amount of the compound required to produce an effect of given intensity. It refers to the amount of the compound required to achieve a defined biological effect; the smaller the dose required, the more potent the drug. Potency is normally expressed as an $IC_{50}$ value, in nM unless otherwise stated. $IC_{50}$ is the median inhibitory concentration of an ALK7-binding protein (e.g., an anti-ALK7 antibody). In functional assays, $IC_{50}$ is the concentration that reduces a biological response by 50% of its maximum. In ligand-receptor binding studies, $IC_{50}$ is the concentration that reduces ligand-receptor binding by 50% of maximal specific binding level. $IC_{50}$ can be calculated by any number of means known in the art. The fold improvement in potency for the antibodies or other binding protein provided herein as compared to a reference anti-ALK7 antibody or other ALK7-binding protein can be at least 2-fold, 4-fold, 6-fold, 8-fold, 10-fold, 20-fold, 30-fold, 40-fold, 50-fold, 60-fold, 70-fold, 80-fold, 90-fold, 100-fold, 110-fold, 120-fold, 130-fold, 140-fold, 150-fold, 160-fold, 170-fold, or at least 180-fold.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the surface of target cells "arm" the cytotoxic cells and are absolutely required for such killing. Lysis of the target cell is extracellular, requires direct cell-to-cell contact, and does not involve complement. It is contemplated that, in addition to antibodies, other proteins comprising Fc regions, specifically Fc fusion proteins, having the capacity to specifically bind to an ALK7-bearing target cell will be able to effect cell-mediated cytotoxicity. For simplicity, the cell-mediated cytotoxicity resulting from the activity of an Fc fusion protein is also referred to herein as ADCC activity.

An ALK7-binding protein (e.g., an ALK7 antibody, including an ALK7-binding fragment, variant, and derivative thereof), polynucleotide, vector, cell, or composition which is "isolated" is a protein (e.g., antibody), polynucleotide, vector, cell, or composition which is in a form not found in nature. Isolated proteins, polynucleotides, vectors, cells or compositions include those which have been purified to a degree that they are no longer in a form in which they are found in nature. In some embodiments, a protein, polynucleotide, vector, cell, or composition which is isolated is substantially pure. Isolated proteins and isolated nucleic acid will be free or substantially free of material with which they are naturally associated such as other polypeptides or nucleic acids with which they are found in their natural environment, or the environment in which they are prepared (e.g., cell culture) when such preparation is by recombinant DNA technology practiced in vitro or in vivo. Proteins and nucleic acid may be formulated with diluents or adjuvants and still for practical purposes be isolated—for example the proteins will normally be mixed with gelatin or other carriers if used to coat microtitre plates for use in immunoassays, or will be mixed with pharmaceutically acceptable carriers or diluents when used in diagnosis or therapy.

The terms "subject," "individual," "animal," "patient," and "mammal," refer to any subject, particularly a mammalian subject, for whom diagnosis, prognosis, or therapy is desired. Mammalian subjects include but are not limited to humans, non-human primates, domestic animals, farm animals, rodents, and the like, which is to be the recipient of a particular treatment.

The term "pharmaceutical composition" refers to a preparation which is in such form as to permit the biological activity of the active ingredient to be effective, and which contains no additional components at concentrations that are unacceptably toxic to a subject to which the composition would be administered. Such composition can be sterile.

An "effective amount" of a polypeptide, e.g., an antigen binding protein including an antibody, as disclosed herein is an amount sufficient to carry out a specifically stated purpose. An "effective amount" can be determined empirically and in a routine manner, in relation to the stated purpose. The term "therapeutically effective amount" refers to an amount of a polypeptide, e.g., an antigen binding protein including an antibody, or other drug effective to "treat" a disease or condition in a subject (e.g., a mammal such as a human) and provides some improvement or benefit to a subject having the disease or condition. Thus, a "therapeutically effective" amount is an amount that provides some alleviation, mitigation, and/or decrease in at least one clinical symptom of an ALK7-mediated disease or condition. Clinical symptoms associated with the diseases or conditions that can be treated by the methods of the disclosure are well known. Further, therapeutic effects need not be complete or curative, as long as some benefit is provided to the subject. In some embodiments, the term "therapeutically effective" refers to an amount of a therapeutic agent that is capable of reducing ALK7 activity in a subject in need thereof. The actual amount administered and rate and time-course of administration, will depend on the nature and severity of what is being treated. Prescription of treatment, e.g., decisions on dosage etc., is within the responsibility of general practitioners and other medical doctors. Appropriate doses of antibodies and antigen binding fragments thereof are generally known; see, Ledermann et al., *Int. J. Cancer* 47:659-664 (1991); Bagshawe et al., *Ant. Immun. and Radiopharm.* 4:915-922 (1991).

A "sufficient amount" or "an amount sufficient to" achieve a particular result in a subject having an ALK7-mediated disease or condition refers to an amount of a therapeutic agent (e.g., an antigen binding protein including an antibody, as disclosed herein) that is effective to produce a desired effect, which is optionally a therapeutic effect (i.e., by administration of a therapeutically effective amount). In some embodiments, such particular result is a reduction in ALK7 activity in a subject in need thereof.

The term "label" refers to a detectable compound or composition which is conjugated directly or indirectly to a moiety such as an anti-ALK7 antibody so as to generate a "labeled" moiety. The label can be detectable by itself (e.g., radioisotope labels or fluorescent labels) or, in the case of an enzymatic label, can catalyze chemical alteration of a substrate compound or composition which is detectable.

Terms such as "treating," or "treatment," "to treat" or "ameliorating" and "to ameliorate" refer to both (a) therapeutic measures that cure, slow down, lessen symptoms of, and/or halt progression of a diagnosed pathologic condition or disorder and (b) prophylactic or preventative measures that prevent and/or slow the development of a targeted disease or condition. Thus, subjects in need of treatment include those already with the disease or condition; those at risk of developing the disease or condition; and those in whom the disease or condition is to be prevented. In certain embodiments, a subject is successfully "treated" according to the methods provided herein if the subject shows, e.g., total, partial, or transient amelioration or elimination of a symptom associated with the disease or condition. In some embodiments, the disclosure provides a method for treating a disease, disorder or condition selected from, obesity (e.g., abdominal obesity); insulin resistance; metabolic syndrome and other metabolic diseases or conditions; a lipid disorder such as, low HDL levels, high LDL levels, hyperlipidemia, hypertriglyceridemia or dyslipidemia; lipoprotein aberrations; decreased triglycerides; inflammation (e.g., liver inflammation and/or inflammation of adipose tissue), fatty liver disease; non-alcoholic fatty liver disease; hyperglycemia; impaired glucose tolerance (IGT); hyperinsulinemia; high cholesterol (e.g., high LDL levels and hypercholesterolemia); cardiovascular disease such as, heart disease including coronary heart disease, congestive heart failure, stroke, peripheral vascular disease, atherosclerosis; arteriosclerosis, and hypertension; Syndrome X; vascular restenosis; neuropathy; retinopathy; neurodegenerative disease; endothelial dysfunction, respiratory dysfunction, renal disease (e.g., nephropathy); pancreatitis; polycystic ovarian syndrome; elevated uric acid levels; haemochromatosis (iron overload); acanthosis nigricans (dark patches on the skin); and cancer (e.g., myeloma (multiple myeloma, plasmacytoma, localized myeloma, or extramedullary myeloma), or an ovarian (e.g., epithelial ovarian), breast, colon, endometrial, liver, kidney, pancreatic, gastric, uterine, or colon cancer); and other disorders/conditions associated with one or more of the above diseases or conditions, or with overweight (e.g., BMI of 25 kg/m$^2$), or with too much body fat.

As used herein, "in combination with" or "combination therapies" refers to any form of administration such that additional therapies (e.g., second, third, fourth, etc.) are still effective in the body (e.g., multiple compounds are simultaneously effective in the subject, which may include synergistic effects of those compounds). Effectiveness may not correlate to measurable concentration of the agent in blood, serum, or plasma. For example, the different therapeutic compounds can be administered either in the same formulation or in separate formulations, either concomitantly or sequentially, and on different schedules. Thus, a subject that receives such treatment can benefit from a combined effect of different therapies. One or more ALK7-binding proteins provided herein can be administered concurrently with, prior to, or subsequent to, one or more other additional agents and/or supportive therapies. In general, each therapeutic agent will be administered at a dose and/or on a time schedule determined for that particular agent. The particular combination to employ in a regimen will take into account compatibility of the antagonist of the present disclosure with therapy and/or the desired outcome.

The methods and techniques of the present disclosure are generally performed according to known conventional methods and as described in various general and more specific references that are cited and discussed throughout the present disclosure unless otherwise indicated. See, e.g., Sambrook et al., Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), all of which are herein incorporated by reference.

The terms "cancer," "tumor," "cancerous," and "malignant" refer to or describe the physiological condition in mammals that is typically characterized by unregulated cell growth. Examples of cancers include but are not limited to, carcinoma including adenocarcinomas, lymphomas, blastomas, melanomas, sarcomas, and leukemias. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, glioma, cervical cancer, ovarian cancer, liver cancer such as hepatic carcinoma and hepatoma, bladder cancer, breast cancer (including hormonally mediated breast cancer, see, e.g., Innes et al., *Br. J. Cancer* 94:1057-1065 (2006)), colon cancer, colorectal cancer, endometrial carcinoma, myeloma (such as multiple myeloma), salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, various types of head and neck cancer and cancers of mucinous origins, such as, mucinous ovarian cancer, cholangiocarcinoma (liver) and renal papillary carcinoma. In a particular embodiment, the cancer is breast, endometrial, or uterine cancer. In another embodiment, the cancer is a myeloma (e.g., multiple myeloma, plasmacytoma, localized myeloma, and extramedullary myeloma), or endometrial, gastric, liver, colon, renal or pancreatic cancer.

The terms "polynucleotide" and "nucleic acid" are used interchangeably and are intended to encompass a singular nucleic acid as well as plural nucleic acids, and refers to an isolated nucleic acid molecule or construct, e.g., messenger RNA (mRNA), complementary DNA (cDNA), or plasmid DNA (pDNA). In certain embodiments, a polynucleotide comprises a conventional phosphodiester bond or a non-conventional bond (e.g., an amide bond, such as found in peptide nucleic acids (PNA)). The term "nucleic acid" refers to any one or more nucleic acid segments, e.g., DNA, cDNA, or RNA fragments, present in a polynucleotide. When applied to a nucleic acid or polynucleotide, the term "isolated" refers to a nucleic acid molecule, DNA or RNA, which has been removed from its native environment, for example, a recombinant polynucleotide encoding an antigen binding protein contained in a vector is considered isolated for the purposes of the present disclosure. Further examples of an isolated polynucleotide include recombinant polynucleotides maintained in heterologous host cells or purified (partially or substantially) from other polynucleotides in a solution. Isolated RNA molecules include in vivo or in vitro RNA transcripts of polynucleotides of the present disclosure. Isolated polynucleotides or nucleic acids according to the present disclosure further include such molecules produced synthetically. In addition, polynucleotides or nucleic acids can include regulatory elements such as promoters, enhancers, ribosome binding sites, or transcription termination signals.

The term "vector" means a construct, which is capable of delivering, and in some embodiments expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "host cell" refers to a cell or a population of cells harboring or capable of harboring a recombinant nucleic acid. Host cells can be prokaryotic (e.g., *E. coli*), or eukaryotic. The host cells can be fungal cells including yeast such as *Saccharomyces cerevisiae, Pichia pastoris*, or *Schizosaccharomyces pombe*. The host cells also be any of various animal cells, such as insect cells (e.g., Sf-9) or mammalian cells (e.g., HEK293F, CHO, COS-7, NIH-3T3, NS0, PER.C6®, and hybridoma). In further embodiments, the host cells is a CHO cell selected from the group consisting of CHO-K, CHO-0 CHO-Lec10, CHO-Lec13, CHO-Lec1, CHO Pro$^-$5, and CHO dhfr$^-$. In particular embodiments, the host cell is a hybridoma.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because in some embodiments the provided ALK7-binding proteins are based upon antibodies, the ALK7-binding proteins can occur as single chains or associated chains.

A "recombinant" polypeptide, protein or antibody refers to polypeptide, protein or antibody produced via recombinant DNA technology. Recombinantly produced polypeptides, proteins and antibodies expressed in host cells are considered isolated for the purpose of the present disclosure, as are native or recombinant polypeptides which have been separated, fractionated, or partially or substantially purified by any suitable technique.

Also included in the present disclosure are fragments, variants, or derivatives of polypeptides, and any combination thereof. The term "fragment" when referring to polypeptides and proteins include any polypeptides or proteins which retain at least some of the properties of the reference polypeptide or protein. Fragments of polypeptides include proteolytic fragments, as well as deletion fragments.

The term "variant" refers to an antibody or polypeptide sequence that differs from that of a parent antibody or polypeptide sequence by virtue of at least one amino acid modification. Variants of antibodies or polypeptides include fragments, and also antibodies or polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

The term "derivatives" as applied to antibodies or polypeptides refers to antibodies or polypeptides which have been altered so as to exhibit additional features not found on the native antibody or polypeptide. An example of a "derivative" antibody is a fusion or a conjugate with a second polypeptide or another molecule (e.g., a polymer such as PEG, a chromophore, or a fluorophore) or atom (e.g., a radioisotope).

The term "amino acid substitution" refers to replacing an amino acid residue present in a parent sequence with another amino acid residue. An amino acid can be substituted in a parent sequence, for example, via chemical peptide synthesis or through known recombinant methods. Accordingly, references to a "substitution at position X" or "substitution at position X" refer to the substitution of an amino acid residue present at position X with an alternative amino acid residue. In some embodiments, substitution patterns can described according to the schema AXY, wherein A is the single letter code corresponding to the amino acid residue naturally present at position X, and Y is the substituting amino acid residue. In other embodiments, substitution patterns can described according to the schema XY, wherein Y is the single letter code corresponding to the amino acid residue substituting the amino acid residue naturally present at position X.

A "conservative amino acid substitution" is one in which the amino acid residue is replaced with an amino acid residue having a similar side chain. Families of amino acid residues having similar side chains have been previously defined, including basic side chains (e.g., Lys, Arg, His), acidic side chains (e.g., Asp, Glu), uncharged polar side chains (e.g., Gly, Asp, Gln, Ser, Thr, Tyr, Cys), nonpolar side chains (e.g., Ala, Val, Leu, Ile, Pro, Phe, Met, Trp), beta-branched side chains (e.g., Thr, Val, Ile) and aromatic side chains (e.g., Tyr, Phe, Trp, His). Thus, if an amino acid residue in a polypeptide is replaced with another amino acid residue from the same side chain family, the substitution is considered to be conservative. In another embodiment, a string of amino acid residues can be conservatively replaced with a structurally similar string that differs in order and/or composition of side chain family members.

Non-conservative substitutions include those in which (a) a residue having an electropositive side chain (e.g., Arg, His, or Lys) is substituted for, or by, an electronegative residue (e.g., Glu or Asp), (b) a hydrophilic residue (e.g., Ser or Thr) is substituted for, or by, a hydrophobic residue (e.g., Ala, Leu, Ile, Phe, or Val), (c) a Cys or Pro is substituted for, or by, any other residue, or (d) a residue having a bulky hydrophobic or aromatic side chain (e.g., Val, His, Ile, or Trp) is substituted for, or by, one having a smaller side chain (e.g., Ala or Ser) or no side chain (e.g., Gly).

Other substitutions can be readily identified. For example, for the amino acid alanine, a substitution can be taken from any one of D-Ala, Gly, beta-Ala, L-Cys and D-Cys. For lysine, a replacement can be any one of D-Lys, Arg, D-Arg, homo-Arg, Met, D-Met, ornithine, or D-ornithine. Generally, substitutions in functionally important regions that can be expected to induce changes in the properties of isolated polypeptides are those in which (a) a polar residue (e.g., Ser or Thr) is substituted for (or by) a hydrophobic residue (e.g., Leu, Ile, Phe, or Ala); (b) a Cys residue is substituted for (or by) any other residue; (c) a residue having an electropositive side chain (e.g., Lys, Arg, or His), is substituted for (or by) a residue having an electronegative side chain (e.g., Glu or Asp); or (d) a residue having a bulky side chain (e.g., Phe)

is substituted for (or by) one not having such a side chain (e.g., Gly). The likelihood that one of the foregoing non-conservative substitutions can alter functional properties of the protein is also correlated to the position of the substitution with respect to functionally important regions of the protein: some non-conservative substitutions can accordingly have little or no effect on biological properties.

The term "amino acid insertion" refers to introducing a new amino acid residue between two amino acid residues present in the parent sequence. An amino acid residue can be inserted in a parent sequence, for example, via chemical peptide synthesis or through recombinant methods known in the art. Accordingly, the phrases "insertion between positions X and Y" or "insertion between Kabat positions X and Y," wherein X and Y correspond to amino acid residue positions (e.g., a cysteine amino acid residue insertion between positions 239 and 240), refers to the insertion of an amino acid residue between the X and Y positions, and also to the insertion in a nucleic acid sequence of a codon encoding an amino acid residue between the codons encoding the amino acid residues at positions X and Y.

The term "percent sequence identity" or "percent identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence. The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software programs. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

The structure for carrying a CDR or a set of CDRs will generally be of an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains and their CDRs can readily be determined by one skilled in the art using programs and known variable domain residue numbering systems such as Chothia, Chothia+, and Kabat can routinely be determined by reference to Kabat (Kabat et al., Sequences of Proteins of Immunological Interest. 4th Edition. U.S. DHHS. 1987, and tools available on the Internet (e.g., at bioinforg.uk/abysis/sequence_input/key_annotation/key_annotation. html; and immuno.bme.n-wu.edu)), herein incorporated by reference in its entirety.

CDRs can also be carried by other scaffolds such as fibronectin, cytochrome B, albumin (e.g., ALBUdAb (Domantis/GSK) and ALB-Kunitz (Dyax)), unstructured repeat sequences of 3 or 6 amino acids (e.g., PASylation® technology and XTEN® technology), and sequences containing elastin-like repeat domains (see, e.g., U.S. Pat. Appl. No. 61/442,106, which is herein incorporated by reference in its entirety).

A CDR amino acid sequence substantially as set out herein can be carried as a CDR in a human variable domain or a substantial portion thereof. The HCDR3 sequences substantially as set out herein represent embodiments of the present disclosure and each of these may be carried as a HCDR3 in a human heavy chain variable domain or a substantial portion thereof.

Variable domains employed in the present disclosure can be obtained from any germ-line or rearranged human variable domain, or can be a synthetic variable domain based on consensus sequences of known human variable domains. A CDR sequence (e.g., CDR3) can be introduced into a repertoire of variable domains lacking a CDR (e.g., CDR3), using recombinant DNA technology.

For example, Marks et al., (Bio/Technology 10:779-783 (1992); which is herein incorporated by reference in its entirety) provide methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al., further describe how this repertoire can be combined with a CDR3 of a particular antibody. Using analogous techniques, the CDR3-derived sequences of the present disclosure can be shuffled with repertoires of VH or VL domains lacking a CDR3, and the shuffled complete VH or VL domains combined with a cognate VL or VH domain to provide antigen binding proteins. The repertoire can then be displayed in a suitable host system such as the phage display system of Intl. Appl. Publ. No. WO92/01047 or any of a subsequent large body of literature, including Kay et al., (1996) Phage Display of Peptides and Proteins: A Laboratory Manual, San Diego: Academic Press, so that suitable antigen binding proteins may be selected. A repertoire can consist of from anything from 104 individual members upwards, for example from $10^6$ to $10^8$, or $10^{10}$, members. Other suitable host systems include yeast display, bacterial display, T7 display, and ribosome display. For a review of ribosome display for see Lowe et al., Curr. Pharm. Biotech. 517-527 (2004) and Intl. Appl. Publ. No. WO92/01047, each of which is herein incorporated by reference herein in its entirety. Analogous shuffling or combinatorial techniques are also disclosed by Stemmer (Nature 370:389-391 (1994), which is herein incorporated by reference in its entirety), which describes the technique in relation to a β-lactamase gene but observes that the approach may be used for the generation of antibodies.

An ALK7-binding protein (e.g., an anti-ALK7 antibody) is said to "compete" with a reference molecule for binding to ALK7 if it binds to ALK7 to the extent that it blocks, to some degree, binding of the reference molecule to ALK7. The ability of proteins to compete for binding to ALK7 and thus to interfere with, block or "cross-block" one another's binding to ALK7 can be determined by any standard competitive binding assay known in the art including, for example, a competition ELISA assay, surface plasmon resonance (SPR; BIACORE®, Biosensor, Piscataway, N.J.) or according to methods described by Scatchard et al. (*Ann. N.Y. Acad. Sci.* 51:660-672 (1949)). An ALK7-binding protein may be said to competitively inhibit binding of the reference molecule to ALK7, for example, by at least 90%, at least 80%, at least 70%, at least 60%, or at least 50%. According to some embodiments, the ALK7-binding protein competitively inhibits binding of the reference molecule to ALK7, by at least 90%, at least 80%, at least 70%, at least 60%, or at least 50%. According to other embodiments, the ALK7-binding protein competitively inhibits binding of a reference molecule to ALK7, by at least 90%, at least 80%, at least 70%, at least 60%, or at least 50%.

ALK7-Binding Proteins

Proteins that specifically bind ALK7 are provided. In some embodiments, antagonist ALK-7 binding proteins are provided. In some embodiments, the ALK7 binding proteins are antibodies. In further embodiments, the antibodies are antagonist anti-ALK7 antibodies.

As used herein, the term "ALK7" refers to a family of activin receptor-like kinase-7 proteins from any species and variants derived from such ALK7 proteins by mutagenesis or other modification. Reference to ALK7 herein is understood to be a reference to any one of the currently identified forms. Members of the ALK7 family are generally transmembrane proteins, composed of a ligand-binding extracellular domain with a cysteine-rich region, a transmembrane domain, and a cytoplasmic domain with predicted serine/threonine kinase activity. There are various naturally occurring isoforms of human ALK7. The sequence of canonical human ALK7 isoform 1 precursor protein (NCBI Ref Seq NP_660302.2) is as follows:

In some embodiments, BIACORE® analysis is used to determine the ability of an ALK7-binding protein (e.g., an anti-ALK7 antibody) to compete with/block the binding to ALK7 protein by a reference ALK7-binding protein (e.g., an anti-ALK7 antibody). In a further embodiment in which a BIACORE® instrument (for example the BIACORE® 3000) is operated according to the manufacturer's recommendations, ALK7-Fc fusion protein is captured on a CM5 BIACORE® chip by previously attached anti-niFc IgG to generate an ALK7-coated surface. Typically 200-800 resonance units of ALK7-Fc (dimeric) would be coupled to the chip (an amount that gives easily measurable levels of binding but that is readily saturable by the concentrations of test reagent being used).

The two ALK7-binding proteins (termed A* and B*) to be assessed for their ability to compete with/block each other are mixed at a one to one molar ratio of binding sites in a suitable buffer to create a test mixture. When calculating the concentrations on a binding site basis the molecular weight of an ALK7-binding protein is assumed to be the total molecular weight of the ALK7-binding protein divided by the number of ALK7-binding sites on that ALK7-binding protein. The concentration of each ALK7-binding protein (i.e., A* and B*) in the test mixture should be high enough to readily saturate the binding sites for that ALK7-binding protein on the ALK7-Fc molecules captured on the BIACORE® chip. The A* and B* ALK7-binding proteins in the mixture are at the same molar concentration (on a binding basis) and that concentration would typically be between 1.00 and 1.5 micromolar (on a binding site basis). Separate solutions containing ALK7-binding protein A* alone and ALK7-binding protein B* alone are also prepared. ALK7-binding protein A* and ALK7-binding protein B* in these solutions should be in the same buffer and at the same concentration as in the test mixture. The test mixture is passed over the ALK7-Fc-coated BIACORE® chip and the total amount of binding recorded. The chip is then treated in such a way as to remove the bound ALK7-binding proteins

```
                                                         (SEQ ID NO: 85)
  1   MTRALCSALR QALLLLAAAA ELSPGLKCVC LLCDSSNFTC QTEGACWASV MLTNGKEQVI

61   KSCVSLPELN AQVFCHSSNN VTKTECCFTD FCNNITLHLP TASPNAPKLG PMELAIIITV

121   PVCLLSIAAM LTVWACQGRQ CSYRKKKRPN VEEPLSECNL VNAGKTLKDL IYDVTASGSG

181   SGLPLLVQRT IARTIVLQEI VGKGRFGEVW HGRWCGEDVA VKIFSSRDER SWFREAEIYQ

241   TVMLRHENIL GFIAADNKDN GTWTQLWLVS EYHEQGSLYD YLNRNIVTVA GMIKLALSIA

301   SGLAHLHMEI VGTQGKPAIA HRDIKSKNIL VKKCETCAIA DLGLAVKHDS ILNTIDIPQN

361   PKVGTKRYMA PEMLDDTMNV NIFESFKRAD IYSVGLVYWE IARRCSVGGI VEEYQLPYYD

421   MVPSDPSIEE MRKVVCDQKF RPSIPNQWQS CEALRVMGRI MRECWYANGA ARLTALRIKK

481   TISQLCVKED CKA
```

The signal peptide is indicated by a single underline and the extracellular domain is indicated in bold font.

In some embodiments, the ALK7-binding protein binds ALK7 with an affinity that is at least, 100, 500, or 1000 times greater than the affinity of the ALK7-binding protein for a control protein that is not a TGF-beta receptor family member. In certain embodiments, the ALK7-binding protein binds ALK7 and has a dissociation constant ($K_D$) of <1 µM, <100 nM, <10 nM, <1 nM, <0.1 nM, <10 pM, <1 pM, or <0.1 pM. In some embodiments, the ALK7-binding protein has a $K_D$ for human ALK7 within the range of ≤1 µM and ≥0.1 pM, ≤100 µM and ≥0.1 pM, or ≤100 µM and ≥1 pM.

without damaging the chip-bound ALK7-Fc. Typically, this is done by treating the chip with 30 mM HCl for 60 seconds. The solution of ALK7-binding protein A* alone is then passed over the ALK7-Fc-coated surface and the amount of binding recorded. The chip is again treated to remove the bound antibody without damaging the chip-bound ALK7-Fc. The solution of ALK7-binding protein B* alone is then passed over the ALK7-Fc-coated surface and the amount of binding recorded. The maximum theoretical binding of the mixture of ALK7-binding protein A* and ALK7-binding protein B* is next calculated, and is the sum of the binding of each ALK7-binding protein when passed over the ALK7 surface alone. If the actual recorded binding of the mixture is less than this theoretical maximum then the two ALK7-binding proteins are competing with/blocking each other. Thus, in general, a blocking ALK7-binding protein is one which will bind to ALK7 in the above BIACORE® blocking assay such that during the assay and in the presence of a second ALK7-binding protein the recorded binding is between 80% and 0.1% (e.g., 80%> to 4%) of the maximum theoretical binding, specifically between 75% and 0.1% (e.g., 75% to 4%) of the maximum theoretical binding, and more specifically between 70% and 0.1% (e.g., 70% to 4%) of maximum theoretical binding (as defined above) of the two ALK7-binding proteins in combination.

The BIACORE® assay described above is an exemplary assay used to determine if two ALK7-binding proteins such as anti-ALK7 antibodies compete with/block each other for binding ALK7. On rare occasions, particular ALK7-binding proteins may not bind to ALK7-Fc coupled via anti-Fc IgG to a CMS BIACORE® chip (this might occur when the relevant binding site on ALK7 is masked or destroyed by ALK7 linkage to Fc). In such cases, blocking can be determined using a tagged version of ALK7, for example C-terminal His-tagged ALK7. In this particular format, an anti-His antibody would be coupled to the BIACORE® chip and then the His-tagged ALK7 would be passed over the surface of the chip and captured by the anti-His antibody. The cross-blocking analysis would be carried out essentially as described above, except that after each chip regeneration cycle, new His-tagged ALK7 would be loaded back onto the surface coated with anti-His antibody. Moreover, various other known tags and tag binding protein combinations can be used for such a blocking analysis (e.g., HA tag with anti-HA antibodies; FLAG tag with anti-FLAG antibodies; biotin tag with streptavidin). The following generally describes an ELISA assay for determining whether an ALK7-binding protein blocks or is capable of blocking the binding of a reference ALK7-binding protein to ALK7.

In some embodiments, an ELISA is used to determine the ability of an ALK7-binding protein (e.g., an anti-ALK7 antibody) to compete for binding to ALK7 with a reference ALK7-binding protein (e.g., an anti-ALK7 antibody or ALK7 ligand). The general principle of such an assay is to have a reference ALK7-binding protein (e.g., an anti-ALK7 antibody) coated onto the wells of an ELISA plate. An excess amount of a second potentially blocking, test ALK7-binding protein is added in solution (i.e., not bound to the ELISA plate). A limited amount of ALK7 (or alternatively ALK7-Fc) is then added to the wells. The coated reference ALK7-binding protein and the test ALK7-binding protein in solution compete for binding of the limited number of ALK7 (or ALK7-Fc) molecules. The plate is washed to remove ALK7 that has not been bound by the coated reference ALK7-binding protein and to also remove the test, solution-phase ALK7-binding protein as well as any complexes formed between the test, solution-phase ALK7-binding protein and ALK7. The amount of bound ALK7 is then measured using an appropriate ALK7 detection reagent. A test ALK7-binding protein in solution that is able to block binding of the coated reference ALK7-binding protein to ALK7 will be able to cause a decrease in the number of ALK7 molecules that the coated reference ALK7-binding protein can bind relative to the number of ALK7 molecules that the coated reference ALK7-binding protein can bind in the absence of the second, solution-phase test ALK7-binding protein. The background signal for the assay is defined as the signal obtained in wells with the coated reference ALK7-binding protein, solution-phase test ALK7-binding protein, ALK7 buffer only (i.e., no ALK7) and ALK7 detection reagents. The positive control signal for the assay is defined as the signal obtained in wells with the coated reference ALK7-binding protein, solution-phase test ALK7-binding protein buffer only (i.e., no solution-phase test ALK7-binding protein), ALK7 and an ActRII receptor (e.g., ActRIIA or ActRIIB) detection reagents. The ELISA assay is be run in such a manner so as to have the positive control signal at least 3 times the background signal. As a control for methodologic artifacts, the cross-blocking assay may be run in the format just described and also reversed, with the test ALK7-binding protein as the coated antibody and the reference ALK7-binding protein as the solution-phase antibody.

In some embodiments, the ALK7-binding protein binds ALK7 with an affinity that is at least, 100, 500, or 1000 times greater than the affinity of the ALK7-binding protein for a control protein that is not a TGF-beta receptor family member. In additional embodiments, the ALK7-binding protein binds ALK7 with an affinity that is at least, 100, 500, or 1000 times greater than the affinity of the ALK7-binding protein for a control protein that is not a TGF-beta receptor family member. In certain embodiments, the ALK7-binding protein binds ALK7 and has a dissociation constant ($K_D$) of <1 µM, <100 nM, <10 nM, <1 nM, <0.1 nM, <10 pM, <1 pM, or <0.1 pM. In some embodiments, the ALK7-binding protein has a $K_D$ for human ALK7 within the range of ≤1 µM and ≥0.1 pM, ≤100 µM and ≥0.1 pM, or ≤100 µM and ≥1 pM.

In some embodiments, a cell-based lipolysis inhibition assay is used to determine the ability of an ALK7-binding protein (e.g., an antagonist anti-ALK7 antibody) to reduce (inhibit) ALK7-mediated inhibition of lipolysis in mammalian white adipoctyes. In some embodiments, the lipolysis inhibition assay is performed using mature whit adipocytes (e.g., human, mouse, or rat) to determine the ability of an ALK7-binding protein (e.g., an anti-ALK7 antibody) to reduce ALK7 activity. Kits, reagents and methods for conducting a lipolysis assay are commercially available and known in the art. In particular embodiments, the lipolysis inhibition assay is performed as provided in the Examples herein. In other embodiments, the assay is performed according to the instructions and reagents as provided in a commercially available lipolysis assay kit (e.g., BioAssay Systems, EnzyChrom™ Adipolysis Assay Kit, Cat. No. EAPL-200; Abcam Cat. No. ab185433; Zen-Bio, Cat. No. LIP-1-NCL1; BioVision, Cat. No. K577-100; Sigma-Aldrich, Cat. No. MAK211; and AdipoLyze™ Lipolysis Detection Assay, Lonza, Cat. No. 193339).

In some embodiments, the ALK7-binding protein, an ALK7-binding protein is an ALK7 antagonist and increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a mature white adipose cell by 5% to 100%, 10% 95%, 10 to 90%, 10 to 85%, 10 to 80%, 10 to 75%, 10 to 70%, 10 to 65%, 10 to 60%, 10 to 55%, 10 to 50%, or 10 to 45%, as determined using standard techniques and conditions in a lipolysis inhibition assay performed in the presence of activin B (50 ng/ml) (e.g., as described in the examples herein). In another embodiment, an ALK7-binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a mature white adipose cell by at least 5%, 10%, 20%, 30%, 40%, 50%, 60%, 70%, 80%, 90%, or 95%, or by about 100%, as determined, using standard techniques and conditions in a lipolysis inhibition assay performed in the presence of activin B (50 ng/ml) (e.g., as described in the examples herein).

Pharmacodynamic parameters dependent on ALK7 signaling can be measured as endpoints for in vivo testing of ALK7-binding proteins in order to identify those binding proteins that are able to neutralize ALK7 and provide a therapeutic benefit. An ALK7 neutralizing binding agent is defined as one capable of causing a statistically significant change, as compared to vehicle-treated animals, in such a pharmacodynamic parameter. Such in vivo testing can be performed in any suitable mammal (e.g., mouse, rat, or monkey In some embodiments, an ALK7-binding protein is an antibody that specifically binds ALK7. In additional embodiments, the ALK7-binding protein is a full-length anti-ALK7 antibody. In additional embodiments, the antibody is a monoclonal antibody, a recombinant antibody, a human antibody, a humanized antibody, a chimeric antibody, a bi-specific antibody, a multi-specific antibody, or an ALK7-binding antibody fragment thereof.

In some embodiments, the anti-ALK7 antibody is an ALK7-binding antibody fragment. In some embodiments, the ALK7-binding antibody fragment is a: Fab, Fab', F(ab')$_2$, Fv fragment, diabody, or single chain antibody molecule. In additional embodiments, the ALK7-antibody is a Fd, single chain Fv(scFv), disulfide linked Fv, V-NAR domain, IgNar, intrabody, IgGΔCH2, minibody, F(ab')$_3$, tetrabody, triabody, diabody, single-domain antibody, DVD-Ig, Fcab, mAb$^2$, (scFv)$_2$, scFv-Fc or bis-scFv.

In additional embodiments the ALK7-binding protein is an antibody that includes a VH and a VL. In some embodiments the anti-ALK7 antibody further includes a heavy chain constant region or fragment thereof. In some embodiments, the antibody comprises a heavy chain immunoglobulin constant region selected from the group consisting of: (a) a human IgA constant region, or fragment thereof; (b) a human IgD constant region, or fragment thereof; (c) a human IgE constant domain, or fragment thereof; (d) a human IgG1 constant region, or fragment thereof; (e) a human IgG2 constant region, or fragment thereof; (f) a human IgG3 constant region, or fragment thereof; (g) a human IgG4 constant region, or fragment thereof; and (h) a human IgM constant region, or fragment thereof. In certain embodiments an ALK7-binding protein comprises a heavy chain constant region or fragment thereof, e.g., a human IgG constant region or fragment thereof. In further embodiments, the ALK7-binding protein comprises a heavy chain immunoglobulin constant domain that has, or has been mutated to have altered effector function and/or half-life.

In particular embodiments, the ALK7-binding protein is an antibody that comprises an IgG1 heavy chain constant region containing a mutation that decreases effector function (see, e.g., Idusogie et al., *J. Immunol.* 166:2571-2575 (2001); Sazinsky et al., *PNAS USA* 105:20167-20172 (2008); Davis et al., *J. Rheumatol.* 34:2204-2210 (2007); Bolt et al., *Eur. J. Immunol.* 23:403-411 (1993); Alegre et al., *Transplantation* 57:1537-1543 (1994); Xu et al., *Cell Immunol.* 200:16-26 (2000); Cole et al., *Transplantation* 68:563-571 (1999); Hutchins et al., *PNAS USA* 92:11980-11984 (1995); Reddy et al., *J. Immunol.* 164:1925-1933 (2000); WO97/11971, and WO07/106585; U.S. Appl. Publ. 2007/0148167A1; McEarchern et al., *Blood* 109:1185-1192 (2007); Strohl, *Curr. Op. Biotechnol.* 20:685-691 (2009); and Kumagai et al., *J. Clin. Pharmacol.* 47:1489-1497 (2007), each of which is herein incorporated by reference in its entirety).

In some embodiments, the heavy chain constant region or fragment thereof includes one or more amino acid substitutions relative to a wild-type IgG constant domain wherein the modified IgG has decreased ADCC compared to the half-life of an IgG having the wild-type IgG constant domain. Examples of Fc sequence engineering modifications contained in the provided antibodies that decrease ADCC include one or more modifications corresponding to: IgG1-K326W, E333S; IgG2-E333S; IgG1-N297A; IgG1-L234A, L235A; IgG2-V234A, G237A; IgG4-L235A, G237A, E318A; IgG4-S228P, L236E; IgG2-EU sequence 118-260; IgG4-EU sequence 261-447; IgG2-H268Q, V309L, A330S, A331S; IgG1-C220S, C226S, C229S, P238S; IgG1-C226S, C229S, E233P, L234V, L235A; and IgG1-L234F, L235E, P331S, wherein the position numbering is according to the EU index as in Kabat.

In certain embodiments an ALK7-binding protein comprises a heavy chain immunoglobulin constant domain that has, or has been mutated to have, reduced CDC activity. In particular embodiments, the ALK7-binding protein is an antibody that comprises an IgG1 heavy chain constant region containing a mutation that decreases CDC activity (see, e.g., WO97/11971 and WO07/106585; U.S. Appl. Publ. 2007/0148167A1; McEarchern et al., *Blood* 109:1185-1192 (2007); Hayden-Ledbetter et al., *Clin. Cancer* 15:2739-2746 (2009); Lazar et al., *PNAS USA* 103:4005-4010 (2006); Bruckheimer et al., *Neoplasia* 11:509-517 (2009); Strohl, *Curr. Op. Biotechnol.* 20:685-691 (2009); and Sazinsky et al., *PNAS USA* 105:20167-20172 (2008); each of which is herein incorporated by reference in its entirety). Examples of Fc sequence engineering modifications contained in an anti-ALK7 antibody that decrease CDC include one or more modifications corresponding to: IgG1-S239D, A330L, I332E; IgG2 EU sequence 118-260; IgG4-EU sequence 261-447; IgG2-H268Q, V309L, A330S, A331S; IgG1-C226S, C229S, E233P, L234V, L235A; IgG1-L234F, L235E, P331S; and IgG1-C226S, P230S.

In further embodiments, the heavy chain constant region or fragment thereof includes one or more amino acid substitutions relative to a wild-type IgG constant domain wherein the modified IgG has an increased half-life compared to the half-life of an IgG having the wild-type IgG constant domain. For example, the IgG constant domain can contain one or more amino acid substitutions of amino acid residues at positions 251-257, 285-290, 308-314, 385-389, and 428-436, wherein the amino acid position numbering is according to the EU index as set forth in Kabat. In certain embodiments the IgG constant domain can contain one or more of a substitution of the amino acid at Kabat position 252 with Tyr, Phe, Trp, or Thr; a substitution of the amino acid at Kabat position 254 with Thr; a substitution of the amino acid at Kabat position 256 with Ser, Arg, Gln, Glu, Asp, or Thr; a substitution of the amino acid at Kabat position 257 with Leu; a substitution of the amino acid at Kabat position 309 with Pro; a substitution of the amino acid at Kabat position 311 with Ser; a substitution of the amino acid at Kabat position 428 with Thr, Leu, Phe, or Ser; a substitution of the amino acid at Kabat position 433 with Arg, Ser, Iso, Pro, or Gln; or a substitution of the amino acid at Kabat position 434 with Trp, Met, Ser, His, Phe, or Tyr. More specifically, the IgG constant domain can contain amino acid substitutions relative to a wild-type human IgG constant domain including a substitution of the amino acid at Kabat position 252 with Tyr, a substitution of the amino acid at Kabat position 254 with Thr, and a substitution of the amino acid at Kabat position 256 with Glu.

In additional embodiments, the ALK7-binding protein is an antibody that comprises a light chain immunoglobulin constant region. In a further embodiment, the antibody comprises a human Ig kappa constant region or a human Ig lambda constant region.

In some embodiments, the ALK7-binding protein comprises a set of CDRs: VH-CDR1, VH-CDR2, VH-CDR3, VL-CDR1, VL-CDR2 and VL-CDR3, wherein the CDRs are present in a VH and a VL pair disclosed in Table 1A. In further embodiments, the ALK7-binding protein comprises a set of CDRs wherein the CDRs are present in a VH and a VL pair selected from the group consisting of: (a) a VH sequence of SEQ ID NO:4, and a VL sequence of SEQ ID NO:13; (b) a VH sequence of SEQ ID NO:22, and a VL sequence of SEQ ID NO:31; (c) a VH sequence of SEQ ID NO:40, and a VL sequence of SEQ ID NO:49; and (d) a VH sequence of SEQ ID NO:58 and a VL sequence of SEQ ID NO:67; and wherein the protein binds ALK7.

In some embodiments, the ALK7-binding protein comprises a set of CDRs: VH-CDR1, VH-CDR2, VH-CDR3, VL-CDR1, VL-CDR2 and VL-CDR3, wherein the CDRs are present in a VH and a VL pair disclosed in Table 1B. In further embodiments, the ALK7-binding protein comprises a set of CDRs wherein the CDRs are present in a VH and a VL pair selected from the group consisting of: (a) a VH sequence of SEQ ID NO:152, and a VL sequence of SEQ ID NO:98; (b) a VH sequence of SEQ ID NO:159, and a VL sequence of SEQ ID NO:110; and (c) a VH sequence of SEQ ID NO:165, and a VL sequence of SEQ ID NO:171; and wherein the protein binds ALK7.

In some embodiments, the ALK7-binding protein comprises a set of CDRs: VH-CDR1, VH-CDR2, VH-CDR3, VL-CDR1, VL-CDR2 and VL-CDR3, wherein the CDRs are present in a VH and a VL pair disclosed in Table 3. In further embodiments, the ALK7-binding protein comprises a set of CDRs wherein the CDRs are present in a VH and a VL pair selected from the group consisting of: (a) a VH sequence of SEQ ID NO:91, and a VL sequence of SEQ ID NO:98; (b) a VH sequence of SEQ ID NO:105, and a VL sequence of SEQ ID NO:110; (c) a VH sequence of SEQ ID NO:117, and a VL sequence of SEQ ID NO:124; (d) a VH sequence of SEQ ID NO:128 and a VL sequence of SEQ ID NO:135; and (d) a VH sequence of SEQ ID NO:140 and a VL sequence of SEQ ID NO:148; and wherein the protein binds ALK7.

In some embodiments an ALK7-binding protein comprises a set of CDRs: (a) VH-CDR1, VH-CDR2, and VH-CDR3, or (b) VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs disclosed herein. In further embodiments, the ALK7-binding protein comprises a set of CDRs, wherein the set of CDRs is identical to, or has a total of one, two, three, four, five, six, seven, eight, nine, ten, or fewer than ten, amino acid substitutions, deletions, and/or insertions from a reference set of CDRs in a VH or VL sequence disclosed in Table 1A.

In some embodiments an ALK7-binding protein comprises a set of CDRs: (a) VH-CDR1, VH-CDR2, and VH-CDR3, or (b) VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs disclosed herein. In further embodiments, the ALK7-binding protein comprises a set of CDRs, wherein the set of CDRs is identical to, or has a total of one, two, three, four, five, six, seven, eight, nine, ten, or fewer than ten, amino acid substitutions, deletions, and/or insertions from a reference set of CDRs in a VH or VL sequence disclosed in Table 1B.

In some embodiments an ALK7-binding protein comprises a set of CDRs: VH-CDR1, VH-CDR2, VH-CDR3, VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs disclosed herein. In further embodiments, the ALK7-binding protein comprises a set of CDRs, wherein the set of CDRs is identical to, or has a total of one, two, three, four, five, six, seven, eight, nine, ten, or fewer than ten, amino acid substitutions, deletions, and/or insertions from a reference set of CDRs in a VH and VL sequence pair disclosed in Table 3.

In additional embodiments, the ALK7-binding protein specifically binds ALK7 and comprises a set of CDRs: VH-CDR1, VH-CDR2, VH-CDR3, VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (a)(i) VH-CDR1 comprises the amino acid sequence of SEQ ID NO:1; (ii) VH-CDR2 comprises the amino acid sequence of SEQ ID NO:2; (iii) VH-CDR3 comprises the amino acid sequence of SEQ ID NO:3; (iv) VL-CDR1 comprises the amino acid sequence of SEQ ID NO:10; (v) VL-CDR2 comprises the amino acid sequence of SEQ ID NO:11; and (vi) VL-CDR3 comprises the amino acid sequence of SEQ ID NO:12; (b)(i) VH-CDR1 comprises the amino acid sequence of SEQ ID NO:19; (ii) VH-CDR2 comprises the amino acid sequence of SEQ ID NO:20; (iii) VH-CDR3 comprises the amino acid sequence of SEQ ID NO:21; (iv) VL-CDR1 comprises the amino acid sequence of SEQ ID NO:28; (v) VL-CDR2 comprises the amino acid sequence of SEQ ID NO:29; and (vi) VL-CDR3 comprises the amino acid sequence of SEQ ID NO:30; (c)(i) VH-CDR1 comprises the amino acid sequence of SEQ ID NO:37; (ii) VH-CDR2 comprises the amino acid sequence of SEQ ID NO:38; (iii) VH-CDR3 comprises the amino acid sequence of SEQ ID NO:39; (iv) VL-CDR1 comprises the amino acid sequence of SEQ ID NO:46; (v) VL-CDR2 comprises the amino acid sequence of SEQ ID NO:47; and (vi) VL-CDR3 comprises the amino acid sequence of SEQ ID NO:48; or (d)(i) VH-CDR1 comprises the amino acid sequence of SEQ ID NO:55; (ii) VH-CDR2 comprises the amino acid sequence of SEQ ID NO:56; (iii) VH-CDR3 comprises the amino acid sequence of SEQ ID NO:57; (iv) VL-CDR1 comprises the amino acid sequence of SEQ ID NO:64; (v) VL-CDR2 comprises the amino acid sequence of SEQ ID NO:65; and (vi) VL-CDR3 comprises the amino acid sequence of SEQ ID NO:66; and wherein the protein binds to ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the type II receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis) and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK7-binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In additional embodiments, the ALK7-binding protein specifically binds ALK7 and comprises a set of CDRs: VH-CDR1, VH-CDR2, VH-CDR3, VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (a)(i) VH-CDR1 comprises the amino acid sequence of SEQ ID NO:37; (ii) VH-CDR2 comprises the amino acid sequence of SEQ ID NO:56; (iii) VH-CDR3 comprises the amino acid sequence of SEQ ID NO:90; (iv) VL-CDR1 comprises the amino acid sequence of SEQ ID NO:95; (v) VL-CDR2 comprises the amino acid sequence of SEQ ID NO:96; and (vi) VL-CDR3 comprises the amino acid sequence of SEQ ID NO:97; (b)(i) VH-CDR1 comprises the amino acid sequence of SEQ ID NO:156; (ii) VH-CDR2 comprises the amino acid sequence of SEQ ID NO:157; (iii) VH-CDR3 comprises the amino acid sequence of SEQ ID NO:184; (iv) VL-CDR1 comprises the amino acid sequence of SEQ ID NO:107; (v) VL-CDR2 comprises the amino acid sequence of SEQ ID NO:108; and (vi) VL-CDR3 comprises the amino acid sequence of SEQ ID NO:109; and (c)(i) VH-CDR1 comprises the amino acid sequence of SEQ ID NO:1; (ii) VH-CDR2 comprises the amino acid sequence of SEQ ID NO:163; (iii) VH-CDR3 comprises the amino acid sequence of SEQ ID NO:164; (iv) VL-CDR1 comprises the amino acid sequence of SEQ ID NO:167; (v) VL-CDR2 comprises the amino acid sequence of SEQ ID NO:168; and (vi) VL-CDR3 comprises the amino acid sequence of SEQ ID NO:169; and wherein the protein binds to ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the type II receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis) and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK7-binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In additional embodiments, the ALK7-binding protein specifically binds ALK7 and comprises a set of CDRs: VH-CDR1, VH-CDR2, VH-CDR3, VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (a)(i) VH-CDR1 comprises the amino acid sequence of SEQ ID NO:88; (ii) VH-CDR2 comprises the amino acid sequence of SEQ ID NO:89; (iii) VH-CDR3 comprises the amino acid sequence of SEQ ID NO:90; (iv) VL-CDR1 comprises the amino acid sequence of SEQ ID NO:95; (v) VL-CDR2 comprises the amino acid sequence of SEQ ID NO:96; and (vi) VL-CDR3 comprises the amino acid sequence of SEQ ID NO:97; (b)(i) VH-CDR1 comprises the amino acid sequence of SEQ ID NO:102; (ii) VH-CDR2 comprises the amino acid sequence of SEQ ID NO:103; (iii) VH-CDR3 comprises the amino acid sequence of SEQ ID NO:104; (iv) VL-CDR1 comprises the amino acid sequence of SEQ ID NO:107; (v) VL-CDR2 comprises the amino acid sequence of SEQ ID NO:108; and (vi) VL-CDR3 comprises the amino acid sequence of SEQ ID NO:109; (c)(i) VH-CDR1 comprises the amino acid sequence of SEQ ID NO:114; (ii) VH-CDR2 comprises the amino acid sequence of SEQ ID NO:115; (iii) VH-CDR3 comprises the amino acid sequence of SEQ ID NO:116; (iv) VL-CDR1 comprises the amino acid sequence of SEQ ID NO:121; (v) VL-CDR2 comprises the amino acid sequence of SEQ ID NO:122; and (vi) VL-CDR3 comprises the amino acid sequence of SEQ ID NO:123; (d)(i) VH-CDR1 comprises the amino acid sequence of SEQ ID NO:125; (ii) VH-CDR2 comprises the amino acid sequence of SEQ ID NO:126; (iii) VH-CDR3 comprises the amino acid sequence of SEQ ID NO:127; (iv) VL-CDR1 comprises the amino acid sequence of SEQ ID NO:132; (v) VL-CDR2 comprises the amino acid sequence of SEQ ID NO:133; and (vi) VL-CDR3 comprises the amino acid sequence of SEQ ID NO:134; or (e)(i) VH-CDR1 comprises the amino acid sequence of SEQ ID NO:137; (ii) VH-CDR2 comprises the amino acid sequence of SEQ ID NO:138; (iii) VH-CDR3 comprises the amino acid sequence of SEQ ID NO:139; (iv) VL-CDR1 comprises the amino acid sequence of SEQ ID NO:145; (v) VL-CDR2 comprises the amino acid sequence of SEQ ID NO:146; and (vi) VL-CDR3 comprises the amino acid sequence of SEQ ID NO:147; and wherein the protein binds to ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the type II receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis) and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK7-binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In additional embodiments, the ALK7-binding protein specifically binds ALK7 and comprises a set of CDRs: VH-CDR1, VH-CDR2, VH-CDR3, VL-CDR1, VL-CDR2, and VL-CDR3, wherein: (a)(i) VH-CDR1 comprises the amino acid sequence of SEQ ID NO:1; (ii) VH-CDR2 comprises the amino acid sequence of SEQ ID NO:2; (iii) VH-CDR3 comprises the amino acid sequence of SEQ ID NO:3; (iv) VL-CDR1 comprises the amino acid sequence of SEQ ID NO:10; (v) VL-CDR2 comprises the amino acid sequence of SEQ ID NO:11; and (vi) VL-CDR3 comprises the amino acid sequence of SEQ ID NO:12; (b)(i) VH-CDR1 comprises the amino acid sequence of SEQ ID NO:19; (ii) VH-CDR2 comprises the amino acid sequence of SEQ ID NO:20; (iii) VH-CDR3 comprises the amino acid sequence of SEQ ID NO:21; (iv) VL-CDR1 comprises the amino acid sequence of SEQ ID NO:28; (v) VL-CDR2 comprises the amino acid sequence of SEQ ID NO:29; and (vi) VL-CDR3 comprises the amino acid sequence of SEQ ID NO:30; (c)(i) VH-CDR1 comprises the amino acid sequence of SEQ ID NO:37; (ii) VH-CDR2 comprises the amino acid sequence of SEQ ID NO:38; (iii) VH-CDR3 comprises the amino acid sequence of SEQ ID NO:39; (iv) VL-CDR1 comprises the amino acid sequence of SEQ ID NO:46; (v) VL-CDR2 comprises the amino acid sequence of SEQ ID NO:47; and (vi) VL-CDR3 comprises the amino acid sequence of SEQ ID NO:48; or (d)(i) VH-CDR1 comprises the amino acid sequence of SEQ ID NO:55; (ii) VH-CDR2 comprises the amino acid sequence of SEQ ID NO:56; (iii) VH-CDR3 comprises the amino acid sequence of SEQ ID NO:57; (iv) VL-CDR1 comprises the amino acid sequence of SEQ ID NO:64; (v) VL-CDR2 comprises the amino acid sequence of SEQ ID NO:65; and (vi) VL-CDR3 comprises the amino acid sequence of SEQ ID NO:66; and wherein the protein binds ALK7.

In additional embodiments, the ALK7-binding protein specifically binds ALK7 and comprises a set of CDRs: VH-CDR1, VH-CDR2, VH-CDR3, VL-CDR1, VL-CDR2, and VL-CDR3, wherein: (a)(i) VH-CDR1 comprises the amino acid sequence of SEQ ID NO:37; (ii) VH-CDR2 comprises the amino acid sequence of SEQ ID NO:56; (iii) VH-CDR3 comprises the amino acid sequence of SEQ ID NO:90; (iv) VL-CDR1 comprises the amino acid sequence of SEQ ID NO:95; (v) VL-CDR2 comprises the amino acid sequence of SEQ ID NO:96; and (vi) VL-CDR3 comprises the amino acid sequence of SEQ ID NO:97; (b)(i) VH-CDR1 comprises the amino acid sequence of SEQ ID NO:156; (ii) VH-CDR2 comprises the amino acid sequence of SEQ ID NO:157; (iii) VH-CDR3 comprises the amino acid sequence of SEQ ID NO:104; (iv) VL-CDR1 comprises the amino acid sequence of SEQ ID NO:107; (v) VL-CDR2 comprises the amino acid sequence of SEQ ID NO:108; and (vi) VL-CDR3 comprises the amino acid sequence of SEQ ID NO:109; and (c)(i) VH-CDR1 comprises the amino acid sequence of SEQ ID NO:1; (ii) VH-CDR2 comprises the amino acid sequence of SEQ ID NO:163; (iii) VH-CDR3 comprises the amino acid sequence of SEQ ID NO:1164; (iv) VL-CDR1 comprises the amino acid sequence of SEQ ID NO:107; (v) VL-CDR2 comprises the amino acid sequence of SEQ ID NO:168; and (vi) VL-CDR3 comprises the amino acid sequence of SEQ ID NO:169; and wherein the protein binds ALK7.

In additional embodiments, the ALK7-binding protein specifically binds ALK7 and comprises a set of CDRs: VH-CDR1, VH-CDR2, VH-CDR3, VL-CDR1, VL-CDR2, and VL-CDR3, wherein: (a)(i) VH-CDR1 comprises the amino acid sequence of SEQ ID NO:88; (ii) VH-CDR2 comprises the amino acid sequence of SEQ ID NO:89; (iii) VH-CDR3 comprises the amino acid sequence of SEQ ID NO:90; (iv) VL-CDR1 comprises the amino acid sequence of SEQ ID NO:95; (v) VL-CDR2 comprises the amino acid sequence of SEQ ID NO:96; and (vi) VL-CDR3 comprises the amino acid sequence of SEQ ID NO:97; (b)(i) VH-CDR1 comprises the amino acid sequence of SEQ ID NO:102; (ii) VH-CDR2 comprises the amino acid sequence of SEQ ID NO:103; (iii) VH-CDR3 comprises the amino acid sequence of SEQ ID NO:104; (iv) VL-CDR1 comprises the amino acid sequence of SEQ ID NO:107; (v) VL-CDR2 comprises the amino acid sequence of SEQ ID NO:108; and (vi) VL-CDR3 comprises the amino acid sequence of SEQ ID NO:109; (c)(i) VH-CDR1 comprises the amino acid sequence of SEQ ID NO:114; (ii) VH-CDR2 comprises the amino acid sequence of SEQ ID NO:115; (iii) VH-CDR3 comprises the amino acid sequence of SEQ ID NO:116; (iv) VL-CDR1 comprises the amino acid sequence of SEQ ID NO:121; (v) VL-CDR2 comprises the amino acid sequence of SEQ ID NO:122; and (vi) VL-CDR3 comprises the amino acid sequence of SEQ ID NO:123; (d)(i) VH-CDR1 comprises the amino acid sequence of SEQ ID NO:125; (ii) VH-CDR2 comprises the amino acid sequence of SEQ ID NO:126; (iii) VH-CDR3 comprises the amino acid sequence of SEQ ID NO:127; (iv) VL-CDR1 comprises the amino acid sequence of SEQ ID NO:132; (v) VL-CDR2 comprises the amino acid sequence of SEQ ID NO:133; and (vi) VL-CDR3 comprises the amino acid sequence of SEQ ID NO:134; or (e)(i) VH-CDR1 comprises the amino acid sequence of SEQ ID NO:137; (ii) VH-CDR2 comprises the amino acid sequence of SEQ ID NO:138; (iii) VH-CDR3 comprises the amino acid sequence of SEQ ID NO:139; (iv) VL-CDR1 comprises the amino acid sequence of SEQ ID NO:145; (v) VL-CDR2 comprises the amino acid sequence of SEQ ID NO:146; and (vi) VL-CDR3 comprises the amino acid sequence of SEQ ID NO:147; and wherein the protein binds ALK7.

In some embodiments, the ALK7-binding protein specifically binds ALK7 and comprises a set of CDRs that has a total of one, two, three, four, five, six, seven, eight, nine, ten, fewer than ten, or zero, amino acid substitutions, deletions, and/or insertions from a reference set of CDRs in which: (a)(i) VH-CDR1 comprises the amino acid sequence of SEQ ID NO:1; (ii) VH-CDR2 comprises the amino acid sequence of SEQ ID NO:2; (iii) VH-CDR3 comprises the amino acid sequence of SEQ ID NO:3; (iv) VL-CDR1 comprises the amino acid sequence of SEQ ID NO:10; (v) VL-CDR2 comprises the amino acid sequence of SEQ ID NO:11; and (vi) VL-CDR3 comprises the amino acid sequence of SEQ ID NO:12; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and activin B on the surface of cells expressing ALK7 and the ActRII receptor in the presence of the one or more TGF-beta superfamily ligands; (b) competes with ActRIIA or ActRIIB for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and an ActRII receptor (e.g., ActRIIA or ActRIIB) in the presence of GDF1, GDF3, GDF8, activin B, activin A/B, and/or Nodal; (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein specifically binds ALK7 and comprises a set of CDRs that has a total of one, two, three, four, five, six, seven, eight, nine, ten, fewer than ten, or zero, amino acid substitutions, deletions, and/or insertions from a reference set of CDRs in which: (i) VH-CDR1 comprises the amino acid sequence of SEQ ID NO:19; (ii) VH-CDR2 comprises the amino acid sequence of SEQ ID NO:20; (iii) VH-CDR3 comprises the amino acid sequence of SEQ ID NO:21; (iv) VL-CDR1 comprises the amino acid sequence of SEQ ID NO:28; (v) VL-CDR2 comprises the amino acid sequence of SEQ ID NO:29; and (vi) VL-CDR3 comprises the amino acid sequence of SEQ ID NO:30; and wherein the protein binds ALK7. In further embodiments, the ALK7-binding protein has at least one characteristic selected from the group consisting of: (a) decreases the formation of a complex containing ALK7, a A type II receptor (e.g., ActRIIA or ActRIIB), and activin B on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and an ActRII receptor (e.g., ActRIIA or ActRIIB) in the presence of GDF1, GDF3, GDF8, activin B, activin A/B, and/or Nodal; (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein specifically binds ALK7 and comprises a set of CDRs that has a total of one, two, three, four, five, six, seven, eight, nine, ten, fewer than ten, or zero, amino acid substitutions, deletions, and/or insertions from a reference set of CDRs in which: (i) VH-CDR1 comprises the amino acid sequence of SEQ ID NO:37; (ii) VH-CDR2 comprises the amino acid sequence of SEQ ID NO:38; (iii) VH-CDR3 comprises the amino acid sequence of SEQ ID NO:39; (iv) VL-CDR1 comprises the amino acid sequence of SEQ ID NO:46; (v) VL-CDR2 comprises the amino acid sequence of SEQ ID NO:47; and (vi) VL-CDR3 comprises the amino acid sequence of SEQ ID NO:48; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and an ActRII receptor (e.g., ActRIIA or ActRIIB) in the presence of GDF1, GDF3, GDF8, activin B, activin A/B, and/or Nodal; (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIA-CORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein specifically binds ALK7 and comprises a set of CDRs that has a total of one, two, three, four, five, six, seven, eight, nine, ten, fewer than ten, or zero, amino acid substitutions, deletions, and/or insertions from a reference set of CDRs in which: (i) VH-CDR1 comprises the amino acid sequence of SEQ ID NO:55; (ii) VH-CDR2 comprises the amino acid sequence of SEQ ID NO:56; (iii) VH-CDR3 comprises the amino acid sequence of SEQ ID NO:57; (iv) VL-CDR1 comprises the amino acid sequence of SEQ ID NO:64; (v) VL-CDR2 comprises the amino acid sequence of SEQ ID NO:65; and (vi) VL-CDR3 comprises the amino acid sequence of SEQ ID NO:66; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and an ActRII receptor (e.g., ActRIIA or ActRIIB) in the presence of GDF1, GDF3, GDF8, activin B, activin A/B, and/or Nodal; (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIA-CORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein specifically binds ALK7 and comprises a set of CDRs that has a total of one, two, three, four, five, six, seven, eight, nine, ten, fewer than ten, or zero, amino acid substitutions, deletions, and/or insertions from a reference set of CDRs in which: (a)(i) VH-CDR1 comprises the amino acid sequence of SEQ ID NO:88; (ii) VH-CDR2 comprises the amino acid sequence of SEQ ID NO89; (iii) VH-CDR3 comprises the amino acid sequence of SEQ ID NO:90; (iv) VL-CDR1 comprises the amino acid sequence of SEQ ID NO:95; (v) VL-CDR2 comprises the amino acid sequence of SEQ ID NO:96; and (vi) VL-CDR3 comprises the amino acid sequence of SEQ ID NO:97; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and activin B on the surface of cells expressing ALK7 and the ActRII receptor in the presence of the one or more TGF-beta superfamily ligands; (b) competes with ActRIIA or ActRIIB) for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and an ActRII receptor (e.g., ActRIIA or ActRIIB) in the presence of GDF1, GDF3, GDF8, activin B, activin A/B, and/or Nodal; (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein specifically binds ALK7 and comprises a set of CDRs that has a total of one, two, three, four, five, six, seven, eight, nine, ten, fewer than ten, or zero, amino acid substitutions, deletions, and/or insertions from a reference set of CDRs in which: (i) VH-CDR1 comprises the amino acid sequence of SEQ ID NO:102; (ii) VH-CDR2 comprises the amino acid sequence of SEQ ID NO:103; (iii) VH-CDR3 comprises the amino acid sequence of SEQ ID NO:104; (iv) VL-CDR1 comprises the amino acid sequence of SEQ ID NO:107; (v) VL-CDR2 comprises the amino acid sequence of SEQ ID NO:108; and (vi) VL-CDR3 comprises the amino acid sequence of SEQ ID NO:109; and wherein the protein binds ALK7. In further embodiments, the ALK7-binding protein has at least one characteristic selected from the group consisting of: (a) decreases the formation of a complex containing ALK7, a A type II receptor (e.g., ActRIIA or ActRIIB), and activin B on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and an ActRII receptor (e.g., ActRIIA or ActRIIB) in the presence of GDF1, GDF3, GDF8, activin B, activin A/B, and/or Nodal; (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein specifically binds ALK7 and comprises a set of CDRs that has a total of one, two, three, four, five, six, seven, eight, nine, ten, fewer than ten, or zero, amino acid substitutions, deletions, and/or insertions from a reference set of CDRs in which: (i) VH-CDR1 comprises the amino acid sequence of SEQ ID NO:114; (ii) VH-CDR2 comprises the amino acid sequence of SEQ ID NO:115; (iii) VH-CDR3 comprises the amino acid sequence of SEQ ID NO:116; (iv) VL-CDR1 comprises the amino acid sequence of SEQ ID NO:121; (v) VL-CDR2 comprises the amino acid sequence of SEQ ID NO:122; and (vi) VL-CDR3 comprises the amino acid sequence of SEQ ID NO:123; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and an ActRII receptor (e.g., ActRIIA or ActRIIB) in the presence of GDF1, GDF3, GDF8, activin B, activin A/B, and/or Nodal; (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein specifically binds ALK7 and comprises a set of CDRs that has a total of one, two, three, four, five, six, seven, eight, nine, ten, fewer than ten, or zero, amino acid substitutions, deletions, and/or insertions from a reference set of CDRs in which: (i)

VH-CDR1 comprises the amino acid sequence of SEQ ID NO:125; (ii) VH-CDR2 comprises the amino acid sequence of SEQ ID NO:126; (iii) VH-CDR3 comprises the amino acid sequence of SEQ ID NO:127; (iv) VL-CDR1 comprises the amino acid sequence of SEQ ID NO:132; (v) VL-CDR2 comprises the amino acid sequence of SEQ ID NO:133; and (vi) VL-CDR3 comprises the amino acid sequence of SEQ ID NO:134; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and an ActRII receptor (e.g., ActRIIA or ActRIIB) in the presence of GDF1, GDF3, GDF8, activin B, activin A/B, and/or Nodal; (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIA-CORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein specifically binds ALK7 and comprises a set of CDRs that has a total of one, two, three, four, five, six, seven, eight, nine, ten, fewer than ten, or zero, amino acid substitutions, deletions, and/or insertions from a reference set of CDRs in which: (i) VH-CDR1 comprises the amino acid sequence of SEQ ID NO:137; (ii) VH-CDR2 comprises the amino acid sequence of SEQ ID NO:138; (iii) VH-CDR3 comprises the amino acid sequence of SEQ ID NO:139; (iv) VL-CDR1 comprises the amino acid sequence of SEQ ID NO:145; (v) VL-CDR2 comprises the amino acid sequence of SEQ ID NO:146; and (vi) VL-CDR3 comprises the amino acid sequence of SEQ ID NO:147; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and an ActRII receptor (e.g., ActRIIA or ActRIIB) in the presence of GDF1, GDF3, GDF8, activin B, activin A/B, and/or Nodal; (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIA-CORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, an ALK7-binding protein specifically binds ALK7 and comprises a set of CDRs: VH-CDR1, VH-CDR2, and VH-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VH-CDR1 comprises the amino acid sequence of SEQ ID NO:37; (ii) VH-CDR2 comprises the amino acid sequence of SEQ ID NO:38; and (iii) VH-CDR3 comprises the amino acid sequence of SEQ ID NO:39 or 57; and the protein binds ALK7. In a further embodiment, an ALK7-binding protein specifically binds ALK7 and comprises a set of CDRs: VH-CDR1, VH-CDR2, and VH-CDR3, wherein: (i) VH-CDR1 comprises the amino acid sequence of SEQ ID NO:37; (ii) VH-CDR2 comprises the amino acid sequence of SEQ ID NO:38; and (iii) VH-CDR3 comprises the amino acid sequence of SEQ ID NO:39; and the protein binds ALK7. In a further embodiment, an ALK7-binding protein specifically binds ALK7 and comprises a set of CDRs: VH-CDR1, VH-CDR2, and VH-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VH-CDR1 comprises the amino acid sequence of SEQ ID NO:37; (ii) VH-CDR2 comprises the amino acid sequence of SEQ ID NO:38; and (iii) VH-CDR3 comprises the amino acid sequence of SEQ ID NO:39; and the protein binds ALK7. In a further embodiment, an ALK7-binding protein specifically binds ALK7 and comprises a set of CDRs: VH-CDR1, VH-CDR2, and VH-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VH-CDR1 comprises the amino acid sequence of SEQ ID NO:37; (ii) VH-CDR2 comprises the amino acid sequence of SEQ ID NO:38; and (iii) VH-CDR3 comprises the amino acid sequence of SEQ ID NO:57; and the protein binds ALK7. In a further embodiment, an ALK7-binding protein specifically binds ALK7 and comprises a set of CDRs: VH-CDR1, VH-CDR2, and VH-CDR3, wherein: (i) VH-CDR1 comprises the amino acid sequence of SEQ ID NO:37; (ii) VH-CDR2 comprises the amino acid sequence of SEQ ID NO:38; and (iii) VH-CDR3 comprises the amino acid sequence of SEQ ID NO:57; and the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and an ActRII receptor (e.g., ActRIIA or ActRIIB in the presence of GDF1, GDF3, GDF8, activin B, activin A/B, and/or Nodal; (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, an ALK7-binding protein specifically binds ALK7 and comprises a set of CDRs: VH-CDR1, VH-CDR2, and VH-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VH-CDR1 comprises the amino acid sequence of SEQ ID NO:1; (ii) VH-CDR2 comprises the amino acid sequence of SEQ ID NO:2; and (iii) VH-CDR3 comprises the amino acid sequence of SEQ ID NO:3; and the protein binds ALK7. In some embodiments, an ALK7-binding protein specifically binds ALK7 and comprises a set of CDRs: VH-CDR1, VH-CDR2, and VH-CDR3, wherein: (i) VH-CDR1 comprises the amino acid sequence of SEQ ID NO:1; (ii) VH-CDR2 comprises the amino acid sequence of SEQ ID NO:2; and (iii) VH-CDR3 comprises the amino acid sequence of SEQ ID NO:3; and the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and an ActRII receptor (e.g., ActRIIA or ActRIIB in the presence of GDF1, GDF3, GDF8, activin B, activin A/B, and/or Nodal; (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, an ALK7-binding protein specifically binds ALK7 and comprises a set of CDRs: VH-CDR1, VH-CDR2, and VH-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VH-CDR1 comprises the amino acid sequence of SEQ ID NO:19; (ii) VH-CDR2 comprises the amino acid sequence of SEQ ID NO:20; and (iii) VH-CDR3 comprises the amino acid sequence of SEQ ID NO:21; and the protein binds ALK7. In some embodiments, an ALK7-binding protein specifically binds ALK7 and comprises a set of CDRs: VH-CDR1, VH-CDR2, and VH-CDR3, wherein: (i) VH-CDR1 comprises the amino acid sequence of SEQ ID NO:19; (ii) VH-CDR2 comprises the amino acid sequence of SEQ ID NO:20; and (iii) VH-CDR3 comprises the amino acid sequence of SEQ ID NO:21; and the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and an ActRII receptor (e.g., ActRIIA or ActRIIB in the presence of GDF1, GDF3, GDF8, activin B, activin A/B, and/or Nodal; (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In a further embodiment, an ALK7-binding protein specifically binds ALK7 and comprises a set of CDRs: VH-CDR1, VH-CDR2, and VH-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VH-CDR1 comprises the amino acid sequence of SEQ ID NO:37; (ii) VH-CDR2 comprises the amino acid sequence of SEQ ID NO:38; and (iii) VH-CDR3 comprises the amino acid sequence of SEQ ID NO:39; and the protein binds ALK7. In a further embodiment, an ALK7-binding protein specifically binds ALK7 and comprises a set of CDRs: VH-CDR1, VH-CDR2, and VH-CDR3, wherein (i) VH-CDR1 comprises the amino acid sequence of SEQ ID NO:37; (ii) VH-CDR2 comprises the amino acid sequence of SEQ ID NO:38; and (iii) VH-CDR3 comprises the amino acid sequence of SEQ ID NO:39; and the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and an ActRII receptor (e.g., ActRIIA or ActRIIB in the presence of GDF1, GDF3, GDF8, activin B, activin A/B, and/or Nodal; (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In a further embodiment, an ALK7-binding protein specifically binds ALK7 and comprises a set of CDRs: VH-CDR1, VH-CDR2, and VH-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VH-CDR1 comprises the amino acid sequence of SEQ ID NO:55; (ii) VH-CDR2 comprises the amino acid sequence of SEQ ID NO:56; and (iii) VH-CDR3 comprises the amino acid sequence of SEQ ID NO:57; and the protein binds ALK7. In a further embodiment, an ALK7-binding protein specifically binds ALK7 and comprises a set of CDRs: VH-CDR1, VH-CDR2, and VH-CDR3, wherein (i) VH-CDR1 comprises the amino acid sequence of SEQ ID NO:55; (ii) VH-CDR2 comprises the amino acid sequence of SEQ ID NO:56; and (iii) VH-CDR3 comprises the amino acid sequence of SEQ ID NO:57; and the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and an ActRII receptor (e.g., ActRIIA or ActRIIB in the presence of GDF1, GDF3, GDF8, activin B, activin A/B, and/or Nodal; (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, an ALK7-binding protein specifically binds ALK7 and comprises a set of CDRs: VH-CDR1, VH-CDR2, and VH-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VH-CDR1 comprises the amino acid sequence of SEQ ID NO:88; (ii) VH-CDR2 comprises the amino acid sequence of SEQ ID NO:89; and (iii) VH-CDR3 comprises the amino acid sequence of SEQ ID NO:90; and the protein binds ALK7. In some embodiments, an ALK7-binding protein specifically binds ALK7 and comprises a set of CDRs: VH-CDR1, VH-CDR2, and VH-CDR3, wherein: (i) VH-CDR1 comprises the amino acid sequence of SEQ ID NO:88; (ii) VH-CDR2 comprises the amino acid sequence of SEQ ID NO:89; and (iii) VH-CDR3 comprises the amino acid sequence of SEQ ID NO:90; and the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and an ActRII receptor (e.g., ActRIIA or ActRIIB in the presence of GDF1, GDF3, GDF8, activin B, activin A/B, and/or Nodal; (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, an ALK7-binding protein specifically binds ALK7 and comprises a set of CDRs: VH-CDR1, VH-CDR2, and VH-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VH-CDR1 comprises the amino acid sequence of SEQ ID NO:102; (ii) VH-CDR2 comprises the amino acid sequence of SEQ ID NO:103; and (iii) VH-CDR3 comprises the amino acid sequence of SEQ ID NO:104; and the protein binds ALK7. In some embodiments, an ALK7-binding protein specifically binds ALK7 and comprises a set of CDRs: VH-CDR1, VH-CDR2, and VH-CDR3, wherein: (i) VH-CDR1 comprises the amino acid sequence of SEQ ID NO:102; (ii) VH-CDR2 comprises the amino acid sequence of SEQ ID NO:103; and (iii) VH-CDR3 comprises the amino acid sequence of SEQ ID NO:104; and the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and an ActRII receptor (e.g., ActRIIA or ActRIIB in the presence of GDF1, GDF3, GDF8, activin B, activin A/B, and/or Nodal; (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In a further embodiment, an ALK7-binding protein specifically binds ALK7 and comprises a set of CDRs: VH-CDR1, VH-CDR2, and VH-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VH-CDR1 comprises the amino acid sequence of SEQ ID NO:114; (ii) VH-CDR2 comprises the amino acid sequence of SEQ ID NO:115; and (iii) VH-CDR3 comprises the amino acid sequence of SEQ ID NO:116; and the protein binds ALK7. In a further embodiment, an ALK7-binding protein specifically binds ALK7 and comprises a set of CDRs: VH-CDR1, VH-CDR2, and VH-CDR3, wherein (i) VH-CDR1 comprises the amino acid sequence of SEQ ID NO:114; (ii) VH-CDR2 comprises the amino acid sequence of SEQ ID NO:115; and (iii) VH-CDR3 comprises the amino acid sequence of SEQ ID NO:116; and the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and an ActRII receptor (e.g., ActRIIA or ActRIIB in the presence of GDF1, GDF3, GDF8, activin B, activin A/B, and/or Nodal; (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In a further embodiment, an ALK7-binding protein specifically binds ALK7 and comprises a set of CDRs: VH-CDR1, VH-CDR2, and VH-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VH-CDR1 comprises the amino acid sequence of SEQ ID NO:125; (ii) VH-CDR2 comprises the amino acid sequence of SEQ ID NO:126; and (iii) VH-CDR3 comprises the amino acid sequence of SEQ ID NO:127; and the protein binds ALK7. In a further embodiment, an ALK7-binding protein specifically binds ALK7 and comprises a set of CDRs: VH-CDR1, VH-CDR2, and VH-CDR3, wherein (i) VH-CDR1 comprises the amino acid sequence of SEQ ID NO:125; (ii) VH-CDR2 comprises the amino acid sequence of SEQ ID NO:126; and (iii) VH-CDR3 comprises the amino acid sequence of SEQ ID NO:127; and the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and an ActRII receptor (e.g., ActRIIA or ActRIIB in the presence of GDF1, GDF3, GDF8, activin B, activin A/B, and/or Nodal; (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In a further embodiment, an ALK7-binding protein specifically binds ALK7 and comprises a set of CDRs: VH-CDR1, VH-CDR2, and VH-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VH-CDR1 comprises the amino acid sequence of SEQ ID NO:137; (ii) VH-CDR2 comprises the amino acid sequence of SEQ ID NO:138; and (iii) VH-CDR3 comprises the amino acid sequence of SEQ ID NO:139; and the protein binds ALK7. In a further embodiment, an ALK7-binding protein specifically binds ALK7 and comprises a set of CDRs: VH-CDR1, VH-CDR2, and VH- CDR3, wherein (i) VH-CDR1 comprises the amino acid sequence of SEQ ID NO:137; (ii) VH-CDR2 comprises the amino acid sequence of SEQ ID NO:138; and (iii) VH-CDR3 comprises the amino acid sequence of SEQ ID NO:139; and the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and an ActRII receptor (e.g., ActRIIA or ActRIIB in the presence of GDF1, GDF3, GDF8, activin B, activin A/B, and/or Nodal; (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, an ALK7-binding protein specifically binds ALK7 and comprises a set of CDRs: VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VL-CDR1 comprises the amino acid sequence of SEQ ID NO:10; (ii) VL-CDR2 comprises the amino acid sequence of SEQ ID NO:11; and (iii) VL-CDR3 comprises the amino acid sequence of SEQ ID NO:12; and wherein the protein binds ALK7. In some embodiments, an ALK7-binding protein specifically binds ALK7 and comprises a set of CDRs: VL-CDR1, VL-CDR2, and VL-CDR3, wherein: (i) VL-CDR1 comprises the amino acid sequence of SEQ ID NO:10; (ii) VL-CDR2 comprises the amino acid sequence of SEQ ID NO:11; and (iii) VL-CDR3 comprises the amino acid sequence of SEQ ID NO:12; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, an ALK7-binding protein specifically binds ALK7 and comprises a set of CDRs: VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VL-CDR1 comprises the amino acid sequence of SEQ ID NO:28; (ii) VL-CDR2 comprises the amino acid sequence of SEQ ID NO:29; and (iii) VL-CDR3 comprises the amino acid sequence of SEQ ID NO:30; and wherein the protein binds ALK7. In some embodiments, an ALK7-binding protein specifically binds ALK7 and comprises a set of CDRs: VL-CDR1, VL-CDR2, and VL-CDR3, wherein: (i) VL-CDR1 comprises the amino acid sequence of SEQ ID NO:28; (ii) VL-CDR2 comprises the amino acid sequence of SEQ ID NO:29; and (iii) VL-CDR3 comprises the amino acid sequence of SEQ ID NO:30; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, an ALK7-binding protein specifically binds ALK7 and comprises a set of CDRs: VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VL-CDR1 comprises the amino acid sequence of SEQ ID NO:46; (ii) VL-CDR2 comprises the amino acid sequence of SEQ ID NO:47; and (iii) VL-CDR3 comprises the amino acid sequence of SEQ ID NO:48; and wherein the protein binds ALK7. In some embodiments, an ALK7-binding protein specifically binds ALK7 and comprises a set of CDRs: VL-CDR1, VL-CDR2, and VL-CDR3, wherein: (i) VL-CDR1 comprises the amino acid sequence of SEQ ID NO:46; (ii) VL-CDR2 comprises the amino acid sequence of SEQ ID NO:47; and (iii) VL-CDR3 comprises the amino acid sequence of SEQ ID NO:48; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, an ALK7-binding protein specifically binds ALK7 and comprises a set of CDRs: VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VL-CDR1 comprises the amino acid sequence of SEQ ID NO:64; (ii) VL-CDR2 comprises the amino acid sequence of SEQ ID NO:65; and (iii) VL-CDR3 comprises the amino acid sequence of SEQ ID NO:66; and wherein the protein binds ALK7. In some embodiments, an ALK7-binding protein specifically binds ALK7 and comprises a set of CDRs: VL-CDR1, VL-CDR2, and VL-CDR3, wherein: (i) VL-CDR1 comprises the amino acid sequence of SEQ ID NO:64; (ii) VL-CDR2 comprises the amino acid sequence of SEQ ID NO:65; and (iii) VL-CDR3 comprises the amino acid sequence of SEQ ID NO:66; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, an ALK7-binding protein specifically binds ALK7 and comprises a set of CDRs: VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VL-CDR1 comprises the amino acid sequence of SEQ ID NO:95; (ii) VL-CDR2 comprises the amino acid sequence of SEQ ID NO:96; and (iii) VL-CDR3 comprises the amino acid sequence of SEQ ID NO:97; and wherein the protein binds ALK7. In some embodiments, an ALK7-binding protein specifically binds ALK7 and comprises a set of CDRs: VL-CDR1, VL-CDR2, and VL-CDR3, wherein: (i) VL-CDR1 comprises the amino acid sequence of SEQ ID NO:95; (ii) VL-CDR2 comprises the amino acid sequence of SEQ ID NO:96; and (iii) VL-CDR3 comprises the amino acid sequence of SEQ ID NO:97; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, an ALK7-binding protein specifically binds ALK7 and comprises a set of CDRs: VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VL-CDR1 comprises the amino acid sequence of SEQ ID NO:107; (ii) VL-CDR2 comprises the amino acid sequence of SEQ ID NO:108; and (iii) VL-CDR3 comprises the amino acid sequence of SEQ ID NO:109; and wherein the protein binds ALK7. In some embodiments, an ALK7-binding protein specifically binds ALK7 and comprises a set of CDRs: VL-CDR1, VL-CDR2, and VL-CDR3, wherein: (i) VL-CDR1 comprises the amino acid sequence of SEQ ID NO:107; (ii) VL-CDR2 comprises the amino acid sequence of SEQ ID NO:108; and (iii) VL-CDR3 comprises the amino acid sequence of SEQ ID NO:109; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, an ALK7-binding protein specifically binds ALK7 and comprises a set of CDRs: VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VL-CDR1 comprises the amino acid sequence of SEQ ID NO:121; (ii) VL-CDR2 comprises the amino acid sequence of SEQ ID NO:122; and (iii) VL-CDR3 comprises the amino acid sequence of SEQ ID NO:123; and wherein the protein binds ALK7. In some embodiments, an ALK7-binding protein specifically binds ALK7 and comprises a set of CDRs: VL-CDR1, VL-CDR2, and VL-CDR3, wherein: (i) VL-CDR1 comprises the amino acid sequence of SEQ ID NO:121; (ii) VL-CDR2 comprises the amino acid sequence of SEQ ID NO:122; and (iii) VL-CDR3 comprises the amino acid sequence of SEQ ID NO:123; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, an ALK7-binding protein specifically binds ALK7 and comprises a set of CDRs: VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VL-CDR1 comprises the amino acid sequence of SEQ ID NO:132; (ii) VL-CDR2 comprises the amino acid sequence of SEQ ID NO:133; and (iii) VL-CDR3 comprises the amino acid sequence of SEQ ID NO:134; and wherein the protein binds ALK7. In some embodiments, an ALK7-binding protein specifically binds ALK7 and comprises a set of CDRs: VL-CDR1, VL-CDR2, and VL-CDR3, wherein: (i) VL-CDR1 comprises the amino acid sequence of SEQ ID NO:132; (ii) VL-CDR2 comprises the amino acid sequence of SEQ ID NO:133; and (iii) VL-CDR3 comprises the amino acid sequence of SEQ ID NO:134; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, an ALK7-binding protein specifically binds ALK7 and comprises a set of CDRs: VL-CDR1, VL-CDR2, and VL-CDR3, wherein the set of CDRs is identical to, or has a total of one, two, three, four, five, six, seven, eight, nine, ten, or fewer than ten, amino acid substitutions, deletions, and/or insertions from a reference set of CDRs in which: (i) VL-CDR1 comprises the amino acid sequence of SEQ ID NO:145; (ii) VL-CDR2 comprises the amino acid sequence of SEQ ID NO:146; and (iii) VL-CDR3 comprises the amino acid sequence of SEQ ID NO:147; and wherein the protein binds ALK7. In some embodiments, an ALK7-binding protein specifically binds ALK7 and comprises a set of CDRs: VL-CDR1, VL-CDR2, and VL-CDR3, wherein: (i) VL-CDR1 comprises the amino acid sequence of SEQ ID NO:145; (ii) VL-CDR2 comprises the amino acid sequence of SEQ ID NO:146; and (iii) VL-CDR3 comprises the amino acid sequence of SEQ ID NO:147; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments an ALK7-binding protein comprises a VH-CDR3 or a VL-CDR3 sequence disclosed herein. In further embodiments, the ALK7-binding protein comprises a VH-CDR3 or a VL-CDR3 sequence disclosed in Table 1A. In some embodiments an ALK7-binding protein comprises a VH-CDR3 and a VL-CDR3 sequence disclosed herein. In further embodiments, the ALK7-binding protein comprises a VH-CDR3 and a VL-CDR3 sequence disclosed in Table 1A. In some embodiments, the ALK7-binding protein comprises a VH-CDR3 or a VL-CDR3 sequence disclosed in Table 1B. In further embodiments, the ALK7-binding protein comprises a VH-CDR3 and a VL-CDR3 sequence disclosed in Table 1B. In some embodiments, the ALK7-binding protein comprises a VH-CDR3 or a VL-CDR3 sequence disclosed in Table 3. In further embodiments, the ALK7-binding protein comprises a VH-CDR3 and a VL-CDR3 sequence disclosed in Table 3.

In some embodiments, the disclosure provides an ALK7-binding protein comprising a VH-CDR3 having the amino acid sequence of SEQ ID NO:3. In further embodiments the ALK7-binding protein comprises a VH-CDR3 having the amino acid sequence of SEQ ID NO:3 and a VH-CDR2 having the amino acid sequence of SEQ ID NO:2. In further embodiments, the ALK7-binding protein comprises a VH-CDR3 having the amino acid sequence of SEQ ID NO:3, a VH-CDR2 having the amino acid sequence of SEQ ID NO:2, and a VH-CDR1 having the amino acid sequence of SEQ ID NO:1. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type I receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the disclosure provides an ALK7-binding protein comprising a VH-CDR3 having the amino acid sequence of SEQ ID NO:21. In further embodiments the ALK7-binding protein comprises a VH-CDR3 having the amino acid sequence of SEQ ID NO:21 and a VH-CDR2 having the amino acid sequence of SEQ ID NO:20. In further embodiments, the ALK7-binding protein comprises a VH-CDR3 having the amino acid sequence of SEQ ID NO:21, a VH-CDR2 having the amino acid sequence of SEQ ID NO:20, and a VH-CDR1 having the amino acid sequence of SEQ ID NO:19. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein comprises a VH-CDR3 having the amino acid sequence of SEQ ID NO:39. In further embodiments the ALK7-binding protein comprises a VH-CDR3 having the amino acid sequence of SEQ ID NO:39 and a VH-CDR2 having the amino acid sequence of SEQ ID NO:38. In further embodiments, the ALK7-binding protein comprises a VH-CDR3 having the amino acid sequence of SEQ ID NO:39, a VH-CDR2 having the amino acid sequence of SEQ ID NO:38, and a VH-CDR1 having the amino acid sequence of SEQ ID NO:37. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein comprises a VH-CDR3 having the amino acid sequence of SEQ ID NO:57. In further embodiments the ALK7-binding protein comprises a VH-CDR3 having the amino acid sequence of SEQ ID NO:57 and a VH-CDR2 having the amino acid sequence of SEQ ID NO:56. In further embodiments, the ALK7-binding protein comprises a VH-CDR3 having the amino acid sequence of SEQ ID NO:57, a VH-CDR2 having the amino acid sequence of SEQ ID NO:56, and a VH-CDR1 having the amino acid sequence of SEQ ID NO:55. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In further embodiments, the disclosure provides an ALK7-binding protein comprising a VH-CDR1 having the amino acid sequence of SEQ ID NO:1. In further embodiments, the disclosure provides an ALK7-binding protein comprising a VH-CDR1 having the amino acid sequence of SEQ ID NO:1 and a VH-CDR2 having the amino acid sequence of SEQ ID NO:2. In further embodiments, the disclosure provides an ALK7-binding protein comprising a VH-CDR1 having the amino acid sequence of SEQ ID NO:1, a VH-CDR2 having the amino acid sequence of SEQ ID NO:2, and a VH-CDR3 having the amino acid sequence of SEQ ID NO:3 or 21.

In further embodiments, the disclosure provides an ALK7-binding protein comprising a VH-CDR2 having the amino acid sequence of SEQ ID NO:2. In further embodiments the ALK7-binding protein comprises a VH-CDR2 having the amino acid sequence of SEQ ID NO:2 and a VH-CDR1 having the amino acid sequence of SEQ ID NO:1. In further embodiments, the ALK7-binding protein comprises a VH-CDR2 having the amino acid sequence of SEQ ID NO:2, a VH-CDR1 having the amino acid sequence of SEQ ID NO:1, and a VH-CDR3 having the amino acid sequence of SEQ ID NO:3 or 21.

In further embodiments, the disclosure provides an ALK7-binding protein comprising a VH-CDR1 having the amino acid sequence of SEQ ID NO:38. In further embodiments, the disclosure provides an ALK7-binding protein comprising a VH-CDR1 having the amino acid sequence of SEQ ID NO:37 and a VH-CDR2 having the amino acid sequence of SEQ ID NO:38. In further embodiments, the disclosure provides an ALK7-binding protein comprising a VH-CDR1 having the amino acid sequence of SEQ ID NO:37, a VH-CDR2 having the amino acid sequence of SEQ ID NO:38, and a VH-CDR3 having the amino acid sequence of SEQ ID NO:39 or 57.

In further embodiments, the disclosure provides an ALK7-binding protein comprising a VH-CDR2 having the amino acid sequence of SEQ ID NO:38. In further embodiments the ALK7-binding protein comprises a VH-CDR2 having the amino acid sequence of SEQ ID NO:38 and a VH-CDR1 having the amino acid sequence of SEQ ID NO:37. In further embodiments, the ALK7-binding protein comprises a VH-CDR2 having the amino acid sequence of SEQ ID NO:38, a VH-CDR1 having the amino acid sequence of SEQ ID NO:37, and a VH-CDR3 having the amino acid sequence of SEQ ID NO:39 or 57.

In some embodiments, the disclosure provides an ALK7-binding protein comprising a VH-CDR3 having the amino acid sequence of SEQ ID NO:90. In further embodiments the ALK7-binding protein comprises a VH-CDR3 having the amino acid sequence of SEQ ID NO:90 and a VH-CDR2 having the amino acid sequence of SEQ ID NO:89. In further embodiments, the ALK7-binding protein comprises a VH-CDR3 having the amino acid sequence of SEQ ID NO:90, a VH-CDR2 having the amino acid sequence of SEQ ID NO:89, and a VH-CDR1 having the amino acid sequence of SEQ ID NO:88. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the disclosure provides an ALK7-binding protein comprising a VH-CDR3 having the amino acid sequence of SEQ ID NO:104. In further embodiments the ALK7-binding protein comprises a VH-CDR3 having the amino acid sequence of SEQ ID NO:104 and a VH-CDR2 having the amino acid sequence of SEQ ID NO:103. In further embodiments, the ALK7-binding protein comprises a VH-CDR3 having the amino acid sequence of SEQ ID NO:104, a VH-CDR2 having the amino acid sequence of SEQ ID NO:103, and a VH-CDR1 having the amino acid sequence of SEQ ID NO:102. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein comprises a VH-CDR3 having the amino acid sequence of SEQ ID NO:116. In further embodiments the ALK7-binding protein comprises a VH-CDR3 having the amino acid sequence of SEQ ID NO:116 and a VH-CDR2 having the amino acid sequence of SEQ ID NO:115. In further embodiments, the ALK7-binding protein comprises a VH-CDR3 having the amino acid sequence of SEQ ID NO:116, a VH-CDR2 having the amino acid sequence of SEQ ID NO:115, and a VH-CDR1 having the amino acid sequence of SEQ ID NO:114. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein comprises a VH-CDR3 having the amino acid sequence of SEQ ID NO:127. In further embodiments the ALK7-binding protein comprises a VH-CDR3 having the amino acid sequence of SEQ ID NO:127 and a VH-CDR2 having the amino acid sequence of SEQ ID NO:126. In further embodiments, the ALK7-binding protein comprises a VH-CDR3 having the amino acid sequence of SEQ ID NO:127, a VH-CDR2 having the amino acid sequence of SEQ ID NO:126, and a VH-CDR1 having the amino acid sequence of SEQ ID NO:125. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the disclosure provides an ALK7-binding protein comprising a VH-CDR3 having the amino acid sequence of SEQ ID NO:164. In further embodiments the ALK7-binding protein comprises a VH-CDR3 having the amino acid sequence of SEQ ID NO:164 and a VH-CDR2 having the amino acid sequence of SEQ ID NO:138 or 163. In further embodiments, the ALK7-binding protein comprises a VH-CDR3 having the amino acid sequence of SEQ ID NO:164, a VH-CDR2 having the amino acid sequence of SEQ ID NO:103, and a VH-CDR1 having the amino acid sequence of SEQ ID NO:1 or 137. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein comprises a VH-CDR3 having the amino acid sequence of SEQ ID NO:139. In further embodiments the ALK7-binding protein comprises a VH-CDR3 having the amino acid sequence of SEQ ID NO:139 and a VH-CDR2 having the amino acid sequence of SEQ ID NO:138. In further embodiments, the ALK7-binding protein comprises a VH-CDR3 having the amino acid sequence of SEQ ID NO:139, a VH-CDR2 having the amino acid sequence of SEQ ID NO:138, and a VH-CDR1 having the amino acid sequence of SEQ ID NO:137. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In further embodiments, the disclosure provides an ALK7-binding protein comprising a VH-CDR1 having the amino acid sequence of SEQ ID NO:88. In further embodiments, the disclosure provides an ALK7-binding protein comprising a VH-CDR1 having the amino acid sequence of SEQ ID NO:88 and a VH-CDR2 having the amino acid sequence of SEQ ID NO:89. In further embodiments, the disclosure provides an ALK7-binding protein comprising a VH-CDR1 having the amino acid sequence of SEQ ID NO:88, a VH-CDR2 having the amino acid sequence of SEQ ID NO:89, and a VH-CDR3 having the amino acid sequence of SEQ ID NO:90.

In further embodiments, the disclosure provides an ALK7-binding protein comprising a VH-CDR2 having the amino acid sequence of SEQ ID NO:89. In further embodiments the ALK7-binding protein comprises a VH-CDR2 having the amino acid sequence of SEQ ID NO:89 and a VH-CDR1 having the amino acid sequence of SEQ ID NO:88. In further embodiments, the ALK7-binding protein comprises a VH-CDR2 having the amino acid sequence of SEQ ID NO:89, a VH-CDR1 having the amino acid sequence of SEQ ID NO:88, and a VH-CDR3 having the amino acid sequence of SEQ ID NO:90.

In further embodiments, the disclosure provides an ALK7-binding protein comprising a VH-CDR1 having the amino acid sequence of SEQ ID NO:102. In further embodiments, the disclosure provides an ALK7-binding protein comprising a VH-CDR1 having the amino acid sequence of SEQ ID NO:102 and a VH-CDR2 having the amino acid sequence of SEQ ID NO:103. In further embodiments, the disclosure provides an ALK7-binding protein comprising a VH-CDR1 having the amino acid sequence of SEQ ID NO:102, a VH-CDR2 having the amino acid sequence of SEQ ID NO:103, and a VH-CDR3 having the amino acid sequence of SEQ ID NO:104.

In further embodiments, the disclosure provides an ALK7-binding protein comprising a VH-CDR2 having the amino acid sequence of SEQ ID NO:103. In further embodiments the ALK7-binding protein comprises a VH-CDR2 having the amino acid sequence of SEQ ID NO:103 and a VH-CDR1 having the amino acid sequence of SEQ ID NO:102. In further embodiments, the ALK7-binding protein comprises a VH-CDR2 having the amino acid sequence of SEQ ID NO:103, a VH-CDR1 having the amino acid sequence of SEQ ID NO:102, and a VH-CDR3 having the amino acid sequence of SEQ ID NO:104.

In further embodiments, the disclosure provides an ALK7-binding protein comprising a VH-CDR1 having the amino acid sequence of SEQ ID NO:114. In further embodiments, the disclosure provides an ALK7-binding protein comprising a VH-CDR1 having the amino acid sequence of SEQ ID NO:114 and a VH-CDR2 having the amino acid sequence of SEQ ID NO:115. In further embodiments, the disclosure provides an ALK7-binding protein comprising a VH-CDR1 having the amino acid sequence of SEQ ID NO:114, a VH-CDR2 having the amino acid sequence of SEQ ID NO:115, and a VH-CDR3 having the amino acid sequence of SEQ ID NO:116.

In further embodiments, the disclosure provides an ALK7-binding protein comprising a VH-CDR2 having the amino acid sequence of SEQ ID NO:115. In further embodiments the ALK7-binding protein comprises a VH-CDR2 having the amino acid sequence of SEQ ID NO:115 and a VH-CDR1 having the amino acid sequence of SEQ ID NO:114. In further embodiments, the ALK7-binding protein comprises a VH-CDR2 having the amino acid sequence of SEQ ID NO:115, a VH-CDR1 having the amino acid sequence of SEQ ID NO:114, and a VH-CDR3 having the amino acid sequence of SEQ ID NO:116.

In further embodiments, the disclosure provides an ALK7-binding protein comprising a VH-CDR1 having the amino acid sequence of SEQ ID NO:125. In further embodiments, the disclosure provides an ALK7-binding protein comprising a VH-CDR1 having the amino acid sequence of SEQ ID NO:125 and a VH-CDR2 having the amino acid sequence of SEQ ID NO:126. In further embodiments, the disclosure provides an ALK7-binding protein comprising a VH-CDR1 having the amino acid sequence of SEQ ID NO:125, a VH-CDR2 having the amino acid sequence of SEQ ID NO:126, and a VH-CDR3 having the amino acid sequence of SEQ ID NO:127.

In further embodiments, the disclosure provides an ALK7-binding protein comprising a VH-CDR2 having the amino acid sequence of SEQ ID NO:126. In further embodiments the ALK7-binding protein comprises a VH-CDR2 having the amino acid sequence of SEQ ID NO:126 and a VH-CDR1 having the amino acid sequence of SEQ ID NO:125. In further embodiments, the ALK7-binding protein comprises a VH-CDR2 having the amino acid sequence of SEQ ID NO:126, a VH-CDR1 having the amino acid sequence of SEQ ID NO:125, and a VH-CDR3 having the amino acid sequence of SEQ ID NO:127.

In further embodiments, the disclosure provides an ALK7-binding protein comprising a VH-CDR1 having the amino acid sequence of SEQ ID NO:137. In further embodiments, the disclosure provides an ALK7-binding protein comprising a VH-CDR1 having the amino acid sequence of SEQ ID NO:137 and a VH-CDR2 having the amino acid sequence of SEQ ID NO:138. In further embodiments, the disclosure provides an ALK7-binding protein comprising a VH-CDR1 having the amino acid sequence of SEQ ID NO:137, a VH-CDR2 having the amino acid sequence of SEQ ID NO:138, and a VH-CDR3 having the amino acid sequence of SEQ ID NO:139.

In further embodiments, the disclosure provides an ALK7-binding protein comprising a VH-CDR2 having the amino acid sequence of SEQ ID NO:138. In further embodiments the ALK7-binding protein comprises a VH-CDR2 having the amino acid sequence of SEQ ID NO:138 and a VH-CDR1 having the amino acid sequence of SEQ ID NO:137. In further embodiments, the ALK7-binding protein comprises a VH-CDR2 having the amino acid sequence of SEQ ID NO:138, a VH-CDR1 having the amino acid sequence of SEQ ID NO:137, and a VH-CDR3 having the amino acid sequence of SEQ ID NO:139.

In further embodiments, the disclosure provides an ALK7-binding protein comprising a VL-CDR3 having the amino acid sequence of SEQ ID NO:12. In further embodiments the ALK7-binding protein comprises a VL-CDR3 having the amino acid sequence of SEQ ID NO:12 and a VL-CDR2 having the amino acid sequence of SEQ ID NO:11. In further embodiments, the ALK7-binding protein comprises a VL-CDR3 having the amino acid sequence of SEQ ID NO:12, a VL-CDR2 having the amino acid sequence of SEQ ID NO:11, and a VL-CDR1 having the amino acid sequence of SEQ ID NO:10. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In further embodiments, the disclosure provides an ALK7-binding protein comprising a VL-CDR3 having the amino acid sequence of SEQ ID NO:30. In further embodiments the ALK7-binding protein comprises a VL-CDR3 having the amino acid sequence of SEQ ID NO:30 and a VL-CDR2 having the amino acid sequence of SEQ ID NO:29. In further embodiments, the ALK7-binding protein comprises a VL-CDR3 having the amino acid sequence of SEQ ID NO:30, a VL-CDR2 having the amino acid sequence of SEQ ID NO:29, and a VL-CDR1 having the amino acid sequence of SEQ ID NO:28. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In further embodiments, the disclosure provides an ALK7-binding protein comprising a VL-CDR3 having the amino acid sequence of SEQ ID NO:48. In further embodiments the ALK7-binding protein comprises a VL-CDR3 having the amino acid sequence of SEQ ID NO:48 and a VL-CDR2 having the amino acid sequence of SEQ ID NO:47. In further embodiments, the ALK7-binding protein comprises a VL-CDR3 having the amino acid sequence of SEQ ID NO:48, a VL-CDR2 having the amino acid sequence of SEQ ID NO:47, and a VL-CDR1 having the amino acid sequence of SEQ ID NO:46. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein comprises a VL-CDR3 having the amino acid sequence of SEQ ID NO:66. In further embodiments the ALK7-binding protein comprises a VL-CDR3 having the amino acid sequence of SEQ ID NO:66 and a VL-CDR2 having the amino acid sequence of SEQ ID NO:65. In further embodiments, the ALK7-binding protein comprises a VL-CDR3 having the amino acid sequence of SEQ ID NO:66, a VL-CDR2 having the amino acid sequence of SEQ ID NO:65, and a VL-CDR1 having the amino acid sequence of SEQ ID NO:64. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In further embodiments, the disclosure provides an ALK7-binding protein comprising a VL-CDR3 having the amino acid sequence of SEQ ID NO:97. In further embodiments the ALK7-binding protein comprises a VL-CDR3 having the amino acid sequence of SEQ ID NO:97 and a VL-CDR2 having the amino acid sequence of SEQ ID NO:96. In further embodiments, the ALK7-binding protein comprises a VL-CDR3 having the amino acid sequence of SEQ ID NO:97, a VL-CDR2 having the amino acid sequence of SEQ ID NO:96, and a VL-CDR1 having the amino acid sequence of SEQ ID NO:95. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In further embodiments, the disclosure provides an ALK7-binding protein comprising a VL-CDR3 having the amino acid sequence of SEQ ID NO:109. In further embodiments the ALK7-binding protein comprises a VL-CDR3 having the amino acid sequence of SEQ ID NO:109 and a VL-CDR2 having the amino acid sequence of SEQ ID NO:108. In further embodiments, the ALK7-binding protein comprises a VL-CDR3 having the amino acid sequence of SEQ ID NO:109, a VL-CDR2 having the amino acid sequence of SEQ ID NO:108, and a VL-CDR1 having the amino acid sequence of SEQ ID NO:107. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In further embodiments, the disclosure provides an ALK7-binding protein comprising a VL-CDR3 having the amino acid sequence of SEQ ID NO:123. In further embodiments the ALK7-binding protein comprises a VL-CDR3 having the amino acid sequence of SEQ ID NO:123 and a VL-CDR2 having the amino acid sequence of SEQ ID NO:122. In further embodiments, the ALK7-binding protein comprises a VL-CDR3 having the amino acid sequence of SEQ ID NO:123, a VL-CDR2 having the amino acid sequence of SEQ ID NO:122, and a VL-CDR1 having the amino acid sequence of SEQ ID NO:121. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein comprises a VL-CDR3 having the amino acid sequence of SEQ ID NO:134. In further embodiments the ALK7-binding protein comprises a VL-CDR3 having the amino acid sequence of SEQ ID NO:134 and a VL-CDR2 having the amino acid sequence of SEQ ID NO:133. In further embodiments, the ALK7-binding protein comprises a VL-CDR3 having the amino acid sequence of SEQ ID NO:134, a VL-CDR2 having the amino acid sequence of SEQ ID NO:133, and a VL-CDR1 having the amino acid sequence of SEQ ID NO:132. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein comprises a VL-CDR3 having the amino acid sequence of SEQ ID NO:147. In further embodiments the ALK7-binding protein comprises a VL-CDR3 having the amino acid sequence of SEQ ID NO:147 and a VL-CDR2 having the amino acid sequence of SEQ ID NO:146. In further embodiments, the ALK7-binding protein comprises a VL-CDR3 having the amino acid sequence of SEQ ID NO:147, a VL-CDR2 having the amino acid sequence of SEQ ID NO:146, and a VL-CDR1 having the amino acid sequence of SEQ ID NO:145. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB)

in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In further embodiments, the disclosure provides an ALK7-binding protein comprising a VH-antigen binding domain 3 (ABD3) having the amino acid sequence of SEQ ID NO:75, 78, 81, or 84. In one embodiment, the ALK7-binding protein comprises a VH-ABD3 having the amino acid sequence of SEQ ID NO:75. In one embodiment, the ALK7-binding protein comprises a VH-ABD3 having the amino acid sequence of SEQ ID NO:75 and a VH-antigen binding domain 2 (VH-ABD2) having the amino acid sequence of SEQ ID NO:74. In further embodiments, the ALK7-binding protein comprises a VH-ABD3 having the amino acid sequence of SEQ ID NO:75, a VH-ABD2 having the amino acid sequence of SEQ ID NO:74, and a VH-antigen binding domain 1 (VH-ABD1) having the amino acid sequence of SEQ ID NO:73. In one embodiment, the ALK7-binding protein comprises a VH-ABD3 having the amino acid sequence of SEQ ID NO:75. In one embodiment, the ALK7-binding protein comprises a VH-ABD3 having the amino acid sequence of SEQ ID NO:75 and a VH-antigen binding domain 2 (VH-ABD2) having the amino acid sequence of SEQ ID NO:74. In further embodiments, the ALK7-binding protein comprises a VH-ABD3 having the amino acid sequence of SEQ ID NO:75, a VH-ABD2 having the amino acid sequence of SEQ ID NO:74, and a VH-antigen binding domain 1 (VH-ABD1) having the amino acid sequence of SEQ ID NO:73. In one embodiment, the ALK7-binding protein comprises a VH-ABD3 having the amino acid sequence of SEQ ID NO:78. In one embodiment, the ALK7-binding protein comprises a VH-ABD3 having the amino acid sequence of SEQ ID NO:78 and a VH-antigen binding domain 2 (VH-ABD2) having the amino acid sequence of SEQ ID NO:77. In further embodiments, the ALK7-binding protein comprises a VH-ABD3 having the amino acid sequence of SEQ ID NO:78, a VH-ABD2 having the amino acid sequence of SEQ ID NO:77, and a VH-antigen binding domain 1 (VH-ABD1) having the amino acid sequence of SEQ ID NO:76. In one embodiment, the ALK7-binding protein comprises a VH-ABD3 having the amino acid sequence of SEQ ID NO:81. In one embodiment, the ALK7-binding protein comprises a VH-ABD3 having the amino acid sequence of SEQ ID NO:81 and a VH-antigen binding domain 2 (VH-ABD2) having the amino acid sequence of SEQ ID NO:80. In further embodiments, the ALK7-binding protein comprises a VH-ABD3 having the amino acid sequence of SEQ ID NO:81, a VH-ABD2 having the amino acid sequence of SEQ ID NO:80, and a VH-antigen binding domain 1 (VH-ABD1) having the amino acid sequence of SEQ ID NO:79. In one embodiment, the ALK7-binding protein comprises a VH-ABD3 having the amino acid sequence of SEQ ID NO:84. In one embodiment, the ALK7-binding protein comprises a VH-ABD3 having the amino acid sequence of SEQ ID NO:84 and a VH-antigen binding domain 2 (VH-ABD2) having the amino acid sequence of SEQ ID NO:83. In further embodiments, the ALK7-binding protein comprises a VH-ABD3 having the amino acid sequence of SEQ ID NO:84, a VH-ABD2 having the amino acid sequence of SEQ ID NO:83, and a VH-antigen binding domain 1 (VH-ABD1) having the amino acid sequence of SEQ ID NO:82. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments an ALK7-binding protein comprises a VH or a VL which has a total of one, two, three, four, five, six, seven, eight, nine, ten, fewer than fifteen, or zero, amino acid substitutions, deletions, and/or insertions compared to a reference VH or VL disclosed herein. In further embodiments, the ALK7-binding protein comprises a VH or a VL which has a total of one, two, three, four, five, six, seven, eight, nine, ten, fewer than fifteen, or zero, amino acid substitutions, deletions, and/or insertions compared to a reference VH or VL disclosed in Table 1B. In some embodiments an ALK7-binding protein comprises a VH and a VL pair which has a total of one, two, three, four, five, six, seven, eight, nine, ten, fewer than fifteen, or zero, amino acid substitutions, deletions, and/or insertions compared to a reference VH and VL pair disclosed herein. In further embodiments, the ALK7-binding protein comprises a VH and VL pair which has a total of one, two, three, four, five, six, seven, eight, nine, ten, fewer than fifteen, or zero, amino acid substitutions, deletions, and/or insertions compared to a reference VH and VL pair disclosed in Table 1B.

In further embodiments, the ALK7-binding protein comprises a VH or a VL which has a total of one, two, three, four, five, six, seven, eight, nine, ten, fewer than fifteen, or zero, amino acid substitutions, deletions, and/or insertions compared to a reference VH or VL disclosed in Table 3. In further embodiments, the ALK7-binding protein comprises a VH and VL pair which has a total of one, two, three, four, five, six, seven, eight, nine, ten, fewer than fifteen, or zero, amino acid substitutions, deletions, and/or insertions compared to a reference VH and VL pair disclosed in Table 1B or Table 3.

In some embodiments, the ALK7-binding protein a VH and a VL pair selected from the group consisting of: (a)(i) a VH sequence having a total of one, two, three, four, five, six, seven, eight, nine, ten, fewer than fifteen, or zero, amino acid substitutions, deletions, and/or insertions from a reference VH sequence selected from the group consisting of SEQ ID NO:4, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:13; (b)(i) a VH sequence having a total of one, two, three, four, five, six, seven, eight, nine, ten, fewer than fifteen, or zero, amino acid substitutions, deletions, and/or insertions from a reference VH sequence of SEQ ID NO:22, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:31; (c)(i) a VH sequence having a total of one, two, three, four, five, six, seven, eight, nine, ten, fewer than fifteen, or zero, amino acid substitutions, deletions, and/or insertions from a reference VH sequence of SEQ ID NO:40, 170, or 171, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:49; and (d)(i) a VH sequence having a total of one, two, three, four, five, six, seven, eight, nine, ten, fewer than fifteen, or zero, amino acid substitutions, deletions, and/or insertions from a reference VH sequence of SEQ ID NO:58, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:67; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocytes cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein a VH and a VL pair selected from the group consisting of: (a)(i) a VH sequence having a total of one, two, three, four, five, six, seven, eight, nine, ten, fewer than fifteen, or zero, amino acid substitutions, deletions, and/or insertions from a reference VH sequence selected from the group consisting of SEQ ID NO:91, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:98; (b)(i) a VH sequence having a total of one, two, three, four, five, six, seven, eight, nine, ten, fewer than fifteen, or zero, amino acid substitutions, deletions, and/or insertions from a reference VH sequence of SEQ ID NO:105, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:110; (c)(i) a VH sequence having a total of one, two, three, four, five, six, seven, eight, nine, ten, fewer than fifteen, or zero, amino acid substitutions, deletions, and/or insertions from a reference VH sequence of SEQ ID NO:117, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:124; (d)(i) a VH sequence having a total of one, two, three, four, five, six, seven, eight, nine, ten, fewer than fifteen, or zero, amino acid substitutions, deletions, and/or insertions from a reference VH sequence of SEQ ID NO:128, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:135; and (e)(i) a VH sequence having a total of one, two, three, four, five, six, seven, eight, nine, ten, fewer than fifteen, or zero, amino acid substitutions, deletions, and/or insertions from a reference VH sequence of SEQ ID NO:140, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:148; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein a VH and a VL pair selected from the group consisting of: (a)(i) a VH sequence having a total of one, two, three, four, five, six, seven, eight, nine, ten, fewer than fifteen, or zero, amino acid substitutions, deletions, and/or insertions from a reference VH sequence selected from the group consisting of SEQ ID NO:152, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:98; (b)(i) a VH sequence having a total of one, two, three, four, five, six, seven, eight, nine, ten, fewer than fifteen, or zero, amino acid substitutions, deletions, and/or insertions from a reference VH sequence of SEQ ID NO:159, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:110; and (c)(i) a VH sequence having a total of one, two, three, four, five, six, seven, eight, nine, ten, fewer than fifteen, or zero, amino acid substitutions, deletions, and/or insertions from a reference VH sequence of SEQ ID NO:165, and (ii) a VL sequence having a total of one, two, three, four, five, six, seven, eight, nine, ten, fewer than fifteen, or zero, amino acid substitutions, deletions, and/or insertions from a reference VL sequence of SEQ ID NO:171; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In a further embodiment, the ALK7-binding protein comprises a VH and a VL pair wherein the VH sequence has a total of one, two, three, four, five, six, seven, eight, nine, ten, fewer than fifteen, or zero, amino acid substitutions, deletions, and/or insertions from a reference VH sequence of SEQ ID NO:4; and the VL sequence has a total of one, two, three, four, five, six, seven, eight, nine, ten, fewer than fifteen, or zero, amino acid substitutions, deletions, and/or insertions from a reference VL sequence of SEQ ID NO:13; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c)

competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In a further embodiment, the ALK7-binding protein comprises a VH and a VL pair wherein the VH sequence has a total of one, two, three, four, five, six, seven, eight, nine, ten, fewer than fifteen, or zero, amino acid substitutions, deletions, and/or insertions from a reference VH sequence of SEQ ID NO:22; and the VL sequence has a total of one, two, three, four, five, six, seven, eight, nine, ten, fewer than fifteen, or zero, amino acid substitutions, deletions, and/or insertions from a reference VL sequence of SEQ ID NO:31; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In a further embodiment, the ALK7-binding protein comprises a VH and a VL pair wherein the VH sequence has a total of one, two, three, four, five, six, seven, eight, nine, ten, fewer than fifteen, or zero, amino acid substitutions, deletions, and/or insertions from a reference VH sequence of SEQ ID NO:40; and the VL sequence has a total of one, two, three, four, five, six, seven, eight, nine, ten, fewer than fifteen, or zero, amino acid substitutions, deletions, and/or insertions from a reference VL sequence of SEQ ID NO:49; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In a further embodiment, the ALK7-binding protein comprises a VH and a VL pair wherein the VH sequence has a total of one, two, three, four, five, six, seven, eight, nine, ten, fewer than fifteen, or zero, amino acid substitutions, deletions, and/or insertions from a reference VH sequence of SEQ ID NO:58 and the VL sequence has a total of one, two, three, four, five, six, seven, eight, nine, ten, fewer than fifteen, or zero, amino acid substitutions, deletions, and/or insertions from a reference VL sequence of SEQ ID NO:67; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In a further embodiment, the ALK7-binding protein comprises a VH and a VL pair wherein the VH sequence has a total of one, two, three, four, five, six, seven, eight, nine, ten, fewer than fifteen, or zero, amino acid substitutions, deletions, and/or insertions from a reference VH sequence of SEQ ID NO:91; and the VL sequence has a total of one, two, three, four, five, six, seven, eight, nine, ten, fewer than fifteen, or zero, amino acid substitutions, deletions, and/or insertions from a reference VL sequence of SEQ ID NO:98; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In a further embodiment, the ALK7-binding protein comprises a VH and a VL pair wherein the VH sequence has a total of one, two, three, four, five, six, seven, eight, nine, ten, fewer than fifteen, or zero, amino acid substitutions, deletions, and/or insertions from a reference VH sequence of SEQ ID NO:105; and the VL sequence has a total of one, two, three, four, five, six, seven, eight, nine, ten, fewer than fifteen, or zero, amino acid substitutions, deletions, and/or insertions from a reference VL sequence of SEQ ID NO:110; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3)

in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In a further embodiment, the ALK7-binding protein comprises a VH and a VL pair wherein the VH sequence has a total of one, two, three, four, five, six, seven, eight, nine, ten, fewer than fifteen, or zero, amino acid substitutions, deletions, and/or insertions from a reference VH sequence of SEQ ID NO:117; and the VL sequence has a total of one, two, three, four, five, six, seven, eight, nine, ten, fewer than fifteen, or zero, amino acid substitutions, deletions, and/or insertions from a reference VL sequence of SEQ ID NO:124; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In a further embodiment, the ALK7-binding protein comprises a VH and a VL pair wherein the VH sequence has a total of one, two, three, four, five, six, seven, eight, nine, ten, fewer than fifteen, or zero, amino acid substitutions, deletions, and/or insertions from a reference VH sequence of SEQ ID NO:128 and the VL sequence has a total of one, two, three, four, five, six, seven, eight, nine, ten, fewer than fifteen, or zero, amino acid substitutions, deletions, and/or insertions from a reference VL sequence of SEQ ID NO:135; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In a further embodiment, the ALK7-binding protein comprises a VH and a VL pair wherein the VH sequence has a total of one, two, three, four, five, six, seven, eight, nine, ten, fewer than fifteen, or zero, amino acid substitutions, deletions, and/or insertions from a reference VH sequence of SEQ ID NO:140 and the VL sequence has a total of one, two, three, four, five, six, seven, eight, nine, ten, fewer than fifteen, or zero, amino acid substitutions, deletions, and/or insertions from a reference VL sequence of SEQ ID NO:148; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein comprises a VH sequence having a total of one, two, three, four, five, six, seven, eight, nine, ten, fewer than fifteen, or zero, amino acid substitutions, deletions, and/or insertions from a reference VH sequence selected from the group consisting of (a) SEQ ID NO:4, (b) SEQ ID NO:22, (c) SEQ ID NO:40, and (d) SEQ ID NO:58; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein In some embodiments, the ALK7-binding protein comprises a VH sequence having a total of one, two, three, four, five, six, seven, eight, nine, ten, fewer than fifteen, or zero, amino acid substitutions, deletions, and/or insertions from a reference VH sequence selected from the group consisting of (a) SEQ ID NO:91, (b) SEQ ID NO:105, (c) SEQ ID NO:117, (d) SEQ ID NO:128, and (e) SEQ ID NO:140; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein comprises a VL sequence having a total of one, two, three, four, five, six, seven, eight, nine, ten, fewer than fifteen, or zero, amino acid substitutions, deletions, and/or insertions from a reference VL sequence of (a) SEQ ID NO:13; (b) SEQ ID NO:31; (c) SEQ ID NO:49; and (d) SEQ ID NO:67; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein comprises a VL sequence having a total of one, two, three, four, five, six, seven, eight, nine, ten, fewer than fifteen, or zero, amino acid substitutions, deletions, and/or insertions from a reference VL sequence of (a) SEQ ID NO:98; (b) SEQ ID NO:110; (c) SEQ ID NO:124; (d) SEQ ID NO:135, and (e) SEQ ID NO:148; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments an ALK7-binding protein comprises a VH or a VL which has at least 90%, 95%, 96%, 97%, 98%, 99%, or 100% sequence identity to a reference VH or VL disclosed herein. In further embodiments, the ALK7-binding protein comprises a VH or a VL which has at least 90%, 95%, 96%, 97%, 98%, 99%, or 100% sequence identity to a reference VH or VL disclosed in Table 1A. In further embodiments, the ALK7-binding protein comprises a VH or a VL which has at least 90%, 95%, 96%, 97%, 98%, 99%, or 100% sequence identity to a reference VH or VL disclosed in Table 1B. In further embodiments, the ALK7-binding protein comprises a VH or a VL which has at least 90%, 95%, 96%, 97%, 98%, 99%, or 100% sequence identity to a reference VH or VL disclosed in Table 3. In some embodiments an ALK7-binding protein comprises a VH and VL which has at least 90%, 95%, 96%, 97%, 98%, 99%, or 100% sequence identity to a reference VH and VL disclosed herein. In further embodiments, the ALK7-binding protein comprises a VH and VL which has at least 90%, 95%, 96%, 97%, 98%, 99%, or 100% sequence identity to a reference VH and VL disclosed in Table 1A. In further embodiments, the ALK7-binding protein comprises a VH and VL which has at least 90%, 95%, 96%, 97%, 98%, 99%, or 100% sequence identity to a reference VH and VL disclosed in Table 1B. In further embodiments, the ALK7-binding protein comprises a VH and VL which has at least 90%, 95%, 96%, 97%, 98%, 99%, or 100% sequence identity to a reference VH and VL disclosed in Table 3. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein specifically binds ALK7 and comprises a VH having (a) at least 90%, 95%, 96%, 97%, 98%, 99%, or 100% sequence identity to SEQ ID NO:4; (b) at least 90%, 95%, 96%, 97%, 98%, 99%, or 100% sequence identity to SEQ ID NO:22; (c) at least 90%, 95%, 96%, 97%, 98%, 99%, or 100% sequence identity to SEQ ID NO:40; and (d) a VH having at least 90%, 95%, 96%, 97%, 98%, 99%, or 100% sequence identity to SEQ ID NO:58; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK.-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein specifically binds ALK7 and comprises a VH having (a) at least 90%, 95%, 96%, 97%, 98%, 99%, or 100% sequence identity to SEQ ID NO:91; (b) at least 90%, 95%, 96%, 97%, 98%, 99%, or 100% sequence identity to SEQ ID NO:105; (c) at least 90%, 95%, 96%, 97%, 98%, 99%, or 100% sequence identity to SEQ ID NO:117; (d) a VH having at least 90%, 95%, 96%, 97%, 98%, 99%, or 100% sequence identity to SEQ ID NO:128; and (e) a VH having at least 90%, 95%, 96%, 97%, 98%, 99%, or 100% sequence identity to SEQ ID NO:140; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein specifically binds ALK7 and comprises a VL having: (a) at least 90%, 95%, 96%, 97%, 98%, 99%, or 100% sequence identity to SEQ ID NO:13; (b) at least 90%, 95%, 96%, 97%, 98%, 99%, or 100% sequence identity to SEQ ID NO:31; (c) at least 90%, 95%, 96%, 97%, 98%, 99%, or 100% sequence identity to SEQ ID NO:49; and (d) at least 90%, 95%, 96%, 97%, 98%, 99%, or 100% sequence identity to SEQ ID NO:67; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein specifically binds ALK7 and comprises a VL having: (a) at least 90%, 95%, 96%, 97%, 98%, 99%, or 100% sequence identity to SEQ ID NO:98; (b) at least 90%, 95%, 96%, 97%, 98%, 99%, or 100% sequence identity to SEQ ID NO:110; (c) at least 90%, 95%, 96%, 97%, 98%, 99%, or 100% sequence identity to SEQ ID NO:124; (d) at least 90%, 95%, 96%, 97%, 98%, 99%, or 100% sequence identity to SEQ ID NO:135; and (e) at least 90%, 95%, 96%, 97%, 98%, 99%, or 100% sequence identity to SEQ ID NO:148; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein specifically binds ALK7 and comprises a VH and a VL pair selected from the group consisting of: (a)(i) a VH having at least 90%, 95%, 96%, 97%, 98%, 99%, or 100% sequence identity to SEQ ID NO:4, and (ii) a VL having at least 90%, 95%, 96%, 97%, 98%, 99%, or 100% sequence identity to SEQ ID NO:13; (b)(i) a VH having at least 90%, 95%, 96%, 97%, 98%, 99%, or 100% sequence identity to SEQ ID NO:22, and (ii) a VL having at least 90%, 95%, 96%, 97%, 98%, 99%, or 100% sequence identity to SEQ ID NO:31; (c)(i) a VH having at least 90%, 95%, 96%, 97%, 98%, 99%, or 100% sequence identity to SEQ ID NO:40, and (ii) a VL having at least 90%, 95%, 96%, 97%, 98%, 99%, or 100% sequence identity to SEQ ID NO:49; and (d)(i) a VH having at least 90%, 95%, 96%, 97%, 98%, 99%, or 100% sequence identity to SEQ ID NO:58, and (ii) a VL having at least 90%, 95%, 96%, 97%, 98%, 99%, or 100% sequence identity to SEQ ID NO:67; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein specifically binds ALK7 and comprises a VH and a VL pair selected from the group consisting of: (a)(i) a VH having at least 90%, 95%, 96%, 97%, 98%, 99%, or 100% sequence identity to SEQ ID NO:152, and (ii) a VL having at least 90%, 95%, 96%, 97%, 98%, 99%, or 100% sequence identity to SEQ ID NO:98; (b)(i) a VH having at least 90%, 95%, 96%, 97%, 98%, 99%, or 100% sequence identity to SEQ ID NO:159, and (ii) a VL having at least 90%, 95%, 96%, 97%, 98%, 99%, or 100% sequence identity to SEQ ID NO:110; and (c)(i) a VH having at least 90%, 95%, 96%, 97%, 98%, 99%, or 100% sequence identity to SEQ ID NO:165, and (ii) a VL having at least 90%, 95%, 96%, 97%, 98%, 99%, or 100% sequence identity to SEQ ID NO:171; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In some embodiments, the ALK7-binding protein specifically binds ALK7 and comprises a VH and a VL pair selected from the group consisting of: (a)(i) a VH having at least 90%, 95%, 96%, 97%, 98%, 99%, or 100% sequence identity to SEQ ID NO:91, and (ii) a VL having at least 90%, 95%, 96%, 97%, 98%, 99%, or 100% sequence identity to SEQ ID NO:98; (b)(i) a VH having at least 90%, 95%, 96%, 97%, 98%, 99%, or 100%, sequence identity to SEQ ID NO:105, and (ii) a VL having at least 90%, 95%, 96%, 97%, 98%, 99%, or 100% sequence identity to SEQ ID NO:110; (c)(i) a VH having at least 90%, 95%, 96%, 97%, 98%, 99%, or 100% sequence identity to SEQ ID NO:117, and (ii) a VL having at least 90%, 95%, 96%, 97%, 98%, 99%, or 100% sequence identity to SEQ ID NO:124; (d)(i) a VH having at least 90%, 95%, 96%, 97%, 98%, 99%, or 100° sequence identity to SEQ ID NO:128, and (ii) a VL having at least 90%, 95%, 96%, 97%, 98%, 99%, or 100% sequence identity to SEQ ID NO:135; and (e)(i) a VH having at least 90%, 95%, 96%, 97%, 98%, 99%, or 100% sequence identity to SEQ ID NO:140, and (ii) a VL having at least 90%, 95%, 96%, 97%, 98%, 99%, or 100% sequence identity to SEQ ID NO:148; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In one embodiment, the ALK7-binding protein specifically binds ALK7 and comprises a VH having at least 90%, 95%, 96%, 97%, 98%, 99%, or 100% sequence identity to SEQ ID NO:4, and a VL having at least 90%, 95%, 96%, 97%, 98%, 99%, or 100% sequence identity to SEQ ID NO:13. In one embodiment, the ALK7-binding protein specifically binds ALK7 and comprises a VH of SEQ ID NO:4 and a VL of SEQ ID NO:13. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In one embodiment, the ALK7-binding protein specifically binds ALK7 and comprises a VH having at least 90%, 95%, 96%, 97%, 98%, 99%, or 100% sequence identity to SEQ ID SEQ ID NO:22, and a VL having at least 90%, 95%, 96%, 97%, 98%, 99%, or 100% sequence identity to SEQ ID NO:31. In one embodiment, the ALK7-binding protein specifically binds ALK7 and comprises a VH of SEQ ID SEQ ID NO:22 and a VL of SEQ ID NO:31. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In one embodiment, the ALK7-binding protein specifically binds ALK7 and comprises a VH having at least 90%, 95%, 96%, 97%, 98%, 99%, or 100% sequence identity to SEQ ID NO:40, and a VL having at least 90%, 95%, 96%, 97%, 98%, 99%, or 100% sequence identity to SEQ ID NO:49. In one embodiment, the ALK7-binding protein specifically binds ALK7 and comprises a VH of SEQ ID NO:40 and a VL of SEQ ID NO:49. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In one embodiment, the ALK7-binding protein specifically binds ALK7 and comprises a VH having at least 90%, 95%, 96%, 97%, 98%, 99%, or 100% sequence identity to SEQ ID NO:58, and a VL having at least 90%, 95%, 96%, 97%, 98%, 99%, or 100% sequence identity to SEQ ID NO:67. In one embodiment, the ALK7-binding protein specifically binds ALK7 and comprises a VH of SEQ ID NO:58 and a VL of SEQ ID NO:67. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In one embodiment, the ALK7-binding protein specifically binds ALK7 and comprises a VH having at least 90%, 95%, 96%, 97%, 98%, 99%, or 100% sequence identity to SEQ ID NO:91, and a VL having at least 90%, 95%, 96%, 97%, 98%, 99%, or 100% sequence identity to SEQ ID NO:98. In one embodiment, the ALK7-binding protein specifically binds ALK7 and comprises a VH of SEQ ID NO:91 and a VL of SEQ ID NO:98. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In one embodiment, the ALK7-binding protein specifically binds ALK7 and comprises a VH having at least 90%, 95%, 96%, 97%, 98%, 99%, or 100% sequence identity to SEQ ID SEQ ID NO:105, and a VL having at least 90%, 95%, 96%, 97%, 98%, 99%, or 100% sequence identity to SEQ ID NO:110. In one embodiment, the ALK7-binding protein specifically binds ALK7 and comprises a VH of SEQ ID SEQ ID NO:105 and a VL of SEQ ID NO:110. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In one embodiment, the ALK7-binding protein specifically binds ALK7 and comprises a VH having at least 90%, 95%, 96%, 97%, 98%, 99%, or 100% sequence identity to SEQ ID NO:117, and a VL having at least 90%, 95%, 96%, 97%, 98%, 99%, or 100% sequence identity to SEQ ID NO:124. In one embodiment, the ALK7-binding protein specifically binds ALK7 and comprises a VH of SEQ ID NO:117 and a VL of SEQ ID NO:124. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In one embodiment, the ALK7-binding protein specifically binds ALK7 and comprises a VH having at least 90%, 95%, 96%, 97%, 98%, 99%, or 100% sequence identity to SEQ ID NO:128, and a VL having at least 90%, 95%, 96%, 97%, 98%, 99%, or 100% sequence identity to SEQ ID NO:135. In one embodiment, the ALK7-binding protein specifically binds ALK7 and comprises a VH of SEQ ID NO:128 and a VL of SEQ ID NO:135. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c)

competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In one embodiment, the ALK7-binding protein specifically binds ALK7 and comprises a VH having at least 90%, 95%, 96%, 97%, 98%, 99%, or 100% sequence identity to SEQ ID NO:140, and a VL having at least 90%, 95%, 96%, 97%, 98%, 99%, or 100% sequence identity to SEQ ID NO:148. In one embodiment, the ALK7-binding protein specifically binds ALK7 and comprises a VH of SEQ ID NO:140 and a VL of SEQ ID NO:148. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In a further embodiment, the ALK7-binding protein comprises a VH and a VL pair selected from the group consisting of: (a) a VH sequence of SEQ ID NO:4 and a VL sequence of SEQ ID NO:13; (b) a VH sequence of SEQ ID NO:22, and a VL sequence of SEQ ID NO:31; (c) a VH sequence of SEQ ID NO:40, and a VL sequence of SEQ ID NO:49; and (d) a VH sequence of SEQ ID NO:58 and a VL sequence of SEQ ID NO:67; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and ActRIIA/B in the presence of GDF1, GDF3, GDF8, activin B, activin A/B, and/or Nodal; (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In a further embodiment, the ALK7-binding protein comprises a VH and a VL pair selected from the group consisting of: (a) a VH sequence of SEQ ID NO:91 and a VL sequence of SEQ ID NO:98; (b) a VH sequence of SEQ ID NO:105, and a VL sequence of SEQ ID NO:110; (c) a VH sequence of SEQ ID NO:117, and a VL sequence of SEQ ID NO:124; (d) a VH sequence of SEQ ID NO:128 and a VL sequence of SEQ ID NO:135; and (e) a VH sequence of SEQ ID NO:140 and a VL sequence of SEQ ID NO:148; and wherein the protein binds ALK7. In further embodiments, the ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and ActRIIA/B in the presence of GDF1, GDF3, GDF8, activin B, activin A/B, and/or Nodal; (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In additional embodiments an ALK7-binding protein cross-blocks or competes for binding to ALK7 with an antibody comprising a VH and a VL sequence pair disclosed herein. In additional embodiments an ALK7-binding protein cross-blocks or competes for binding to ALK7 with an antibody comprising a VH and a VL sequence pair disclosed in Table 1A. In some embodiments, the ALK7-binding protein specifically binds ALK7 and comprises a VH of SEQ ID NO:4, 22, 40, or 58. In additional embodiments, the ALK7-binding protein specifically binds ALK7 and comprises a VL of SEQ ID NO:13, 31, 49, or 67. In further embodiments, the ALK7-binding protein specifically binds ALK7 and comprises a VH of SEQ ID NO: 4, 22, 40, or 58; and a VL of SEQ ID NO: 13, 31, 49, or 67. In certain embodiments, an ALK7-binding protein binds to the same epitope as an ALK7-binding protein disclosed herein. In additional embodiments, an ALK7-binding protein binds to the same epitope as an ALK7-binding protein disclosed in Table 1A. The ability of an ALK7-binding protein to compete for binding with and/or bind the same epitope of ALK7 as a reference ALK7-binding protein can readily be determined using techniques disclosed herein or otherwise known in the art.

In additional embodiments an ALK7-binding protein cross-blocks or competes for binding to ALK7 with an antibody comprising a VH and a VL sequence pair disclosed in Table 1B. In some embodiments, the ALK7-binding protein specifically binds ALK7 and comprises a VH of SEQ ID NO:152, 159, or 166. In additional embodiments, the ALK7-binding protein specifically binds ALK7 and comprises a VL of SEQ ID NO:98, 110, or 171. In further embodiments, the ALK7-binding protein specifically binds ALK7 and comprises a VH of SEQ ID NO: 152, 159, or 166; and a VL of SEQ ID NO: 98, 110, or 171. In certain embodiments, an ALK7-binding protein binds to the same epitope as an ALK7-binding protein disclosed herein. In additional embodiments, an ALK7-binding protein binds to the same epitope as an ALK7-binding protein disclosed in Table 1A. The ability of an ALK7-binding protein to compete for binding with and/or bind the same epitope of ALK7 as a reference ALK7-binding protein can readily be determined using techniques disclosed herein or otherwise known in the art.

In additional embodiments an ALK7-binding protein cross-blocks or competes for binding to ALK7 with an antibody comprising a VH and a VL sequence pair disclosed in Table 1B or Table 3. In some embodiments, the ALK7-binding protein specifically binds ALK7 and comprises a VH of SEQ ID NO: 91, 105, 117, 128, or 140. In additional embodiments, the ALK7-binding protein specifically binds ALK7 and comprises a VL of SEQ ID NO: 98, 110, 124, 135, or 148. In further embodiments, the ALK7-binding protein specifically binds ALK7 and comprises a VH of SEQ ID NO: 91, 105, 117, 128, or 140; and a VL of SEQ ID NO: 98, 110, 124, 135, or 148. In certain embodiments, an ALK7-binding protein binds to the same epitope as an ALK7-binding protein disclosed herein. In additional embodiments, an ALK7-binding protein binds to the same epitope as an ALK7-binding protein disclosed in Table 1A. In additional embodiments, an ALK7-binding protein binds to the same epitope as an ALK7-binding protein disclosed in Table 1B or Table 3. The ability of an ALK7-binding protein to compete for binding with and/or bind the same epitope of ALK7 as a reference ALK7-binding protein can readily be determined using techniques disclosed herein or otherwise known in the art.

In some embodiments, the ALK7-binding protein comprises a VH sequence of SEQ ID NO:40 and a VL sequence of SEQ ID NO:49. In some embodiments, an ALK7-binding protein cross-blocks or competes for binding to ALK7 with an antibody comprising a VH sequence of SEQ ID NO:40 and a VL sequence of SEQ ID NO:49. In further embodiments, the ALK7-binding protein binds the same epitope of ALK7 as an antibody comprising a VH sequence of SEQ ID NO:40 and a VL sequence of SEQ ID NO:49.

In some embodiments, the ALK7-binding protein comprises a VH sequence of SEQ ID NO:58 and a VL sequence of SEQ ID NO:67. In some embodiments, an ALK7-binding protein cross-blocks or competes for binding to ALK7 with an antibody comprising a VH sequence of SEQ ID NO:58 and a VL sequence of SEQ ID NO:67. In further embodiments, the ALK7-binding protein binds the same epitope of ALK7 as an antibody comprising a VH sequence of SEQ ID NO:58 and a VL sequence of SEQ ID NO:67.

In some embodiments, the ALK7-binding protein comprises a VH and a VL sequence of antibody J01. In some embodiments, the ALK7-binding protein comprises a VH sequence of SEQ ID NO:152 and a VL sequence of SEQ ID NO:98. In some embodiments, an ALK7-binding protein cross-blocks or competes for binding to ALK7 with an antibody comprising a VH sequence of SEQ ID NO:152 and a VL sequence of SEQ ID NO:98. In further embodiments, the ALK7-binding protein binds the same epitope of ALK7 as an antibody comprising a VH sequence of SEQ ID NO:152 and a VL sequence of SEQ ID NO:98.

In some embodiments, the ALK7-binding protein comprises a VH and a VL sequence of antibody J02. In some embodiments, the ALK7-binding protein comprises a VH sequence of SEQ ID NO:91 and a VL sequence of SEQ ID NO:98. In some embodiments, an ALK7-binding protein cross-blocks or competes for binding to ALK7 with an antibody comprising a VH sequence of SEQ ID NO:91 and a VL sequence of SEQ ID NO:98. In further embodiments, the ALK7-binding protein binds the same epitope of ALK7 as an antibody comprising a VH sequence of SEQ ID NO:91 and a VL sequence of SEQ ID NO:98.

In some embodiments, the ALK7-binding protein comprises a VH and a VL sequence of antibody K01. In some embodiments, the ALK7-binding protein comprises a VH sequence of SEQ ID NO:159 and a VL sequence of SEQ ID NO:110. In some embodiments, an ALK7-binding protein cross-blocks or competes for binding to ALK7 with an antibody comprising a VH sequence of SEQ ID NO:159 and a VL sequence of SEQ ID NO:110. In further embodiments, the ALK7-binding protein binds the same epitope of ALK7 as an antibody comprising a VH sequence of SEQ ID NO:159 and a VL sequence of SEQ ID NO:110.

In some embodiments, the ALK7-binding protein comprises a VH and a VL sequence of antibody K02. In some embodiments, the ALK7-binding protein comprises a VH sequence of SEQ ID NO:105 and a VL sequence of SEQ ID NO:110. In some embodiments, an ALK7-binding protein cross-blocks or competes for binding to ALK7 with an antibody comprising aVH sequence of SEQ ID NO:105 and a VL sequence of SEQ ID NO:110. In further embodiments, the ALK7-binding protein binds the same epitope of ALK7 as an antibody comprising aVH sequence of SEQ ID NO:105 and a VL sequence of SEQ ID NO:110.

In some embodiments, the ALK7-binding protein comprises a VH and a VL sequence of antibody G04. In some embodiments, the ALK7-binding protein comprises a VH sequence of SEQ ID NO:4 and a VL sequence of SEQ ID NO:13. In some embodiments, an ALK7-binding protein cross-blocks or competes for binding to ALK7 with an antibody comprising a VH sequence of SEQ ID NO:4 and a VL sequence of SEQ ID NO:13. In further embodiments, the ALK7-binding protein binds the same epitope of ALK7 as an antibody comprising a VH sequence of SEQ ID NO:4 and a VL sequence of SEQ ID NO:13.

In some embodiments, the ALK7-binding protein comprises a VH and a VL sequence of antibody G05. In some embodiments, the ALK7-binding protein comprises a VH sequence of SEQ ID NO:117 and a VL sequence of SEQ ID NO:124. In some embodiments, an ALK7-binding protein cross-blocks or competes for binding to ALK7 with an antibody comprising a VH sequence of SEQ ID NO:117 and a VL sequence of SEQ ID NO:124. In further embodiments, the ALK7-binding protein binds the same epitope of ALK7 as an antibody comprising a VH sequence of SEQ ID NO:117 and a VL sequence of SEQ ID NO:124.

In some embodiments, the ALK7-binding protein comprises a VH and a VL sequence of antibody C02. In some embodiments, the ALK7-binding protein comprises a VH sequence of SEQ ID NO:22 and a VL sequence of SEQ ID NO:31. In some embodiments, an ALK7-binding protein cross-blocks or competes for binding to ALK7 with an antibody comprising aVH sequence of SEQ ID NO:22 and a VL sequence of SEQ ID NO:31. In further embodiments, the ALK7-binding protein binds the same epitope of ALK7 as an antibody comprising aVH sequence of SEQ ID NO:22 and a VL sequence of SEQ ID NO:31.

In some embodiments, the ALK7-binding protein comprises a VH and a VL sequence of antibody C03. In some embodiments, the ALK7-binding protein comprises a VH sequence of SEQ ID NO:128 and a VL sequence of SEQ ID NO:135. In some embodiments, an ALK7-binding protein cross-blocks or competes for binding to ALK7 with an antibody comprising a VH sequence of SEQ ID NO:128 and a VL sequence of SEQ ID NO:135. In further embodiments, the ALK7-binding protein binds the same epitope of ALK7 as an antibody comprising a VH sequence of SEQ ID NO:128 and a VL sequence of SEQ ID NO:135.

In some embodiments, the ALK7-binding protein comprises a VH and a VL sequence of antibody L01. In some embodiments, the ALK7-binding protein comprises a VH sequence of SEQ ID NO:165 and a VL sequence of SEQ ID NO:171. In some embodiments, an ALK7-binding protein cross-blocks or competes for binding to ALK7 with an antibody comprising a VH sequence of SEQ ID NO:165 and a VL sequence of SEQ ID NO:171. In further embodiments, the ALK7-binding protein binds the same epitope of ALK7 as an antibody comprising a VH sequence of SEQ ID NO:165 and a VL sequence of SEQ ID NO:171.

In some embodiments, the ALK7-binding protein comprises a VH and a VL sequence of antibody L02. In some embodiments, the ALK7-binding protein comprises a VH sequence of SEQ ID NO:140 and a VL sequence of SEQ ID NO:148. In some embodiments, an ALK7-binding protein cross-blocks or competes for binding to ALK7 with an antibody comprising a VH sequence of SEQ ID NO:140 and a VL sequence of SEQ ID NO:148. In further embodiments, the ALK7-binding protein binds the same epitope of ALK7 as an antibody comprising a VH sequence of SEQ ID NO:140 and a VL sequence of SEQ ID NO:148.

In some embodiments, the ALK7-binding protein is an antibody that specifically binds ALK7. In some embodiments, the anti-ALK7 antibody is a murine antibody, a humanized antibody, a chimeric antibody, a monoclonal antibody, a polyclonal antibody, a recombinant antibody, a multispecific antibody, or any combination thereof. In some embodiments the anti-ALK7 antibody is an Fv fragment, an Fab fragment, an F(ab')2 fragment, an Fab' fragment, a dsFv fragment, an scFv fragment, or an sc(Fv)2 fragment.

In some embodiments, the ALK7-binding protein specifically binds ALK7 and blocks an activity of an ALK7-ligand (e.g., GDF1, GDF3, GDF8, activin B, activin A/B, or Nodal). In some embodiments, the ALK7-binding protein specifically binds ALK7 and blocks an activity of a co-receptor (e.g., cripto). In some embodiments the ALK7-binding protein specifically binds ALK7 and decreases the fat formation associated with the activity of an ALK7 ligand (e.g., GDF1, GDF3, GDF8, activin B, activin A/B, or Nodal). In some embodiments the ALK7-binding protein specifically binds ALK7 and treats or ameliorates one or more disease or conditions associated with excess weight, obesity or a metabolic disorder. In some embodiments, the disease or condition is type II diabetes. In some embodiments, the disease or condition is hypertension. In some embodiments the metabolic disorder is dyslipidemia, insulin resistance, hyperinsulinemia or hyperglycemia.

In particular embodiments, the ALK7-binding protein (e.g., an anti-ALK7 antibody) decreases ALK7-mediated Smad signaling. In another embodiment, an ALK7-binding protein antagonizes ALK7-mediated inhibition of lipolysis in white and/or brown adipose cells by 5% to 100%, 10% to 95%, 10 to 90%, 10 to 85%, 10 to 80%, 10 to 75%, 10 to 70%, 10 to 75%, 10 to 70%, 10 to 60%, 10 to 55%, 10 to 50%, or 10 to 45%, as determined in a lipolysis assay. In another embodiment, an ALK7-binding protein reduces or decreases ALK7-mediated inhibition of lipolysis in white and/or brown adipose cells by at least 5%, 10%, 20%, 30%, 40%, 50%, 60%, 70%, 80%, 90%, or 95%, or by about 100%, as determined in a lipolysis assay. In some embodiments the lipolysis assay is performed in the presence of one or more ALK7 ligands. In further embodiments, the lipolysis assay is performed in the presence of one or more ALK7 ligands selected from the group consisting of GDF1, GDF3, GDF8, activin B, activin A/B, and Nodal). In some embodiments the ALK7-binding protein binds ALK7 and inhibits or decreases one or more conditions associated with overweight, obesity, insulin resistance, diabetes, atherosclerosis, hypertension, inflammation, and/or NAFLD (e.g., fatty liver and/or NASH).

In particular embodiments, the ALK7-binding protein (e.g., an anti-ALK7 antibody) decreases ALK7-mediated Smad signaling. In another embodiment, the ALK7-binding protein inhibits ALK7-mediated inhibition of lipolysis in white adipose cells by 5% to 100%, 10% to 95%, 10 to 90%, 10 to 85%, 10 to 80%, 10 to 75%, 10 to 70%, 10 to 75%, 10 to 70%, 10 to 60%, 10 to 55%, 10 to 50%, or 10 to 45%, as determined using standard techniques and conditions in a lipolysis inhibition assay performed in the presence of activin B (50 ng/ml) (e.g., as described in the examples herein). In another embodiment, an ALK7-binding protein reduces or decreases ALK7-mediated inhibition of lipolysis in white adipose cells by at least 5%, 10%, 20%, 30%, 40%, 50%, 60%, 70%, 80%, 90%, or 95%, or by about 100%, as determined, using standard techniques and conditions in a lipolysis inhibition assay performed in the presence of activin B (50 ng/ml) (e.g., as described in the examples herein). In some embodiments the ALK7-binding protein binds ALK7 and inhibits or decreases one or more conditions associated with overweight, obesity, insulin resistance, diabetes, atherosclerosis, hypertension, inflammation, and/or NAFLD (e.g., fatty liver and/or NASH).

In certain embodiments, the blocking of ALK7 activity by an ALK7-binding protein (e.g., an anti-ALK7 antibody) described herein, inhibits or decreases one or more conditions associated with excess body weight, insulin resistance, obesity or diabetes, such as hypertension, cancer, and neuropathy, retinopathy, and cardiovascular, pulmonary and kidney disease. In further embodiments the blocking of ALK7 inhibits or decreases one or more conditions associated with metabolic disease. In particular embodiments, the ALK7-binding protein (e.g., an anti-ALK7 antibody) inhibits or decreases the binding to ALK7 by activin B, GDF8, or Nodal. In another embodiment the ALK7-binding protein inhibits or decreases the inhibition of lipolysis by a Smad-dependent pathway.

As noted above, in some embodiments, an anti-ALK7 antibody (e.g., a full-length ALK7-antibody and an ALK7-binding antibody fragment, and a variant and derivative thereof) containing a VH and/or VL amino acid sequence that binds ALK7 can have at least 85%, 90%, 95%, 96%, 97%, 98% 99%, or 100% sequence identity to a sequence set forth herein. In some embodiments, the VH and/or VL amino acid sequence(s) that binds ALK7 comprise 8, 7, 6, 5, 4, 3, 2, 1 amino acid additions, substitutions (e.g., conservative substitutions) or deletions relative to a sequence set forth herein. In additional embodiments, the VH and/or VL amino acid sequence that binds ALK7 comprise 1, 2, 3, 4, 5 or more amino acid additions, substitutions (e.g., conservative substitutions) or deletions relative to a sequence set forth herein. An anti-ALK7 antibody containing VH and VL regions having a certain percent similarity to a VH region or VL region, or having one or more substitutions, deletions and/or insertions (e.g., conservative substitutions) can be obtained by mutagenesis (e.g., site-directed or PCR-mediated mutagenesis) of nucleic acid molecules encoding VH and/or VL regions described herein, followed by testing of the encoded altered antibody for binding to ALK7 and optionally testing for retained function using the functional assays described herein or an assay known in the art that can routinely be modified to test the retained function.

The affinity or avidity of an ALK7-binding protein such as, an anti-ALK7 antibody (e.g., a full-length ALK7-antibody and an ALK7-binding antibody fragment, and a variant and derivative thereof) for hALK7, or murALK7, can be determined experimentally using any suitable method known in the art, e.g., flow cytometry, enzyme-linked immunosorbent assay (ELISA), or radioimmunoassay (RIA), or kinetics (e.g., BIACORE® or KINEXA® analysis). Direct binding assays and competitive binding assay formats can be readily employed. (See, for example, Berzofsky et al., "Antibody-Antigen Interactions," In Fundamental Immunology, Paul, W. E., Ed., Raven Press: New York, N.Y. (1984); Kuby, Immunology, W. H. Freeman and Company: New York, N.Y. (1992); and methods described herein.) The measured affinity of a particular antibody-antigen interaction can vary if measured under different conditions (e.g., salt concentration, pH, temperature). Thus, measurements of affinity and other ALK7-binding parameters (e.g., $K_D$ or Kd, $K_{on}$, $K_{off}$) are made with standardized solutions of ALK7-binding proteins and ALK7 and the measurements are performed using standardized conditions and methods, as described herein or otherwise known in the art.

The disclosure further provides an ALK7-binding protein such as, an anti-ALK7 antibody as described herein, where the ALK7-binding protein is conjugated to a heterologous agent. In certain embodiments the heterologous agent is an antimicrobial agent, a therapeutic agent, a prodrug, a peptide, a protein, an enzyme, a lipid, a biological response modifier, a pharmaceutical agent, a lymphokine, a heterologous antibody or antibody fragment, a detectable label, or a polyethylene glycol (PEG). Heteroconjugate ALK7-binding proteins are discussed in more detail elsewhere herein.

In certain embodiments, the ALK7-binding protein is not an anti-ALK7 antibody. A variety of methods for identifying and producing non-antibody polypeptides that bind with high affinity to a protein target are known in the art. See, e.g., Skerra, Curr. Opin. Biotech. 18:295-304 (2007); Hosse et al., Protein Science 15:14-27 (2006); Gill et al., Curr. Opin. Biotechnol. 17:653-658 (2006); Nygren, FEBS J. 275:2668-2676 (2008); and Skerra, FEBS J. 275:2677-2683 (2008), each of which is incorporated by reference herein in its entirety. In some embodiments, phage display technology can been used to identify/produce an ALK7-binding protein. In some embodiments, the ALK7-binding protein comprises a protein scaffold based on a type selected from the group consisting of VASP polypeptides, avian pancreatic polypeptide (aPP), tetranectin (based on CTLD3), affilin (based on yB-crystallin/ubiquitin), a knottin, an SH3 domain, a PDZ domain, tendamistat, transferrin, an ankyrin consensus repeat domain (e.g., DARPins), a lipocalin protein fold (e.g., anticalins and Duocalins), a Protein Epitope Mimetic (PEM), a maxybody/avimer, a domain antibody a fibronectin domain (e.g., 10 Fn3, see, e.g., U.S. Appl. Publ. Nos. 2003/0170753 and 20090155275, each of which is herein incorporated by reference in its entirety), a domain of protein A (e.g., Affibodies), and thioredoxin.

In some embodiments the disclosure provides an ALK7-binding protein (e.g., an anti-ALK7 antibody such as, a full-length anti-ALK7 antibody and an ALK7-binding antibody fragment) that cross-blocks or competes for binding ALK7 with an anti-ALK7 antibody provided herein. In some embodiments the disclosure provides an ALK7-binding protein that binds to the same epitope of ALK7 as an ALK7-binding protein provided herein. The ability of a test ALK7-binding protein to inhibit the binding of, for example, a reference binding protein such as an antibody comprising a VH sequence of SEQ ID NO:4 and a VL sequence of SEQ ID NO:13, a VH sequence of SEQ ID NO:22 and a VL sequence of SEQ ID NO:31, a VH sequence of SEQ ID NO:40 and a VL sequence of SEQ ID NO:49, or a VH sequence of SEQ ID NO:58 and a VL sequence of SEQ ID NO:67, to ALK7 demonstrates that the test ALK7-binding protein can compete with the reference antibody for binding to ALK7. Such an ALK7-binding protein can, according to non-limiting theory, bind to the same or a related (e.g., a structurally similar or spatially proximal) epitope on ALK7 as the ALK7-reference antibody with which it competes. In one embodiment, the ALK7-binding protein binds to the same epitope on ALK7 as an antibody comprising a VH sequence of SEQ ID NO:4 and a VL sequence of SEQ ID NO:13, a VH sequence of SEQ ID NO:22 and a VL sequence of SEQ ID NO:31, a VH sequence of SEQ ID NO:40 and a VL sequence of SEQ ID NO:49, or a VH sequence of SEQ ID NO:58 and a VL sequence of SEQ ID NO:67, respectively.

Likewise, the ability of a test ALK7-binding protein to inhibit the binding of, for example, a reference binding protein such as an antibody comprising a VH sequence of SEQ ID NO:91 and a VL sequence of SEQ ID NO:98, a VH sequence of SEQ ID NO:105 and a VL sequence of SEQ ID NO:110, a VH sequence of SEQ ID NO:117 and a VL sequence of SEQ ID NO:124, a VH sequence of SEQ ID NO:128 and a VL sequence of SEQ ID NO:135, or a VH sequence of SEQ ID NO:140 and a VL sequence of SEQ ID NO:148, to ALK7 demonstrates that the test ALK7-binding protein can compete with the reference antibody for binding to ALK7. Such an ALK7-binding protein can, according to non-limiting theory, bind to the same or a related (e.g., a structurally similar or spatially proximal) epitope on ALK7 as the ALK7-reference antibody with which it competes. In one embodiment, the ALK7-binding protein binds to the same epitope on ALK7 as an antibody comprising a VH sequence of SEQ ID NO:91 and a VL sequence of SEQ ID NO:98, a VH sequence of SEQ ID NO:105 and a VL sequence of SEQ ID NO:110, a VH sequence of SEQ ID NO:117 and a VL sequence of SEQ ID NO:124, a VH sequence of SEQ ID NO:128 and a VL sequence of SEQ ID NO:135, or a VH sequence of SEQ ID NO:140 and a VL sequence of SEQ ID NO:148, respectively.

In general, type 1 TGF-beta receptor family members such as, ALK7, are known to be phosphorylated by type II receptors (e.g., ActRIIA and ActRIIB) and to signal through the phosphorylation of Smads (e.g., Smad2 and/or Smad3). In some embodiments, an ALK7-binding protein (e.g., an anti-ALK7 antibody) can decrease phosphorylation of ALK7 by one or more type II receptors (e.g., ActRIIA and/or ActRIIB) in an ALK7 and type II receptor-expressing cell (e.g., adipocyte). In some embodiments, an ALK7-binding protein (e.g., an anti-ALK7 antibody) can decrease ALK7-mediated phosphorylation of Smads (e.g., Smad2 and/or Smad3) in an ALK7 and type II receptor-expressing cell (e.g., adipocyte). In some embodiments the ALK7 receptor expressing cell is murine. In some embodiments the ALK7 receptor expressing cell is human. In some embodiments the ALK7 receptor expressing cell is an adipocyte.

In some embodiments, an ALK7-binding protein has at least one characteristic selected from: (a) decreasing the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competing with one or more type II receptors for binding to ALK7; (c) competing with one or more TGF-beta superfamily ligands (e.g., activin B, activin AB, Nodal, GDF1, GDF3 and/or GDF8) for binding to ALK7; (d) decreasing the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreasing the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binding to ALK7 with a $K_D$ of ≤1 nM and ≥1 pM (e.g., as determined by BIACORE® analysis), and (g) decreasing the formation of a complex containing ALK7, a co-receptor (e.g., cripto and/or cryptic), and one or more TGF-beta superfamily ligands (e.g., Nodal). In some embodiments, the ALK7-binding protein has 2, 3, or 4 of the above characteristics. In some embodiments, the ALK7-binding protein has at least 2, at least 3, or at least 4, of the above characteristics. In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In further embodiments, the ALK7-binding protein cross-blocks or competes for binding to ALK7 with an antibody having an ALK7-binding VH and VL pair disclosed herein. In further embodiments, the ALK7-binding protein is an anti-ALK7 antibody or an ALK7-binding antibody fragment.

In some embodiments, an ALK7-binding protein decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more of the TGF-beta superfamily ligands. In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In further embodiments, the ALK7-binding protein cross-blocks or competes for binding to ALK7 with an antibody having an ALK7-binding VH and VL pair disclosed herein. In further embodiments, the ALK7-binding protein is an anti-ALK7 antibody or an ALK7-binding antibody fragment.

In some embodiments, an ALK7-binding competes with one or more type II receptors for binding to ALK7. In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In further embodiments, the ALK7-binding protein cross-blocks or competes for binding to ALK7 with an antibody having an ALK7-binding VH and VL pair disclosed herein. In further embodiments, the ALK7-binding protein is an anti-ALK7 antibody or an ALK7-binding antibody fragment.

In some embodiments, an ALK7-binding protein (e.g., an anti-ALK7 antibody) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal). In some embodiments, the ALK7-binding protein decreases the phosphorylation of Smads as measured using a cell-based assay. In some embodiments, an ALK7-binding protein decreases ALK7-mediated phosphorylation with an $IC_{50}$ lower than 500 pM, lower than 350 pM, lower than 250 pM, lower than 150 pM, lower than 100 pM, lower than 75 pM, lower than 60 pM, lower than 50 pM, lower than 40 pM, lower than 30 pM, lower than 20 pM, lower than 15 pM, lower than 10 pM, or lower than 5 pM, as measured using a cell-based assay. In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In further embodiments, the ALK7-binding protein cross-blocks or competes for binding to ALK7 with an antibody having an ALK7-binding VH and VL pair disclosed herein. In further embodiments, the ALK7-binding protein is an anti-ALK7 antibody or an ALK7-binding antibody fragment.

In some embodiments, an ALK7-binding protein binds to ALK7 with a $K_D$ of $\leq 1$ nM and $\geq 1$ pM (e.g., as determined by BIACORE® analysis). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In further embodiments, the ALK7-binding protein cross-blocks or competes for binding to ALK7 with an antibody having an ALK7-binding VH and VL pair disclosed herein. In further embodiments, the ALK7-binding protein is an anti-ALK7 antibody or an ALK7-binding antibody fragment.

In some embodiments, an ALK7-binding protein decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In further embodiments, the ALK7-binding protein cross-blocks or competes for binding to ALK7 with an antibody having an ALK7-binding VH and VL pair disclosed herein. In further embodiments, the ALK7-binding protein is an anti-ALK7 antibody or an ALK7-binding antibody fragment.

Preparation of ALK7-Binding Proteins

In some embodiments, the ALK7-binding protein binds the extracellular domain of ALK7. In further embodiments, the ALK7-binding protein is an anti-ALK7 antibody such as, a full-length anti-ALK7 antibody or an ALK7-binding antibody fragment, and variants, and derivatives thereof.

ALK7-binding proteins can be readily prepared using known techniques. Monoclonal anti-ALK7 antibodies can be prepared using techniques known in the art, including hybridoma methods, such as those described by Kohler and Milstein, *Nature* 256:495-497 (1975). Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line to form hybridoma cells that can then be selected away from unfused lymphocytes and myeloma cells. Hybridomas that produce monoclonal antibodies directed specifically against ALK7 such as hALK7, as determined by immunoprecipitation, immunoblotting, or by an in vitro binding assay (e.g., radioimmunoassay (RIA); enzyme-linked immunosorbent assay (ELISA)) can then be propagated either in in vitro culture using standard methods (see, e.g., Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

The provided monoclonal antibodies can also be made using recombinant DNA methods as described in U.S. Pat. No. 4,816,567, wherein the polynucleotides encoding a monoclonal antibody are isolated from mature B-cells or a hybridoma cell, such as by RT-PCR using oligonucleotide primers that specifically amplify the genes encoding the heavy and light chains of the antibody, and their sequence is determined using known procedures. The isolated polynucleotides encoding the heavy and light chains are then cloned into suitable expression vectors, which when transfected into host cells such as E. coli cells, simian COS cells, Chinese hamster ovary (CHO) cells, Per. C6 cells, or myeloma cells (e.g., NS0 cells) that do not otherwise produce immunoglobulin protein, monoclonal antibodies are generated by the host cells. Recombinant anti-ALK7 monoclonal antibodies can also readily be isolated from phage display libraries expressing CDRs of the desired species using known techniques (see, e.g., McCafferty et al., Nature 348:552-554 (1990); Clackson et al., Nature 352:624-628 (1991); and Marks et al., J. Mol. Biol. 222:581-597 (1991)).

The anti-ALK7 antibodies can optionally be humanized, resurfaced, and engineered to display high affinity for the ALK7 antigen and other favorable biological properties. For example, a humanized (or human) anti-ALK7 antibody, can readily be designed and prepared using commonly available three-dimensional immunoglobulin modeling and known procedures for selecting framework (FW) residues, consensus sequences, and germline sequences to provide a desired antibody characteristic, such as increased affinity for ALK7.

Affinity maturation strategies and chain shuffling strategies are known in the art and can be employed to generate high affinity anti-ALK7 antibodies as well as derivatives and variants of the ALK7-binding proteins disclosed herein. See, e.g., Marks et al., Bio/Technology 10:779-783 (1992), which is herein incorporated by reference in its entirety. An additional strategy for generating high affinity anti-ALK7 antibodies as well as derivatives and variants of the ALK7-binding proteins disclosed herein is to generate novel VH or VL regions carrying CDR-derived sequences of the disclosure using random mutagenesis of one or more selected VH and/or VL genes to generate mutations within the entire variable domain. Such a technique that uses error-prone PCR is described by Gram et al. (PNAS USA 89:3576-3580 (1992)). In some embodiments, one or two amino acid substitutions are made within a set of VH CDRs and/or VL CDRs. A further strategy used direct mutagenesis to CDR regions of VH or VL genes encoding anti-ALK7 antibodies disclosed herein. Examples of such techniques are disclosed by Barbas et al. (PNAS USA 91:3809-3813 (1994)) and Schier et al. (J. Mol. Biol. 263:551-567 (1996)).

Humanization, resurfacing or engineering of anti-ALK7 antibodies of the disclosure can be performed using any known method including, but not limited to, those described in Jones et al., Nature 321:522 (1986); Riechmann et al., Nature 332:323 (1988); Verhoeyen et al., Science 239:1534 (1988)), Sims et al., J. Immunol. 151: 2296 (1993); Chothia et al., J. Mol. Biol. 196:901 (1987), Carter et al., PNAS USA 89:4285 (1992); Presta et al., J. Immunol. 151:2623 (1993), U.S. Pat. Nos. 5,639,641, 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567, 7,557,189; 7,538,195; and 7,342,110; Intl. Appl. Nos. PCT/US98/16280; PCT/US96/18978; PCT/US91/09630; PCT/US91/05939; PCT/US94/01234; PCT/GB89/01334; PCT/GB91/01134; PCT/GB92/01755; Intl. Appl. Publ. Nos. WO90/14443; WO90/14424; WO90/14430; and EP Pat. Publ. No. EP 229246; each of which is herein incorporated by reference in is entirely. Likewise, known assays are available for readily selecting anti-ALK7-antibodies displaying desirable features (e.g., assays for determining binding affinity to ALK7; cross-blocking assays such as the BIACORE®-based human ALK7-binding protein competition binding assays described herein).

Methods for engineering, humanizing or resurfacing non-human or human antibodies can also be used and are known in the art. A humanized, resurfaced or similarly engineered antibody can have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence. Such imported sequences can be used to reduce immunogenicity or reduce, enhance or modify binding, affinity, on-rate, off-rate, avidity, specificity, half-life, or any other suitable characteristic, as known in the art. Preferably, part or all of the non-human or human CDR sequences are maintained while the non-human sequences of the variable and constant regions can be replaced with human or other amino acids.

Nucleic acid(s) encoding an ALK7-binding protein, such as a full-length anti-ALK7 antibody can further be modified in a number of different manners using recombinant DNA technology to generate alternative antibodies. In some embodiments, nucleic acid(s) encoding the constant domains of the light and heavy chains of, for example, a mouse monoclonal antibody can be substituted (a) for those coding regions of, for example, a human antibody to generate a chimeric antibody or (b) for non-immunoglobulin encoding nucleic acid(s) to generate a fusion antibody. In some embodiments, the constant regions are truncated or removed to generate the desired antibody fragment of a monoclonal antibody. Site-directed or high-density mutagenesis of the variable region coding sequence can be used to optimize specificity, affinity, etc. of a monoclonal antibody.

Anti-ALK7 human antibodies can be directly prepared using any of the numerous techniques known in the art. (See, e.g., Cole et al., Monoclonal Antibodies and Cancer Therapy, Alan R. Liss, p. 77 (1985); Boemer et al., J. Immunol. 147(1):86-95 (1991); and U.S. Pat. No. 5,750, 373). Similarly, human anti-ALK7 antibodies can readily be obtained from immortalized human B lymphocyte immunized in vitro or isolated from an immunized individual that produces an antibody directed against ALK7.

Human anti-ALK7 antibodies can also be selected from a phage library that expresses human antibodies, as described, for example, in Vaughan et al., Nat. Biotech. 14:309-314 (1996), Sheets et al., PNAS 95:6157-6162 (1998), Hoogenboom and Winter, J. Mol. Biol. 227:381 (1991), and Marks et al., J. Mol. Biol. 222:581 (1991). Techniques for the generating and screening antibody phage libraries are also described in U.S. Pat. Nos. 5,969,108; 6,172,197; 5,885, 793; 6,521,404; 6,544,731; 6,555,313; 6,582,915; 6,593, 081; 6,300,064; 6,653,068; 6,706,484; and 7,264,963; and Rothe et al., J. Mol. Biol. 376(4):1182-1200 (2008)(each of which is herein incorporated by reference in its entirety).

Human anti-ALK7 antibodies can also be made in transgenic mice containing human immunoglobulin loci that are capable upon immunization of producing human antibodies in the absence of endogenous immunoglobulin production. This approach is described for example, in U.S. Pat. Nos. 5,545,807; 5,545,806; 5,569,825; 5,625,126; 5,633,425; and 5,661,016.

Human anti-ALK7 antibodies can also be selected and/or isolated from yeast-based antibody presentation libraries, as disclosed in, for example, WO012/009568; WO09/036379; WO10/105256; WO03/074679 and U.S. Appl. Publ. No. US2002/0177170, the contents of each of which is herein incorporated by reference in its entirety. Such libraries are designed in silico to be reflective of the diversity afforded by the human preimmune repertoire.

Alternatively, anti-ALK7 antibodies may be selected from a yeast-displayed antibody library see, for example: Blaise et al., Gene 342(2):211-218 (2004); Boder et al., Nat Biotechnol. 15(6):553-557 (1997); Kuroda et al., Biotechnol. Lett. 33(1):1-9 (2011). Review; Lauer et al., J. Pharm. Sci. 101(1):102-15 (2012); Orcutt K. D. and Wittrup K. D. Antibody Engineering, yeast display and selection (2010), 207-233; Rakestraw et al., Protein Eng. Des. Sel. 24(6):525-30 (2011); and U.S. Pat. Nos. 6,423,538; 6,696,251; and 6,699,658.

Various techniques are known for the production of antigen-binding antibody fragments. Traditionally, these fragments are derived via proteolytic digestion of intact antibodies (see, e.g., Morimoto et al., J. Biochem. Biophys. Meth. 24:107-117 (1993); and Brennan et al., Science 229: 81 (1985)). In certain embodiments an ALK7-binding antibody fragments produced recombinantly. Fab, Fv, and scFv antibody fragments can all be expressed in and secreted from E. coli or other host cells, thus allowing the production of large amounts of these fragments. Such an ALK7-binding antibody fragments can additionally be isolated from the antibody phage libraries discussed above. In some embodiments, the ALK7-binding antibody fragment is a linear antibody as described in U.S. Pat. No. 5,641,870. Other techniques for the production of antigen-binding antibody fragments are known in the art.

Known techniques can be readily adapted for the production of single-chain antibodies that bind ALK7 (see, e.g., U.S. Pat. No. 4,946,778). In addition, known methods can routinely be adapted for the construction of Fab expression libraries (see, e.g., Huse et al., Science 246:1275-1281 (1989)) to allow rapid and effective identification of monoclonal Fab fragments with the desired specificity for ALK7. ALK7-binding antibody fragments can be produced by techniques known in the art including, but not limited to: (a) a F(ab')2 fragment produced by pepsin digestion of an antibody; (b) a Fab fragment generated by reducing the disulfide bridges of an F(ab')2 fragment, (c) a Fab fragment generated by the treatment of the anti-ALK7 antibody with papain and a reducing agent, and (d) Fv fragments.

In certain embodiments, an ALK7-binding protein (e.g., an anti-ALK7 antibody) can be modified in order to increase its serum half-life. This can be achieved, for example, by incorporation of a salvage receptor binding epitope into the ALK7-binding protein by mutation of an appropriate region in the ALK7-binding protein or by incorporating the salvage receptor epitope into a peptide tag that is then fused to the ALK7-binding protein at either end or in the middle (e.g., by DNA or peptide synthesis). Other methods to increase the serum half-life of an ALK7-binding protein, e.g., conjugation to a heterologous molecule such as PEG are known in the art.

Heteroconjugate ALK7-binding proteins (e.g., anti-ALK7 antibodies, such as a full-length anti-ALK7 antibodies and ALK7-binding antibody fragments, and variants and derivatives thereof) are also within the scope of the disclosure. Heteroconjugate ALK7-binding proteins are composed of two covalently joined proteins. It is contemplated that the heteroconjugate ALK7-binding proteins can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

ALK7-binding proteins can comprise any type of variable region that provides for the association of the antibody with ALK7. Such variable region can comprise or be derived from any mammal that can be induced to mount a humoral response and generate immunoglobulins against the ALK7 antigen. The variable region of an anti-ALK7 antibody can be, for example, of human, murine, non-human primate (e.g., cynomolgus monkeys, macaques, etc.) or lupine origin. In some embodiments both the variable and constant regions of the modified anti-ALK7 antibodies are human. In other embodiments the variable regions of compatible antibodies (usually derived from a non-human source) can be engineered or specifically tailored to improve the binding properties or reduce the immunogenicity of the molecule. In this respect, variable regions useful according to the disclosure can be humanized or otherwise altered through the inclusion of imported amino acid sequences using affinity maturation, mutagenesis procedures, chain shuffling strategies and/or other methods described herein or otherwise know in the art.

In certain embodiments, the variable domains in both the heavy and light chains of an anti-ALK7 antibody are altered by at least partial replacement of one or more CDRs and/or by partial framework region replacement and sequence changing. Although the CDRs can be derived from an antibody of the same class or even subclass as the antibody from which the framework regions are derived, it is envisaged that the CDRs will be derived from an antibody of different class and in certain embodiments from an antibody from a different species. It is not necessary to replace all of the CDRs with the complete CDRs from the donor variable region to transfer the antigen-binding capacity of one variable domain to another. Rather, it is only necessary to transfer those residues that are necessary to maintain the activity of the antigen-binding site. It is well within the competence of those of ordinary skill in the art, to routinely obtain a functional antibody with reduced immunogenicity. See, e.g., U.S. Pat. Nos. 5,585,089, 5,693,761 and 5,693, 762.

Alterations to the variable region notwithstanding, those of ordinary skill in the art will appreciate that the modified anti-ALK7 antibody of the disclosure will comprise antibodies in which at least a fraction of one or more of the constant region domains has been deleted or otherwise altered so as to provide desired biochemical characteristics such as decreased ADCC or increased serum half-life when compared with an antibody of approximately the same immunogenicity comprising a native or unaltered constant region. In some embodiments, the constant region of the modified anti-ALK7 antibodies comprise a human constant region. Modifications to the constant region can include additions, deletions or substitutions of one or more amino acids in one or more domains. The modified anti-ALK7 antibodies disclosed herein can comprise alterations or modifications to one or more of the three heavy chain constant domains (CH1, CH2 or CH3) and/or to the light chain constant domain (CL). In some embodiments, the modified anti-ALK7 antibodies comprise constant regions wherein one or more domains are partially or entirely deleted are contemplated. In some embodiments, the modified anti-ALK7 antibodies comprise domain deleted constructs or variants wherein the entire CH2 domain has been removed (ΔCH2 constructs). In some embodiments, the omitted constant region domain can be replaced by a short amino acid spacer (e.g., 10 residues) that provides some of the molecular flexibility typically imparted by the absent constant region.

It is generally understood that the constant region mediates several effector functions. For example, binding of the C1 component of complement to antibodies activates the complement system. Activation of complement is important in the opsonization and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors that are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In certain embodiments, an anti-ALK7 antibody has an altered effector function that, in turn, affects the biological profile of the administered anti-ALK7 antibody. For example, the deletion or inactivation (through point mutations or other means) of a constant region domain can reduce Fc receptor binding of the circulating modified antibody. In other cases the constant region modifications, can moderate complement binding and thus reduce the serum half-life and nonspecific association of a conjugated cytotoxin. Yet other modifications of the constant region can be used to eliminate disulfide linkages or oligosaccharide moieties that allow for enhanced localization due to increased antigen specificity or antibody flexibility. Similarly, modifications to the constant region in accordance with this disclosure can easily be made using biochemical or molecular engineering techniques known to those of ordinary skill in the art.

In some embodiments, an ALK7-binding protein provided herein is an ALK7 antibody that does not have one or more effector functions. For instance, in some embodiments, the anti-ALK7 antibody has no antibody-dependent cellular cytoxicity (ADCC) activity and/or no complement-dependent cytoxicity (CDC) activity. In certain embodiments, the anti-ALK7 antibody does not bind to an Fc receptor and/or complement factors. In certain embodiments, the anti-ALK7 antibody has no effector function. Examples of Fc sequence engineering modifications that reduce or eliminate ADCC and/or CDC activity and Fc receptor and/or complement factor binding are described herein or otherwise know in the art, as are assays and procedures for testing the same.

In some embodiments, an anti-ALK7 antibody is engineered to fuse the CH3 domain directly to the hinge region of the respective modified antibody. In other constructs a peptide spacer is inserted between the hinge region and the modified CH2 and/or CH3 domains. For example, compatible constructs can be expressed in which the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. Amino acid spacers can, in some cases, prove to be immunogenic and elicit an unwanted immune response against the construct. Accordingly, in certain embodiments, any spacer added to the construct can be relatively non-immunogenic, or even omitted altogether, so as to maintain the desired biochemical qualities of the modified anti-ALK7 antibody.

In additional embodiments anti-ALK7 antibodies are modified by the partial deletion or substitution of a few or even a single amino acid in a constant region. For example, the mutation of a single amino acid in selected areas of the CH2 domain can be enough to substantially reduce Fc binding and thereby. Similarly one or more constant region domains that control the effector function (e.g., complement C1Q binding) can be fully or partially deleted. Such partial deletions of the constant regions can improve selected characteristics of the anti-ALK7 antibody (e.g., serum half-life) while leaving other desirable functions associated with the corresponding constant region domain intact. In some embodiments the constant region of the anti-ALK7 antibody is modified through the mutation or substitution of one or more amino acids that enhances the profile of the resulting construct. In this respect it is possible to disrupt the activity provided by a conserved binding site (e.g., Fc binding) while substantially maintaining the configuration and immunogenic profile of the modified anti-ALK7 antibody. The disclosure also provides an anti-ALK7 antibody that contains the addition of one or more amino acids to the constant region to enhance desirable characteristics such, as decreasing or increasing effector function or providing attachments sites for one or more cytotoxin, labeling or carbohydrate moieties. In such embodiments it can be desirable to insert or replicate specific sequences derived from selected constant region domains.

The disclosure also provides an ALK7-binding protein that is a variant to an ALK7-binding protein provided herein (e.g., murine, chimeric, humanized and human ALK7-binding proteins). In particular embodiments, the variant ALK7-binding protein has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

The provided ALK7-binding proteins, such as anti-ALK7 antibodies, can be derivatized to contain additional chemical moieties known in the art for improving for example, the solubility, biological half-life, bioavailability, and to otherwise improve the stability, formulation and/or therapeutic properties of the ALK7-binding protein. A non-exhaustive overview for such moieties can be found for example, in Remington's Pharmaceutical Sciences, 20th ed., Mack Publishing Co., Easton, Pa. (2000).

Nucleic Acids Encoding ALK7-Binding Proteins and Their Expression

Nucleic acid molecules and combinations of nucleic acid molecules that encode an ALK7-binding protein are also provided. In some embodiments, the nucleic acids molecules encode an anti-ALK7 antibody, such as a full-length anti-ALK7 antibody and an ALK7-binding antibody fragment. In further embodiments, the disclosure provides nucleic acid molecules that encode a variant or derivative of a full-length anti-ALK7 antibody or an ALK7-binding antibody fragment provided herein.

The nucleic acid molecules disclosed herein can be in the form of RNA or in the form of DNA. DNA includes cDNA, genomic DNA, and synthetic DNA; and can be double-stranded or single-stranded, and if single stranded can be the coding strand/or non-coding (anti-sense) strand. In certain embodiments, the nucleic acid molecule is isolated. In additional embodiments, a nucleic acid molecule is substantially pure. In some embodiments the nucleic acid is cDNA or is derived from cDNA. In some embodiments the nucleic acid is be recombinantly produced.

In some embodiments, the nucleic acid molecule comprises an ALK7-binding protein coding sequence operably linked to a control sequence that controls the expression of the coding sequence in a host cell or in vitro. In particular embodiments, the coding sequence is a cDNA. The disclosure also relates to vectors containing nucleic acid molecules comprises an ALK7-binding protein coding sequence operably linked to a control sequence that controls the expression of the coding sequence in a host cell or in vitro.

In some embodiments, the nucleic acid molecule comprises a coding sequence for a mature ALK7-binding protein that is fused in the same reading frame to a heterologous polynucleotide sequence. In some embodiments, the heterologous polynucleotide sequence encodes a leader peptide sequence that facilitates the secretion of the expressed protein from the host cell transformed with the ALK7-binding protein encoding nucleic acid molecule(s). A protein containing a leader sequence is referred to as a preprotein and can have the leader sequence cleaved by the host cell to form the mature form of the ALK7-binding protein. Such leader peptide sequences and their use facilitating the secretion of recombinant proteins in host cells is generally known in the art. In additional embodiments, the heterologous polynucleotide sequence encodes additional 5' amino acid residues that can function for example, to facilitate purification, add or improve protein stability and/or therapeutic or diagnostic properties of the recombinantly expressed ALK7-binding protein.

In some embodiments the disclosure provides isolated nucleic acids such as an ALK7-binding protein encoding cDNA fragments, sufficient for use as a hybridization probe, PCR primer or sequencing primer.

In some embodiments, the nucleic acid molecules encode an ALK7-binding protein that has at least one characteristic selected from the group consisting of: (a) decreases the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competes with one or more type II receptors for binding to ALK7; (c) competes with one or more TGF-beta superfamily ligands (e.g., activin B, activin AB, Nodal, GDF1, GDF3 and/or GDF8) for binding to ALK7; (d) decreases the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreases the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binds to ALK7 with a $K_D$ of ≤1 nM and ≥1 pM (e.g., as determined by BIACORE® analysis), and (g) decreases the formation of a complex containing ALK7, a co-receptor (e.g., cripto and/or cryptic), and one or more TGF-beta superfamily ligands (e.g., Nodal). In some embodiments, the encoded ALK7-binding protein is an ALK7 antagonist (e.g., a neutralizing anti-ALK7 antibody). In further embodiments, the encoded ALK-7 binding protein increases lipolysis in adipose cells expressing ALK7. In some embodiments, the encoded ALK7-binding protein has 2, 3, or 4 of the above characteristics. In some embodiments, the encoded ALK7-binding protein has at least 2, at least 3, or at least 4, of the above characteristics. In some embodiments, the encoded ALK7-binding protein cross-blocks or competes for binding to ALK7 with an antibody having an ALK7-binding VH and VL pair disclosed herein. In additional embodiments, the encoded ALK7-binding protein binds to the same epitope of ALK7 as an antibody disclosed herein. In some embodiments, the encoded ALK7-binding protein cross-blocks or competes for binding to ALK7 with an ALK7 binding antibody having a VH and VL pair disclosed herein. In additional embodiments, the encoded ALK7-binding protein binds to the same epitope of ALK7 as an antibody disclosed herein. In further embodiments, the nucleic acid molecules encode an ALK7-binding protein that specifically binds ALK7 and comprises a VH and a VL In some embodiments, the disclosure provides vectors and sets of vectors containing nucleic acids and sets of nucleic acids encoding the ALK7-binding proteins provided herein. Host cells transformed with these nucleic acids, sets of nucleic acids, vectors, and sets of vectors are also provided, as are methods of making an using the ALK7-binding proteins.

In some embodiments, the disclosure provides a host cell comprising a nucleic acid molecule or combination of nucleic acid molecules or a vector as provided above, where the host cell can, in some instances express an ALK7-binding protein (e.g., an anti-ALK7 antibody such as, a full-length ALK7-antibody and an ALK7-binding antibody fragment), that specifically binds to ALK7. In further embodiments, the disclosure provides a host cell transformed with a nucleic acid molecule or combination of nucleic acid molecules or a vector as provided above, where the host cell can, in some instances express an ALK7-binding protein that specifically binds to ALK7. Such host cells can be utilized in a method of making an ALK7-binding protein as provided herein, where the method includes (a) culturing the host cell and (b) isolating the ALK7-binding proteins expressed from the host cell.

The disclosure also provides a method for making an ALK7-binding protein comprising culturing a host cell (e.g., a hybridoma or transformed mammalian host cell) capable of expressing the ALK7-binding protein under suitable conditions and optionally provides a method for isolating the ALK7-binding protein secreted from the host cell. And the disclosure additionally provides the ALK7-binding protein isolated using the disclosed methods.

In certain embodiments the polynucleotides comprise the coding sequence(s) for the mature ALK7-binding protein(s) (e.g., an ALK7-antibody, such as a full-length antibody and an ALK7-binding antibody fragment) fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used.

Nucleic acid variants encoding an ALK7-binding protein such as, an anti-ALK7 antibody and an ALK7-binding antibody fragment, are also provided. Nucleic acid variants can contain alterations in the coding regions, non-coding regions, or both. In some embodiments the nucleic acid variants contain alterations that produce silent substitutions, additions, or deletions, but do not alter the properties or activities of the encoded polypeptide. In some embodiments, the nucleic acid variants are produced by silent substitutions due to the degeneracy of the genetic code. Nucleic acid variants can be produced for a variety of reasons, e.g., to optimize codon expression for a particular host (change codons in the human mRNA to those preferred by a bacterial host such as *E. coli*). Vectors and cells comprising the nucleic acids described herein are also provided.

In some embodiments a nucleic acid sequence encoding an ALK7-binding protein (e.g., an anti-ALK7 antibody such as a full-length antibody and an ALK7-binding antibody fragment) is constructed by chemical synthesis using an oligonucleotide synthesizer. Such oligonucleotides can be designed based on the amino acid sequence of the desired polypeptide and codon optimization based on the host cell preferences. Standard methods can routinely be applied to synthesize an isolate polynucleotide sequences encoding ALK7-binding proteins.

Once assembled (by synthesis, site-directed mutagenesis or another method), the nucleic acid sequences encoding ALK7-binding proteins can routinely be operably linked to a control sequence appropriate for expression of the ALK7-binding protein in a desired host. In some embodiments, the nucleic acid sequence(s) encoding an ALK7-binding protein is inserted into one or more expression vectors and operably linked to a control sequence(s) appropriate for expression of the protein in a desired host. In order to obtain high expression levels of a transfected coding sequence in a host, the coding sequence can be operably linked to or associated with transcriptional and translational expression control sequences that are functional in the chosen expression host.

In certain embodiments, recombinant expression vectors are used to amplify and express DNA encoding an ALK7-binding protein, such as, an anti-ALK7 antibody or an ALK7-binding antibody fragment. Recombinant expression vectors are replicable DNA constructs which have synthetic or cDNA-derived DNA fragments encoding a polypeptide chain of an ALK7-binding protein operably linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Structural elements intended for use in yeast expression systems include a leader sequence enabling extracellular secretion of translated protein by a host cell. Alternatively, where a recombinant protein is expressed without a leader or transport sequence, the protein can include an N-terminal methionine residue. This residue can optionally be subsequently cleaved from the expressed recombinant protein to provide a final protein. In certain embodiments, the disclosure provides a composition, e.g., a pharmaceutical composition, comprising a nucleic acid or vector of as described above or elsewhere herein, optionally further comprising one or more carriers, diluents, excipients, or other additives.

Also provided is a host cell transformed with the nucleic acid molecule or cDNA molecules and/or the vectors disclosed herein. The disclosure also provides host cells transformed with the disclosed nucleic acid molecule or molecules operably linked to a control sequence and optionally inserted into a vector. In some embodiments, the host cell is a mammalian host cell. In further embodiments, the mammalian host cell is a NS0 murine myeloma cell, a PER.C6® human cell, or a Chinese hamster ovary (CHO) cell. In other embodiments, the host cell is a hybridoma.

In additional embodiments, the disclosure provides a method of making an ALK7-binding protein (e.g., an anti-ALK7 antibody such as, a full-length ALK7-antibody and an ALK7-binding antibody fragment, and variants and derivatives thereof) provided herein comprising culturing a transformed host cell or a hybridoma disclosed herein under suitable conditions for producing the ALK7-binding protein. The disclosure optionally provides isolating the ALK7-binding protein secreted from the host cell. The disclosure also optionally provides the ALK7-binding protein produced using this method and pharmaceutical compositions comprising the ALK7-binding protein and a pharmaceutically acceptable carrier.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR1, pBR322, pMB9 and their derivatives, and also wider host range plasmids, such as M13 and filamentous single-stranded DNA phages.

Suitable host cells for expression of an ALK7-binding protein, include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Additional information regarding methods of protein production, including antibody production, can be found, e.g., in U.S. Appl. Publ. No. 2008/0187954, U.S. Pat. Nos. 6,413,746 and 6,660,501, and Intl. Appl. Publ. No. WO04/009823, each of which is herein incorporated by reference in its entirety.

Various mammalian or insect cell culture systems can also be advantageously employed to express recombinant ALK7-binding proteins (e.g., an anti-ALK7 antibody such as, a full-length ALK7-antibody and an ALK7-binding antibody fragment, and variants and derivatives thereof). Expression of recombinant ALK7-binding proteins in mammalian cells can be performed because such proteins are generally correctly folded, appropriately modified and completely functional. Examples of suitable mammalian host cell lines include HEK-293 and HEK-293T, the COS-7 lines of monkey kidney cells, described by Gluzman (*Cell* 23:175 (1981)), and other cell lines including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins In sect cells are reviewed by Luckow and Summers, *BioTechnology* 6:47 (1988).

ALK7-binding proteins produced by a transformed host cell or hybridoma can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. ALK7-binding proteins can also be physically characterized using such techniques as proteolysis, nuclear magnetic resonance and x-ray crystallography.

For example, supernatants from systems that secrete recombinant ALK7-binding proteins into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify an ALK7-binding protein. Some or all of the foregoing purification steps, in various combinations, can also routinely be employed to provide a homogeneous recombinant ALK7-binding proteins.

A recombinant ALK7-binding protein (e.g., an anti-ALK7 antibody such as, a full-length ALK7-antibody and an ALK7-binding antibody fragment and variants and derivatives thereof) produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying target binding proteins such as full-length antibodies and antigen-binding antibody fragments also include, for example, those described in U.S. Appl. Publ. Nos. 2008/0312425, 2008/0177048, and 2009/0187005, each of which is incorporated herein by reference herein in its entirety.

In certain embodiments, the ALK7-binding protein is not an antibody. A variety of methods are known for identifying and producing non-antibody polypeptides that bind with high affinity to a protein target. See, e.g., Skerra, *Curr. Opin. Biotechnol.* 18:295-304 (2007), Hosse et al., *Protein Science* 15:14-27 (2006), Gill et al., *Curr. Opin. Biotechnol.* 17:653-658 (2006), Nygren, *FEBS J.* 275:2668-2676 (2008), and Skerra, *FEBS J.* 275:2677-2683 (2008), each of which is herein incorporated by reference in its entirety. In certain embodiments, phage display technology is used to identify/produce the ALK7-binding protein. In certain embodiments, the polypeptide comprises a protein scaffold of a type selected from the group consisting of protein A, a lipocalin, a fibronectin domain (e.g., Fibronectin type III (Fn3)), an ankyrin consensus repeat domain, and thioredoxin.

Methods of Use and Pharmaceutical Compositions

The provided ALK7-binding proteins (including antibodies, immunoconjugates, and polypeptides) are useful in a variety of applications including, but not limited to, diagnostic methods and methods of treating and/or ameliorating various diseases and conditions with an ALK7-binding protein (e.g., an anti-ALK7 antibody). Methods are provided for the use of an ALK7-binding protein (e.g., an anti-ALK7 antibody such as, a full-length antibody that specifically binds ALK7 and an ALK7-binding antibody fragment, and variants and derivatives thereof) to treat subjects having a disease or condition associated with ALK7 signaling, altered ALK7 expression, and/or can be ameliorated by reduced ALK7 signaling. In additional embodiments, the disclosure provides a pharmaceutical composition containing an ALK7-binding protein provided herein and a pharmaceutically acceptable carrier. In some embodiments, the disclosure provides a pharmaceutical composition containing an ALK7-binding protein provided herein and a pharmaceutically acceptable carrier, for use as a medicament. The disclosure also provides the use of the pharmaceutical compositions disclosed herein for treating and/or ameliorating a disease or condition associated with ALK7 signaling, altered ALK7 expression, and/or that can be ameliorated by reduced ALK7 signaling. In some embodiments, the disease or condition treated using the pharmaceutical composition provided herein is obesity (e.g., abdominal obesity); overweight; insulin resistance; metabolic syndrome and other metabolic diseases or conditions; a lipid disorder such as, low HDL levels, high LDL levels, hyperlipidemia, hypertriglyceridemia or dyslipidemia; lipoprotein aberrations; decreased triglycerides; inflammation (e.g., liver inflammation and/or inflammation of adipose tissue), fatty liver disease; non-alcoholic fatty liver disease; hyperglycemia; impaired glucose tolerance (IGT); hyperinsulinemia; high cholesterol (e.g., high LDL levels and hypercholesterolemia); cardiovascular disease such as, heart disease including coronary heart disease, congestive heart failure, stroke, peripheral vascular disease, atherosclerosis; arteriosclerosis, and hypertension; Syndrome X; vascular restenosis; neuropathy; retinopathy; neurodegenerative disease; endothelial dysfunction, respiratory dysfunction, renal disease (e.g., nephropathy); pancreatitis; polycystic ovarian syndrome; elevated uric acid levels; haemochromatosis (iron overload); acanthosis nigricans (dark patches on the skin); or cancer such as, myeloma (e.g., multiple myeloma, plasmacytoma, localized myeloma, and extramedullary myeloma), ovarian, breast, endometrial, and colon cancer); or a another disorders/conditions associated with one or more of the above diseases or conditions. In some embodiments, the disease or condition treated using the pharmaceutical composition provided herein is associated with overweight (e.g., BMI of ≥25 kg/m²), or with too much body fat.

In some embodiments, a pharmaceutical composition contains an ALK7-binding protein (e.g., an anti-ALK antagonist antibody) and a pharmaceutically acceptable carrier, and the ALK7 binding protein further comprises a labeling group or an effector group. A "label" refers to one or more elements, isotopes, or chemical compounds attached to enable the detection in a screen. Labels generally fall into three classes: (a) isotopic labels, which may be radioactive or heavy isotopes, (b) small molecule labels, which may include fluorescent and colorimetric dyes, or molecules such as biotin that enable other labeling methods, and (c) immune labels, which may be an epitope incorporated as a fusion partner that is recognized by an antibody, "Labeling group" refers to any detectable label. In some embodiments, the labeling group is coupled to the ALK7-binding protein via a spacer (e.g., a peptide spacer) to reduce potential steric hindrance. Labels may be incorporated into the compound at any position and may be incorporated in vitro or in vivo during protein expression. Various methods for labeling proteins are known in the art and may be used in performing the provided methods. In additional embodiments, the labeling group is selected from the group consisting of: isotopic labels, magnetic labels, redox active moieties, optical dyes, biotinylated groups and polypeptide epitopes recognized by a secondary reporter. In some embodiments, the labeling group is a fluorescent protein such as a Green Fluorescent Protein or derivative thereof (e.g., enhanced GFP, blue fluorescent protein or derivative thereof (e.g., EBFP (Enhanced Blue Fluorescent Protein), EBFP2, Azurite, mKalamal, cyan fluorescent protein or derivative thereof (e.g., ECFP (Enhanced Cyan Fluorescent Protein), Cerulean, CyPet), yellow fluorescent protein or derivative thereof (e.g., YFP, Citrine, Venus, YPet). In some embodiments, the polypeptide epitope is a member selected from a biotin signaling peptide, histidine peptide (his), hemagglutinin (HA), Flag, gold binding peptide. In additional embodiments the effector group is selected from the group consisting of a radioisotope, radionucleotide, a toxin, a therapeutic and a chemotherapeutic agent.

The ALK7-binding proteins of the present disclosure have applications in in vitro and in vivo diagnostic and therapeutic utilities. For example, the ALK7-binding proteins can be administered to cells in culture, e.g., in vitro or in vivo, or in a subject, to treat, prevent or diagnose a variety of diseases or conditions. In some embodiments, the ALK7-binding proteins are human antibodies, murine antibodies, or humanized antibodies.

Also provided are methods of blocking ALK7 activity. In some embodiments, the method comprises contacting ALK7 with an antagonist ALK7-binding protein. In further embodiments, the antagonist ALK7-binding protein is an anti-ALK7 antibody. In some instances the method is performed in vivo. In other instances, the method is performed in vitro. In some embodiments the blocked ALK7 activity is selected from (a) decreasing the formation of a complex containing ALK7, a type II receptor (e.g., ActRIIA or ActRIIB), and one or more TGF-beta superfamily ligands (e.g., activin B, activin AB, Nodal, GDF1, GDF3 and/or GDF8) on the surface of cells expressing ALK7 and the ActRII receptor in the presence of the one or more TGF-beta superfamily ligands; (b) competing with one or more type II receptors for binding to ALK7; (c) competing with one or more TGF-beta superfamily ligands (e.g., activin B, activin AB, Nodal, GDF1, GDF3 and/or GDF8) for binding to ALK7; (d) decreasing the phosphorylation of ALK7 in cells expressing ALK7 and a type II receptor (e.g., ActRIIA or ActRIIB) in the presence of one or more TGF-beta super family ligands (e.g., GDF1, GDF3, GDF8, activin B, activin AB, and/or Nodal); (e) decreasing the phosphorylation of Smads (e.g., Smad2 and/or Smad3) in cells expressing ALK7 and a type II receptor (e.g., ActRIIA and/or ActRIIB) in the presence of one or more TGF-beta ligands (e.g., GDF1, GDF3, GDF8, activin B, activin AB, and/or Nodal); (f) binding to ALK7 with a $K_D$ of ≤1 nM and ≥1 pM (e.g., as determined by BIACORE® analysis), and (g) decreasing the formation of a complex containing ALK7, a co-receptor (e.g., cripto and/or cryptic), and one or more TGF-beta superfamily ligands (e.g., Nodal). In some embodiments, the ALK7-binding protein is an ALK7 antagonist (e.g., a neutralizing anti-ALK7 antibody). In further embodiments, the ALK-7 binding protein increases lipolysis by 5% to 100%, 10% to 80%, or 10% to 60%. In some embodiments, the ALK7-binding protein increase lipolysis in adipocyte cells by 5% to 100%, 10% to 80%, or 10% to 60%. In some embodiments, the ALK7-binding protein increase lipolysis in a lipolysis assay using adipocyte cells (e.g., white adipocytes) by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the ALK7-binding protein has 2, 3, or 4 of the above characteristics. In some embodiments, the ALK7-binding protein has at least 2, at least 3, or at least 4, of the above characteristics.

In one embodiment, the disclosure provides for the treatment, prevention and/or amelioration of a disease or condition that comprises administering an ALK7-binding protein (e.g., an anti-ALK antagonist antibody) to a subject that has a disease or condition, or is at risk of developing a disease or condition, associated with ALK7 signaling, altered ALK7 expression, and/or can be ameliorated by reduced ALK7 signaling. In another embodiment the treatment includes the administration of an ALK7-binding protein to an isolated tissue or cells from a subject, where the subject has a disease or condition, or is at risk of developing a disease or condition, associated with ALK7 expression or ALK7 signaling.

The disclosure provides pharmaceutical compositions comprising an ALK7-binding protein and a pharmaceutically acceptable carrier. Also provided are methods for treating and/or ameliorating conditions associated with an ALK7-mediated activity in a subject, comprising administering to a subject in need thereof an effective amount of a pharmaceutical composition comprising an ALK7-binding protein provided herein. In some embodiments, the ALK7-binding protein is administered alone. In other embodiments, the ALK7-binding protein is administered as a combination therapy. Also provided are methods of reducing ALK7 activity in a subject comprising administering an effective amount of an ALK7-binding protein to a subject in need thereof.

As provided herein, an effective amount of an ALK7-binding protein (e.g., an antagonist anti-ALK7 antibody that specifically binds ALK7 or an antagonist ALK7-binding antibody fragment) can be administered for reducing body weight (e.g., promoting weight loss), reducing body weight gain (e.g., preventing weight gain), and/or treating obesity. In some embodiments, the ALK7-binding protein is an antibody disclosed herein. In some embodiments, the ALK7-binding protein is an ALK7 antagonist antibody. In some embodiments, the administered anti-ALK7-antibody cross-blocks or competes for binding ALK7 with an antibody having a VH and a VL pair disclosed in Table 1A. In some embodiments, the administered anti-ALK7-antibody binds to the same epitope of ALK7 as an antibody having a VH and a VL pair disclosed in Table 1A. In some embodiments, the administered anti-ALK7-antibody cross-blocks or competes for binding ALK7 with an antibody having a VH and a VL pair disclosed in Table 1B or Table 3. In some embodiments, the administered anti-ALK7-antibody binds to the same epitope of ALK7 as an antibody having a VH and a VL pair disclosed in Table 1B or Table 3. In certain instances, the subject has type 2 diabetes mellitus.

In one embodiment, the disclosure provides a method of reducing body weight comprising administering to a subject desiring to reduce body weight, or in need thereof, an effective amount of an ALK7-binding protein (e.g., an antagonist antibody that specifically binds ALK7 or an antagonist ALK7-binding antibody fragment). In some embodiments, the ALK7-binding protein is an antibody disclosed herein. In some embodiments, the ALK7-binding protein is an ALK7 antagonist antibody. In some embodiments, the administered antagonist anti-ALK7-antibody cross-blocks or competes for binding ALK7 with an antibody having a VH and a VL pair disclosed in Table 1A. In some embodiments, the administered antagonist anti-ALK7-antibody binds to the same epitope of ALK7 as an antibody having a VH and a VL pair disclosed in Table 1A. In some embodiments, the administered antagonist anti-ALK7-antibody cross-blocks or competes for binding ALK7 with an antibody having a VH and a VL pair disclosed in Table 1B or Table 3. In some embodiments, the administered antagonist anti-ALK7-antibody binds to the same epitope of ALK7 as an antibody having a VH and a VL pair disclosed in Table 1B or Table 3. In some embodiments, the subject is overweight (e.g., pre-obese). In some embodiments, the subject has a body mass index (BMI) of 25 kg/m$^2$ or greater. In further embodiments, the subject has a BMI of 25 kg/m$^2$ to 29.9 kg/m$^2$, 30 kg/m$^2$ to 39.9 mkg/m$^2$, 25 kg/m$^2$ to 39.9 kg/m$^2$, or 25 kg/m$^2$ to 50 kg/m$^2$. In some embodiments, the subject is obese. In some embodiments, the subject has a BMI of 30 kg/m$^2$ or greater (e.g., 30 to 39.9 kg/m$^2$ or 30 kg/m$^2$ to 50 kg/m$^2$). In some embodiments, the subject is morbidly obese. In some embodiments, the subject has a BMI of 40 kg/m$^2$ or greater. In further embodiments, the subject has a BMI of 40 kg/m$^2$ to 45 kg/m$^2$, or 40 kg/m$^2$ to 50 kg/m$^2$. In some embodiments, the subject has central obesity (e.g., excess adiposity in the abdominal region, including belly fat and/or visceral fat). In some embodiments, the subject has a waist/hip circumference ratio (WHR) of 0.85 or greater. In some embodiments, the subject has peripheral obesity (e.g., excess adiposity on the hips). In some embodiments, the subject has type 2 diabetes mellitus. The ALK7-binding protein is administered alone or as a combination therapy. In some embodiments, the administration is an adjunct to diet and/or exercise.

In one embodiment, the disclosure provides a method of reducing weight gain comprising administering to a subject desiring to reduce weight gain, or in need thereof, an effective amount of an ALK7-binding protein (e.g., an antagonist antibody that specifically binds ALK7 or an antagonist ALK7-binding antibody fragment). In some embodiments, the ALK7-binding protein is an antibody disclosed herein. In some embodiments, the ALK7-binding protein is an ALK7 antagonist antibody. In some embodiments, the administered antagonist anti-ALK7-antibody cross-blocks or competes for binding ALK7 with an antibody having a VH and a VL pair disclosed in Table 1A. In some embodiments, the administered antagonist anti-ALK7-antibody binds to the same epitope of ALK7 as an antibody having a VH and a VL pair disclosed in Table 1A. In some embodiments, the administered antagonist anti-ALK7-antibody cross-blocks or competes for binding ALK7 with an antibody having a VH and a VL pair disclosed in Table 1B or Table 3. In some embodiments, the administered antagonist anti-ALK7-antibody binds to the same epitope of ALK7 as an antibody having a VH and a VL pair disclosed in Table 1B or Table 3. In some embodiments, the subject is overweight (e.g., pre-obese). In some embodiments, the subject has a BMI of 25 kg/m$^2$ or greater. In further embodiments, the subject has a BMI of 25 kg/m$^2$ to 29.9 kg/m$^2$, 30 kg/m$^2$ to 39.9 mkg/m$^2$, 25 kg/m$^2$ to 39.9 kg/m$^2$, or 25 kg/m$^2$ to 50 kg/m$^2$. In some embodiments, the subject is obese. In some embodiments, the subject has a BMI of 30 kg/m$^2$ or greater (e.g., 30 to 39.9 kg/m$^2$ or 30 kg/m$^2$ to 50 kg/m$^2$). In some embodiments, the subject is morbidly obese. In some embodiments, the subject has a BMI of 40 kg/m$^2$ or greater. In further embodiments, the subject has a BMI of 40 kg/m$^2$ to 45 kg/m$^2$, or 40 kg/m$^2$ to 50 kg/m$^2$. In some embodiments, the subject has type 2 diabetes mellitus.

Also provided is a method of treating or preventing a disease or condition associated with excess body weight, comprising administering to a subject in need of treatment or prevention, an effective amount of an ALK7-binding protein (e.g., an antagonist antibody that specifically binds ALK7 or an antagonist ALK7-binding antibody fragment). In some embodiments, the administered ALK7-binding protein (e.g., an antagonist antibody) binds to the same epitope of ALK7 as an antibody having a VH and a VL pair disclosed in Table 1A. In some embodiments, the administered ALK7-binding protein binds to the same epitope of ALK7 as an antibody having a VH and a VL pair disclosed in Table 1B or Table 3. In one embodiment, the treated or prevented disease or condition is obesity. In one embodiment, the treated or prevented disease or condition is insulin resistance. In one embodiment, the treated or prevented disease or condition is a member selected from the group consisting of: dyslipidemia, hyperlipidemia (total cholesterol level >240 mg/dL), hypercholesterolemia (e.g., total cholesterol level of >200 mg/dL, >220 mg/dL, >240 mg/dL, >250 mg/dL, or >275 mg/dL), low HDL serum level (e.g., <40 mg/dL, <45 mg/dL, or <50 mg/dL), high LDL serum level (e.g., ≥100 mg/dL, ≥130 mg/dL, ≥160 mg/dL, or ≥190 mg/dL), and hypertriglyceridemia (e.g., a fasting TG level of ≥150 mg/dL, ≥175 mg/dL, ≥200 mg/dL, ≥300 mg/dL, ≥400 mg/dL, or ≥499 mg/dL). In certain instances, the administration is an adjunct to diet and/or exercise.

In another embodiment the disclosure provides a method of reducing body weight in a subject who is overweight. The method includes administering to an overweight subject an effective amount of an ALK7-binding protein (e.g., an antagonist antibody that specifically binds ALK7 or an antagonist ALK7-binding antibody fragment). In some embodiments, the administered ALK7-binding protein (e.g., an antagonist antibody) cross-blocks or competes for binding ALK7 with an antibody having a VH and a VL pair disclosed in Table 1A. In some embodiments, the administered ALK7-binding protein (e.g., an antagonist antibody) cross-blocks or competes for binding ALK7 with an antibody having a VH and a VL pair disclosed in Table 1A. In some embodiments, the administered ALK7-binding protein (e.g., an antagonist antibody) binds to the same epitope of ALK7 as an antibody having a VH and a VL pair disclosed in Table 1A. In some embodiments, the administered ALK7-binding protein (e.g., an antagonist antibody) cross-blocks or competes for binding ALK7 with an antibody having a VH and a VL pair disclosed in Table 1B or Table 3. In some embodiments, the administered ALK7-binding protein (e.g., an antagonist antibody) cross-blocks or competes for binding ALK7 with an antibody having a VH and a VL pair disclosed in Table 1B or Table 3. In some embodiments, the administered ALK7-binding protein (e.g., an antagonist antibody) binds to the same epitope of ALK7 as an antibody having a VH and a VL pair disclosed in Table 1B or Table 3. In some embodiments, the subject has a body mass index (BMI) of 25 kg/m$^2$ or greater. In further embodiments, the subject has a BMI of 25 kg/m$^2$ to 29.9 kg/m$^2$, 30 kg/m$^2$ to 39.9 mkg/m$^2$, 25 kg/m$^2$ to 39.9 kg/m$^2$, or 25 kg/m$^2$ to 50 kg/m$^{2'}$ or 27 to 40 kg/m$^2$. In some embodiments, the subject is obese. In some embodiments, the subject has a BMI of 30 kg/m$^2$ or greater (e.g., 30 to 39.9 kg/m$^2$ or 30 kg/m$^2$ to 50 kg/m$^2$). The ALK7-binding protein is administered alone or as a combination therapy. In some embodiments, the administration is an adjunct to diet and/or exercise.

In one embodiment the disclosure provides a method of reducing body weight in an obese subject. The method includes administering to the subject an effective amount of an ALK7-binding protein (e.g., an antagonist antibody that specifically binds ALK7 or an antagonist ALK7-binding antibody fragment). In some embodiments, the administered ALK7-binding protein (e.g., an antagonist antibody) cross-blocks or competes for binding ALK7 with an antibody having a VH and a VL pair disclosed in Table 1A. In some embodiments, the administered ALK7-binding protein (e.g., an antagonist antibody) binds to the same epitope of ALK7 as an antibody having a VH and a VL pair disclosed in Table 1A. In some embodiments, the administered ALK7-binding protein (e.g., an antagonist antibody) cross-blocks or competes for binding ALK7 with an antibody having a VH and a VL pair disclosed in Table 1B or Table 3. In some embodiments, the administered ALK7-binding protein (e.g., an antagonist antibody) binds to the same epitope of ALK7 as an antibody having a VH and a VL pair disclosed in Table 1B or Table 3. In some embodiments, the subject has a BMI of 30 kg/m$^2$ or greater (e.g., 30 to 39.9 kg/m$^2$ or 30 kg/m$^{2'}$ to 50 kg/m$^{2'}$ In some embodiments, the subject has a BMI of 40 kg/m$^2$ or greater. In some embodiments, the subject has central obesity (e.g., excess adiposity in the abdominal region, including belly fat and/or visceral fat). In some embodiments, the subject has a waist/hip circumference ratio (WHR) of 0.85 or greater. In some embodiments, the subject has peripheral obesity (e.g., excess adiposity on the hips). The ALK7-binding protein is administered alone or as a combination therapy. In some embodiments, the administration is an adjunct to diet and/or exercise.

In another embodiment, the disclosure provides a method of treating and/or ameliorating obesity or a disease or condition associated with obesity, comprising administering to an obese subject, an effective amount of an ALK7-binding protein (e.g., an antagonist antibody that specifically binds ALK7 or an antagonist ALK7-binding antibody fragment). In some embodiments, the antagonist ALK7-binding protein is an antibody disclosed herein. In some embodiments, the ALK7-binding protein is an antibody disclosed herein. In some embodiments, the ALK7-binding protein is an ALK7 antagonist antibody. In some embodiments, the administered antagonist anti-ALK7-antibody cross-blocks or competes for binding ALK7 with an antibody having a VH and a VL pair disclosed in Table 1A. In some embodiments, the administered antagonist anti-ALK7-antibody binds to the same epitope of ALK7 as an antibody having a VH and a VL pair disclosed in Table 1A. In some embodiments, the administered antagonist anti-ALK7-antibody cross-blocks or competes for binding ALK7 with an antibody having a VH and a VL pair disclosed in Table 1B or Table 3. In some embodiments, the administered antagonist anti-ALK7-antibody binds to the same epitope of ALK7 as an antibody having a VH and a VL pair disclosed in Table 1B or Table 3. In some embodiments, the subject has a BMI of 30 kg/m$^2$ or greater. In further embodiments, the subject has a BMI of 30 to 39.9 kg/m$^2$ or 30 kg/m$^2$ to 50 kg/m$^2$. In some embodiments, the subject is morbidly obese. In some embodiments, the subject has a body BMI of 40 kg/m$^2$ or greater. In further embodiments, the subject has a BMI of 40 kg/m$^2$ to 45 kg/m$^2$, or 40 kg/m$^2$ to 50 kg/m$^2$ In some embodiments, the subject has type 2 diabetes mellitus. In some embodiments, the subject has a BMI of 30 kg/m$^2$ or greater (e.g., 30 to 39.9 kg/m$^2$). In some embodiments, the subject has a BMI of at least 40 kg/m$^2$. In some embodiments, the subject has central obesity (e.g., excess adiposity in the abdominal region, including belly fat and/or visceral fat). In some embodiments, the subject has a waist/hip circumference ratio (WHR) of 0.85 or greater. In some embodiments, the subject has peripheral obesity (e.g., excess adiposity on the hips). The ALK7-binding protein is administered alone or as a combination therapy. In some embodiments, the administration is an adjunct to diet and/or exercise.

Also provided is a method of treating or preventing a disease or condition associated with obesity, comprising administering to a subject in need of treatment or prevention, an effective amount of an ALK7-binding protein (e.g., an antagonist antibody that specifically binds ALK7 or an antagonist ALK7-binding antibody fragment). In some embodiments, the administered ALK7-binding protein (e.g., an antagonist antibody) cross-blocks or competes for binding ALK7 with an antibody having a VH and a VL pair disclosed in Table 1A. In some embodiments, the administered ALK7-binding protein (e.g., an antagonist antibody) binds to the same epitope of ALK7 as an antibody having a VH and a VL pair disclosed in Table 1A. In some embodiments, the administered ALK7-binding protein (e.g., an antagonist antibody) cross-blocks or competes for binding ALK7 with an antibody having a VH and a VL pair disclosed in Table 1B or Table 3. In some embodiments, the administered ALK7-binding protein (e.g., an antagonist antibody) binds to the same epitope of ALK7 as an antibody having a VH and a VL pair disclosed in Table 1B or Table 3. In one embodiment, the treated or prevented disease or condition is a member selected from the group consisting of: dyslipidemia, hyperlipidemia (total cholesterol level >240 mg/dL), hypercholesterolemia (e.g., total cholesterol level of >200 mg/dL, >220 mg/dL, >240 mg/dL, >250 mg/dL, or >275 mg/dL), low HDL serum level (e.g., <40 mg/dL, <45 mg/dL, or <50 mg/dL), high LDL serum level (e.g., ≥100 mg/dL, >130 mg/dL, ≥160 mg/dL, or ≥190 mg/dL), and hypertriglyceridemia (e.g., a fasting TG level of ≥150 mg/dL, ≥175 mg/dL, ≥200 mg/dL, ≥300 mg/dL, ≥400 mg/dL, or ≥499 mg/dL). In one embodiment, the treated or prevented disease or condition is cardiovascular disease. In an additional embodiment, the treated or prevented disease or condition is hypertension (high blood pressure), myocardial infarction, stroke, peripheral artery disease, vasoregulatoin dysfunction, arteriosclerosis congestive heart failure, atherosclerosis, coronary heart disease, or microvascular disease. In one embodiment, the treated or prevented disease or condition is inflammation. In another embodiment, the treated or prevented disease or condition is a member selected from the group: retinopathy, bowel disease, ulcerative colitis, and asthma, inflammation (e.g., inflammation of the liver and/or inflammation of adipose tissue). In one embodiment, the treated or prevented disease or condition is liver disease. In one embodiment, the treated or prevented liver disease or condition is NAFLD. In one embodiment, the liver disease is fatty liver. In one embodiment, the liver disease is NASH. In another embodiment, the treated or prevented disease or condition is a member selected from the group: steatohepatitis, steatosis, fibrosis, and/or cirrhosis. In one embodiment, the treated or prevented disease or condition is a member selected from the group consisting of: cataract, macular degeneration, obstructive sleep apnea, phlebitis, gout, osteoarthritis, gallbladder disease, renal disease, pulmonary disease (e.g., asthma, hypoventilation syndrome, or respiratory dysfunction), and/or cancer (e.g., ovarian, breast, endometrial, liver, kidney, and/or colon cancer, and/or cancer metastasis (e.g., lymphatic metastasis, bloodstream metastasis, and/or tumor growth and invasion). In one embodiment, the treated or prevented disease or condition is infection. In one embodiment, the treated or prevented disease or condition is a slow healing or nonhealing wound. In certain instances, the administration is an adjunct to diet and/or exercise.

In one embodiment, the disclosure provides a method of reducing liver fat comprising administering an effective amount of an ALK7-binding protein (e.g., an antagonist antibody that specifically binds ALK7 or an antagonist ALK7-binding antibody fragment) to a subject in need thereof. In some embodiments, the ALK7-binding protein is an antibody disclosed herein. In some embodiments, the ALK7-binding protein is an ALK7 antagonist antibody. In some embodiments, the administered antagonist anti-ALK7-antibody cross-blocks or competes for binding ALK7 with an antibody having a VH and a VL pair disclosed in Table 1A. In some embodiments, the administered antagonist anti-ALK7-antibody binds to the same epitope of ALK7 as an antibody having a VH and a VL pair disclosed in Table 1A. In some embodiments, the administered antagonist anti-ALK7-antibody cross-blocks or competes for binding ALK7 with an antibody having a VH and a VL pair disclosed in Table 1B or Table 3. In some embodiments, the administered antagonist anti-ALK7-antibody binds to the same epitope of ALK7 as an antibody having a VH and a VL pair disclosed in Table 1B or Table 3. In some embodiments, the subject is overweight (e.g., pre-obese). In some embodiments, the subject has a body mass index (BMI) of 25 kg/m$^2$ or greater. In further embodiments, the subject has a BMI of 25 kg/m$^2$ to 29.9 kg/m$^2$, 30 kg/m$^2$ to 39.9 mkg/m$^2$, 25 kg/m$^2$ to 39.9 kg/m$^2$, or 25 kg/m$^2$ to 50 kg/m$^2$. In some embodiments, the subject is obese. In some embodiments, the subject has a BMI of 30 kg/m$^2$ or greater (e.g., 30 to 39.9 kg/m$^2$ or 30 kg/m$^2$ to 50 kg/m$^2$). In some embodiments, the subject is morbidly obese. In some embodiments, the subject has a BMI of 40 kg/m$^2$ or greater. In further embodiments, the subject has a BMI of 40 kg/m$^2$ to 45 kg/m$^2$, or 40 kg/m$^2$ to 50 kg/m$^2$. In some embodiments, the subject has central obesity (e.g., excess adiposity in the abdominal region, including belly fat and/or visceral fat). In some embodiments, the subject has a waist/hip circumference ratio (WHR) of 0.85 or greater. In some embodiments, the subject has peripheral obesity (e.g., excess adiposity on the hips). In some embodiments, the subject has type 2 diabetes mellitus. The ALK7-binding protein is administered alone or as a combination therapy. In some embodiments, the administration is an adjunct to diet and/or exercise.

In another embodiment, the disclosure provides a method of treating, ameliorating, and/or preventing type 2 diabetes mellitus or a disease or condition associated with diabetes comprising administering to a subject having type 2 diabetes mellitus, or at risk of developing type 2 diabetes, an effective amount of an ALK7-binding protein (e.g., an antagonist antibody that specifically binds ALK7 or an antagonist ALK7-binding antibody fragment). In some embodiments, the ALK7-binding protein is an antibody disclosed herein. In some embodiments, the ALK7-binding protein is an ALK7 antagonist antibody. In some embodiments, the administered antagonist anti-ALK7-antibody cross-blocks or competes for binding ALK7 with an antibody having a VH and a VL pair disclosed in Table 1A. In some embodiments, the administered antagonist anti-ALK7-antibody binds to the same epitope of ALK7 as an antibody having a VH and a VL pair disclosed in Table 1A. In some embodiments, the administered antagonist anti-ALK7-antibody cross-blocks or competes for binding ALK7 with an antibody having a VH and a VL pair disclosed in Table 1B or Table 3. In some embodiments, the administered antagonist anti-ALK7-antibody binds to the same epitope of ALK7 as an antibody having a VH and a VL pair disclosed in Table 1B or Table 3. In some embodiments, the subject has a body mass index BMI of 30 kg/m$^2$ or greater (e.g., 30 to 39.9 kg/m$^2$). In some embodiments, the subject has a BMI of at least 40 kg/m$^2$. In some embodiments, the subject has central obesity (e.g., excess adiposity in the abdominal region, including belly fat and/or visceral fat). In some embodiments, the subject has a WHR of 0.85 or greater. In some embodiments, the subject has peripheral obesity (e.g., excess adiposity on the hips). The ALK7-binding protein is administered alone or as a combination therapy. In some embodiments, the administration is an adjunct to diet and/or exercise.

Also provided is a method of treating, ameliorating or preventing a disease or condition associated with diabetes, comprising administering to a subject having diabetes, an effective amount of an ALK7-binding protein (e.g., an antagonist antibody that specifically binds ALK7 or an antagonist ALK7-binding antibody fragment). In some embodiments, the administered ALK7-binding protein (e.g., an antagonist antibody) cross-blocks or competes for binding ALK7 with an antibody having a VH and a VL pair disclosed in Table 1A. In some embodiments, the administered ALK7-binding protein (e.g., an antagonist antibody) binds to the same epitope of ALK7 as an antibody having a VH and a VL pair disclosed in Table 1A. In some embodiments, the administered ALK7-binding protein (e.g., an antagonist antibody) cross-blocks or competes for binding ALK7 with an antibody having a VH and a VL pair disclosed in Table 1B or Table 3. In some embodiments, the administered ALK7-binding protein (e.g., an antagonist antibody) binds to the same epitope of ALK7 as an antibody having a VH and a VL pair disclosed in Table 1B or Table 3. In one embodiment, the treated or prevented disease or condition is a member selected from the group consisting of: dyslipidemia, hyperlipidemia (total cholesterol level >240 mg/dL), hypercholesterolemia (e.g., total cholesterol level of >200 mg/dL, >220 mg/dL, >240 mg/dL, >250 mg/dL, or >275 mg/dL), low HDL serum level (e.g., <40 mg/dL, <45 mg/dL, or <50 mg/dL), high LDL serum level (e.g., ≥100 mg/dL, >130 mg/dL, ≥160 mg/dL, or ≥190 mg/dL), and hypertriglyceridemia (e.g., a fasting TG level of ≥150 mg/dL, ≥175 mg/dL, ≥200 mg/dL, ≥300 mg/dL, ≥400 mg/dL, or ≥499 mg/dL). In one embodiment, the treated or prevented disease or condition is cardiovascular disease. In an additional embodiment, the treated or prevented disease or condition is hypertension (high blood pressure), myocardial infarction, stroke, peripheral artery disease, vasoregulatoin dysfunction, or arteriosclerosis. In one embodiment, the treated or prevented disease or condition is inflammation (e.g., systemic inflammation, inflammation of the liver, and inflammation of adipose tissue). In another embodiment, the treated or prevented disease or condition is a member selected from the group: atherosclerosis, retinopathy, bowel disease, ulcerative colitis, asthma, inflammation of the liver, and/or inflammation of adipose tissue). In one embodiment, the treated or prevented disease or condition is liver disease. In another embodiment, the treated or prevented disease or condition is a member selected from the group: fatty liver disease, Steatohepatitis, steatosis, and/or cirrhosis. In one embodiment, the treated or prevented disease or condition is a member selected from the group consisting of: cataract, macular degeneration, obstructive sleep apnea, phlebitis, gout, osteoarthritis, gallbladder disease, high cholesterol, pulmonary disease (e.g., asthma, and/or hypoventilation syndrome), neuropathy, retinopathy, vasculopathy microangiopathy, nephropathy, renal failure, and/or cancer (e.g., ovarian, breast, endometrial, liver, kidney, pancreatic, and/or colon cancer), and cancer metastasis (e.g., lymphatic metastasis, bloodstream metastasis, and/or tumor growth and invasion). In one embodiment, the treated or prevented disease or condition is infection or a nonhealing wound. In certain instances, the administration is an adjunct to diet and/or exercise.

The disclosure also provides a method for improving the blood-lipid profile in a subject, comprising administering to a subject in need of such treatment an effective amount of an ALK7-binding protein (e.g., an antagonist (neutralizing) antibody that specifically binds ALK7 or an antagonist ALK7-binding antibody fragment). In some embodiments, the antagonist ALK7-binding protein is an antibody disclosed herein. In some embodiments, the ALK7-binding protein is an antibody disclosed herein. In some embodiments, the ALK7-binding protein is an ALK7 antagonist antibody. In some embodiments, the administered antagonist anti-ALK7-antibody cross-blocks or competes for binding ALK7 with an antibody having a VH and a VL pair disclosed in Table 1A. In some embodiments, the administered antagonist anti-ALK7-antibody binds to the same epitope of ALK7 as an antibody having a VH and a VL pair disclosed in Table 1A. In some embodiments, the ALK7-binding protein is an ALK7 antagonist antibody. In some embodiments, the administered antagonist anti-ALK7-antibody cross-blocks or competes for binding ALK7 with an antibody having a VH and a VL pair disclosed in Table 1B or Table 3. In some embodiments, the administered antagonist anti-ALK7-antibody binds to the same epitope of ALK7 as an antibody having a VH and a VL pair disclosed in Table 1B or Table 3. In some embodiments, the disclosure provides a method for reducing levels of LDL cholesterol or increasing levels of HDL-cholesterol. In one embodiment, the subject has dyslipidemia. In another embodiment, the subject has elevated serum lipids (e.g., cholesterol (hypercholesterolemia) and/or triglycerides (e.g., hypertriglyceridemia). In one embodiment the subject has an LDL-C≥100 mg/dL, ≥130 mg/dL, or ≥160 mg/dL). In one embodiment the subject has a TG≥150 mg/dL, ≥160 mg/dL, ≥170 mg/dL). In one embodiment, the subject has elevated plasma insulin levels (hyperinsulinemia; e.g., fasting insulin level of ≥20 ug/ml can exceed 100). In some embodiments, the subject has type II diabetes.

According to one embodiment, the disclosure provides a method of treating or preventing a metabolic disease or disorder or a condition associated with a metabolic disease or disorder, comprising administering an ALK7-binding protein (e.g., an antagonist antibody that specifically binds ALK7 or an antagonist ALK7-binding antibody fragment) to a subject in need thereof. In one embodiment, the treated metabolic disease, disorder, or condition is hyperglycemia (e.g., >130 mg/dL in the fasting state or following glucose administration during an oral glucose tolerance test). In one embodiment, the treated metabolic disease, disorder, or condition is a lipid metabolism disease, disorder, or condition. In one embodiment, the treated metabolic disease, disorder, or condition is dislipidemia. In a further embodiment, the lipid metabolism disease, disorder, or condition is a member selected from: low HDL levels, high LDL levels, high triglyceride levels, hyperlipidemia, and a lipoprotein aberration. In one embodiment, the subject to which the ALK-7 binding protein is administered has a total cholesterol level of >200 mg/dL, >220 mg/dL, >240 mg/dL, >250 mg/dL, or >275 mg/dL. In one embodiment, the subject to which the ALK-7 binding protein is administered has a HDL serum level of <40 mg/dL, <45 mg/dL, or <50 mg/dL). In one embodiment, the subject to which the ALK-7 binding protein is administered has a LDL serum level ≥100 mg/dL, ≥130 mg/dL, ≥160 mg/dL, or ≥190 mg/dL. In one embodiment, the subject to which the ALK-7 binding protein is administered has, fasting TG level of ≥150 mg/dL, ≥175 mg/dL, ≥200 mg/dL, ≥300 mg/dL, ≥400 mg/dL, or >499 mg/dL. In one embodiment, the treated metabolic disease, disorder, or condition is a glucose metabolism disease, disorder, or condition. In a further embodiment, the glucose metabolism disease, disorder, or condition is a member selected from: glucose intolerance, insulin resistance, impaired glucose tolerance (IGT), impaired fasting glucose (IFG). In one embodiment, the treated metabolic disease, disorder, or condition is a member selected from the group consisting of: high uric acid levels, NAFLD, fatty liver, NASH, and polycystic ovarian syndrome. In one embodiment, the treated subject has hyperinsulinemia. In one embodiment, the treated subject is obese (e.g., the subject has visceral or abdominal obesity). In another embodiment, the treated subject has type II diabetes.

Metabolic syndrome is a condition involving a set of disorders that enhances the risk of heart disease. The major components of metabolic syndrome are excess weight, the cardiovascular parameters (high blood pressure, dyslipidemia, high levels of triglycerides and/or low levels of HDL in the blood), atherosclerosis, diabetes, and/or insulin resistance. A subject having several of these components, i.e. metabolic syndrome, is highly prone to heart disease, though each component is a risk factor. The disclosure also provides a method for treating or preventing 1, 2, 3, or more of the above components of metabolic syndrome, comprising administering to a subject in need of treatment an effective amount of an ALK7-binding protein (e.g., an antagonist antibody that specifically binds ALK7 or an antagonist ALK7-binding antibody fragment).

Additionally provided is a method of treating, preventing or ameliorating a cardiovascular disease or condition, comprising administering an ALK7-binding protein (e.g., an antagonist antibody that specifically binds ALK7 or an antagonist ALK7-binding antibody fragment) to a subject in need thereof. In one embodiment, the treated, prevented, or ameliorated cardiovascular disease or condition is atherosclerosis. In one embodiment, the treated, prevented, or ameliorated cardiovascular disease or condition is hypertension (e.g., blood pressure >130/80 mmHg or >140/90 mmHg, in a resting state). In one embodiment, the cardiovascular disease or condition is peripheral vascular disease, a microvascular or microvascular complication, stroke, and/or retinopathy. In one embodiment, the cardiovascular disease is atherosclerosis (coronary heart disease disease).

In one embodiment, the disclosure provides a method for treating and/or ameliorating an inflammatory disease or condition that comprises administering an ALK7-binding protein (e.g., an antagonist antibody that specifically binds ALK7 or an antagonist ALK7-binding antibody fragment) to a subject in need thereof. In one embodiment, the inflammatory disease or condition is chronic inflammation. In another embodiment, the inflammatory disease or condition is inflammation of adipose tissue. In another embodiment, the disease or condition is inflammation of the liver. In one embodiment, the disease or condition is NAFLD. In a further embodiment, the disease or condition is fatty liver. In a further embodiment, the disease or condition is steatosis (e.g., nonalcoholic Steatohepatitis (NASH).

This disclosure also provides a method of improving glycemic control, comprising administering to a subject in need of treatment an effective amount of an ALK7-binding protein (e.g., an antagonist antibody that specifically binds ALK7 or an antagonist ALK7-binding antibody fragment). In one embodiment, the subject to which the ALK7-binding protein is administered has a fasting blood sugar level of >130, >135, >140, >145, or >150 mg/dL. In one embodiment, the subject to which the ALK7-binding protein is administered has a postprandial blood sugar level of >180, >185, >190, >195, or >200 mg/dL 2 hours after eating. In certain instances, the administration is an adjunct to diet and/or exercise. The administration can also reduce body weight or treat obesity. In certain instances, the subject has type 2 diabetes mellitus. In certain instances, the subject has a BMI of 27 to 40 kg/m2. In certain instances, the subject has a BMI of 30 to 39.9 kg/m2. In certain instances, the subject has a BMI of at least 40. In certain instances, the subject is overweight. In certain instances, the subject is obese. An improvement in glycemic control can be assessed using techniques known in the art such as a mixed-meal test.

The disclosure also provides compositions and methods for treating, preventing or ameliorating hyperglycemia or a condition associated with hyperglycemia in a subject comprising administering to a subject in need of such treatment an effective amount of an ALK7-binding protein (e.g., an antagonist anti-ALK7 antibody that specifically binds ALK7 or an antagonist ALK7-binding antibody fragment). In one embodiment, the subject to which the ALK7-binding protein is administered has a fasting blood sugar level of >130, >135, >140, >145, or >150 mg/dL. In one embodiment, the subject to which the ALK7-binding protein is administered has a postprandial blood sugar level of >180, >185, >190, >195, or >200 mg/dL 2 hours after eating. In one embodiment, the result of the treatment, prevention or amelioration is a member selected from the group consisting of: a decrease in serum levels of glucose, a decrease in serum levels of triglycerides, a decrease in serum levels of insulin, and/or a decrease in serum levels of non-esterified fatty acids, as compared to serum levels in the subject prior to treatment. In one embodiment, the result of the treatment, prevention or amelioration is an increase in body temperature of about 0.4° C. to 1° C. as compared to body temperature of the subject prior to treatment. In some embodiments, the ALK7-binding protein is an antagonist anti-ALK7 protein. In some embodiments, the ALK7-binding protein is an antagonist anti-ALK7 antibody or an ALK7-binding fragment thereof. In some embodiments, the ALK7-binding protein is an antagonist anti-ALK7 antibody or an ALK7-binding fragment thereof disclosed herein. In some embodiments, the administered antagonist anti-ALK7-antibody cross-blocks or competes for binding ALK7 with an antibody having a VH and a VL pair disclosed in Table 1A. In some embodiments, the administered antagonist anti-ALK7-antibody binds to the same epitope of ALK7 as an antibody having a VH and a VL pair disclosed in Table 1A. In some embodiments, the administered antagonist anti-ALK7-antibody cross-blocks or competes for binding ALK7 with an antibody having a VH and a VL pair disclosed in Table 1B or Table 3. In some embodiments, the administered antagonist anti-ALK7-antibody binds to the same epitope of ALK7 as an antibody having a VH and a VL pair disclosed in Table 1B or Table 3. In some embodiments, the administration also reduces body weight of the subject.

In another embodiment, the disclosure provides a method of decreasing plasma insulin levels in a subject, comprising administering an effective amount of an ALK7-binding protein (e.g., an antagonist anti-ALK7 antibody that specifically binds ALK7 or an antagonist ALK7-binding antibody fragment) to a subject in need of such treatment. In one embodiment, the subject to which the ALK7-binding protein is administered has a fasting blood sugar level of >130, >135, >140, >145, or >150 mg/dL. In one embodiment, the subject to which the ALK7-binding protein is administered has a postprandial blood sugar level of >180, >185, >190, >195, or >200 mg/dL 2 hours after eating. In one embodiment, the subject is overweight. In one embodiment, the subject is obese. In another embodiment, the subject has type 2 diabetes. In some embodiments, the ALK7-binding protein is an antagonist anti-ALK7 protein. In some embodiments, the ALK7-binding protein is an antagonist anti-ALK7 antibody or an ALK7-binding fragment thereof. In some embodiments, the ALK7-binding protein is an antagonist anti-ALK7 antibody or an ALK7-binding fragment thereof disclosed herein. In some embodiments, the administered antagonist anti-ALK7-antibody cross-blocks or competes for binding ALK7 with an antibody having a VH and a VL pair disclosed in Table 1A. In some embodiments, the administered antagonist anti-ALK7-antibody binds to the same epitope of ALK7 as an antibody having a VH and a VL pair disclosed in Table 1A. In some embodiments, the administered antagonist anti-ALK7-antibody cross-blocks or competes for binding ALK7 with an antibody having a VH and a VL pair disclosed in Table 1B or Table 3. In some embodiments, the administered antagonist anti-ALK7-antibody binds to the same epitope of ALK7 as an antibody having a VH and a VL pair disclosed in Table 1B or Table 3

The disclosure also provides compositions and methods for treating, preventing or ameliorating hyperglycemia or a condition associated with hyperglycemia in a subject comprising administering to a subject in need of such treatment an effective amount of an ALK7-binding protein (e.g., an antagonist anti-ALK7 antibody that specifically binds ALK7 or an antagonist ALK7-binding antibody fragment). In one embodiment, the subject to which the ALK7-binding protein is administered has a fasting blood sugar level of >130, >135, >140, >145, or >150 mg/dL. In one embodiment, the subject to which the ALK7-binding protein is administered has a postprandial blood sugar level of >180, >185, >190, >195, or >200 mg/dL 2 hours after eating. In one embodiment, the result of the treatment, prevention or amelioration is a member selected from the group consisting of: a decrease in serum levels of glucose, a decrease in serum levels of triglycerides, a decrease in serum levels of insulin, and/or a decrease in serum levels of non-esterified fatty acids, as compared to serum levels in the subject prior to treatment. In one embodiment, the result of the treatment, prevention or amelioration is an increase in body temperature of about 0.4° C. to 1° C. as compared to body temperature of the subject prior to treatment. In some embodiments, the ALK7-binding protein is an antagonist anti-ALK7 protein. In some embodiments, the ALK7-binding protein is an antagonist anti-ALK7 antibody or an ALK7-binding fragment thereof. In some embodiments, the ALK7-binding protein is an antagonist anti-ALK7 antibody or an ALK7-binding fragment thereof disclosed herein. In some embodiments, the administered antagonist anti-ALK7-antibody cross-blocks or competes for binding ALK7 with an antibody having a VH and a VL pair disclosed in Table 1A. In some embodiments, the administered antagonist anti-ALK7-antibody binds to the same epitope of ALK7 as an antibody having a VH and a VL pair disclosed in Table 1A. In some embodiments, the administered antagonist anti-ALK7-antibody cross-blocks or competes for binding ALK7 with an antibody having a VH and a VL pair disclosed in Table 1B or Table 3. In some embodiments, the administered antagonist anti-ALK7-antibody binds to the same epitope of ALK7 as an antibody having a VH and a VL pair disclosed in Table 1B or Table 3 In some embodiments, the administration also reduces body weight of the subject.

In another embodiment, the disclosure provides a method of decreasing plasma insulin levels in a subject, comprising administering an effective amount of an ALK7-binding protein (e.g., an antagonist anti-ALK7 antibody that specifically binds ALK7 or an antagonist ALK7-binding antibody fragment) to a subject in need of such treatment. In one embodiment, the subject to which the ALK7-binding protein is administered has a fasting blood sugar level of >130, >135, >140, >145, or >150 mg/dL. In one embodiment, the subject to which the ALK7-binding protein is administered has a postprandial blood sugar level of >180, >185, >190, >195, or >200 mg/dL 2 hours after eating. In one embodiment, the subject is overweight. In one embodiment, the subject is obese. In another embodiment, the subject has type 2 diabetes. In some embodiments, the ALK7-binding protein is an antagonist anti-ALK7 protein. In some embodiments, the ALK7-binding protein is an antagonist anti-ALK7 antibody or an ALK7-binding fragment thereof. In some embodiments, the ALK7-binding protein is an antagonist anti-ALK7 antibody or an ALK7-binding fragment thereof disclosed herein. In some embodiments, the administered antagonist anti-ALK7-antibody cross-blocks or competes for binding ALK7 with an antibody having a VH and a VL pair disclosed in Table 1A. In some embodiments, the administered antagonist anti-ALK7-antibody binds to the same epitope of ALK7 as an antibody having a VH and a VL pair disclosed in Table 1A. In some embodiments, the administered antagonist anti-ALK7-antibody cross-blocks or competes for binding ALK7 with an antibody having a VH and a VL pair disclosed in Table 1B or Table 3. In some embodiments, the administered antagonist anti-ALK7-antibody binds to the same epitope of ALK7 as an antibody having a VH and a VL pair disclosed in Table 1B or Table 3.

In another embodiment, the disclosure provides a method of treating, preventing, or ameliorating liver disease in a subject, comprising administering an effective amount of an ALK7-binding protein (e.g., an antagonist anti-ALK7 antibody that specifically binds ALK7 or an antagonist ALK7-binding antibody fragment) to a subject having a liver disease. In one embodiment, the subject has inflammation of the liver. In one embodiment, the subject has NAFLD. In on embodiment the subject has fatty liver. In another embodiment, the subject has NASH. In one embodiment, the treated, prevented or ameliorated liver disease is fibrosis, scarring, cirrhosis, or liver failure. In another embodiment, the treated, prevented or ameliorated liver disease is liver cancer. In one embodiment, the subject is overweight. In another embodiment, the subject is obese. In another embodiment, the subject has type 2 diabetes. In some embodiments, the ALK7-binding protein is an antagonist anti-ALK7 protein. In some embodiments, the ALK7-binding protein is an antagonist anti-ALK7 antibody or an ALK7-binding fragment thereof. In some embodiments, the ALK7-binding protein is an antagonist anti-ALK7 antibody or an ALK7-binding fragment thereof disclosed herein. In some embodiments, the administered antagonist anti-ALK7-antibody cross-blocks or competes for binding ALK7 with an antibody having a VH and a VL pair disclosed in Table 1A. In some embodiments, the administered antagonist anti-ALK7-antibody binds to the same epitope of ALK7 as an antibody having a VH and a VL pair disclosed in Table 1A. In some embodiments, the administered antagonist anti-ALK7-antibody cross-blocks or competes for binding ALK7 with an antibody having a VH and a VL pair disclosed in Table 1B or Table 3. In some embodiments, the administered antagonist anti-ALK7-antibody binds to the same epitope of ALK7 as an antibody having a VH and a VL pair disclosed in Table 1B or Table 3.

In additional embodiments, the disclosure provides methods of treating and/or ameliorating cancer or a condition associated with cancer, that comprises administering an ALK7-binding protein (e.g., an anti-ALK7 antibody or ALK7-binding fragment thereof) to a subject in need thereof. In some embodiments the ALK7-binding protein is an anti-ALK7 antibody or an ALK7-binding fragment thereof. In some embodiments, the subject has a cancer selected from the group consisting of a myeloma (e.g., multiple myeloma, plasmacytoma, localized myeloma, or extramedullary myeloma), or an ovarian, breast, colon, endometrial, liver, kidney, pancreatic, gastric, uterine or colon cancer. In some embodiments, ALK7-binding protein is administered to treat or prevent lymphatic metastasis, bloodstream metastasis, tumor growth, or tumor invasion.

In one embodiment, the disclosure provides a method of treating cancer that comprises contacting a cancer cell, tumor associated-stromal cell, or endothelial cell expressing ALK7 with an ALK7-binding protein (e.g., an antagonist anti-ALK7 antibody that specifically binds ALK7 or an antagonist ALK7-binding antibody fragment). In additional embodiments the cancer cell is a myeloma (e.g., multiple myeloma, plasmacytoma, localized myeloma, or extramedullary myeloma), ovarian, breast, colon, endometrial, liver, kidney, pancreatic, gastric, uterine and/or colon cancer cell. In some embodiments the contacted cell is from a cancer line. In some embodiments the cancer cell is contacted in vivo.

In one embodiment, the disclosure provides a method of for increasing lipolysis comprising contacting a white adipocyte or adipose tissue with an antagonist ALK7-binding protein (e.g., an antagonist anti-ALK7 antibody that specifically binds ALK7 or an antagonist ALK7-binding antibody fragment). In some embodiments, the ALK-7 binding protein increases lipolysis by 5% to 100%, 10% to 80%, or 10% to 60%. In some embodiments, the ALK7-binding protein increase lipolysis in adipose cells by 5% to 100%, 10% to 80%, or 10% to 60%. In some embodiments, the ALK7-binding protein increase lipolysis in a lipolysis assay by 5% to 100%, 10% to 80%, or 10% to 60%. In further embodiments the lipolysis assay is performed in the presence of one or more ALK7 ligands selected from the group consisting of: GDF1, GDF3, GDF8, activin B, activin A/B, and Nodal. In some embodiments, the antagonist ALK7 binding protein is an antibody. In some embodiments, the antagonist anti-ALK7-antibody comprises an antibody provided herein. In some embodiments the antagonist antibody cross-blocks or competes for binding ALK7 with an antibody having a VH and a VL pair disclosed in Table 1A. In some embodiments, the antagonist anti-ALK7-antibody binds to the same epitope of ALK7 as an antibody having a VH and a VL pair disclosed in Table 1A. In some embodiments, the administered antagonist anti-ALK7-antibody cross-blocks or competes for binding ALK7 with an antibody having a VH and a VL pair disclosed in Table 1B or Table 3. In some embodiments, the administered antagonist anti-ALK7-antibody binds to the same epitope of ALK7 as an antibody having a VH and a VL pair disclosed in Table 1B or Table 3. In some embodiments the white adipose cell or adipose tissue is contacted in vitro. In some embodiments the differentiated white adipose cell or adipose tissue is contacted in vivo. In one embodiment, the method is carried out in vivo, for example, in a mammalian subject (e.g., an animal model). In a further embodiment, the subject is a human. In some embodiments, the method leads to increased glycerol production. In further embodiments, the method leads to increased glycerol and/or free fatty acid in an adipocyte culture. In some embodiments, the method leads to decreased triglyceride (TG) content in the adipose cell or tissue. In some embodiments, the method leads to a decreased plasma TG level in a subject.

In another embodiment, the disclosure provides a method of increasing adrenergic receptor-β (ADRB) signaling in an adipose cell or tissue. The method comprises contacting a differentiated white adipocyte or adipose tissue with an antagonist ALK7-binding protein (e.g., an antagonist anti-ALK7 antibody that specifically binds ALK7 or an antagonist ALK7-binding antibody fragment) in an amount sufficient to increase ADRB signaling. In some embodiments, the antagonist ALK7 binding protein is an antibody. In some embodiments, the antagonist anti-ALK7-antibody comprises an antibody provided herein. In some embodiments the antagonist antibody cross-blocks or competes for binding ALK7 with an antibody having a VH and a VL pair disclosed in Table 1A. In some embodiments, the antagonist anti-ALK7-antibody binds to the same epitope of ALK7 as an antibody having a VH and a VL pair disclosed in Table 1A. In some embodiments, the administered antagonist anti-ALK7-antibody cross-blocks or competes for binding ALK7 with an antibody having a VH and a VL pair disclosed in Table 1B or Table 3. In some embodiments, the administered antagonist anti-ALK7-antibody binds to the same epitope of ALK7 as an antibody having a VH and a VL pair disclosed in Table 1B or Table 3. In some embodiments the differentiated white adipocyte or adipose tissue is contacted in vitro. In some embodiments the differentiated white adipocyte or adipose tissue is contacted in vivo. In one embodiment, the method is carried out in vivo, for example, in a mammalian subject (e.g., an animal model). In a further embodiment, the subject is a human. In some embodiments, the method leads to increased glycerol production. In further embodiments, the method leads to increased glycerol and/or free fatty acid in an adipocyte culture. In some embodiments, the method leads to decreased TG content in the adipose cell or tissue. In some embodiments, the method leads to a decreased plasma TG level in a subject, in some embodiments, the method leads to an increased ADRB signaling in an adipocyte or adipose tissue during nutrient overload.

In another embodiment, the disclosure provides a method of decreasing peroxisome proliferator-activated receptor-gamma (PPAR gamma) signaling in an adipose cell or adipose tissue (e.g., differentiated white adipocytes). The method includes contacting a differentiated white adipocyte or adipose tissue with an antagonist ALK7-binding protein (e.g., an antagonist anti-ALK7 antibody that specifically binds ALK7 or an antagonist ALK7-binding antibody fragment) in an amount effective to decrease PPAR gamma activity. In some embodiments, the antagonist ALK7 binding protein is an antibody. In some embodiments, the antagonist anti-ALK7-antibody comprises an antibody provided herein. In some embodiments the antagonist antibody cross-blocks or competes for binding ALK7 with an antibody having a VH and a VL pair disclosed in Table 1A. In some embodiments, the antagonist anti-ALK7-antibody binds to the same epitope of ALK7 as an antibody having a VH and a VL pair disclosed in Table 1A. In some embodiments, the administered antagonist anti-ALK7-antibody cross-blocks or competes for binding ALK7 with an antibody having a VH and a VL pair disclosed in Table 1B or Table 3. In some embodiments, the administered antagonist anti-ALK7-antibody binds to the same epitope of ALK7 as an antibody having a VH and a VL pair disclosed in Table 1B or Table 3. In some embodiments the differentiated white adipocyte or adipose tissue is contacted in vitro. In some embodiments the differentiated white adipocyte or adipose tissue is contacted in vivo. In one embodiment, the method is carried out in vivo, for example, in a mammalian subject (e.g., an animal model). In a further embodiment, the subject is a human. In some embodiments, the method leads to increased glycerol production. In further embodiments, the method leads to increased glycerol and/or free fatty acid in an adipocyte culture. In some embodiments, the method leads to decreased TG content in the adipose cell or tissue. In some embodiments, the method leads to a decreased plasma TG level in a subject.

In another embodiment, the disclosure provides a method of decreasing insulin resistance in an adipose cell or adipose tissue (e.g., differentiated white adipocytes). The method includes contacting an adipocyte or adipose tissue with an antagonist ALK7-binding protein (e.g., an antagonist anti-ALK7 antibody that specifically binds ALK7 or an antagonist ALK7-binding antibody fragment) in an amount effective to reduce insulin resistance. In some embodiments, the antagonist ALK7 binding protein is an antibody. In some embodiments, the antagonist anti-ALK7-antibody comprises an antibody provided herein. In some embodiments the antagonist antibody cross-blocks or competes for binding ALK7 with an antibody having a VH and a VL pair disclosed in Table 1A. In some embodiments, the antagonist anti-ALK7-antibody binds to the same epitope of ALK7 as an antibody having a VH and a VL pair disclosed in Table 1A. In some embodiments, the administered antagonist anti-ALK7-antibody cross-blocks or competes for binding ALK7 with an antibody having a VH and a VL pair disclosed in Table 1B or Table 3. In some embodiments, the administered antagonist anti-ALK7-antibody binds to the same epitope of ALK7 as an antibody having a VH and a VL pair disclosed in Table 1B or Table 3. In some embodiments the differentiated white adipocyte or adipose tissue is contacted in vitro. In some embodiments the differentiated white adipocyte or adipose tissue is contacted in vivo. In one embodiment, the method is carried out in vivo, for example, in a mammalian subject (e.g., an animal model). In a further embodiment, the subject is a human.

In another embodiment, the disclosure provides a method of increasing the metabolic rate of an adipose cell or tissue. The method includes contacting an adipocyte or adipose tissue with an antagonist ALK7-binding protein (e.g., an antagonist anti-ALK7 antibody that specifically binds ALK7 or an antagonist ALK7-binding antibody fragment) in an amount effective to increase metabolism of the adipocyte or tissue. In some embodiments, the antagonist ALK7 binding protein is an antibody. In some embodiments, the antagonist anti-ALK7-antibody comprises an antibody provided herein. In some embodiments the antagonist antibody cross-blocks or competes for binding ALK7 with an antibody having a VH and a VL pair disclosed in Table 1A. In some embodiments, the antagonist anti-ALK7-antibody binds to the same epitope of ALK7 as an antibody having a VH and a VL pair disclosed in Table 1A. In some embodiments, the administered antagonist anti-ALK7-antibody cross-blocks or competes for binding ALK7 with an antibody having a VH and a VL pair disclosed in Table 1B or Table 3. In some embodiments, the administered antagonist anti-ALK7-antibody binds to the same epitope of ALK7 as an antibody having a VH and a VL pair disclosed in Table 1B or Table 3. In some embodiments the differentiated white adipocyte or adipose tissue is contacted in vitro. In some embodiments the differentiated white adipocyte or adipose tissue is contacted in vivo. In one embodiment, the method is carried out in vivo, for example, in a mammalian subject (e.g., an animal model). In a further embodiment, the subject is a human.

The disclosure provides methods that comprise administering a therapeutically effective amount of a ALK7-binding protein (e.g., an antagonist anti-ALK7 antibody that specifically binds ALK7 or an antagonist ALK7-binding antibody fragment), alone or in combination with one or more additional therapies (e.g., one or more additional therapeutic agents) to a subject having, or at risk for developing, an ALK7-mediated disease and/or condition such as, obesity (e.g., abdominal or visceral obesity); overweight; insulin resistance; metabolic syndrome and other metabolic diseases or conditions; a lipid disorder such as, low HDL levels, high LDL levels, hyperlipidemia, hypertriglyceridemia or dyslipidemia; lipoprotein aberrations; decreased triglycerides; inflammation (e.g., liver inflammation and/or inflammation of adipose tissue), fatty liver disease; non-alcoholic fatty liver disease; hyperglycemia; impaired glucose tolerance (IGT); hyperinsulinemia; high cholesterol (e.g., high LDL levels and/or hypercholesterolemia); cardiovascular disease such as, heart disease including coronary heart disease, congestive heart failure, stroke, peripheral vascular disease, atherosclerosis; arteriosclerosis, and/or hypertension; Syndrome X; vascular restenosis; neuropathy; retinopathy; neurodegenerative disease; endothelial dysfunction, respiratory dysfunction, renal disease (e.g., nephropathy); pancreatitis; polycystic ovarian syndrome; elevated uric acid levels; haemochromatosis (iron overload); acanthosis nigricans (dark patches on the skin); and/or cancer (e.g., myeloma (e.g., multiple myeloma, plasmacytoma, localized myeloma, or extramedullary myeloma), ovarian, breast, colon, endometrial, liver, kidney, pancreatic, gastric, uterine or colon cancer r); and/or other disorders/conditions associated with one or more of the above diseases or conditions, and/or with overweight (e.g., BMI of ≥25 kg/m$^2$), or with too much body fat.

Also provided is the use of an ALK7-binding protein provided herein for diagnostic monitoring of protein levels (e.g., ALK7 levels) in blood or tissue as part of a clinical testing procedure, e.g., to determine the efficacy of a given treatment regimen. For example, detection can be facilitated by coupling an ALK7-binding protein to a detectable substance. Examples of detectable substances include various enzymes, prosthetic groups, fluorescent materials, luminescent materials, bioluminescent materials, and/or radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^3$H.

Pharmaceutical Compositions and Administration Methods

Methods of preparing and administering an ALK7-binding protein to a subject in need thereof are known to or are readily determined by those of ordinary skill in the art. The route of administration of the ALK7-binding proteins can be, for example, oral, parenteral, by inhalation or topical. The term parenteral includes, e.g., intravenous, intraarterial, intraperitoneal, intramuscular, intraocular, subcutaneous, rectal, or vaginal administration. While all these forms of administration are clearly contemplated as being within the scope of the disclosure, another example of a form for administration would be a solution for injection, in particular for intravenous or intraarterial injection or drip. Usually, a suitable pharmaceutical composition can comprise a buffer (e.g., acetate, phosphate or citrate buffer), a surfactant (e.g., polysorbate), optionally a stabilizer agent (e.g., human albumin), etc. In other methods compatible with the teachings herein, ALK7-binding proteins as provided herein can be delivered directly to the organ and/or site of a fibrosis or tumor, thereby increasing the exposure of the diseased tissue to therapeutic agent. In one embodiment, the administration is directly to the airway, e.g., by inhalation or intranasal administration.

As discussed herein, ALK7-binding proteins can be administered in a pharmaceutically effective amount for the in vivo treatment of ALK7-mediated diseases and conditions such as, obesity, diabetes, metabolic disease, dyslipidemia; cardiovascular disease, type 2 diabetes, inflammation, or a cardiovascular, pulmonary, fatty liver disease, neurologic, and hepatic, or renal disease, and and/cancer. In this regard, it will be appreciated that the disclosed ALK7-binding proteins can be formulated so as to facilitate administration and promote stability of the active agent. Pharmaceutical compositions in accordance with the disclosure can comprise a pharmaceutically acceptable, non-toxic, sterile carrier such as physiological saline, non-toxic buffers, preservatives and the like. For the purposes of the instant application, a pharmaceutically effective amount of a ALK7-binding protein, conjugated or unconjugated, means an amount sufficient to achieve effective binding to ALK7 and to achieve a benefit, e.g., to ameliorate symptoms of a disease or condition or to detect a substance or a cell. Suitable formulations for use in therapeutic methods disclosed herein are described in Remington's Pharmaceutical Sciences (Mack Publishing Co.) 16th ed. (1980).

Certain pharmaceutical compositions provided herein can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of an ALK7-binding protein (e.g., an antibody that specifically binds ALK7) that can be combined with carrier materials to produce a single dosage form will vary depending upon the subject treated and the particular mode of administration. The composition can be administered as a single dose, multiple doses or over an established period of time in an infusion. Dosage regimens also can be adjusted to provide the optimum desired response (e.g., a therapeutic or prophylactic response).

ALK7-binding proteins provided herein can be administered to a human or other subject in accordance with the aforementioned methods of treatment in an amount sufficient to produce a therapeutic effect. The ALK7-binding proteins provided herein can be administered to such human or other animal in a conventional dosage form prepared by combining the ALK7-binding proteins with a conventional pharmaceutically acceptable carrier or diluent according to known techniques. The form and character of the pharmaceutically acceptable carrier or diluent can be dictated by the amount of active ingredient with which it is to be combined, the route of administration and other well-known variables. A cocktail comprising one or more different ALK7-binding proteins can also be used.

Therapeutically effective doses of ALK7-binding compositions for treatment of an ALK7-mediated disease or condition such as, obesity, diabetes, metabolic disease, dyslipidemia; cardiovascular disease, type 2 diabetes, inflammation, or a cardiovascular, pulmonary, fatty liver disease, neurologic, and hepatic, or renal disease and/or cancer, vary depending upon many different factors, including means of administration, target site, physiological state of the subject, whether the subject is human or an animal, other medications administered, and whether treatment is prophylactic or therapeutic. Usually, the subject is a human, but non-human mammals including transgenic mammals can also be treated. Treatment dosages can be titrated using routine methods known to those of ordinary skill in the art to optimize safety and efficacy.

To ameliorate the symptoms of a particular disease or condition by administration of an ALK7-binding protein refers to any lessening, whether permanent or temporary, lasting or transient that can be attributed to or associated with administration of the ALK7-binding.

The disclosure also provides for the use of an ALK7-binding protein, such as, an anti-ALK7 antibody in the manufacture of a medicament for example, for treating, preventing or ameliorating obesity, diabetes, metabolic disease, dyslipidemia; cardiovascular disease, type 2 diabetes, inflammation, or a cardiovascular, pulmonary, fatty liver disease, neurologic, and hepatic, or renal disease and/or cancer.

Combination Therapies

In some embodiments, an ALK7-binding protein (e.g., an anti-ALK7 antibody such as, a full-length ALK7-antibody and an ALK7-binding antibody fragment, or a variant or derivative thereof) is administered in combination with one or more other therapies. Such therapies include additional therapeutic agents as well as other medical interventions. Exemplary therapeutic agents that can be administered in combination with the ALK7-binding proteins provided herein include, but are not limited to, anti-SDI-fibrotics, corticosteroids, anti-inflammatories, angiotensin converting enzyme inhibitors, angiotensin receptor blockers, diuretics, antidiabetics, immune suppressants, chemotherapeutic agents, anti-metabolites, and/or immunomodulators. In various embodiments, an ALK7-binding protein is administered to a subject before, during, and/or after a surgical excision/removal procedure.

In some embodiments, an ALK7-binding protein (e.g., an anti-ALK7 antibody such as, a full-length ALK7-antibody and an ALK7-binding antibody fragment, or a variant or derivative thereof) is administered in combination with one or more (a) biguanides (e.g., buformin, metformin, phenformin), (b) insulin, (c) somatostatin, (d) alpha-glucosidase inhibitors (e.g., voglibose, miglitol, acarbose), (e) DPP-IV inhibitors, such as sitagliptin, vildagliptin, alogliptin, saxagliptin (e.g., as disclosed in U.S. Pat. No. 6,699,871B1) (f) LXR modulators, (g) insulin secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and/or repaglinide), (k) CB1 inhibitors, such as, rimonabant, taranabant, and compounds disclosed in Intl. Appl. Publ. Nos. WO03/077847A2 and WO05/000809 A1, or (i). sibutramine, topiramate, orlistat, Qnexa, mevastatin, simvastatin, ezetimibe, atorvastatin, naltrexone, bupriopion, phentermine, hydrochlorothiazide, or losartan.

Diagnostics

The disclosure also provides a diagnostic method useful during diagnosis of ALK7-mediated diseases and conditions (such as, obesity (e.g., abdominal or visceral obesity); overweight; insulin resistance; metabolic syndrome and/or other metabolic diseases or conditions; a lipid disorder such as, low HDL levels, high LDL levels, hyperlipidemia, hypertriglyceridemia or dyslipidemia; lipoprotein aberrations; decreased triglycerides; inflammation (e.g., liver inflammation and/or inflammation of adipose tissue), fatty liver disease; non-alcoholic fatty liver disease; hyperglycemia; impaired glucose tolerance (IGT); hyperinsulinemia; high cholesterol (e.g., high LDL levels and/or hypercholesterolemia); cardiovascular disease such as, heart disease including coronary heart disease, congestive heart failure, stroke, peripheral vascular disease, atherosclerosis; arteriosclerosis, and/or hypertension; Syndrome X; vascular restenosis; neuropathy; retinopathy; neurodegenerative disease; endothelial dysfunction, respiratory dysfunction, renal disease (e.g., nephropathy); pancreatitis; polycystic ovarian syndrome; elevated uric acid levels; haemochromatosis (iron overload); acanthosis nigricans (dark patches on the skin); and/or cancer (e.g., a myeloma (e.g., multiple myeloma, plasmacytoma, localized myeloma, or extramedullary myeloma), or an ovarian, breast, colon, endometrial, liver, kidney, pancreatic, gastric, uterine or colon cancer); and/or other disorders/conditions associated with one or more of the above diseases or conditions, or with too much body fat.), which involves measuring the expression level of ALK7 protein tissue or body fluid from an individual and comparing the measured expression level with a standard ALK7 expression level in normal tissue or body fluid, whereby an increase in ALK7 expression level compared to the standard is indicative of a disorder treatable by an ALK7-binding protein provided herein, such as a full-length anti-ALK7 antibody and ALK7-binding antibody fragment as provided herein.

The ALK7-binding proteins provided herein such as, anti-ALK7 antibodies (e.g., full-length ALK7-antibodies and ALK7-binding antibody fragment, and variants and derivatives thereof) can be used to assay ALK7 levels in a biological sample using classical immunohistological methods known to those of skill in the art (see, e.g., Jalkanen, et al., *J. Cell. Biol.* 101:976-985 (1985); Jalkanen et al., *J. Cell Biol.* 105:3087-3096 (1987)). Other antibody-based methods useful for detecting ALK7 protein expression include immunoassays, such as the enzyme linked immunosorbent assay (ELISA), immunoprecipitation, or Western blotting.

By "assaying the expression level of ALK7 protein" is intended qualitatively or quantitatively measuring or estimating the level of ALK7 protein in a first biological sample either directly (e.g., by determining or estimating absolute protein level) or relatively (e.g., by comparing to the disease associated polypeptide level in a second biological sample). The ALK7 protein expression level in the first biological sample can be measured or estimated and compared to a standard ALK7 protein level, the standard being taken from a second biological sample obtained from an individual not having the disorder or being determined by averaging levels from a population of individuals not having the disorder. As will be appreciated in the art, once the "standard" ALK7 protein level is known, it can be used repeatedly as a standard for comparison.

By "biological sample" is intended any biological sample obtained from an individual, cell line, tissue culture, or other source of cells potentially expressing ALK7. Methods for obtaining tissue biopsies and body fluids from mammals are known in the art.

Kits Comprising ALK7-Binding Proteins

This disclosure further provides kits that include an ALK7-binding protein (e.g., an antibody that specifically binds ALK7 such as, a full-length ALK7-antibody and an ALK7-binding antibody fragment, and variants and derivatives thereof) in suitable packaging, and written material and that can be used to perform the methods described herein. The written material can include any of the following information: instructions for use, discussion of clinical studies, listing of side effects, scientific literature references, package insert materials, clinical trial results, and/or summaries of these and the like. The written material can indicate or establish the activities and/or advantages of the composition, and/or describe dosing, administration, side effects, drug interactions, or other information useful to the health care provider. Such information can be based on the results of various studies, for example, studies using experimental animals involving in vivo models and/or studies based on human clinical trials. The kit can further contain another therapy (e.g., another agent) and/or written material such as that described above that serves to provide information regarding the other therapy (e.g., the other agent).

In certain embodiments, a kit comprises at least one purified ALK7-binding protein in one or more containers. In some embodiments, the kits contain all of the components necessary and/or sufficient to perform a detection assay, including all controls, directions for performing assays, and/or any necessary software for analysis and presentation of results.

Immunoassays

ALK7-binding proteins (e.g., antibodies that specifically bind ALK7 and ACTRIIA/B-binding fragments of antibodies that specifically bind ALK7, and variants, or derivatives thereof) can be assayed for immunospecific binding by any method known in the art. The immunoassays that can be used include, but are not limited to, competitive and non-competitive assay systems using techniques such as Western blots, radioimmunoassays (REA), ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, or protein A immunoassays. Such assays are routine and known in the art (see, e.g., Ausubel et al., eds, (1994) Current Protocols in Molecular Biology (John Wiley & Sons, Inc., NY) Vol. 1, which is herein incorporated by reference in its entirety).

ALK7-binding proteins (e.g., antibodies that specifically binds ALK7 and an ActRII receptor (e.g., ActRIIA or ActRIIB)-binding fragments of antibodies that specifically bind ALK7, and variants, or derivatives thereof) provided herein can be employed histologically, as in immunofluorescence, immunoelectron microscopy or non-immunological assays, for in situ detection of ALK7 or conserved variants or peptide fragments thereof. In situ detection can be accomplished according to methods known in the art. Those of ordinary skill in the art will be able to determine operative and optimal assay conditions for each determination by employing routine experimentation. Methods suitable for determination of binding characteristics of an ALK7-binding protein are described herein or otherwise known in the art. Equipment and software designed for such kinetic analyses are commercially available (e.g., BIA- CORE®, BIAevaluation® software, GE Healthcare; KINEXA® Software, Sapidyne Instruments).

Unless otherwise indicated, the practice of the disclosure employs conventional techniques of cell biology, cell culture, molecular biology, transgenic biology, microbiology, recombinant DNA, and immunology, which are within the skill of the art.

The following examples are offered by way of illustration and not by way of limitation.

EXAMPLES

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

Example 1. Selection, Characterization and Production of ALK7-Binding Antibodies A multi-round selection procedure was used to select for human IgG antibodies that bind ALK7 with high affinity which is detailed below.
Materials and Methods Human ALK7-Fc comprising protein was biotinylated using the EZ-Link Sulfo-NHS-Biotinylation Kit from Pierce. Goat anti-human F(ab')$_2$ kappa-FITC (LC-FITC), Extravidin-PE (EA-PE) and streptavidin-633 (SA-633) were obtained from Southern Biotech, Sigma and Molecular Probes, respectively. Streptavidin MicroBeads and MACS LC separation columns were purchased from Miltenyi Biotec.

Experiments were performed using a Biacore T100/T200 biosensor (Biacore/GE Healthcare) at 25° C. and 37° C. ALK7 antibodies were captured on custom made FAB chip. A concentration series of ALK7-Fc comprising protein was injected over the flow cells at a flow rate of 50 µl/ml. To obtain kinetic rate constants the corrected data were fit to a 1:1 interaction model using BiaEvaluation software (GE Healthcare). The equilibrium binding constant KD was determined by the ratio of binding rate constants kd/ka.

Eight naïve human synthetic yeast libraries each of ~$10^9$ diversity were propagated as described previously (see, e.g., WO09/036379; WO10/105256; WO12/009568). For the first two rounds of selection, a magnetic bead sorting technique utilizing the Miltenyi MACs system was performed, as described (see, e.g., Siegel et al., J. Immunol. Meth. 286(1-2):141-153 (2004)). Briefly, yeast cells (~$10^{10}$ cells/library) were incubated with 3 ml of 10 nM biotinylated ALK7-Fc comprising protein for 15 minute at room temperature in FACS wash buffer (phosphate-buffered saline (PBS)/0.1% bovine serum albumin (BSA)). After washing once with 50 ml ice-cold wash buffer, the cell pellet was resuspended in 40 mL wash buffer, and Streptavidin MicroBeads (500 µl) were added to the yeast and incubated for 15 minutes at 4° C. Next, the yeast were pelleted, resuspended in 5 mL wash buffer, and loaded onto a Miltenyi LS column. After the 5 mL was loaded, the column was washed 3 times with 3 ml FACS wash buffer. The column was then removed from the magnetic field, and the yeast were eluted with 5 mL of growth media and then grown overnight. The following rounds of sorting were performed using flow cytometry. Approximately 1×$10^8$ yeast were pelleted, washed three times with wash buffer, and incubated with decreasing concentrations of biotinylated ALK7-Fc comprising protein (100 to 1 nM) under equilibrium conditions at room temperature. Yeast were then washed twice and stained with LC-FITC (diluted 1:100) and either SA-633 (diluted 1:500) or EA-PE (diluted 1:50) secondary reagents for 15 minutes at 4° C. After washing twice with ice-cold wash buffer, the cell pellets were resuspended in 0.4 mL wash buffer and transferred to strainer-capped sort tubes. Sorting was performed using a FACS ARIA sorter (BD Biosciences) and sort gates were assigned to select for specific binders relative to a background control. Subsequent rounds of selection were employed in order to reduce the number non-specific reagent binders utilizing soluble membrane proteins from CHO cells (See, e.g., WO14/179363 and Xu et al., Protein Eng. Des. Sel. 26(10):663-670 (2013)), and to identify binders with improved affinity to ALK7 using the ALK7-Fc comprising protein. After the final round of sorting, yeast were plated and individual colonies were picked for characterization and for nomination of clones for affinity maturation.
Antibody Production and Purification In order to produce sufficient amounts of selected antibodies for further characterization, the yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over KappaSelect (GE Healthcare LifeSciences).
ForteBio $K_D$ Measurements ForteBio affinity measurements of selected antibodies were performed generally as previously described (see, e.g., Estep et al., Mabs, 5(2):270-278 (2013)). Briefly, ForteBio affinity measurements were performed by loading IgGs on-line onto AHQ sensors. Sensors were equilibrated off-line in assay buffer for 30 minutes and then monitored on-line for 60 seconds for baseline establishment. Sensors with loaded IgGs were exposed to 100 nM antigen for 5 minutes, afterwards they were transferred to assay buffer for 5 minutes for off-rate measurement. Kinetics were analyzed using the 1:1 binding model.
Octet Red384 Epitope Binning/Ligand Blocking Epitope binning/ligand blocking of selected antibodies was performed using a standard sandwich format cross-blocking assay. Control anti-target IgG was loaded onto AHQ sensors and unoccupied Fc-binding sites on the sensor were blocked with an irrelevant human IgG1 antibody. The sensors were then exposed to 100 nM target antigen followed by a second anti-target antibody or ligand. Data was processed using ForteBio's Data Analysis Software 7.0. Additional binding by the second antibody or ligand after antigen association indicates an unoccupied epitope (non-competitor), while no binding indicates epitope blocking (competitor or ligand blocking).

Size Exclusion Chromatography

A TSKgel SuperSW mAb HTP column (22855) was used for fast SEC analysis of yeast-produced mAbs at 0.4 mL/minute with a cycle time of 6 min/run. 200 mM Sodium Phosphate and 250 mM Sodium Chloride was used as the mobile phase.

Dynamic Scanning Fluorimetry 10 uL of 20× Sypro Orange was added to 20 uL of 0.2-1 mg/mL mAb or Fab solution. An RT-PCR instrument (Bio-Rad CFX96 RT PCR) was used to ramp the sample plate temperature from 40° to 95° C. at 0.5° C. increment, with a 2 minute equilibration at each temperature. The negative of the first derivative for the raw data was used to extract Tm.

Example 2. Characterization of ALK7-Binding Antibodies

Exemplary ALK7-binding proteins generated according to the previous example were further characterized by sequence, SPR, and cell-based lipolysis inhibition assay analyses.

Sequences of exemplary ALK7-binding antibodies generated according to the methods described in Example 1 are presented in Table 1A (exemplary CDR sequences are underscored).

TABLE 1A

| Exemplary | ALK7-binding proteins |
|---|---|
| | G04 |
| VH FR1 | QVQLVQSGAEVKKPGSSVKVSCKASGGTFS (SEQ ID NO: 6) |
| VH CDR1 | SYAIS (SEQ ID NO: 1) |
| VH FR2 | WVRQAPGQGLEWMG (SEQ ID NO: 7) |
| VH CDR2 | GIIPIFGTASYAQKFQG (SEQ ID NO: 2) |
| VH FR3 | RVTITADESTSTAYMELSSLRSEDTAVYYCAR (SEQ ID NO: 8) |
| VH CDR3 | TPYYDSSGYLDV (SEQ ID NO: 3) |
| VH FR4 | WGQGTMVTVSS (SEQ ID NO: 9) |
| VH ABRs | ABR1: GTFSSYAIS (SEQ ID NO: 73)     ABR2: GIIPIFGTASYAQKFQG (SEQ ID NO: 74)<br>ABR3: ARTPYYDSSGYLDV (SEQ ID NO: 75) |
| VH DNA | CAGGTGCAGCTGGTGCAGTCTGGGGCTGAGGTGAAGAAGCCTGGGTCCTCGGTGAAGGTCT<br>CCTGCAAGGCTTCTGGAGGCACCTTCAGCAGCTATGCTATCAGCTGGGTGCGACAGGCCCCT<br>GGACAAGGGCTTGAGTGGATGGGAGGGATCATCCCTATCTTTGGTACAGCAAGCTACGCAC<br>AGAAGTTCCAGGGCAGAGTCACGATTACCGCGGACGAATCCACAGCACAGCCTACATGGA<br>GCTGAGCAGCCTGAGATCTGAGGACACGGCGGTGTACTACTGCGCCAGAACTCCTTACTACG<br>ACAGCAGCGGATACCTAGACGTATGGGGTCAGGGTACAATGGTCACCGTCTCCTCA (SEQ ID NO: 5) |
| VH Protein | QVQLVQSGAEVKKPGSSVKVSCKASGGTFS<u>SYAIS</u>WVRQAPGQGLEWMG<u>GIIPIFGTASYAQKF<br>QG</u>RVTITADESTSTAYMELSSLRSEDTAVYYCAR<u>TPYYDSSGYLDV</u>WGQGTMVTVSS (SEQ ID NO: 4) |
| VL FR1 | DIQMTQSPSSLSASVGDRVTITC (SEQ ID NO: 15) |
| VL CDR1 | QASQDISNYLN (SEQ ID NO: 10) |
| VL FR2 | WYQQKPGKAPKLLIY (SEQ ID NO: 16) |
| VL CDR2 | DASNLAT (SEQ ID NO: 11) |
| VL FR3 | GVPSRFSGSGSGTDFTFTISSLQPEDIATYYC (SEQ ID NO: 17) |
| VL CDR3 | QQSLDLPPT (SEQ ID NO: 12) |
| VL FR4 | FGGGTKVEIK (SEQ ID NO: 18) |
| VL DNA | GACATCCAGATGACCCAGTCTCCATCCTCCCTGTCTGCATCTGTAGGAGACAGAGTCACCAT<br>CACTTGCCAGGCGAGTCAGGACATTAGCAACTATTTAAATTGGTATCAGCAGAAACCAGGG<br>AAAGCCCCTAAGCTCCTGATCTACGATGCATCCAATTTGGCAACAGGGGTCCCATCAAGGTT<br>CAGTGGAAGTGGATCTGGGACAGATTTTACTTTCACCATCAGCAGCCTGCAGCCTGAAGATA<br>TTGCAACATATTACTGTCAGCAGTCCCTCGACCTCCCTCCTACTTTTGGCGGAGGGACCAAG<br>GTTGAGATCAAA (SEQ ID NO: 14) |
| VL Protein | DIQMTQSPSSLSASVGDRVTITC<u>QASQDISNYLN</u>WYQQKPGKAPKLLIY<u>DASNLAT</u>GVPSRFSGS<br>GSGTDFTFTISSLQPEDIATYYC<u>QQSLDLPPT</u>FGGGTKVEIK (SEQ ID NO: 13) |

TABLE 1A-continued

| Exemplary | ALK7-binding proteins |
|---|---|

C02

| | |
|---|---|
| VH FR1 | QLQLQESGPGLVKPSETLSLTCTVSGGSIS (SEQ ID NO: 24) |
| VH CDR1 | SSSYYWG (SEQ ID NO: 19) |
| VH FR2 | WIRQPPGKGLEWIG (SEQ ID NO: 25) |
| VH CDR2 | NIYYSGSTYYNPSLKS (SEQ ID NO: 20) |
| VH FR3 | RVTISVDTSKNQFSLKLSSVTAADTAVYYCAR (SEQ ID NO: 26) |
| VH CDR3 | DGRYQSATADYYYGMDV (SEQ ID NO: 21) |
| VH FR4 | WGQGTTVTVSS (SEQ ID NO: 27) |
| VH ABRs | ABR1:GSISSSSYYWG (SEQ ID NO: 76)　　　ABR2: NIYYSGSTYYNPSLKS (SEQ ID NO: 77)<br>ABR3: ARDGRYQSATADYYYGMDV (SEQ ID NO: 78) |
| VH DNA | CAGCTGCAGCTGCAGGAGTCGGGCCCAGGACTGGTGAAGCCTTCGGAGACCCTGTCCCTCA<br>CCTGCACTGTCTCTGGTGGCTCCATCAGCAGTAGTAGTTACTACTGGGGCTGGATCCGCCAG<br>CCCCCAGGGAAGGGGCTGGAGTGGATTGGGAACATCTATTATAGTGGGAGCACCTACTACA<br>ACCCGTCCCTCAAGAGTCGAGTCACCATATCCGTAGACACGTCCAAGAACCAGTTCTCCCTG<br>AAGCTGAGTTCTGTGACCGCCGCAGACACGGCGGTGTACTACTGCGCCAGAGACGGCAGAT<br>ACCAAAGCGCCACAGCCGATTACTATTACGGTATGGATGTCTGGGGCCAGGGAACAACTGT<br>CACCGTCTCCTCA (SEQ ID NO: 23) |
| VH Protein | QLQLQESGPGLVKPSETLSLTCTVSGGSIS<u>SSSYYWG</u>WIRQPPGKGLEWIG<u>NIYYSGSTYYNPSLK</u><u>S</u>RVTISVDTSKNQFSLKLSSVTAADTAVYYCAR<u>DGRYQSATADYYYGMDV</u>WGQGTTVTVSS<br>(SEQ ID NO: 22) |
| VL FR1 | EIVLTQSPGTLSLSPGERATLSC (SEQ ID NO: 33) |
| VL CDR1 | RASQSVSSSYLA (SEQ ID NO: 28) |
| VL FR2 | WYQQKPGQAPRLLIY (SEQ ID NO: 34) |
| VL CDR2 | GASSRAT (SEQ ID NO: 29) |
| VL FR3 | GIPDRFSGSGSGTDFTLTISRLEPEDFAVYYC (SEQ ID NO: 35) |
| VL CDR3 | QQVFSYPFT (SEQ ID NO: 30) |
| VL FR4 | FGGGTKVEIK (SEQ ID NO: 36) |
| VL DNA | GAAATTGTGTTGACGCAGTCTCCAGGCACCCTGTCTTTGTCTCCAGGGGAAAGAGCCACCCT<br>CTCCTGCAGGGCCAGTCAGAGTGTTAGCAGCAGCTACTTAGCCTGGTACCAGCAGAAACCTG<br>GCCAGGCTCCCAGGCTCCTCATCTATGGTGCATCCAGCAGGGCCACTGGCATCCCAGACAGG<br>TTCAGTGGCAGTGGGTCTGGGACAGACTTCACTCTCACCATCAGCAGACTGGAGCCTGAAGA<br>TTTTGCAGTGTATTACTGTCAGCAGGTCTTCAGTTACCCTTTCACTTTTGGCGGAGGGACCAA<br>GGTTGAGATCAAA (SEQ ID NO: 32) |
| VL Protein | EIVLTQSPGTLSLSPGERATLSC<u>RASQSVSSSYLA</u>WYQQKPGQAPRLLIY<u>GASSRAT</u>GIPDRFSGS<br>GSGTDFTLTISRLEPEDFAVYYCQQVFSYPFTFGGGTKVEIK (SEQ ID NO:31) |

D04

| | |
|---|---|
| VH FR1 | EVQLLESGGGLVQPGGSLRLSCAASGFTFS (SEQ ID NO: 42) |
| VH CDR1 | SYAMS (SEQ ID NO: 37) |
| VH FR2 | WVRQAPGKGLEWVS (SEQ ID NO: 43) |
| VH CDR2 | AISGSGGSTYYADSVKG (SEQ ID NO: 38) |
| VH FR3 | RFTISRDNSKNTLYLQMNSLRAEDTAVYYCAR (SEQ ID NO: 44) |
| VH CDR3 | RYRGVSFDI (SEQ ID NO: 39) |
| VH FR4 | WGRGTMVTVSS (SEQ ID NO: 45) |
| VH ABRs | ABR1: FTFSSYAMS (SEQ ID NO: 79)　　　ABR2: AISGSGGSTYYADSVKG (SEQ ID NO: 80)<br>ABR3: ARRYRGVSFDI (SEQ ID NO: 81) |
| VH DNA | GAGGTGCAGCTGTTGGAGTCTGGGGGAGGCTTGGTACAGCCTGGGGGGTCCCTGAGACTCT<br>CCTGTGCAGCCTCTGGATTCACCTTTAGCAGCTATGCCATGAGCTGGGTCCGCCAGGCTCCA<br>GGGAAGGGGCTGGAGTGGGTCTCAGCTATTAGTGGTAGTGGTGGTAGCACATACTACGCAG<br>ACTCCGTGAAGGGCCGGTTCACCATCTCCAGAGACAATTCCAAGAACACGCTGTATCTGCAA |

TABLE 1A-continued

| Exemplary | ALK7-binding proteins |
|---|---|
| | ATGAACAGCCTGAGAGCCGAGGACACGGCGGTGTACTACTGCGCCAGGAGATACAGAGGA<br>GTGTCATTCGACATATGGGGTCGGGGTACAATGGTCACCGTCTCCTCA (SEQ ID NO: 41) |
| VH Protein | EVQLLESGGGLVQPGGSLRLSCAASGFTFS<u>SYAMS</u>WVRQAPGKGLEWVS<u>AISGSGGSTYYADSV<br>KG</u>RFTISRDNSKNTLYLQMNSLRAEDTAVYYCAR<u>RYRGVSFDI</u>WGRGTMVTVSS (SEQ ID NO: 40) |
| VL FR1 | EIVLTQSPGTLSLSPGERATLSC (SEQ ID NO: 51) |
| VL CDR1 | RASQSVSSSYLA (SEQ ID NO: 46) |
| VL FR2 | WYQQKPGQAPRLLIY (SEQ ID NO: 52) |
| VL CDR2 | GASSRAT (SEQ ID NO: 47) |
| VL FR3 | GIPDRFSGSGSGTDFTLTISRLEPEDFAVYYC (SEQ ID NO: 53) |
| VL CDR3 | QQDSIDIT (SEQ ID NO: 48) |
| VL FR4 | FGGGTKVEIK (SEQ ID NO: 54) |
| VL DNA | GAAATTGTGTTGACGCAGTCTCCAGGCACCCTGTCTTTGTCTCCAGGGGAAAGAGCCACCCT<br>CTCCTGCAGGGCCAGTCAGAGTGTTAGCAGCAGCTACTTAGCCTGGTACCAGCAGAAACCTG<br>GCCAGGCTCCCAGGCTCCTCATCTATGGTGCATCCAGCAGGGCCACTGGCATCCCAGACAGG<br>TTCAGTGGCAGTGGGTCTGGGACAGACTTCACTCTCACCATCAGCAGACTGGAGCCTGAAGA<br>TTTTGCAGTGTATTACTGTCAGCAGGACTCCATCGACATCACTTTTGGCGGAGGGACCAAGG<br>TTGAGATCAAA (SEQ ID NO: 50) |
| VL Protein | EIVLTQSPGTLSLSPGERATLSC<u>RASQSVSSSYLA</u>WYQQKPGQAPRLLIY<u>GASSRAT</u>GIPDRFSGS<br>GSGTDFTLTISRLEPEDFAVYYC<u>QQDSIDIT</u>FGGGTKVEIK (SEQ ID NO: 49) |
| | H03 |
| VH FR1 | EVQLLESGGGLVQPGGSLRLSCAASGFTFS (SEQ ID NO: 60) |
| VH CDR1 | SYAMS (SEQ ID NO: 55) |
| VH FR2 | WVRQAPGKGLEWVS (SEQ ID NO: 61) |
| VH CDR2 | AISGSGGSTYYADSVKG (SEQ ID NO: 56) |
| VH FR3 | RFTISRDNSKNTLYLQMNSLRAEDTAVYYCAR (SEQ ID NO: 62) |
| VH CDR3 | PYQARAFDI (SEQ ID NO: 57) |
| VH FR4 | WGQGTMVTVSS (SEQ ID NO: 63) |
| VH ABRs | ABR1: FTFSSYAMS (SEQ ID NO: 82)    ABR2: AISGSGGSTYYADSVKG (SEQ ID NO: 83)<br>ABR3: ARPYQARAFDI (SEQ ID NO: 84) |
| VH DNA | GAGGTGCAGCTGTTGGAGTCTGGGGGAGGCTTGGTACAGCCTGGGGGGTCCCTGAGACTCT<br>CCTGTGCAGCCTCTGGATTCACCTTTAGCAGCTATGCCATGAGCTGGGTCCGCCAGGCTCCA<br>GGGAAGGGGCTGGAGTGGGTCTCAGCTATTAGTGGTAGTGGTGGTAGCACATACTACGCAG<br>ACTCCGTGAAGGGCCGGTTCACCATCTCCAGAGACAATTCCAAGAACACGCTGTATCTGCAA<br>ATGAACAGCCTGAGAGCCGAGGACACGGCGGTGTACTACTGCGCCAGACCTTACCAAGCCA<br>GAGCCTTTGATATTTGGGGTCAGGGTACAATGGTCACCGTCTCCTCA (SEQ ID NO: 59) |
| VH Protein | EVQLLESGGGLVQPGGSLRLSCAASGFTFS<u>SYAMS</u>WVRQAPGKGLEWVS<u>AISGSGGSTYYADSV<br>KG</u>RFTISRDNSKNTLYLQMNSLRAEDTAVYYCAR<u>PYQARAFDI</u>WGQGTMVTVSS (SEQ ID NO: 58) |
| VL FR1 | EIVLTQSPGTLSLSPGERATLSC (SEQ ID NO: 51) |
| VL CDR1 | RASQSVSSSFLA (SEQ ID NO: 64) |
| VL FR2 | WYQQKPGQAPRLLIY (SEQ ID NO: 52) |
| VL CDR2 | GASSRAT (SEQ ID NO: 65) |
| VL FR3 | GIPDRFSGSGSGTDFTLTISRLEPEDFAVYYC (SEQ ID NO: 53) |
| VL CDR3 | QQYVVAPIT (SEQ ID NO: 66) |
| VL FR4 | FGGGTKVEIK (SEQ ID NO: 54) |
| VL DNA | GAAATTGTGTTGACGCAGTCTCCAGGCACCCTGTCTTTGTCTCCAGGGGAAAGAGCCACCCT<br>CTCCTGCAGGGCCAGTCAGAGTGTTAGCAGCAGCTTCTTAGCCTGGTACCAGCAGAAACCTG<br>GCCAGGCTCCCAGGCTCCTCATCTATGGTGCATCCAGCAGGGCCACTGGCATCCCAGACAGG |

TABLE 1A-continued

| Exemplary | ALK7-binding proteins |
|---|---|
| | TTCAGTGGCAGTGGGTCTGGGACAGACTTCACTCTCACCATCAGCAGACTGGAGCCTGAAGA<br>TTTTGCAGTGTATTACTGTCAGCAGTACGTCGTCGCCCCTATCACTTTTGGCGGAGGGACCA<br>AGGTTGAGATCAAA (SEQ ID NO: 68) |
| VL Protein | EIVLTQSPGTLSLSPGERATLSC<u>RASQSVSSSFLA</u>WYQQKPGQAPRLLIY<u>GASSRAT</u>GIPDRFSGSG<br>SGTDFTLTISRLEPEDFAVYYC<u>QQYVVAPIT</u>FGGGTKVEIK (SEQ ID NO: 67) |

TABLE 1B

Additional exemplary ALK7-binding proteins

J01 †

| VH FR1 | EVQLLESGGGLVQPGGSLRLSCAASGFTFS (SEQ ID NO:42) |
|---|---|
| VH CDR1 | SYAMS (SEQ ID NO: 37) |
| VH FR2 | WVRQAPGKGLEWVS (SEQ ID NO: 43) |
| VH CDR2 | AISGSGGSTYYADSVKG (SEQ ID NO: 56) |
| VH FR3 | RFTISRDNSKNTLYLQMNSLRAEDTAVYYCAK (SEQ ID NO: 93) |
| VH CDR3 | PSYQPIY (SEQ ID NO: 90) |
| VH FR4 | WGQGTLVTVSS (SEQ ID NO:94) |
| VH ABRs | ABR1: FTFSSYAMS (SEQ ID NO: 153)    ABR2: AISGSGGSTYYADSVKG (SEQ ID NO: 154)<br>ABR3: AKPSYQPIY (SEQ ID NO: 155) |
| VH DNA | GAGGTGCAGCTGTTGGAGTCTGGGGGAGGCTTGGTACAGCCTGGGGGGTCCCTGAGACTCT<br>CCTGTGCAGCCTCTGGATTCACCTTTAGCAGCTATGCCATGAGCTGGGTCCGCCAGGCTCCA<br>GGGAAGGGGCTGGAGTGGGTCTCAGCTATTAGTGGTAGTGGTGGTAGCACATACTACGCAG<br>ACTCCGTGAAGGGCCGGTTCACCATCTCCAGAGACAATTCCAAGAACACGCTGTATCTGCA<br>AATGAACAGCCTGAGAGCCGAGGACACGGCCGTGTACTACTGCGCCAAGCCTTCTTACCAA<br>CCAATATACTGGGGACAGGGTACATTGGTCACCGTCTCCTCA (SEQ ID NO: 151) |
| VH Protein | EVQLLESGGGLVQPGGSLRLSCAASGFTFS<u>SYAMS</u>WVRQAPGKGLEWVS<u>AISGSGGSTYYADS<br>VKG</u>RFTISRDNSKNTLYLQMNSLRAEDTAVYYCAK<u>PSYQPIY</u>WGQGTLVTVSS (SEQ ID<br>NO: 152) |
| VL FR1 | DIQMTQSPSSVSASVGDRVTITC (SEQ ID NO: 100) |
| VL CDR1 | RASQGISSWLA (SEQ ID NO: 95) |
| VL FR2 | WYQQKPGKAPKLLIY (SEQ ID NO: 16) |
| VL CDR2 | AASSLQS (SEQ ID NO: 96) |
| VL FR3 | GVPSRFSGSGSGTDFTLTISSLQPEDFATYYC (SEQ ID NO: 101) |
| VL CDR3 | QQAASYPLT (SEQ ID NO: 97) |
| VL FR4 | FGGGTKVEI (SEQ ID NO: 18) |
| VL DNA | GACATCCAGATGACCCAGTCTCCATCTTCCGTGTCTGCATCTGTAGGAGACAGAGTCACCAT<br>CACTTGTCGGGCGAGTCAGGGTATTAGCAGCTGGTTAGCCTGGTATCAGCAGAAACCAGGG<br>AAAGCCCCTAAGCTCCTGATCTATGCTGCATCCAGTTTGCAAAGTGGGGTCCCATCAAGGTT<br>CAGCGGCAGTGGATCTGGGACAGATTTCACTCTCACCATCAGCAGCCTGCAGCCTGAAGAT<br>TTTGCAACTTATTACTGTCAGCAGGCAGCCAGTTACCCTCTCACTTTTGGCGGAGGGACCAAG<br>GTTGAGATCAAA (SEQ ID NO: 99) |
| VL Protein | DIQMTQSPSSVSASVGDRVTITC<u>RASQGISSWLA</u>WYQQKPGKAPKLLIY<u>AASSLQS</u>GVPSRFSGS<br>GSGTDFTLTISSLQPEDFATYYC<u>QQAASYPLT</u>FGGGTKVEIK (SEQ ID NO: 98) |

K01

| VH FR1 | QVQLVQSGAEVKKPGSSVKVSCKASGGTFS (SEQ ID NO: 6) |
|---|---|
| VH CDR1 | NYAIS (SEQ ID NO: 156) |
| VH FR2 | WVRQAPGQGLEWMG (SEQ ID NO: 7) |
| VH CDR2 | GIIPIFGTANYAQKFQG (SEQ ID NO: 157) |
| VH FR3 | RVTITADESTSTAYMELSSLRSEDTAVYYCAR (SEQ ID NO: 8) |
| VH CDR3 | DPREYIHVFDI (SEQ ID NO: 104) |
| VH FR4 | WGQGTMVTVSS (SEQ ID NO: 9) |

TABLE 1B-continued

Additional exemplary ALK7-binding proteins

| | |
|---|---|
| VH ABRs | ABR1: GTFSNYAIS (SEQ ID NO: 160)  ABR2: GIIPIFGTANYAQKFQG (SEQ ID NO: 161)<br>ABR3: ARDPREYIHVFDI (SEQ ID NO: 162) |
| VH DNA | CAGGTGCAGCTGGTGCAGTCTGGGGCTGAGGTGAAGAAGCCTGGGTCCTCGGTGAAGGTCT<br>CCTGCAAGGCTTCTGGAGGCACCTTCAGCAACTATGCTATCAGCTGGGTGCGACAGGCCCCT<br>GGACAAGGGCTTGAGTGGATGGGAGGGATCATCCCTATCTTTGGTACAGCAAACTACGCAC<br>AGAAGTTCCAGGGCAGAGTCACGATTACCGCGGACGAATCCACGAGCACAGCCTACATGGA<br>GCTGAGCAGCCTGAGATCTGAGGACACGGCCGTGTACTACTGCGCCAGAGATCCAAGAGAA<br>TATATCCACGTATTCGACATATGGGGTCAGGGTACAATGGTCACCGTCTCCTCA (SEQ ID<br>NO: 158) |
| VH Protein | QVQLVQSGAEVKKPGSSVKVSCKASGGTFS<u>NYAIS</u>WVRQAPGQGLEWMG<u>GIIPIFGTANYAQKF<br>QG</u>RVTITADESTSTAYMELSSLRSEDTAVYYCAR WGQGTMVTVSS (SEQ ID<br>NO: 159) |
| VL FR1 | DIQMTQSPSSLSASVGDRVTITC (SEQ ID NO: 15) |
| VL CDR1 | RASQSISSYLN (SEQ ID NO: 107) |
| VL FR2 | WYQQKPGKAPKLLIY (SEQ ID NO: 16) |
| VL CDR2 | GASSLQS (SEQ ID NO: 108) |
| VL FR3 | GVPSRFSGSGSGTDFTLTISSLQPEDFATYYC (SEQ ID NO: 112) |
| VL CDR3 | QQAYSFPWT (SEQ ID NO: 109) |
| VL FR4 | FGGGIKVEIK (SEQ ID NO: 113) |
| VL DNA | GACATCCAGATGACCCAGTCTCCATCCTCCCTGTCTGCATCTGTAGGAGACAGAGTCACC<br>ATCACTTGCCGGGCAAGTCAGAGCATTAGCAGCTATTTAAATTGGTATCAGCAGAAACCA<br>GGGAAAGCCCCTAAGCTCCTGATCTATGGTGCATCCAGTTTGCAAAGTGGGGTCCCATCA<br>AGGTTCAGTGGCAGTGGATCTGGGACAGATTTCACTCTCACCATCAGCAGTCTGCAACCT<br>GAAGATTTTGCAACTTACTACTGTCAGCAAGCATACAGTTTCCCTTGGACTTTTGGCGGA<br>GGGATCAAGGTTGAGATCAAA (SEQ ID NO: 111) |
| VL Protein | DIQMTQSPSSLSASVGDRVTITC<u>RASQSISSYLN</u>WYQQKPGKAPKLLIY<u>GASSLQS</u>GVPSRFSGSG<br>SGTDFTLTISSLQPEDFATYYC<u>QQAYSFPWT</u>FGGGIKVEIK (SEQ ID NO: 110) |

L01

| | |
|---|---|
| VH FR1 | QVQLVQSGAEVKKPGSSVKVSCKASGGTFS (SEQ ID NO: 6) |
| VH CDR1 | SYAIS (SEQ ID NO:1) |
| VH FR2 | WVRQAPGQGLEWMG (SEQ ID NO: 7) |
| VH CDR2 | SIIPIFGTANYAQKFQG (SEQ ID NO: 163) |
| VH FR3 | RVTITADESTSTAYMELSSLRSEDTAVYYCAR (SEQ ID NO: 8) |
| VH CDR3 | DPVGARYEVFDY (SEQ ID NO: 164) |
| VH FR4 | WGQGTLVTVSS (SEQ ID NO: 94) |
| VH ABRs | ABR1: GTFSSYAIS (SEQ ID NO: 172)  ABR2: SIIPIFGTANYAQKFQG (SEQ ID NO: 173)<br>ABR3: ARDPVGARYEVFDY (SEQ ID NO: 174) |
| VH DNA | CAGGTGCAGCTGGTGCAGTCTGGGGCTGAGGTGAAGAAGCCTGGGTCCTCGGTGAAGGTCT<br>CCTGCAAGGCTTCTGGAGGCACCTTCAGCAGCTATGCTATCAGCTGGGTGCGACAGGCCCCT<br>GGACAAGGGCTTGAGTGGATGGGAAGCATCATCCCTATCTTTGGTACAGCAAACTACGCAC<br>AGAAGTTCCAGGGCAGAGTCACGATTACCGCGGACGAATCCACGAGCACAGCCTACATGGA<br>GCTGAGCAGCCTGAGATCTGAGGACACGGCCGTGTACTACTGCGCCAGAGACCCTGTCGGA<br>GCAAGATACGAGGTTTTCGATTACTGGGGACAGGGTACATTGGTCACCGTCTCCTCA (SEQ<br>ID NO: 165) |
| VH Protein | QVQLVQSGAEVKKPGSSVKVSCKASGGTFS<u>SYAIS</u>WVRQAPGQGLEWMG<u>SIIPIFGTANYAQKF<br>QG</u>RVTITADESTSTAYMELSSLRSEDTAVYYCAR<u>DPVGARYEVFDY</u>WGQGTLVTVSS (SEQ ID<br>NO: 166) |
| VL FR1 | EIVMTQSPATLSVSPGERATLSC (SEQ ID NO: 150) |
| VL CDR1 | RASQSVSSNLA (SEQ ID NO: 167) |
| VL FR2 | WYQQKPGQAPRLLIY (SEQ ID NO: 34) |
| VL CDR2 | SASTRAT (SEQ ID NO: 168) |

TABLE 1B-continued

Additional exemplary ALK7-binding proteins

| | |
|---|---|
| VL FR3 | GIPARFSGSGSGTEFTLTISSLQSEDFAVYYC (SEQ ID NO: 151) |
| VL CDR3 | QQANTFPLT (SEQ ID NO: 169) |
| VL FR4 | FGGGTKVEIK (SEQ ID NO: 54) |
| VL DNA | GAAATAGTGATGACGCAGTCTCCAGCCACCCTGTCTGTGTCTCCAGGGGAAAGAGCCACCCT<br>CTCCTGCAGGGCCAGTCAGAGTGTTAGCAGCAACTTAGCCTGGTACCAGCAGAAACCTGGC<br>CAGGCTCCCAGGCTCCTCATCTATAGCGCATCCACCAGGGCCACTGGTATCCCAGCCAGGTT<br>CAGTGGCAGTGGGTCTGGGACAGAGTTCACTCTCACCATCAGCAGCCTGCAGTCTGAAGATT<br>TTGCAGTTTATTACTGTCAGCAGGCCAATACCTTCCCTCTCACTTTTGGCGGAGGGACCAAG<br>GTTGAGATCAAA (SEQ ID NO: 170) |
| VL Protein | EIVMTQ SPATLSVSPGERATLSCRASQSVSSNLAWYQQKPGQAPRLLIYSASTRATGIPARFSGSG<br>SGTEFTLTISSLQSEDFAVYYCQQANTFPLTFGGGTKVEIK (SEQ ID NO: 171) |

SPR (BIACORE™-based analysis) and a cell-based lipolysis inhibition assay was used to more fully characterize and exemplary set of the ALK7-binding proteins described in Table 1A, Table 1B, or Table 3.

Surface Plasmon Resonance Analysis

Experiments were performed using a Biacore T100/T200 biosensor (Biacore/GE Healthcare) at 25 and 37° C. ALK7 antibodies were captured on custom made FAB chip. A concentration series of ALK7-Fc comprising protein was injected over the flow cells at a flow rate of 50 µl/ml. To obtain kinetic rate constants the corrected data were fit to a 1:1 interaction model using BiaEvaluation software (GE Healthcare). The equilibrium binding constant KD was determined by the ratio of binding rate constants kd/ka.

Lipolysis Inhibition Assay

Lipolysis is the hydrolysis of triglycerides within the cell into glycerol and free fatty acids. The glycerol and free fatty acids are then released into the bloodstream or culture media. While lipolysis occurs in essentially all cells, it is most abundant in white and brown adipocytes. 3T3-L1 cells (supplied by ATCC; ATCC® CL-173™) were grown in Dulbecco's Modified Eagle Medium (ATCC; ATCC® 30-2002™) containing 10% Bovine Serum (Life Technologies; 16170-060) until reaching confluency. To induce differentiation, at 2 days post-confluency medium was replaced by fresh Dulbecco's Modified Eagle Medium (ATCC; ATCC® 30-2002™) containing 10% fetal Bovine serum (Life Technologies; Ser. No. 10/082,147), dexamethasone (Sigma, D8893), IBMX (Sigma, 17018) and insulin (Sigma, 10516) for 2 weeks. Accumulation of lipid droplets on the cells, as determined by microscopy, was used to confirm a complete differentiation into mature adipocyte cells. Adipocytes were treated overnight with vehicle (PBS), activin B (50 ng/ml) or co-treated with activin B (50 ng/ml) and ALK7 antibodies (5 µg/ml). Cells were washed two times with PBS and incubated with lipolysis assay buffer (supplied by Abcam; ab185433). Lipolysis assay buffer was collected after 3 hours and glycerol levels were measured according to manufacturer's instruction (Abcam; ab185433).

Results of the SPR are presented in Table 2A and 2B and cell-based lipolysis inhibition assay for exemplary ALK-7 binding proteins are presented in Table 2A.

Results of the SPR and cell-based lipolysis inhibition assay for exemplary ALK-7 binding proteins are presented in Table 3.

TABLE 2A

Binding characterization and activity of exemplary ALK7-binding proteins

| | Binding to human ALK7-Fc comprising protein | | | Binding to rat Alk7-Fc comprising protein | | | Increase in lipolysis activity |
|---|---|---|---|---|---|---|---|
| | $k_{on}$ (M$^{-1}$s$^{-1}$) | $k_{off}$ (s$^{-1}$) | $K_D$ (nM) | $k_{on}$ (M$^{-1}$s$^{-1}$) | koff (s$^{-1}$) | $K_D$ (nM) | (%) |
| C02 | $2.31 \times 10^4$ | $1.42 \times 10^{-3}$ | 61.2 | N/A | | | 55.8% |
| D04 | $7.40 \times 10^4$ | $3.78 \times 10^{-3}$ | 51.1 | $6.13 \times 10^3$ | $1.38 \times 10^{-3}$ | 225 | 109.2% |
| G04 | $8.96 \times 10^4$ | $2.22 \times 10^{-2}$ | 247 | N/A | | | 45.8% |
| H03 | $1.79 \times 10^5$ | $4.32 \times 10^{-3}$ | 24.1 | $1.07 \times 10^4$ | $1.54 \times 10^{-3}$ | 144 | 91.8% |

TABLE 2B

Binding characterization of exemplary ALK7-binding proteins

| | Binding to human ALK7-Fc comprising protein | | | Binding to rat Alk7-Fc comprising protein | | |
|---|---|---|---|---|---|---|
| | $k_{on}$ (M$^{-1}$s$^{-1}$) | $k_{off}$ (s$^{-1}$) | $K_D$ (nM) | $k_{on}$ (M$^{-1}$ s$^{-1}$) | koff (s$^{-1}$) | $K_D$ (nM) |
| J01 | | N/A | | $1.62 \times 10^4$ | $4.78 \times 10^{-2}$ | 29.5 |
| K01 | $4.56 \times 10^4$ | $9.16 \times 10^{-3}$ | 200.8 | $1.71 \times 10^4$ | $1.39 \times 10^{-4}$ | 8.14 |
| L01 | $2.43 \times 10^4$ | $3.67 \times 10^4$ | 15.1 | $1.18 \times 10^4$ | $2.71 \times 10^{-4}$ | 22.9 |

ALK7 signaling is thought to suppress lipolysis and to consequently lead to fat accumulation in adipocytes and adipose tissue. The ability of antibodies H03, D04, C02, and G04 to interfere with ALK7-mediated inhibition of lipolysis was assessed in a cell-based lipolysis inhibition assay. The antibodies H03, D04, C02, and G04 increased lipolysis activity by 91.8%, 109.2%, 55.8%, and 45.8%, respectively. Accordingly, these data indicate that ALK7 antibodies can be used to antagonize ALK7-mediated suppression of lipolysis and thereby increase fatty acid breakdown in adipocytes. Together, these data indicate that ALK7 antibodies may be used to treat a variety of disorder or conditions associated with low lipolysis activity and/or excessive fatty acid accumulation in cells, particularly adipocytes (adipose cells), including for example, obesity, diabetes, insulin resistance; metabolic syndrome fatty liver disease and other metabolic diseases or conditions.

The extracellular domain of human ALK7 (SEQ ID NO: 85) and rat ALK7 (SEQ ID NO: 86) share 97% sequence identity. The binding of antibodies H03, G04. C02 and D04 to human ALK7 and rat ALK7 was determined using SPR. The antibodies H03, D04, K01, and L01 bind to both human ALK7 and rat ALK7. F03 and C02 only bound human ALK7. J01 only bound rat ALK7.

Example 3. Binding Optimization of ALK7 Antibodies

Binding optimization of naïve clones was carried out utilizing three maturation strategies: light chain diversification; diversification of CDRH and/CDRH2; and performing sequential VH and VL mutagenesis.

Light chain diversification: Heavy chain plasmids were extracted naïve outputs (described above) and transformed into a light chain library with a diversity of $1 \times 10^6$. Selections were performed as described above with one round of MACS sorting and two rounds of FACS sorting using 10 nM or 1 nM biotinylated ALK7-Fc antigen (for respective rounds.

CDRH1 and CDRH2 selection: The CDRH3s from clones selected from the light chain diversification procedure of was recombined into a premade library with CDRH1 and CDRH2 variants of a diversity of $1 \times 10^8$ and selections were performed using ALK7, as described above. Affinity pressures were applied by incubating the biotinylated antigen-antibody yeast complex with unbiotinylated antigen for different amounts of time to select for the highest affinity antibodies.

VHmut/VKmut selection: Clones obtained from the CDRH1 and CDRH2 selection procedure were subject to additional rounds of affinity maturation via error prone PCR-based mutagenesis of the heavy chain and/or light chain. Selections were performed using ALK7 as antigen generally as described in Example 2 above, but with the addition of employing FACS sorting for all selection rounds. Antigen concentration was reduced and cold antigen competition times were increased to pressure further for optimal affinity.

The sequence of exemplary optimized ALK7 antibodies is provided in Table 3.

TABLE 3

Exemplary affinity matured ALK7-binding proteins

J02

| | | |
|---|---|---|
| VH FR1 | EVQLLESGGGLVQPGGSLRLSCAASGFTFS (SEQ ID NO: 42) | |
| VH CDR1 | VYAMS (SEQ ID NO: 88) | |
| VH FR2 | WVRQAPGKGLEWVS (SEQ ID NO: 43) | |
| VH CDR2 | AISGSGDSTVYADSVKG (SEQ ID NO: 89) | |
| VH FR3 | RFTISRDNSKNTLYLQMNSLRAEDTAVYYCAK (SEQ ID NO: 93) | |
| VH CDR3 | PSYQPIY (SEQ ID NO: 90) | |
| VH FR4 | WGQGTLVTVSS (SEQ ID NO: 94) | |
| VH ABRs | ABR1: FTFSVYAMS (SEQ ID NO: 175) | ABR2: AISGSGDSTVYADSVKG (SEQ ID NO: 176) |
| | ABR3: AKPSYQPIY (SEQ ID NO: 177) | |
| VH DNA | GAGGTGCAGCTGTTGGAGTCTGGGGGAGGCTTGGTACAGCCTGGGGGGTCCCTGAGACTCT CCTGTGCAGCCTCTGGATTCACCTTTTCGGTGTATGCCATGAGCTGGGTCCGCCAGGCTCCA GGGAAGGGGCTGGAGTGGGTCTCAGCTATTAGTGGAAGTGGTGATAGCACAGTGTACGCAG ACTCCGTGAAGGGCCGGTTCACCATCTCCAGAGACAATTCCAAGAACACGCTGTATCTGCA AATGAACAGCCTGAGAGCCGAGGACACGGCGGTGTACTACTGCGCCAAGCCTTCTTACCAA CCAATATACTGGGGACAGGGTACATTGGTCACCGTCTCCTCA (SEQ ID NO: 92) | |
| VH Protein | EVQLLESGGGLVQPGGSLRLSCAASGFTFS<u>VYAMS</u>WVRQAPGKGLEWVS<u>AISGSGDSTVYADS VKG</u>RFTISRDNSKNTLYLQMNSLRAEDTAVYYCAK<u>PSYQPI</u>YWGQGTLVTVSS (SEQ ID NO: 91) | |
| VL FR1 | DIQMTQSPSSVSASVGDRVTITC (SEQ ID NO: 100) | |
| VL CDR1 | RASQGISSWLA (SEQ ID NO: 95) | |
| VL FR2 | WYQQKPGKAPKLLIY (SEQ ID NO: 16) | |
| VL CDR2 | AASSLQS (SEQ ID NO: 96) | |
| VL FR3 | GVPSRFSGSGSGTDFTLTISSLQPEDFATYYC (SEQ ID NO: 101) | |
| VL CDR3 | QQAASYPLT (SEQ ID NO: 97) | |

TABLE 3-continued

Exemplary affinity matured ALK7-binding proteins

| | |
|---|---|
| VL FR4 | FGGGTKVEIK (SEQ ID NO: 18) |
| VL DNA | GACATCCAGATGACCCAAAGCCCTAGTTCCGTCTCTGCAAGCGTGGGAGATAGGGTCACAA<br>TCACATGTAGAGCTTCTCAGGGGATCTCTAGCTGGCTGGCTTGGTATCAGCAGAAGCCCGGT<br>AAGGCCCCAAAGCTCTTGATATACGCCGCCTCTTCTCTTCAATCTGGGGTGCCATCCCGCTTC<br>TCAGGGAGCGGTAGCGGGACCGATTTCACCCTCACTATCAGCAGCCTGCAGCCTGAAGACTT<br>TGCTACCTACTACTGCCAGCAAGCCGCTTCTTATCCTCTGACTTTCGGTGGGGGTACTAAAGT<br>GGAGATTAAA (SEQ ID NO: 99) |
| VL Protein | DIQMTQSPSSVSASVGDRVTITC<u>RASQGISSWLA</u>WYQQKPGKAPKLLIY<u>AASSLQS</u>GVPSRFSGS<br>GSGTDFTLTISSLQPEDFATYYC<u>QQAASYPLT</u>FGGGTKVEIK (SEQ ID NO: 98) |

K02

| | |
|---|---|
| VH FR1 | QVQLVQSGAEVKKPGSSVKVSCKASGGTFS (SEQ ID NO: 6) |
| VH CDR1 | SSAIG (SEQ ID NO: 102) |
| VH FR2 | WVRQAPGQGLEWMG (SEQ ID NO: 7) |
| VH CDR2 | GIWPIFGTALYAQKFQG (SEQ ID NO: 103) |
| VH FR3 | RVTITADESTSTAYMELSSLRSEDTAVYYCAR (SEQ ID NO: 8) |
| VH CDR3 | DPREYIHVFDI (SEQ ID NO: 104) |
| VH FR4 | WGQGTMVTVSS (SEQ ID NO: 9) |
| VH ABRs | ABR1: GTFSSSAIG (SEQ ID NO: 178)      ABR2: GIWPIFGTALYAQKFQG (SEQ ID NO: 179)<br>ABR3: ARDPREYIHVFDI (SEQ ID NO: 180) |
| VH DNA | CAGGTGCAGCTGGTGCAGTCTGGGGCTGAGGTGAAGAAGCCTGGGTCCTCGGTGAAGGTCT<br>CCTGCAAGGCTTCTGGAGGCACCTTCAGCAGCAGTGCTATCGGGTGGGTGCGACAGGCCCCT<br>GGACAAGGGCTTGAGTGGATGGGAGGGATCTGGCCTATCTTTGGTACAGCACTTTACGCACA<br>GAAGTTCCAGGGCAGAGTCACGATTACCGCGGACGAATCCACGAGCACAGCCTACATGGAG<br>CTGAGCAGCCTGAGATCTGAGGACACGGCGGTGTACTACTGCGCCAGAGATCAAGAGAAT<br>ATATCCACGTATTCGACATATGGGGTCAGGGTACAATGGTCACCGTCTCCTCA (SEQ ID<br>NO: 106) |
| VH Protein | QVQLVQSGAEVKKPGSSVKVSCKASGGTFS<u>SSAIG</u>WVRQAPGQGLEWMG<u>GIWPIFGTALYAQK<br>F</u>RVTITADESTSTAYMELSSLRSEDTAVYYCAR<u>DPREYIHVFDI</u>WGQGTMVTVSS (SEQ ID<br>NO: 105) |
| VL FR1 | DIQMTQSPSSLSASVGDRVTITC (SEQ ID NO: 15) |
| VL CDR1 | RASQSISSYLN (SEQ ID NO: 107) |
| VL FR2 | WYQQKPGKAPKLLIY (SEQ ID NO: 16) |
| VL CDR2 | GASSLQS (SEQ ID NO: 108) |
| VL FR3 | GVPSRFSGSGSGTDFTLTISSLQPEDFATYYC (SEQ ID NO: 112) |
| VL CDR3 | QQAYSFPWT (SEQ ID NO: 109) |
| VL FR4 | FGGGIKVEIK (SEQ ID NO: 113) |
| VL DNA | GATATTCAGATGACACAGTCACCTAGCAGTCTGAGCGCATCAGTGGGTGATCGAGTGACAA<br>TCACTTGTAGAGCTTCCCAGTCTATTAGCTCATACCTGAACTGGTATCAGCAAAAGCCTGGG<br>AAGGCTCCTAAGCTGTTGATCTATGGAGCATCTAGCCTGCAGTCCGGCGTGCCATCCCGCTT<br>CAGCGGGAGCGGCTCCGGGACCGATTTTACCCTGACAATCTCTAGCCTGCAGCCTGAAGAC<br>TTTGCAACCTACTACTGCCAGCAGGCATACAGCTTCCCCTGGACATTCGGAGGTGGCATAAAA<br>GTTGAAATCAAA (SEQ ID NO: 111) |
| VL Protein | DIQMTQSPSSLSASVGDRVTITC<u>RASQSISSYLN</u>WYQQKPGKAPKLLIY<u>GASSLQS</u>GVPSRFSGSG<br>SGTDFTLTISSLQPEDFATYYC<u>QQAYSFPWT</u>FGGGIKVEIK (SEQ ID NO:110) |

G05

| | |
|---|---|
| VH FR1 | QVQLVQSGAEVKKPGSSVKVSCKASGGTFS (SEQ ID NO: 6) |
| VH CDR1 | GQAIS (SEQ ID NO: 114) |
| VH FR2 | WVRQAPGQGLEWMG (SEQ ID NO: 7) |
| VH CDR2 | GIIPSFGTARYAQKFQG (SEQ ID NO: 115) |
| VH FR3 | RVTITADESTSTAYMELSSLRSEDTAVYYCAR (SEQ ID NO: 119) |

TABLE 3-continued

Exemplary affinity matured ALK7-binding proteins

| | |
|---|---|
| VH CDR3 | TPYYDSSGYLDV (SEQ ID NO: 116) |
| VH FR4 | WGQGTMVTVS (SEQ ID NO: 120) |
| VH ABRs | ABR1: GTFSGQAIS (SEQ ID NO: 181)    ABR2: GIIPSFGTARYAQKFQG (SEQ ID NO: 182)<br>ABR3: ARTPYYDSSGYLDV (SEQ ID NO: 183) |
| VH DNA | CAGGTGCAGCTGGTGCAGTCTGGGGCTGAGGTGAAGAAGCCTGGGTCCTCGGTGAAGGTCT<br>CCTGCAAGGCTTCTGGAGGCACCTTCAGCGGTCAGGCTATCAGCTGGGTGCGACAGGCCCCT<br>GGACAAGGGCTTGAGTGGATGGGAGGGATCATCCCTTCGTTTGGTACAGCACGGTACGCAC<br>AGAAGTTCCAGGGCAGAGTCACGATTACCGCGGACGAATCCACGAGCACAGCCTACATGGA<br>GCTGAGCAGCCTGAGATCTGAGGACACGGCGGTGTACTACTGCGCCAGAACTCCTTACTACG<br>ACAGCAGCGGATACCTAGACGTATGGGGTCAGGGTACAATGGTCACCGTCTCCTCA (SEQ<br>ID NO: 118) |
| VH Protein | QVQLVQSGAEVKKPGSSVKVSCKASGGTFSGQAISWVRQAPGQGLEWMGGIIPSFGTARYAQK<br>FQGRVTITADESTSTAYMELSSLRSEDTAVYYCARTPYYDSSGYLDVWGQGTMVTVS (SEQ ID<br>NO: 117) |
| VL FR1 | DIQMTQSPSSLSASVGDRVTITC (SEQ ID NO: 15) |
| VL CDR1 | QASHDIDNYLN (SEQ ID NO: 121) |
| VL FR2 | WYQQKPGKAPKLLIY (SEQ ID NO: 16) |
| VL CDR2 | YASNLKT (SEQ ID NO: 122) |
| VL FR3 | GVPSRFSGSGSGTDFTFTISSLQPEDIATYYC (SEQ ID NO: 17) |
| VL CDR3 | QQSRASPPT (SEQ ID NO: 123) |
| VL FR4 | FGGGTKVEIK (SEQ ID NO: 18) |
| VL DNA | GACATCCAGATGACACAGTCCCCTAGCAGCTTGTCAGCCTCAGTGGGCGATAGAGTGACCAT<br>CACCTGTCAAGCCAGCCATGATATAGACAACTATCTCAATTGGTACCAGCAGAAACCAGGC<br>AAGGCACCAAAGCTCCTGATCTATTACGCCTCAAACCTTAAGACCGGCGTCCCAAGCCGGTT<br>TTCAGGCAGCGGCAGCGGGACAGATTTCACCTTCACAATTTCATCACTGCAACCTGAGGATA<br>TAGCCACTTACTATTGTCAGCAGAGCAGAGCCAGCCCCCCTACCTTCGGCGGCGGTACCAAA<br>GTTGAAATCAAG (SEQ ID NO: 125) |
| VL Protein | DIQMTQSPSSLSASVGDRVTITCQASHDIDNYLNWYQQKPGKAPKLLIYYASNLKTGVPSRFSGS<br>GSGTDFTFTISSLQPEDIATYYCQQSRASPPTFGGGTKVEIK (SEQ ID NO: 124) |
| | C03 |
| VH FR1 | QLQLQESGPGLVKPSETLSLTCTVS (SEQ ID NO: 130) |
| VH CDR1 | GGSISSSAY (SEQ ID NO: 125) |
| VH FR2 | YWAWIRQPPGKGLEWIG (SEQ ID NO: 131) |
| VH CDR2 | SIYLSGSTTYNPSLKS (SEQ ID NO: 126) |
| VH FR3 | RVTISVDTSKNQFSLKLSSVTAADTAVYYCAR (SEQ ID NO: 26) |
| VH CDR3 | DGRYQSRSPDYYYGMDV (SEQ ID NO: 127) |
| VH FR4 | WGQGTTVTVSS (SEQ ID NO: 27) |
| VH ABRs | ABR1: GSISSSAYYWA (SEQ ID NO: 184)    ABR2: SIYLSGSTTYNPSLKS (SEQ ID NO: 185)<br>ABR3: ARDGRYQSRSPDYYYGMDV (SEQ ID NO: 186) |
| VH DNA | CAGCTGCAGCTGCAGGAGTCGGGCCCAGGACTGGTGAAGCCTTCGGAGACCCTGTCCCTCA<br>CCTGCACTGTCTCTGGTGGCTCCATCAGCAGTAGTGCTTACTACTGGGCTGGATCCGCCAG<br>CCCCCAGGGAAGGGGCTGGAGTGGATTGGGAGTATCTATTTGAGTGGGAGCACCACTTACA<br>ACCCGTCCCTCAAGAGTCGAGTCACCATATCCGTAGACACGTCCAAGAACCAGTTCTCCCTG<br>AAGCTGAGTTCTGTGACCGCCGCAGACACGGCCGTGTACTACTGCGCCAGAGACGGCAGAT<br>ACCAAAGCAGGTCGCCGGATTACTATTACGGTATGGATGTCTGGGGCCAGGGAACAACGGT<br>CACCGTCTCCTCA (SEQ ID NO: 129) |
| VH Protein | QLQLQESGPGLVKPSETLSLTCTVSGGSISSSAYYWAWIRQPPGKGLEWIGSIYLSGSTTYNPSLK<br>SRVTISVDTSKNQFSLKLSSVTAADTAVYYCARDGRYQSRSPDYYYGMDVWGQGTTVTVSS<br>(SEQ ID NO: 128) |
| VL FR1 | EIVLTQSPGTLSLSPGERATLSC (SEQ ID NO: 33) |
| VL CDR1 | KASQSVSSSYLA (SEQ ID NO: 132) |

TABLE 3-continued

Exemplary affinity matured ALK7-binding proteins

| | |
|---|---|
| VL FR2 | WYQQKPGQAPRLLIY (SEQ ID NO: 34) |
| VL CDR2 | GAFSRAN (SEQ ID NO: 133) |
| VL FR3 | GIPDRFSGSGSGTDFTLTISRLEPEDFAVYYC (SEQ ID NO: 35) |
| VL CDR3 | QQLVSYPFT (SEQ ID NO: 134) |
| VL FR4 | FGGGTKVEIK (SEQ ID NO: 18) |
| VL DNA | GAGATAGTCTTGACCCAGTCACCAGGCACCCTTAGCTTGTCTCCCGGGGAACGCGCCACACT<br>CAGCTGTAAAGCCTCTCAGTCAGTTTCTAGTTCCTACCTCGCTTGGTATCAACAAAAGCCCG<br>GACAAGCACCAAGGCTGTTGATCTACGGAGCTTTCAGTCGCGCAAATGGCATTCCCGACCGA<br>TTCTCTGGCAGTGGTAGTGGCACCGACTTCACTCTCACAATTTCTAGGTTGGAACCTGAGGA<br>CTTTGCTGTGTACTACTGTCAACAACTGGTTTCTTATCCCTTTACATTCGGTGGCGGCACAAA<br>AGTCGAGATTAAA (SEQ ID NO: 136) |
| VL Protein | EIVLTQSPGTLSLSPGERATLSC<u>KASQSVSSSYLA</u>WYQQKPGQAPRLLIY<u>GAFSRAN</u>GIPDRFSGS<br>GSGTDFTLTISRLEPEDFAVYYC<u>QQLVSYPFT</u>FGGGTKVEIK (SEQ ID NO: 135) |

L02

| | |
|---|---|
| VH FR1 | QVQLVQSGAEVKKPGASVKVSCKASGYTFA (SEQ ID NO: 142) |
| VH CDR1 | GYNMH (SEQ ID NO: 137) |
| VH FR2 | WVRQAPGQGLEWVGII (SEQ ID NO: 143) |
| VH CDR2 | NPNSGW (SEQ ID NO: 138) |
| VH FR3 | TNYAQKFQGRVTMTRDTSVSAAYMELSRLRSDDTAVYYCAR (SEQ ID NO: 152) |
| VH CDR3 | DPVGARYEVFDY (SEQ ID NO: 139) |
| VH FR4 | WGQGTLVTVSS (SEQ ID NO: 144) |
| VH ABRs | ABR1: YTFAGYNMH (SEQ ID NO: 187)    ABR2: IINPNSGWTNYAQKFQG (SEQ ID NO: 188)<br>ABR3: ARDPVGARYEVFDY (SEQ ID NO: 189) |
| VH DNA | CAGGTGCAGCTGGTGCAGTCTGGGGCTGAGGTGAAGAAGCCTGGGGCCTCAGTGAAGGTCT<br>CCTGCAAGGCTTCTGGATACACCTTCGCTGGCTACAATATGCACTGGGTGCGACAGGCCCCT<br>GGACAAGGGCTTGAGTGGGTGGGAATTATCAACCCTAACAGTGGTTGGACAAACTATGCAC<br>AGAAGTTCCAGGGCAGGGTCACGATGACCAGGGACACGTCGTCAGCGCAGCCTACATGGA<br>GCTGAGCAGGCTGAGATCTGACGACACGGCGGTGTACTACTGCGCCAGAGACCCTGTCGGA<br>GCAAGATACGAGGTTTTCGATTACTGGGGACAGGGTACATTGGTCACCGTCTCCTCA (SEQ<br>ID NO: 141) |
| VH Protein | QVQLVQSGAEVKKPGASVKVSCKASGYTFA<u>GYNMH</u>WVRQAPGQGLEWVGII<u>NPNSGW</u>TNYA<br>QKFQGRVTMTRDTSVSAAYMELSRLRSDDTAVYYCAR<u>DPVGARYEVFDY</u>WGQGTLVTVSS<br>(SEQ ID NO: 140) |
| VL FR1 | EIVMTQSPATLSVSPGERATLSC (SEQ ID NO: 150) |
| VL CDR1 | RASQSVSSALA (SEQ ID NO: 145) |
| VL FR2 | WYQQKPGQAPRLLIY (SEQ ID NO: 34) |
| VL CDR2 | SAFTRAS (SEQ ID NO: 146) |
| VL FR3 | GIPARFSGSGSGTEFTLTISSLQSEDFAVYYC (SEQ ID NO: 151) |
| VL CDR3 | QQAWAFPLT (SEQ ID NO: 147) |
| VL FR4 | FGGGTKVEIK (SEQ ID NO: 18) |
| VL DNA | GAAATCGTGATGACCCAATCACCTGCCACTCTGTCTGTTAGCCCTGGGGAACGGGCCACCCT<br>CAGTTGTAGGGCCAGTCAGAGTGTTAGTTCAGCTTTGGCTTGGTATCAGCAGAAGCCCGGAC<br>AGGCCCCAAGGCTGCTGATCTACTCTGCTTTCACCCGCGCAAGCGGCATCCCCGCACGCTTT<br>AGCGGCTCCGGAAGCGGCACCGAGTTTACTCTTACTATTTCTTCTTTGCAGAGTGAGGATTTT<br>GCCGTGTACTACTGCCAGCAGGCTTGGGCATTTCCACTCACTTTCGGGGGCGGGACCAAGGT<br>CGAAATCAAG (SEQ ID NO: 149) |
| VL Protein | EIVMTQSPATLSVSPGERATLSC<u>RASQSVSSALA</u>WYQQKPGQAPRLLIY<u>SAFTRAS</u>GIPARFSGSG<br>SGTEFTLTISSLQSEDFAVYYC<u>QQAWAFPLT</u>FGGGTKVEIK (SEQ ID NO:148) |

SPR (BIACORE™-based analysis) was used to more fully characterize the affinity matured ALK7 antibodies described in Table 3.

Surface Plasmon Resonance Analysis

Experiments were performed using a Biacore T100/T200 biosensor (Biacore/GE Healthcare) at 25 and 37° C. ALK7 antibodies were captured on custom made FAB chip. A concentration series of ALK7-Fc comprising protein was injected over the flow cells at a flow rate of 50 µl/ml. To obtain kinetic rate constants the corrected data were fit to a 1:1 interaction model using BiaEvaluation software (GE Healthcare). The equilibrium binding constant KD was determined by the ratio of binding rate constants kd/ka.

Results of the SPR performed as described above are presented in Table 4.

TABLE 4

Binding characterization of exemplary affinity matured ALK7 antibodies

| | Binding to ALK7-Fc comprising protein (25° C.) | | | Parental |
|---|---|---|---|---|
| | $k_{on}$ (M$^{-1}$s$^{-1}$) | $k_{off}$ (s$^{-1}$) | $K_D$ (nM) | Antibody |
| J02 | $2.36 \times 10^4$ | $1.26 \times 10^{-4}$ | 5.33 | J01 |
| K02 | $2.35 \times 10^4$ | $2.91 \times 10^{-4}$ | 12.42 | K01 |
| G05 | $2.99 \times 10^4$ | $2.59 \times 10^{-5}$ | 0.87 | G04 |
| C03 | $3.83 \times 10^4$ | $1.27 \times 10^{-5}$ | 0.33 | C02 |
| L02 | $2.74 \times 10^4$ | $1.21 \times 10^{-5}$ | 0.44 | L01 |

Example 4. The Effects of ALK7 Abs on Adiposity and Lean Body Mass in Obese Mice Applicants investigated the effect of several human monoclonal ALK7 antibodies (ALK7 mAbs) on fat and lean tissue mass in a murine model of diet-induced obesity.

Male mice (n=8 per group) were assessed at baseline for fat and lean muscle amounts using NMR. Mice were then divided into different treatments groups: 1) mice fed a standard chow diet (SD) and treated subcutaneously twice per week with TBS vehicle; 2) mice fed a high fat diet (HFD) and treated subcutaneously twice per week with TBS vehicle; 3) HDF mice treated subcutaneously twice per week with 10 mg/kg of the ALK7 mAb J02; 4) HDF mice treated subcutaneously twice per week with 10 mg/kg of the ALK7 mAb K02; 5) HDF mice treated subcutaneously twice per week with 10 mg/kg of the ALK7 mAb G05; 6) HDF mice treated subcutaneously twice per week with 10 mg/kg of the ALK7 mAb C03; and 7) HDF mice treated subcutaneously twice per week with 10 mg/kg of the ALK7 mAb L02. After three weeks, mice were again subjected to whole-body NMR scan to assess for fat and lean tissue mass amounts, and these measurements were compared to the baseline amounts of fat and lean muscle.

TBS treated HFD mice displayed significantly higher amounts of adipose tissue compared to TBS treated SD mice (FIG. 1). On average, treatment with each ALK7 mAb resulted in significant less adipose tissue accumulation in HFD mice (approximately −30% less) compared to the TBS treated HFD mice (FIG. 1). In contrast, while all mice displayed increases in muscle mass from baseline, there was no significant difference among the treatment groups (FIG. 2).

Together, these data demonstrate that ALK7 mAbs can be used to reduce adipose levels in vivo. Therefore, the data indicate that ALK7 antibodies may be useful in treating various disorders and complications associated with undesirably high fat levels, particularly in obese patients. Moreover, the show that fat reduction may be achieved without concurrently increasing lean body mass, indicating that ALK7 Abs may be particularly useful in treating patients where it is desirable to reduce body fat content without also increasing muscle mass.

What is claimed is:

1. An activin receptor-like kinase 7 (ALK7)-binding protein comprising a heavy chain variable region (VH) comprising the amino acid sequence of SEQ ID NO: 105 and a light chain variable region (VL) comprising the amino acid sequence of SEQ ID NO: 110, wherein the protein binds to ALK7.

2. An activin receptor-like kinase 7 (ALK7)-binding protein comprising a set of CDRs in which:
   (i) VH-CDR1 comprises the amino acid sequence of SEQ ID NO: 102;
   (ii) VH-CDR2 comprises the amino acid sequence of SEQ ID NO: 103;
   (iii) VH-CDR3 comprises the amino acid sequence of SEQ ID NO:104
   (iv) VL-CDR1 comprises the amino acid sequence of SEQ ID NO: 107;
   (v) VL-CDR2 comprises the amino acid sequence of SEQ ID NO: 108; and
   (vi) VL-CDR3 comprises the amino acid sequence of SEQ ID NO: 109;
   wherein the protein binds to ALK7.

3. The ALK7-binding protein of claim 2, wherein the ALK7-binding protein is an antibody, wherein the antibody is a monoclonal antibody, a recombinant antibody, a humanized antibody, a chimeric antibody, a bi-specific antibody, a multi-specific antibody, or an ALK7-binding antibody fragment.

4. The ALK7-binding protein of claim 3, wherein the ALK7-binding antibody fragment is a Fab fragment, a Fab' fragment, a F(ab')2 fragment, a Fv fragment, a diabody, or a single chain antibody molecule.

5. The ALK7-binding protein of claim 3, wherein the antibody further comprises a heavy chain immunoglobulin constant domain selected from the group consisting of:
   (a) a human IgA constant domain;
   (b) a human IgD constant domain;
   (c) a human IgE constant domain;
   (d) a human IgG1 constant domain;
   (e) a human IgG2 constant domain;
   (f) a human IgG3 constant domain;
   (g) a human IgG4 constant domain; and
   (h) a human IgM constant domain.

6. The ALK7-binding protein of claim 3, wherein the antibody further comprises a light chain immunoglobulin constant domain selected from the group consisting of:
   (a) a human Ig kappa constant domain; and
   (b) a human Ig lambda constant domain.

7. The ALK7-binding protein of claim 3, wherein the antibody further comprises a human IgG1 heavy chain constant domain and a human lambda light chain constant domain.

* * * * *

SEQUENCE LISTING

```
<160> NUMBER OF SEQ ID NOS: 189

<210> SEQ ID NO 1
<211> LENGTH: 5
<212> TYPE: PRT
<213> ORGANISM: homo sapiens

<400> SEQUENCE: 1

Ser Tyr Ala Ile Ser
1               5

<210> SEQ ID NO 2
<211> LENGTH: 17
<212> TYPE: PRT
<213> ORGANISM: homo sapiens

<400> SEQUENCE: 2

Gly Ile Ile Pro Ile Phe Gly Thr Ala Ser Tyr Ala Gln Lys Phe Gln
1               5                   10                  15

Gly

<210> SEQ ID NO 3
<211> LENGTH: 12
<212> TYPE: PRT
<213> ORGANISM: homo sapiens

<400> SEQUENCE: 3
```

Thr Pro Tyr Tyr Asp Ser Ser Gly Tyr Leu Asp Val
1               5                   10

<210> SEQ ID NO 4
<211> LENGTH: 121
<212> TYPE: PRT
<213> ORGANISM: homo sapiens

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Ser Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Pro Tyr Tyr Asp Ser Ser Gly Tyr Leu Asp Val Trp Gly
            100                 105                 110

Gln Gly Thr Met Val Thr Val Ser Ser
        115                 120

<210> SEQ ID NO 5
<211> LENGTH: 363
<212> TYPE: DNA
<213> ORGANISM: homo sapiens

<400> SEQUENCE: 5
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatcccta tctttggtac agcaagctac     180
gcacagaagt tccagggcag agtcacgatt accgcggacg aatccacgag cacagcctac     240
atggagctga gcagcctgag atctgaggac acggcggtgt actactgcgc cagaactcct     300
tactacgaca gcagcggata cctagacgta tggggtcagg gtacaatggt caccgtctcc     360
tca                                                                  363

<210> SEQ ID NO 6
<211> LENGTH: 30
<212> TYPE: PRT
<213> ORGANISM: homo sapiens

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser
            20                  25                  30

<210> SEQ ID NO 7
<211> LENGTH: 14
<212> TYPE: PRT
<213> ORGANISM: homo sapiens

<400> SEQUENCE: 7

```
Trp Val Arg Gln Ala Pro Gly Gln Gly Leu Glu Trp Met Gly
1               5                   10
```

<210> SEQ ID NO 8
<211> LENGTH: 32
<212> TYPE: PRT
<213> ORGANISM: homo sapiens

<400> SEQUENCE: 8

```
Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30
```

<210> SEQ ID NO 9
<211> LENGTH: 11
<212> TYPE: PRT
<213> ORGANISM: homo sapiens

<400> SEQUENCE: 9

```
Trp Gly Gln Gly Thr Met Val Thr Val Ser Ser
1               5                   10
```

<210> SEQ ID NO 10
<211> LENGTH: 11
<212> TYPE: PRT
<213> ORGANISM: homo sapiens

<400> SEQUENCE: 10

```
Gln Ala Ser Gln Asp Ile Ser Asn Tyr Leu Asn
1               5                   10
```

<210> SEQ ID NO 11
<211> LENGTH: 7
<212> TYPE: PRT
<213> ORGANISM: homo sapiens

<400> SEQUENCE: 11

```
Asp Ala Ser Asn Leu Ala Thr
1               5
```

<210> SEQ ID NO 12
<211> LENGTH: 9
<212> TYPE: PRT
<213> ORGANISM: homo sapiens

<400> SEQUENCE: 12

```
Gln Gln Ser Leu Asp Leu Pro Pro Thr
1               5
```

<210> SEQ ID NO 13
<211> LENGTH: 107
<212> TYPE: PRT
<213> ORGANISM: homo sapiens

<400> SEQUENCE: 13

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45
```

```
Tyr Asp Ala Ser Asn Leu Ala Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Ser Leu Asp Leu Pro Pro
                 85                  90                  95

Thr Phe Gly Gly Gly Thr Lys Val Glu Ile Lys
                100                 105

<210> SEQ ID NO 14
<211> LENGTH: 321
<212> TYPE: DNA
<213> ORGANISM: homo sapiens

<400> SEQUENCE: 14
gacatccaga tgacccagtc tccatcctcc ctgtctgcat ctgtaggaga cagagtcacc      60
atcacttgcc aggcgagtca ggacattagc aactatttaa attggtatca gcagaaacca     120
gggaaagccc ctaagctcct gatctacgat gcatccaatt tggcaacagg ggtcccatca     180
aggttcagtg gaagtggatc tgggacagat tttactttca ccatcagcag cctgcagcct     240
gaagatattg caacatatta ctgtcagcag tccctcgacc tccctcctac ttttggcgga     300
gggaccaagg ttgagatcaa a                                               321

<210> SEQ ID NO 15
<211> LENGTH: 23
<212> TYPE: PRT
<213> ORGANISM: homo sapiens

<400> SEQUENCE: 15

Asp Ile Gln Met Thr Gln Ser Pro Ser Ser Leu Ser Ala Ser Val Gly
 1               5                  10                  15

Asp Arg Val Thr Ile Thr Cys
                 20

<210> SEQ ID NO 16
<211> LENGTH: 15
<212> TYPE: PRT
<213> ORGANISM: homo sapiens

<400> SEQUENCE: 16

Trp Tyr Gln Gln Lys Pro Gly Lys Ala Pro Lys Leu Leu Ile Tyr
 1               5                  10                  15

<210> SEQ ID NO 17
<211> LENGTH: 32
<212> TYPE: PRT
<213> ORGANISM: homo sapiens

<400> SEQUENCE: 17

Gly Val Pro Ser Arg Phe Ser Gly Ser Gly Ser Gly Thr Asp Phe Thr
 1               5                  10                  15

Phe Thr Ile Ser Ser Leu Gln Pro Glu Asp Ile Ala Thr Tyr Tyr Cys
                 20                  25                  30

<210> SEQ ID NO 18
<211> LENGTH: 10
<212> TYPE: PRT
<213> ORGANISM: homo sapiens

<400> SEQUENCE: 18
```

Phe Gly Gly Gly Thr Lys Val Glu Ile Lys
1               5                   10

<210> SEQ ID NO 19
<211> LENGTH: 7
<212> TYPE: PRT
<213> ORGANISM: homo sapiens

<400> SEQUENCE: 19

Ser Ser Ser Tyr Tyr Trp Gly
1               5

<210> SEQ ID NO 20
<211> LENGTH: 16
<212> TYPE: PRT
<213> ORGANISM: homo sapiens

<400> SEQUENCE: 20

Asn Ile Tyr Tyr Ser Gly Ser Thr Tyr Tyr Asn Pro Ser Leu Lys Ser
1               5                   10                  15

<210> SEQ ID NO 21
<211> LENGTH: 17
<212> TYPE: PRT
<213> ORGANISM: homo sapiens

<400> SEQUENCE: 21

Asp Gly Arg Tyr Gln Ser Ala Thr Ala Asp Tyr Tyr Gly Met Asp
1               5                   10                  15
Val

<210> SEQ ID NO 22
<211> LENGTH: 127
<212> TYPE: PRT
<213> ORGANISM: homo sapiens

<400> SEQUENCE: 22

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Arg Tyr Gln Ser Ala Thr Ala Asp Tyr Tyr Tyr
            100                 105                 110

Gly Met Asp Val Trp Gly Gln Gly Thr Thr Val Thr Val Ser Ser
        115                 120                 125

<210> SEQ ID NO 23
<211> LENGTH: 381
<212> TYPE: DNA
<213> ORGANISM: homo sapiens

<400> SEQUENCE: 23
cagctgcagc tgcaggagtc gggcccagga ctggtgaagc cttcggagac cctgtccctc     60

```
acctgcactg tctctggtgg ctccatcagc agtagtagtt actactgggg ctggatccgc    120
cagcccccag ggaagggct ggagtggatt gggaacatct attatagtgg gagcacctac    180
tacaacccgt ccctcaagag tcgagtcacc atatccgtag acacgtccaa gaaccagttc    240
tccctgaagc tgagttctgt gaccgccgca gacacggcgg tgtactactg cgccagagac    300
ggcagatacc aaagcgccac agccgattac tattacggta tggatgtctg gggccaggga    360
acaactgtca ccgtctcctc a                                              381
```

<210> SEQ ID NO 24
<211> LENGTH: 30
<212> TYPE: PRT
<213> ORGANISM: homo sapiens

<400> SEQUENCE: 24

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser
            20                  25                  30

<210> SEQ ID NO 25
<211> LENGTH: 14
<212> TYPE: PRT
<213> ORGANISM: homo sapiens

<400> SEQUENCE: 25

Trp Ile Arg Gln Pro Pro Gly Lys Gly Leu Glu Trp Ile Gly
1               5                   10

<210> SEQ ID NO 26
<211> LENGTH: 32
<212> TYPE: PRT
<213> ORGANISM: homo sapiens

<400> SEQUENCE: 26

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 27
<211> LENGTH: 11
<212> TYPE: PRT
<213> ORGANISM: homo sapiens

<400> SEQUENCE: 27

Trp Gly Gln Gly Thr Thr Val Thr Val Ser Ser
1               5                   10

<210> SEQ ID NO 28
<211> LENGTH: 12
<212> TYPE: PRT
<213> ORGANISM: homo sapiens

<400> SEQUENCE: 28

Arg Ala Ser Gln Ser Val Ser Ser Ser Tyr Leu Ala
1               5                   10

<210> SEQ ID NO 29
<211> LENGTH: 7
<212> TYPE: PRT
<213> ORGANISM: homo sapiens

<400> SEQUENCE: 29

Gly Ala Ser Ser Arg Ala Thr
1               5

<210> SEQ ID NO 30
<211> LENGTH: 9
<212> TYPE: PRT
<213> ORGANISM: homo sapiens

<400> SEQUENCE: 30

Gln Gln Val Phe Ser Tyr Pro Phe Thr
1               5

<210> SEQ ID NO 31
<211> LENGTH: 108
<212> TYPE: PRT
<213> ORGANISM: homo sapiens

<400> SEQUENCE: 31

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Val Phe Ser Tyr Pro
                85                  90                  95

Phe Thr Phe Gly Gly Gly Thr Lys Val Glu Ile Lys
            100                 105

<210> SEQ ID NO 32
<211> LENGTH: 324
<212> TYPE: DNA
<213> ORGANISM: homo sapiens

<400> SEQUENCE: 32
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag caggtcttca gttaccettt cacttttggc     300 ggagggacca aggttgagat caaa                                             324

<210> SEQ ID NO 33
<211> LENGTH: 23
<212> TYPE: PRT
<213> ORGANISM: homo sapiens

<400> SEQUENCE: 33

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 34
<211> LENGTH: 15
<212> TYPE: PRT
<213> ORGANISM: homo sapiens

<400> SEQUENCE: 34

Trp Tyr Gln Gln Lys Pro Gly Gln Ala Pro Arg Leu Leu Ile Tyr
1               5                   10                  15

<210> SEQ ID NO 35
<211> LENGTH: 32
<212> TYPE: PRT
<213> ORGANISM: homo sapiens

<400> SEQUENCE: 35

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 36
<211> LENGTH: 10
<212> TYPE: PRT
<213> ORGANISM: homo sapiens

<400> SEQUENCE: 36

Phe Gly Gly Gly Thr Lys Val Glu Ile Lys
1               5                   10

<210> SEQ ID NO 37
<211> LENGTH: 5
<212> TYPE: PRT
<213> ORGANISM: homo sapiens

<400> SEQUENCE: 37

Ser Tyr Ala Met Ser
1               5

<210> SEQ ID NO 38
<211> LENGTH: 17
<212> TYPE: PRT
<213> ORGANISM: homo sapiens

<400> SEQUENCE: 38

Ala Ile Ser Gly Ser Gly Gly Ser Thr Tyr Tyr Ala Asp Ser Val Lys
1               5                   10                  15

Gly

<210> SEQ ID NO 39
<211> LENGTH: 9
<212> TYPE: PRT
<213> ORGANISM: homo sapiens

<400> SEQUENCE: 39

Arg Tyr Arg Gly Val Ser Phe Asp Ile
1               5

<210> SEQ ID NO 40
<211> LENGTH: 118
<212> TYPE: PRT
<213> ORGANISM: homo sapiens

<400> SEQUENCE: 40

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Tyr Arg Gly Val Ser Phe Asp Ile Trp Gly Arg Gly Thr
            100                 105                 110

Met Val Thr Val Ser Ser
            115
```

<210> SEQ ID NO 41
<211> LENGTH: 354
<212> TYPE: DNA
<213> ORGANISM: homo sapiens

<400> SEQUENCE: 41

```
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggcggtgt actactgcgc caggagatac     300
agaggagtgt cattcgacat atggggtcgg ggtacaatgg tcaccgtctc ctca           354
```

<210> SEQ ID NO 42
<211> LENGTH: 30
<212> TYPE: PRT
<213> ORGANISM: homo sapiens

<400> SEQUENCE: 42

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30
```

<210> SEQ ID NO 43
<211> LENGTH: 14
<212> TYPE: PRT
<213> ORGANISM: homo sapiens

<400> SEQUENCE: 43

```
Trp Val Arg Gln Ala Pro Gly Lys Gly Leu Glu Trp Val Ser
1               5                   10
```

<210> SEQ ID NO 44
<211> LENGTH: 32
<212> TYPE: PRT
<213> ORGANISM: homo sapiens

<400> SEQUENCE: 44

Arg Phe Thr Ile Ser Arg Asp Asn Ser Lys Asn Thr Leu Tyr Leu Gln

```
1               5                   10                  15
Met Asn Ser Leu Arg Ala Glu Asp Thr Ala Val Tyr Tyr Cys Ala Arg
            20                  25                  30
```

<210> SEQ ID NO 45
<211> LENGTH: 11
<212> TYPE: PRT
<213> ORGANISM: homo sapiens

<400> SEQUENCE: 45

```
Trp Gly Arg Gly Thr Met Val Thr Val Ser Ser
1               5                   10
```

<210> SEQ ID NO 46
<211> LENGTH: 12
<212> TYPE: PRT
<213> ORGANISM: homo sapiens

<400> SEQUENCE: 46

```
Arg Ala Ser Gln Ser Val Ser Ser Ser Tyr Leu Ala
1               5                   10
```

<210> SEQ ID NO 47
<211> LENGTH: 7
<212> TYPE: PRT
<213> ORGANISM: homo sapiens

<400> SEQUENCE: 47

```
Gly Ala Ser Ser Arg Ala Thr
1               5
```

<210> SEQ ID NO 48
<211> LENGTH: 8
<212> TYPE: PRT
<213> ORGANISM: homo sapiens

<400> SEQUENCE: 48

```
Gln Gln Asp Ser Ile Asp Ile Thr
1               5
```

<210> SEQ ID NO 49
<211> LENGTH: 107
<212> TYPE: PRT
<213> ORGANISM: homo sapiens

<400> SEQUENCE: 49

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Ser Ile Asp Ile
                85                  90                  95

Thr Phe Gly Gly Gly Thr Lys Val Glu Ile Lys
            100                 105
```

```
<210> SEQ ID NO 50
<211> LENGTH: 321
<212> TYPE: DNA
<213> ORGANISM: homo sapiens

<400> SEQUENCE: 50
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag caggactcca tcgacatcac ttttggcgga     300
gggaccaagg ttgagatcaa a                                                321

<210> SEQ ID NO 51
<211> LENGTH: 23
<212> TYPE: PRT
<213> ORGANISM: homo sapiens

<400> SEQUENCE: 51

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 52
<211> LENGTH: 15
<212> TYPE: PRT
<213> ORGANISM: homo sapiens

<400> SEQUENCE: 52

Trp Tyr Gln Gln Lys Pro Gly Gln Ala Pro Arg Leu Leu Ile Tyr
1               5                   10                  15

<210> SEQ ID NO 53
<211> LENGTH: 32
<212> TYPE: PRT
<213> ORGANISM: homo sapiens

<400> SEQUENCE: 53

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 54
<211> LENGTH: 10
<212> TYPE: PRT
<213> ORGANISM: homo sapiens

<400> SEQUENCE: 54

Phe Gly Gly Gly Thr Lys Val Glu Ile Lys
1               5                   10

<210> SEQ ID NO 55
<211> LENGTH: 5
<212> TYPE: PRT
<213> ORGANISM: homo sapiens

<400> SEQUENCE: 55

Ser Tyr Ala Met Ser
1               5
```

<210> SEQ ID NO 56
<211> LENGTH: 17
<212> TYPE: PRT
<213> ORGANISM: homo sapiens

<400> SEQUENCE: 56

Ala Ile Ser Gly Ser Gly Gly Ser Thr Tyr Tyr Ala Asp Ser Val Lys
1               5                   10                  15

Gly

<210> SEQ ID NO 57
<211> LENGTH: 9
<212> TYPE: PRT
<213> ORGANISM: homo sapiens

<400> SEQUENCE: 57

Pro Tyr Gln Ala Arg Ala Phe Asp Ile
1               5

<210> SEQ ID NO 58
<211> LENGTH: 118
<212> TYPE: PRT
<213> ORGANISM: homo sapiens

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Tyr Gln Ala Arg Ala Phe Asp Ile Trp Gly Gln Gly Thr
            100                 105                 110

Met Val Thr Val Ser Ser
        115

<210> SEQ ID NO 59
<211> LENGTH: 354
<212> TYPE: DNA
<213> ORGANISM: homo sapiens

<400> SEQUENCE: 59
gaggtgcagc tgttggagtc tgggggaggc ttggtacagc ctggggggtc cctgagactc      60
tcctgtgcag cctctggatt cacctttagc agctatgcca tgagctgggt ccgccaggct    120
ccagggaagg ggctggagtg gtctcagct attagtggta gtggtggtag cacatactac     180
gcagactccg tgaagggccg gttcaccatc tccagagaca attccaagaa cacgctgtat    240
ctgcaaatga acagcctgag agccgaggac acggcggtgt actactgcgc cagaccttac    300
caagccagag cctttgatat ttggggtcag ggtacaatgg tcaccgtctc ctca          354

<210> SEQ ID NO 60

```
<211> LENGTH: 30
<212> TYPE: PRT
<213> ORGANISM: homo sapiens

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 61
<211> LENGTH: 14
<212> TYPE: PRT
<213> ORGANISM: homo sapiens

<400> SEQUENCE: 61

Trp Val Arg Gln Ala Pro Gly Lys Gly Leu Glu Trp Val Ser
1               5                   10

<210> SEQ ID NO 62
<211> LENGTH: 32
<212> TYPE: PRT
<213> ORGANISM: homo sapiens

<400> SEQUENCE: 62

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 63
<211> LENGTH: 11
<212> TYPE: PRT
<213> ORGANISM: homo sapiens

<400> SEQUENCE: 63

Trp Gly Gln Gly Thr Met Val Thr Val Ser Ser
1               5                   10

<210> SEQ ID NO 64
<211> LENGTH: 12
<212> TYPE: PRT
<213> ORGANISM: homo sapiens

<400> SEQUENCE: 64

Arg Ala Ser Gln Ser Val Ser Ser Ser Phe Leu Ala
1               5                   10

<210> SEQ ID NO 65
<211> LENGTH: 7
<212> TYPE: PRT
<213> ORGANISM: homo sapiens

<400> SEQUENCE: 65

Gly Ala Ser Ser Arg Ala Thr
1               5

<210> SEQ ID NO 66
<211> LENGTH: 9
<212> TYPE: PRT
<213> ORGANISM: homo sapiens

<400> SEQUENCE: 66

Gln Gln Tyr Val Val Ala Pro Ile Thr
```

<210> SEQ ID NO 67
<211> LENGTH: 108
<212> TYPE: PRT
<213> ORGANISM: homo sapiens

<400> SEQUENCE: 67

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Phe Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Val Val Ala Pro
                85                  90                  95
Ile Thr Phe Gly Gly Gly Thr Lys Val Glu Ile Lys
            100                 105

<210> SEQ ID NO 68
<211> LENGTH: 324
<212> TYPE: DNA
<213> ORGANISM: homo sapiens

<400> SEQUENCE: 68
gaaattgtgt tgacgcagtc tccaggcacc ctgtctttgt ctccagggga aagagccacc      60
ctctcctgca gggccagtca gagtgttagc agcagcttct tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtacgtcg tcgcccctat cacttttggc     300
ggagggacca aggttgagat caaa                                            324

<210> SEQ ID NO 69
<211> LENGTH: 23
<212> TYPE: PRT
<213> ORGANISM: homo sapiens

<400> SEQUENCE: 69

Glu Ile Val Leu Thr Gln Ser Pro Gly Thr Leu Ser Leu Ser Pro Gly
1               5                   10                  15
Glu Arg Ala Thr Leu Ser Cys
            20

<210> SEQ ID NO 70
<211> LENGTH: 15
<212> TYPE: PRT
<213> ORGANISM: homo sapiens

<400> SEQUENCE: 70

Trp Tyr Gln Gln Lys Pro Gly Gln Ala Pro Arg Leu Leu Ile Tyr
1               5                   10                  15

<210> SEQ ID NO 71
<211> LENGTH: 32

```
<212> TYPE: PRT
<213> ORGANISM: homo sapiens

<400> SEQUENCE: 71

Gly Ile Pro Asp Arg Phe Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 72
<211> LENGTH: 10
<212> TYPE: PRT
<213> ORGANISM: homo sapiens

<400> SEQUENCE: 72

Phe Gly Gly Gly Thr Lys Val Glu Ile Lys
1               5                   10

<210> SEQ ID NO 73
<211> LENGTH: 9
<212> TYPE: PRT
<213> ORGANISM: homo sapiens

<400> SEQUENCE: 73

Gly Thr Phe Ser Ser Tyr Ala Ile Ser
1               5

<210> SEQ ID NO 74
<211> LENGTH: 17
<212> TYPE: PRT
<213> ORGANISM: homo sapiens

<400> SEQUENCE: 74

Gly Ile Ile Pro Ile Phe Gly Thr Ala Ser Tyr Ala Gln Lys Phe Gln
1               5                   10                  15

Gly

<210> SEQ ID NO 75
<211> LENGTH: 14
<212> TYPE: PRT
<213> ORGANISM: homo sapiens

<400> SEQUENCE: 75

Ala Arg Thr Pro Tyr Tyr Asp Ser Ser Gly Tyr Leu Asp Val
1               5                   10

<210> SEQ ID NO 76
<211> LENGTH: 11
<212> TYPE: PRT
<213> ORGANISM: homo sapiens

<400> SEQUENCE: 76

Gly Ser Ile Ser Ser Ser Ser Tyr Tyr Trp Gly
1               5                   10

<210> SEQ ID NO 77
<211> LENGTH: 16
<212> TYPE: PRT
<213> ORGANISM: homo sapiens

<400> SEQUENCE: 77

Asn Ile Tyr Tyr Ser Gly Ser Thr Tyr Tyr Asn Pro Ser Leu Lys Ser
1               5                   10                  15
```

<210> SEQ ID NO 78
<211> LENGTH: 19
<212> TYPE: PRT
<213> ORGANISM: homo sapiens

<400> SEQUENCE: 78

Ala Arg Asp Gly Arg Tyr Gln Ser Ala Thr Ala Asp Tyr Tyr Tyr Gly
1               5                   10                  15
Met Asp Val

<210> SEQ ID NO 79
<211> LENGTH: 9
<212> TYPE: PRT
<213> ORGANISM: homo sapiens

<400> SEQUENCE: 79

Phe Thr Phe Ser Ser Tyr Ala Met Ser
1               5

<210> SEQ ID NO 80
<211> LENGTH: 17
<212> TYPE: PRT
<213> ORGANISM: homo sapiens

<400> SEQUENCE: 80

Ala Ile Ser Gly Ser Gly Gly Ser Thr Tyr Tyr Ala Asp Ser Val Lys
1               5                   10                  15
Gly

<210> SEQ ID NO 81
<211> LENGTH: 11
<212> TYPE: PRT
<213> ORGANISM: homo sapiens

<400> SEQUENCE: 81

Ala Arg Arg Tyr Arg Gly Val Ser Phe Asp Ile
1               5                   10

<210> SEQ ID NO 82
<211> LENGTH: 9
<212> TYPE: PRT
<213> ORGANISM: homo sapiens

<400> SEQUENCE: 82

Phe Thr Phe Ser Ser Tyr Ala Met Ser
1               5

<210> SEQ ID NO 83
<211> LENGTH: 17
<212> TYPE: PRT
<213> ORGANISM: homo sapiens

<400> SEQUENCE: 83

Ala Ile Ser Gly Ser Gly Gly Ser Thr Tyr Tyr Ala Asp Ser Val Lys
1               5                   10                  15
Gly

<210> SEQ ID NO 84
<211> LENGTH: 11
<212> TYPE: PRT
<213> ORGANISM: homo sapiens

<400> SEQUENCE: 84

Ala Arg Pro Tyr Gln Ala Arg Ala Phe Asp Ile
1               5                   10

<210> SEQ ID NO 85
<211> LENGTH: 493
<212> TYPE: PRT
<213> ORGANISM: homo sapiens

<400> SEQUENCE: 85

Met Thr Arg Ala Leu Cys Ser Ala Leu Arg Gln Ala Leu Leu Leu
1               5                   10                  15

Ala Ala Ala Ala Glu Leu Ser Pro Gly Leu Lys Cys Val Cys Leu Leu
            20                  25                  30

Cys Asp Ser Ser Asn Phe Thr Cys Gln Thr Glu Gly Ala Cys Trp Ala
        35                  40                  45

Ser Val Met Leu Thr Asn Gly Lys Glu Gln Val Ile Lys Ser Cys Val
    50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Ala Ser Pro Asn Ala Pro Lys Leu Gly Pro Met
            100                 105                 110

Glu Leu Ala Ile Ile Ile Thr Val Pro Val Cys Leu Leu Ser Ile Ala
        115                 120                 125

Ala Met Leu Thr Val Trp Ala Cys Gln Gly Arg Gln Cys Ser Tyr Arg
    130                 135                 140

Lys Lys Lys Arg Pro Asn Val Glu Glu Pro Leu Ser Glu Cys Asn Leu
145                 150                 155                 160

Val Asn Ala Gly Lys Thr Leu Lys Asp Leu Ile Tyr Asp Val Thr Ala
                165                 170                 175

Ser Gly Ser Gly Ser Gly Leu Pro Leu Leu Val Gln Arg Thr Ile Ala
            180                 185                 190

Arg Thr Ile Val Leu Gln Glu Ile Val Gly Lys Gly Arg Phe Gly Glu
        195                 200                 205

Val Trp His Gly Arg Trp Cys Gly Glu Asp Val Ala Val Lys Ile Phe
    210                 215                 220

Ser Ser Arg Asp Glu Arg Ser Trp Phe Arg Glu Ala Glu Ile Tyr Gln
225                 230                 235                 240

Thr Val Met Leu Arg His Glu Asn Ile Leu Gly Phe Ile Ala Ala Asp
                245                 250                 255

Asn Lys Asp Asn Gly Thr Trp Thr Gln Leu Trp Leu Val Ser Glu Tyr
            260                 265                 270

His Glu Gln Gly Ser Leu Tyr Asp Tyr Leu Asn Arg Asn Ile Val Thr
        275                 280                 285

Val Ala Gly Met Ile Lys Leu Ala Leu Ser Ile Ala Ser Gly Leu Ala
    290                 295                 300

His Leu His Met Glu Ile Val Gly Thr Gln Gly Lys Pro Ala Ile Ala
305                 310                 315                 320

His Arg Asp Ile Lys Ser Lys Asn Ile Leu Val Lys Lys Cys Glu Thr
                325                 330                 335

Cys Ala Ile Ala Asp Leu Gly Leu Ala Val Lys His Asp Ser Ile Leu
            340                 345                 350

Asn Thr Ile Asp Ile Pro Gln Asn Pro Lys Val Gly Thr Lys Arg Tyr

```
                355                 360                 365
Met Ala Pro Glu Met Leu Asp Asp Thr Met Asn Val Asn Ile Phe Glu
    370                 375                 380

Ser Phe Lys Arg Ala Asp Ile Tyr Ser Val Gly Leu Val Tyr Trp Glu
385                 390                 395                 400

Ile Ala Arg Arg Cys Ser Val Gly Gly Ile Val Glu Glu Tyr Gln Leu
                405                 410                 415

Pro Tyr Tyr Asp Met Val Pro Ser Asp Pro Ser Ile Glu Glu Met Arg
            420                 425                 430

Lys Val Val Cys Asp Gln Lys Phe Arg Pro Ser Ile Pro Asn Gln Trp
                435                 440                 445

Gln Ser Cys Glu Ala Leu Arg Val Met Gly Arg Ile Met Arg Glu Cys
    450                 455                 460

Trp Tyr Ala Asn Gly Ala Ala Arg Leu Thr Ala Leu Arg Ile Lys Lys
465                 470                 475                 480

Thr Ile Ser Gln Leu Cys Val Lys Glu Asp Cys Lys Ala
                485                 490
```

<210> SEQ ID NO 86
<211> LENGTH: 88
<212> TYPE: PRT
<213> ORGANISM: homo sapiens

<400> SEQUENCE: 86

```
Leu Lys Cys Val Cys Leu Leu Cys Asp Ser Ser Asn Phe Thr Cys Gln
1               5                   10                  15

Thr Glu Gly Ala Cys Trp Ala Ser Val Met Leu Thr Asn Gly Lys Glu
                20                  25                  30

Gln Val Ile Lys Ser Cys Val Ser Leu Pro Glu Leu Asn Ala Gln Val
            35                  40                  45

Phe Cys His Ser Ser Asn Asn Val Thr Lys Thr Glu Cys Cys Phe Thr
        50                  55                  60

Asp Phe Cys Asn Asn Ile Thr Leu His Leu Pro Thr Ala Ser Pro Asn
65                  70                  75                  80

Ala Pro Lys Leu Gly Pro Met Glu
                85
```

<210> SEQ ID NO 87
<211> LENGTH: 88
<212> TYPE: PRT
<213> ORGANISM: rat

<400> SEQUENCE: 87

```
Leu Lys Cys Val Cys Leu Leu Cys Asp Ser Ser Asn Phe Thr Cys Gln
1               5                   10                  15

Thr Glu Gly Ala Cys Trp Ala Ser Val Met Leu Thr Asn Gly Lys Glu
                20                  25                  30

Gln Val Ser Lys Ser Cys Val Ser Leu Pro Glu Leu Asn Ala Gln Val
            35                  40                  45

Phe Cys His Ser Ser Asn Asn Val Thr Lys Thr Glu Cys Cys Phe Thr
        50                  55                  60

Asp Phe Cys Asn Asn Ile Thr Gln His Leu Pro Thr Ala Ser Pro Asp
65                  70                  75                  80

Ala Pro Arg Leu Gly Pro Thr Glu
                85
```

```
<210> SEQ ID NO 88
<211> LENGTH: 5
<212> TYPE: PRT
<213> ORGANISM: Artificial Sequence
<220> FEATURE:
<223> OTHER INFORMATION: VH CDR1

<400> SEQUENCE: 88

Val Tyr Ala Met Ser
1               5

<210> SEQ ID NO 89
<211> LENGTH: 17
<212> TYPE: PRT
<213> ORGANISM: Artificial Sequence
<220> FEATURE:
<223> OTHER INFORMATION: VH CDR2

<400> SEQUENCE: 89

Ala Ile Ser Gly Ser Gly Asp Ser Thr Val Tyr Ala Asp Ser Val Lys
1               5                   10                  15

Gly

<210> SEQ ID NO 90
<211> LENGTH: 7
<212> TYPE: PRT
<213> ORGANISM: Artificial Sequence
<220> FEATURE:
<223> OTHER INFORMATION: VH CDR3

<400> SEQUENCE: 90

Pro Ser Tyr Gln Pro Ile Tyr
1               5

<210> SEQ ID NO 91
<211> LENGTH: 116
<212> TYPE: PRT
<213> ORGANISM: Artificial Sequence
<220> FEATURE:
<223> OTHER INFORMATION: VH Protein

<400> SEQUENCE: 91

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Ser Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ser Tyr Gln Pro Ile Tyr Trp Gly Gln Gly Thr Leu Val
            100                 105                 110

Thr Val Ser Ser
        115

<210> SEQ ID NO 92
<211> LENGTH: 348
<212> TYPE: DNA
<213> ORGANISM: Artificial Sequence
```

```
<220> FEATURE:
<223> OTHER INFORMATION: VH DNA

<400> SEQUENCE: 92
gaggtgcagc tgttggagtc tgggggaggc ttggtacagc ctgggggtc cctgagactc      60 tcctgtgcag cctctggatt cacctttcg gtgtatgcca tgagctgggt ccgccaggct     120
ccagggaagg gctggagtg gtctcagct attagtggaa gtggtgatag cacagtgtac     180
gcagactccg tgaagggccg gttcaccatc tccagagaca attccaagaa cacgctgtat    240
ctgcaaatga acagcctgag agccgaggac acggcggtgt actactgcgc caagccttct    300
taccaaccaa tatactgggg acagggtaca ttggtcaccg tctcctca                348

<210> SEQ ID NO 93
<211> LENGTH: 32
<212> TYPE: PRT
<213> ORGANISM: Artificial Sequence
<220> FEATURE:
<223> OTHER INFORMATION: VH FR3

<400> SEQUENCE: 93

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
                20                  25                  30

<210> SEQ ID NO 94
<211> LENGTH: 11
<212> TYPE: PRT
<213> ORGANISM: Artificial Sequence
<220> FEATURE:
<223> OTHER INFORMATION: VH FR4

<400> SEQUENCE: 94

Trp Gly Gln Gly Thr Leu Val Thr Val Ser Ser
1               5                   10

<210> SEQ ID NO 95
<211> LENGTH: 11
<212> TYPE: PRT
<213> ORGANISM: Artificial Sequence
<220> FEATURE:
<223> OTHER INFORMATION: VL CDR1

<400> SEQUENCE: 95

Arg Ala Ser Gln Gly Ile Ser Ser Trp Leu Ala
1               5                   10

<210> SEQ ID NO 96
<211> LENGTH: 7
<212> TYPE: PRT
<213> ORGANISM: Artificial Sequence
<220> FEATURE:
<223> OTHER INFORMATION: VL CDR2

<400> SEQUENCE: 96

Ala Ala Ser Ser Leu Gln Ser
1               5

<210> SEQ ID NO 97
<211> LENGTH: 9
<212> TYPE: PRT
<213> ORGANISM: Artificial Sequence
<220> FEATURE:
<223> OTHER INFORMATION: VL CDR3
```

```
<400> SEQUENCE: 97

Gln Gln Ala Ala Ser Tyr Pro Leu Thr
1               5

<210> SEQ ID NO 98
<211> LENGTH: 107
<212> TYPE: PRT
<213> ORGANISM: Artificial Sequence
<220> FEATURE:
<223> OTHER INFORMATION: VL Protein

<400> SEQUENCE: 98

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ala Ser Tyr Pro Leu
                85                  90                  95

Thr Phe Gly Gly Gly Thr Lys Val Glu Ile Lys
            100                 105

<210> SEQ ID NO 99
<211> LENGTH: 321
<212> TYPE: DNA
<213> ORGANISM: Artificial Sequence
<220> FEATURE:
<223> OTHER INFORMATION: VL DNA

<400> SEQUENCE: 99
gacatccaga tgacccaaag ccctagttcc gtctctgcaa gcgtgggaga tagggtcaca      60
atcacatgta gagcttctca ggggatctct agctggctgg cttggtatca gcagaagccc     120
ggtaaggccc caaagctctt gatatacgcc gcctcttctc ttcaatctgg ggtgccatcc     180
cgcttctcag ggagcggtag cgggaccgat ttcaccctca ctatcagcag cctgcagcct     240
gaagactttg ctacctacta ctgccagcaa gccgcttctt atcctctgac tttcggtggg     300
ggtactaaag tggagattaa a                                               321

<210> SEQ ID NO 100
<211> LENGTH: 23
<212> TYPE: PRT
<213> ORGANISM: Artificial Sequence
<220> FEATURE:
<223> OTHER INFORMATION: VL FR1

<400> SEQUENCE: 100

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 101
<211> LENGTH: 32
<212> TYPE: PRT
```

```
<213> ORGANISM: Artificial Sequence
<220> FEATURE:
<223> OTHER INFORMATION: VL FR3

<400> SEQUENCE: 101

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
                20                  25                  30

<210> SEQ ID NO 102
<211> LENGTH: 5
<212> TYPE: PRT
<213> ORGANISM: Artificial Sequence
<220> FEATURE:
<223> OTHER INFORMATION: VH CDR1

<400> SEQUENCE: 102

Ser Ser Ala Ile Gly
1               5

<210> SEQ ID NO 103
<211> LENGTH: 17
<212> TYPE: PRT
<213> ORGANISM: Artificial Sequence
<220> FEATURE:
<223> OTHER INFORMATION: VH CDR2

<400> SEQUENCE: 103

Gly Ile Trp Pro Ile Phe Gly Thr Ala Leu Tyr Ala Gln Lys Phe Gln
1               5                   10                  15

Gly

<210> SEQ ID NO 104
<211> LENGTH: 11
<212> TYPE: PRT
<213> ORGANISM: Artificial Sequence
<220> FEATURE:
<223> OTHER INFORMATION: VH CDR3

<400> SEQUENCE: 104

Asp Pro Arg Glu Tyr Ile His Val Phe Asp Ile
1               5                   10

<210> SEQ ID NO 105
<211> LENGTH: 120
<212> TYPE: PRT
<213> ORGANISM: Artificial Sequence
<220> FEATURE:
<223> OTHER INFORMATION: VH Protein

<400> SEQUENCE: 105

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Ser
                20                  25                  30

Ala Ile Gly Trp Val Arg Gln Ala Pro Gly Gln Gly Leu Glu Trp Met
        35                  40                  45

Gly Gly Ile Trp Pro Ile Phe Gly Thr Ala Leu Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
```

```
                    85                  90                  95
Ala Arg Asp Pro Arg Glu Tyr Ile His Val Phe Asp Ile Trp Gly Gln
            100                 105                 110

Gly Thr Met Val Thr Val Ser Ser
        115                 120
```

<210> SEQ ID NO 106
<211> LENGTH: 360
<212> TYPE: DNA
<213> ORGANISM: Artificial Sequence
<220> FEATURE:
<223> OTHER INFORMATION: VH DNA

<400> SEQUENCE: 106

```
caggtgcagc tggtgcagtc tggggctgag gtgaagaagc ctgggtcctc ggtgaaggtc    60
tcctgcaagg cttctggagg caccttcagc agcagtgcta tcgggtgggt gcgacaggcc   120
cctggacaag gcttgagtg gatgggaggg atctggccta tctttggtac agcactttac   180
gcacagaagt tccagggcag agtcacgatt accgcggacg aatccacgag cacagcctac   240
atggagctga gcagcctgag atctgaggac acggcggtgt actactgcgc cagagatcca   300
agagaatata tccacgtatt cgacatatgg ggtcaggta caatggtcac cgtctcctca   360
```

<210> SEQ ID NO 107
<211> LENGTH: 11
<212> TYPE: PRT
<213> ORGANISM: Artificial Sequence
<220> FEATURE:
<223> OTHER INFORMATION: VL CDR1

<400> SEQUENCE: 107

```
Arg Ala Ser Gln Ser Ile Ser Ser Tyr Leu Asn
1               5                   10
```

<210> SEQ ID NO 108
<211> LENGTH: 7
<212> TYPE: PRT
<213> ORGANISM: Artificial Sequence
<220> FEATURE:
<223> OTHER INFORMATION: VL CDR2

<400> SEQUENCE: 108

```
Gly Ala Ser Ser Leu Gln Ser
1               5
```

<210> SEQ ID NO 109
<211> LENGTH: 9
<212> TYPE: PRT
<213> ORGANISM: Artificial Sequence
<220> FEATURE:
<223> OTHER INFORMATION: VL CDR3

<400> SEQUENCE: 109

```
Gln Gln Ala Tyr Ser Phe Pro Trp Thr
1               5
```

<210> SEQ ID NO 110
<211> LENGTH: 107
<212> TYPE: PRT
<213> ORGANISM: Artificial Sequence
<220> FEATURE:
<223> OTHER INFORMATION: VL Protein

<400> SEQUENCE: 110

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Ser Phe Pro Trp
                85                  90                  95

Thr Phe Gly Gly Gly Ile Lys Val Glu Ile Lys
            100                 105
```

<210> SEQ ID NO 111
<211> LENGTH: 321
<212> TYPE: DNA
<213> ORGANISM: Artificial Sequence
<220> FEATURE:
<223> OTHER INFORMATION: VL DNA

<400> SEQUENCE: 111

```
gatattcaga tgacacagtc acctagcagt ctgagcgcat cagtgggtga tcgagtgaca      60
atcacttgta gagcttccca gtctattagc tcataccctga actggtatca gcaaaagcct    120
gggaaggctc ctaagctgtt gatctatgga gcatctagcc tgcagtccgg cgtgccatcc    180
cgcttcagcg ggagcggctc cgggaccgat tttaccctga caatctctag cctgcagcct    240
gaagattttg caacctacta ctgccagcag gcatacagct tcccctggac attcggaggt    300
ggcataaaag ttgaaatcaa a                                              321
```

<210> SEQ ID NO 112
<211> LENGTH: 32
<212> TYPE: PRT
<213> ORGANISM: Artificial Sequence
<220> FEATURE:
<223> OTHER INFORMATION: VL FR3

<400> SEQUENCE: 112

```
Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30
```

<210> SEQ ID NO 113
<211> LENGTH: 10
<212> TYPE: PRT
<213> ORGANISM: Artificial Sequence
<220> FEATURE:
<223> OTHER INFORMATION: VL FR4

<400> SEQUENCE: 113

```
Phe Gly Gly Gly Ile Lys Val Glu Ile Lys
1               5                   10
```

<210> SEQ ID NO 114
<211> LENGTH: 5
<212> TYPE: PRT
<213> ORGANISM: Artificial Sequence
<220> FEATURE:
<223> OTHER INFORMATION: VH CDR1

-continued

<400> SEQUENCE: 114

Gly Gln Ala Ile Ser
1               5

<210> SEQ ID NO 115
<211> LENGTH: 17
<212> TYPE: PRT
<213> ORGANISM: Artificial Sequence
<220> FEATURE:
<223> OTHER INFORMATION: VH CDR2

<400> SEQUENCE: 115

Gly Ile Ile Pro Ser Phe Gly Thr Ala Arg Tyr Ala Gln Lys Phe Gln
1               5                   10                  15

Gly

<210> SEQ ID NO 116
<211> LENGTH: 12
<212> TYPE: PRT
<213> ORGANISM: Artificial Sequence
<220> FEATURE:
<223> OTHER INFORMATION: VH CDR3

<400> SEQUENCE: 116

Thr Pro Tyr Tyr Asp Ser Ser Gly Tyr Leu Asp Val
1               5                   10

<210> SEQ ID NO 117
<211> LENGTH: 120
<212> TYPE: PRT
<213> ORGANISM: Artificial Sequence
<220> FEATURE:
<223> OTHER INFORMATION: VH Protein

<400> SEQUENCE: 117

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Gly Gln
            20                  25                  30

Ala Ile Ser Trp Val Arg Gln Ala Pro Gly Gln Gly Leu Glu Trp Met
        35                  40                  45

Gly Gly Ile Ile Pro Ser Phe Gly Thr Ala Arg Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Pro Tyr Tyr Asp Ser Ser Gly Tyr Leu Asp Val Trp Gly
            100                 105                 110

Gln Gly Thr Met Val Thr Val Ser
        115                 120

<210> SEQ ID NO 118
<211> LENGTH: 363
<212> TYPE: DNA
<213> ORGANISM: Artificial Sequence
<220> FEATURE:
<223> OTHER INFORMATION: VH DNA

<400> SEQUENCE: 118
caggtgcagc tggtgcagtc tggggctgag gtgaagaagc ctgggtcctc ggtgaaggtc      60

```
tcctgcaagg cttctggagg caccttcagc ggtcaggcta tcagctgggt gcgacaggcc    120
cctggacaag gcttgagtg gatgggaggg atcatccctt cgtttggtac agcacggtac    180
gcacagaagt tccagggcag agtcacgatt accgcggacg aatccacgag cacagcctac    240
atggagctga gcagcctgag atctgaggac acggcggtgt actactgcgc cagaactcct    300
tactacgaca gcagcggata cctagacgta tggggtcagg gtacaatggt caccgtctcc    360
tca                                                                  363
```

<210> SEQ ID NO 119
<211> LENGTH: 32
<212> TYPE: PRT
<213> ORGANISM: Artificial Sequence
<220> FEATURE:
<223> OTHER INFORMATION: VH FR3

<400> SEQUENCE: 119

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 120
<211> LENGTH: 10
<212> TYPE: PRT
<213> ORGANISM: Artificial Sequence
<220> FEATURE:
<223> OTHER INFORMATION: VH FR4

<400> SEQUENCE: 120

Trp Gly Gln Gly Thr Met Val Thr Val Ser
1               5                   10

<210> SEQ ID NO 121
<211> LENGTH: 11
<212> TYPE: PRT
<213> ORGANISM: Artificial Sequence
<220> FEATURE:
<223> OTHER INFORMATION: VL CDR1

<400> SEQUENCE: 121

Gln Ala Ser His Asp Ile Asp Asn Tyr Leu Asn
1               5                   10

<210> SEQ ID NO 122
<211> LENGTH: 7
<212> TYPE: PRT
<213> ORGANISM: Artificial Sequence
<220> FEATURE:
<223> OTHER INFORMATION: VL CDR2

<400> SEQUENCE: 122

Tyr Ala Ser Asn Leu Lys Thr
1               5

<210> SEQ ID NO 123
<211> LENGTH: 9
<212> TYPE: PRT
<213> ORGANISM: Artificial Sequence
<220> FEATURE:
<223> OTHER INFORMATION: VL CDR3

<400> SEQUENCE: 123

Gln Gln Ser Arg Ala Ser Pro Pro Thr

-continued

<210> SEQ ID NO 124
<211> LENGTH: 107
<212> TYPE: PRT
<213> ORGANISM: Artificial Sequence
<220> FEATURE:
<223> OTHER INFORMATION: VL Protein

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Gln Ala Ser His Asp Ile Asp Asn Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Lys Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Arg Ala Ser Pro Pro
                85                  90                  95

Thr Phe Gly Gly Gly Thr Lys Val Glu Ile Lys
            100                 105

<210> SEQ ID NO 125
<211> LENGTH: 9
<212> TYPE: PRT
<213> ORGANISM: Artificial Sequence
<220> FEATURE:
<223> OTHER INFORMATION: VH CDR1

<400> SEQUENCE: 125

Gly Gly Ser Ile Ser Ser Ser Ala Tyr
1               5

<210> SEQ ID NO 126
<211> LENGTH: 16
<212> TYPE: PRT
<213> ORGANISM: Artificial Sequence
<220> FEATURE:
<223> OTHER INFORMATION: VH CDR2

<400> SEQUENCE: 126

Ser Ile Tyr Leu Ser Gly Ser Thr Thr Tyr Asn Pro Ser Leu Lys Ser
1               5                   10                  15

<210> SEQ ID NO 127
<211> LENGTH: 17
<212> TYPE: PRT
<213> ORGANISM: Artificial Sequence
<220> FEATURE:
<223> OTHER INFORMATION: VH CDR3

<400> SEQUENCE: 127

Asp Gly Arg Tyr Gln Ser Arg Ser Pro Asp Tyr Tyr Tyr Gly Met Asp
1               5                   10                  15

Val

<210> SEQ ID NO 128
<211> LENGTH: 127
<212> TYPE: PRT
<213> ORGANISM: Artificial Sequence
<220> FEATURE:
<223> OTHER INFORMATION: VH Protein

<400> SEQUENCE: 128

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ala Tyr Tyr Trp Ala Trp Ile Arg Gln Pro Pro Gly Lys Gly Leu Glu
        35                  40                  45

Trp Ile Gly Ser Ile Tyr Leu Ser Gly Ser Thr Thr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Arg Tyr Gln Ser Arg Ser Pro Asp Tyr Tyr Tyr
            100                 105                 110

Gly Met Asp Val Trp Gly Gln Gly Thr Thr Val Thr Val Ser Ser
        115                 120                 125

<210> SEQ ID NO 129
<211> LENGTH: 381
<212> TYPE: DNA
<213> ORGANISM: Artificial Sequence
<220> FEATURE:
<223> OTHER INFORMATION: VH DNA

<400> SEQUENCE: 129
cagctgcagc tgcaggagtc gggcccagga ctggtgaagc cttcggagac cctgtccctc    60
acctgcactg tctctggtgg ctccatcagc agtagtgctt actactgggc gtggatccgc   120
cagcccccag ggaaggggct ggagtggatt gggagtatct atttgagtgg gagcaccact   180
tacaacccgt ccctcaagag tcgagtcacc atatccgtag acacgtccaa gaaccagttc   240
tccctgaagc tgagttctgt gaccgccgca gacacggcgg tgtactactg cgccagagac   300
ggcagatacc aaagcaggtc gccggattac tattacggta tggatgtctg gggccaggga   360
acaacggtca ccgtctcctc a                                             381

<210> SEQ ID NO 130
<211> LENGTH: 25
<212> TYPE: PRT
<213> ORGANISM: Artificial Sequence
<220> FEATURE:
<223> OTHER INFORMATION: VH FR1

<400> SEQUENCE: 130

Gln Leu Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 131
<211> LENGTH: 17
<212> TYPE: PRT
<213> ORGANISM: Artificial Sequence
<220> FEATURE:
<223> OTHER INFORMATION: VH FR2

<400> SEQUENCE: 131

Tyr Trp Ala Trp Ile Arg Gln Pro Pro Gly Lys Gly Leu Glu Trp Ile
1               5                   10                  15

Gly

<210> SEQ ID NO 132
<211> LENGTH: 12
<212> TYPE: PRT
<213> ORGANISM: Artificial Sequence
<220> FEATURE:
<223> OTHER INFORMATION: VL CDR1

<400> SEQUENCE: 132

Lys Ala Ser Gln Ser Val Ser Ser Ser Tyr Leu Ala
1               5                   10

<210> SEQ ID NO 133
<211> LENGTH: 7
<212> TYPE: PRT
<213> ORGANISM: Artificial Sequence
<220> FEATURE:
<223> OTHER INFORMATION: VL CDR2

<400> SEQUENCE: 133

Gly Ala Phe Ser Arg Ala Asn
1               5

<210> SEQ ID NO 134
<211> LENGTH: 9
<212> TYPE: PRT
<213> ORGANISM: Artificial Sequence
<220> FEATURE:
<223> OTHER INFORMATION: VL CDR3

<400> SEQUENCE: 134

Gln Gln Leu Val Ser Tyr Pro Phe Thr
1               5

<210> SEQ ID NO 135
<211> LENGTH: 108
<212> TYPE: PRT
<213> ORGANISM: Artificial Sequence
<220> FEATURE:
<223> OTHER INFORMATION: VL Protein

<400> SEQUENCE: 135

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Asn Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Val Ser Tyr Pro
                85                  90                  95

Phe Thr Phe Gly Gly Gly Thr Lys Val Glu Ile Lys
            100                 105

<210> SEQ ID NO 136
<211> LENGTH: 324
<212> TYPE: DNA

<213> ORGANISM: Artificial Sequence
<220> FEATURE:
<223> OTHER INFORMATION: VL DNA

<400> SEQUENCE: 136

```
gagatagtct tgacccagtc accaggcacc cttagcttgt ctcccgggga acgcgccaca    60
ctcagctgta aagcctctca gtcagtttct agttcctacc tcgcttggta tcaacaaaag   120
cccggacaag caccaaggct gttgatctac ggagctttca gtcgcgcaaa tggcattccc   180
gaccgattct ctggcagtgg tagtggcacc gacttcactc tcacaatttc taggttggaa   240
cctgaggact ttgctgtgta ctactgtcaa caactggttt cttatccctt tacattcggt   300
ggcggcacaa aagtcgagat taaa                                          324
```

<210> SEQ ID NO 137
<211> LENGTH: 5
<212> TYPE: PRT
<213> ORGANISM: Artificial Sequence
<220> FEATURE:
<223> OTHER INFORMATION: VH CDR1

<400> SEQUENCE: 137

Gly Tyr Asn Met His
1               5

<210> SEQ ID NO 138
<211> LENGTH: 6
<212> TYPE: PRT
<213> ORGANISM: Artificial Sequence
<220> FEATURE:
<223> OTHER INFORMATION: VH CDR2

<400> SEQUENCE: 138

Asn Pro Asn Ser Gly Trp
1               5

<210> SEQ ID NO 139
<211> LENGTH: 12
<212> TYPE: PRT
<213> ORGANISM: Artificial Sequence
<220> FEATURE:
<223> OTHER INFORMATION: VH CDR3

<400> SEQUENCE: 139

Asp Pro Val Gly Ala Arg Tyr Glu Val Phe Asp Tyr
1               5                  10

<210> SEQ ID NO 140
<211> LENGTH: 121
<212> TYPE: PRT
<213> ORGANISM: Artificial Sequence
<220> FEATURE:
<223> OTHER INFORMATION: VH Protein

<400> SEQUENCE: 140

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Ala Gly Tyr
            20                  25                  30

Asn Met His Trp Val Arg Gln Ala Pro Gly Gln Gly Leu Glu Trp Val
        35                  40                  45

Gly Ile Ile Asn Pro Asn Ser Gly Trp Thr Asn Tyr Ala Gln Lys Phe
    50                  55                  60

Gln Gly Arg Val Thr Met Thr Arg Asp Thr Ser Val Ser Ala Ala Tyr
65                  70                  75                  80

Met Glu Leu Ser Arg Leu Arg Ser Asp Asp Thr Ala Val Tyr Tyr Cys
                85                  90                  95

Ala Arg Asp Pro Val Gly Ala Arg Tyr Glu Val Phe Asp Tyr Trp Gly
            100                 105                 110

Gln Gly Thr Leu Val Thr Val Ser Ser
        115                 120

<210> SEQ ID NO 141
<211> LENGTH: 363
<212> TYPE: DNA
<213> ORGANISM: Artificial Sequence
<220> FEATURE:
<223> OTHER INFORMATION: VH DNA

<400> SEQUENCE: 141
caggtgcagc tggtgcagtc tggggctgag gtgaagaagc ctggggcctc agtgaaggtc      60
tcctgcaagg cttctggata caccttcgct ggctacaata tgcactgggt gcgacaggcc     120
cctggacaag gcttgagtg ggtgggaatt atcaacccta acagtggttg acaaactat       180 gcacagaagt tccagggcag ggtcacgatg accaggaca cgtccgtcag cgcagcctac      240
atggagctga gcaggctgag atctgacgac acggcggtgt actactgcgc cagagaccct    300
gtcggagcaa gatacgaggt tttcgattac tggggacagg gtacattggt caccgtctcc    360
tca                                                                  363

<210> SEQ ID NO 142
<211> LENGTH: 30
<212> TYPE: PRT
<213> ORGANISM: Artificial Sequence
<220> FEATURE:
<223> OTHER INFORMATION: VH FR1

<400> SEQUENCE: 142

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala
            20                  25                  30

<210> SEQ ID NO 143
<211> LENGTH: 16
<212> TYPE: PRT
<213> ORGANISM: Artificial Sequence
<220> FEATURE:
<223> OTHER INFORMATION: VH FR2

<400> SEQUENCE: 143

Trp Val Arg Gln Ala Pro Gly Gln Gly Leu Glu Trp Val Gly Ile Ile
1               5                   10                  15

<210> SEQ ID NO 144
<211> LENGTH: 11
<212> TYPE: PRT
<213> ORGANISM: Artificial Sequence
<220> FEATURE:
<223> OTHER INFORMATION: VH FR4

<400> SEQUENCE: 144

Trp Gly Gln Gly Thr Leu Val Thr Val Ser Ser
1               5                   10

```
<210> SEQ ID NO 145
<211> LENGTH: 11
<212> TYPE: PRT
<213> ORGANISM: Artificial Sequence
<220> FEATURE:
<223> OTHER INFORMATION: VL CDR1

<400> SEQUENCE: 145

Arg Ala Ser Gln Ser Val Ser Ala Leu Ala
1               5                   10

<210> SEQ ID NO 146
<211> LENGTH: 7
<212> TYPE: PRT
<213> ORGANISM: Artificial Sequence
<220> FEATURE:
<223> OTHER INFORMATION: VL CDR2

<400> SEQUENCE: 146

Ser Ala Phe Thr Arg Ala Ser
1               5

<210> SEQ ID NO 147
<211> LENGTH: 9
<212> TYPE: PRT
<213> ORGANISM: Artificial Sequence
<220> FEATURE:
<223> OTHER INFORMATION: VL CDR3

<400> SEQUENCE: 147

Gln Gln Ala Trp Ala Phe Pro Leu Thr
1               5

<210> SEQ ID NO 148
<211> LENGTH: 107
<212> TYPE: PRT
<213> ORGANISM: Artificial Sequence
<220> FEATURE:
<223> OTHER INFORMATION: VL Protein

<400> SEQUENCE: 148

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ala
            20                  25                  30

Leu Ala Trp Tyr Gln Gln Lys Pro Gly Gln Ala Pro Arg Leu Leu Ile
        35                  40                  45

Tyr Ser Ala Phe Thr Arg Ala Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ala Trp Ala Phe Pro Leu
                85                  90                  95

Thr Phe Gly Gly Gly Thr Lys Val Glu Ile Lys
            100                 105

<210> SEQ ID NO 149
<211> LENGTH: 321
<212> TYPE: DNA
<213> ORGANISM: Artificial Sequence
<220> FEATURE:
<223> OTHER INFORMATION: VL DNA

<400> SEQUENCE: 149
```

```
gaaatcgtga tgacccaatc acctgccact ctgtctgtta gccctgggga acgggccacc    60
ctcagttgta gggccagtca gagtgttagt tcagctttgg cttggtatca gcagaagccc   120
ggacaggccc caaggctgct gatctactct gctttcaccc gcgcaagcgg catccccgca   180
cgctttagcg gctccggaag cggcaccgag tttactctta ctatttcttc tttgcagagt   240
gaggattttg ccgtgtacta ctgccagcag gcctgggcat ttccactcac tttcggggggc  300 gggaccaagg tcgaaatcaa g                                             321
```

<210> SEQ ID NO 150
<211> LENGTH: 321
<212> TYPE: DNA
<213> ORGANISM: Artificial Sequence
<220> FEATURE:
<223> OTHER INFORMATION: VL DNA

<400> SEQUENCE: 150

```
gacatccaga tgacacagtc ccctagcagc ttgtcagcct cagtgggcga tagagtgacc    60
atcacctgtc aagccagcca tgatatagac aactatctca attggtacca gcagaaacca   120
ggcaaggcac caaagctcct gatctattac gcctcaaacc ttaagaccgg cgtcccaagc   180
cggttttcag gcagcggcag cgggacagat ttcaccttca caatttcatc actgcaacct   240
gaggatatag ccacttacta ttgtcagcag agcagagcca gccccctac cttcggcggc    300 ggtaccaaag ttgaaatcaa g                                             321
```

<210> SEQ ID NO 151
<211> LENGTH: 348
<212> TYPE: DNA
<213> ORGANISM: Artificial Sequence
<220> FEATURE:
<223> OTHER INFORMATION: VH DNA

<400> SEQUENCE: 151

```
gaggtgcagc tgttggagtc tgggggaggc ttggtacagc ctgggggggtc cctgagactc    60 tcctgtgcag cctctggatt cacctttagc agctatgcca tgagctgggt ccgccaggct   120
ccagggaagg ggctggagtg gtctcagct attagtggta gtggtggtag cacatactac   180
gcagactccg tgaagggccg gttcaccatc tccagagaca attccaagaa cacgctgtat   240
ctgcaaatga acagcctgag agccgaggac acggcggtgt actactgcgc caagccttct   300
taccaaccaa tatactgggg acagggtaca ttggtcaccg tctcctca                348
```

<210> SEQ ID NO 152
<211> LENGTH: 116
<212> TYPE: PRT
<213> ORGANISM: Artificial Sequence
<220> FEATURE:
<223> OTHER INFORMATION: VH Protein

<400> SEQUENCE: 152

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                    85                  90                  95

Ala Lys Pro Ser Tyr Gln Pro Ile Tyr Trp Gly Gln Gly Thr Leu Val
                100                 105                 110

Thr Val Ser Ser
        115

<210> SEQ ID NO 153
<211> LENGTH: 9
<212> TYPE: PRT
<213> ORGANISM: Artificial Sequence
<220> FEATURE:
<223> OTHER INFORMATION: VH ABR1

<400> SEQUENCE: 153

Phe Thr Phe Ser Ser Tyr Ala Met Ser
1               5

<210> SEQ ID NO 154
<211> LENGTH: 17
<212> TYPE: PRT
<213> ORGANISM: Artificial Sequence
<220> FEATURE:
<223> OTHER INFORMATION: VH ABR2

<400> SEQUENCE: 154

Ala Ile Ser Gly Ser Gly Gly Ser Thr Tyr Tyr Ala Asp Ser Val Lys
1               5                   10                  15

Gly

<210> SEQ ID NO 155
<211> LENGTH: 9
<212> TYPE: PRT
<213> ORGANISM: Artificial Sequence
<220> FEATURE:
<223> OTHER INFORMATION: VH ABR3

<400> SEQUENCE: 155

Ala Lys Pro Ser Tyr Gln Pro Ile Tyr
1               5

<210> SEQ ID NO 156
<211> LENGTH: 5
<212> TYPE: PRT
<213> ORGANISM: Artificial Sequence
<220> FEATURE:
<223> OTHER INFORMATION: VH CDR1

<400> SEQUENCE: 156

Asn Tyr Ala Ile Ser
1               5

<210> SEQ ID NO 157
<211> LENGTH: 17
<212> TYPE: PRT
<213> ORGANISM: Artificial Sequence
<220> FEATURE:
<223> OTHER INFORMATION: VH CDR2

<400> SEQUENCE: 157

Gly Ile Ile Pro Ile Phe Gly Thr Ala Asn Tyr Ala Gln Lys Phe Gln
1               5                   10                  15

Gly
```

<210> SEQ ID NO 158
<211> LENGTH: 360
<212> TYPE: DNA
<213> ORGANISM: Artificial Sequence
<220> FEATURE:
<223> OTHER INFORMATION: VH DNA

<400> SEQUENCE: 158

```
caggtgcagc tggtgcagtc tggggctgag gtgaagaagc ctgggtcctc ggtgaaggtc      60
tcctgcaagg cttctggagg caccttcagc aactatgcta tcagctgggt gcgacaggcc     120
cctggacaag gcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggcggtgt actactgcgc cagagatcca     300
agagaatata tccacgtatt cgacatatgg ggtcaggta caatggtcac cgtctcctca     360
```

<210> SEQ ID NO 159
<211> LENGTH: 120
<212> TYPE: PRT
<213> ORGANISM: Artificial Sequence
<220> FEATURE:
<223> OTHER INFORMATION: VH Protein

<400> SEQUENCE: 159

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Arg Glu Tyr Ile His Val Phe Asp Ile Trp Gly Gln
            100                 105                 110

Gly Thr Met Val Thr Val Ser Ser
        115                 120

<210> SEQ ID NO 160
<211> LENGTH: 9
<212> TYPE: PRT
<213> ORGANISM: Artificial Sequence
<220> FEATURE:
<223> OTHER INFORMATION: VH ABR1

<400> SEQUENCE: 160

Gly Thr Phe Ser Asn Tyr Ala Ile Ser
1               5

<210> SEQ ID NO 161
<211> LENGTH: 17
<212> TYPE: PRT
<213> ORGANISM: Artificial Sequence
<220> FEATURE:
<223> OTHER INFORMATION: VH ABR2

<400> SEQUENCE: 161

```
Gly Ile Ile Pro Ile Phe Gly Thr Ala Asn Tyr Ala Gln Lys Phe Gln
1               5                   10                  15

Gly

<210> SEQ ID NO 162
<211> LENGTH: 13
<212> TYPE: PRT
<213> ORGANISM: Artificial Sequence
<220> FEATURE:
<223> OTHER INFORMATION: VH ABR3

<400> SEQUENCE: 162

Ala Arg Asp Pro Arg Glu Tyr Ile His Val Phe Asp Ile
1               5                   10

<210> SEQ ID NO 163
<211> LENGTH: 17
<212> TYPE: PRT
<213> ORGANISM: Artificial Sequence
<220> FEATURE:
<223> OTHER INFORMATION: VH CDR2

<400> SEQUENCE: 163

Ser Ile Ile Pro Ile Phe Gly Thr Ala Asn Tyr Ala Gln Lys Phe Gln
1               5                   10                  15

Gly

<210> SEQ ID NO 164
<211> LENGTH: 12
<212> TYPE: PRT
<213> ORGANISM: Artificial Sequence
<220> FEATURE:
<223> OTHER INFORMATION: VH CDR3

<400> SEQUENCE: 164

Asp Pro Val Gly Ala Arg Tyr Glu Val Phe Asp Tyr
1               5                   10

<210> SEQ ID NO 165
<211> LENGTH: 363
<212> TYPE: DNA
<213> ORGANISM: Artificial Sequence
<220> FEATURE:
<223> OTHER INFORMATION: VH DNA

<400> SEQUENCE: 165
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaagc atcatcccta tctttggtac agcaaactac      180
gcacagaagt tccagggcag agtcacgatt accgcggacg aatccacgag cacagcctac     240
atggagctga gcagcctgag atctgaggac acggcggtgt actactgcgc cagagaccct     300
gtcggagcaa gatacgaggt tttcgattac tggggacagg gtacattggt caccgtctcc     360
tca                                                                    363

<210> SEQ ID NO 166
<211> LENGTH: 121
<212> TYPE: PRT
<213> ORGANISM: Artificial Sequence
<220> FEATURE:
<223> OTHER INFORMATION: VH Protein
```

<400> SEQUENCE: 166

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Val Gly Ala Arg Tyr Glu Val Phe Asp Tyr Trp Gly
            100                 105                 110

Gln Gly Thr Leu Val Thr Val Ser Ser
        115                 120

<210> SEQ ID NO 167
<211> LENGTH: 11
<212> TYPE: PRT
<213> ORGANISM: Artificial Sequence
<220> FEATURE:
<223> OTHER INFORMATION: VL CDR1

<400> SEQUENCE: 167

Arg Ala Ser Gln Ser Val Ser Ser Asn Leu Ala
1               5                   10

<210> SEQ ID NO 168
<211> LENGTH: 7
<212> TYPE: PRT
<213> ORGANISM: Artificial Sequence
<220> FEATURE:
<223> OTHER INFORMATION: VL CDR2

<400> SEQUENCE: 168

Ser Ala Ser Thr Arg Ala Thr
1               5

<210> SEQ ID NO 169
<211> LENGTH: 9
<212> TYPE: PRT
<213> ORGANISM: Artificial Sequence
<220> FEATURE:
<223> OTHER INFORMATION: VL CDR3

<400> SEQUENCE: 169

Gln Gln Ala Asn Thr Phe Pro Leu Thr
1               5

<210> SEQ ID NO 170
<211> LENGTH: 321
<212> TYPE: DNA
<213> ORGANISM: Artificial Sequence
<220> FEATURE:
<223> OTHER INFORMATION: VL DNA

<400> SEQUENCE: 170
gaaatagtga tgacgcagtc tccagccacc ctgtctgtgt ctccagggga aagagccacc      60
ctctcctgca gggccagtca gagtgttagc agcaacttag cctggtacca gcagaaacct     120

```
ggccaggctc ccaggctcct catctatagc gcatccacca gggccactgg tatcccagcc    180
aggttcagtg gcagtgggtc tgggacagag ttcactctca ccatcagcag cctgcagtct    240
gaagattttg cagtttatta ctgtcagcag gccaataacct tccctctcac ttttggcgga    300
gggaccaagg ttgagatcaa a                                              321

<210> SEQ ID NO 171
<211> LENGTH: 107
<212> TYPE: PRT
<213> ORGANISM: Artificial Sequence
<220> FEATURE:
<223> OTHER INFORMATION: VL Protein

<400> SEQUENCE: 171

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ala Asn Thr Phe Pro Leu
                85                  90                  95

Thr Phe Gly Gly Gly Thr Lys Val Glu Ile Lys
            100                 105

<210> SEQ ID NO 172
<211> LENGTH: 9
<212> TYPE: PRT
<213> ORGANISM: Artificial Sequence
<220> FEATURE:
<223> OTHER INFORMATION: VH ABR1

<400> SEQUENCE: 172

Gly Thr Phe Ser Ser Tyr Ala Ile Ser
1               5

<210> SEQ ID NO 173
<211> LENGTH: 17
<212> TYPE: PRT
<213> ORGANISM: Artificial Sequence
<220> FEATURE:
<223> OTHER INFORMATION: VH ABR2

<400> SEQUENCE: 173

Ser Ile Ile Pro Ile Phe Gly Thr Ala Asn Tyr Ala Gln Lys Phe Gln
1               5                   10                  15

Gly

<210> SEQ ID NO 174
<211> LENGTH: 14
<212> TYPE: PRT
<213> ORGANISM: Artificial Sequence
<220> FEATURE:
<223> OTHER INFORMATION: VH ABR3

<400> SEQUENCE: 174

Ala Arg Asp Pro Val Gly Ala Arg Tyr Glu Val Phe Asp Tyr
1               5                   10
```

<210> SEQ ID NO 175
<211> LENGTH: 9
<212> TYPE: PRT
<213> ORGANISM: Artificial Sequence
<220> FEATURE:
<223> OTHER INFORMATION: VH ABR1

<400> SEQUENCE: 175

Phe Thr Phe Ser Val Tyr Ala Met Ser
1               5

<210> SEQ ID NO 176
<211> LENGTH: 17
<212> TYPE: PRT
<213> ORGANISM: Artificial Sequence
<220> FEATURE:
<223> OTHER INFORMATION: VH ABR2

<400> SEQUENCE: 176

Ala Ile Ser Gly Ser Gly Asp Ser Thr Val Tyr Ala Asp Ser Val Lys
1               5                   10                  15

Gly

<210> SEQ ID NO 177
<211> LENGTH: 9
<212> TYPE: PRT
<213> ORGANISM: Artificial Sequence
<220> FEATURE:
<223> OTHER INFORMATION: VH ABR3

<400> SEQUENCE: 177

Ala Lys Pro Ser Tyr Gln Pro Ile Tyr
1               5

<210> SEQ ID NO 178
<211> LENGTH: 9
<212> TYPE: PRT
<213> ORGANISM: Artificial Sequence
<220> FEATURE:
<223> OTHER INFORMATION: VH ABR1

<400> SEQUENCE: 178

Gly Thr Phe Ser Ser Ser Ala Ile Gly
1               5

<210> SEQ ID NO 179
<211> LENGTH: 17
<212> TYPE: PRT
<213> ORGANISM: Artificial Sequence
<220> FEATURE:
<223> OTHER INFORMATION: VH ABR2

<400> SEQUENCE: 179

Gly Ile Trp Pro Ile Phe Gly Thr Ala Leu Tyr Ala Gln Lys Phe Gln
1               5                   10                  15

Gly

<210> SEQ ID NO 180
<211> LENGTH: 13
<212> TYPE: PRT
<213> ORGANISM: Artificial Sequence
<220> FEATURE:
<223> OTHER INFORMATION: VH ABR3

<400> SEQUENCE: 180

```
Ala Arg Asp Pro Arg Glu Tyr Ile His Val Phe Asp Ile
1               5                   10
```

<210> SEQ ID NO 181
<211> LENGTH: 9
<212> TYPE: PRT
<213> ORGANISM: Artificial Sequence
<220> FEATURE:
<223> OTHER INFORMATION: VH ABR1

<400> SEQUENCE: 181

```
Gly Thr Phe Ser Gly Gln Ala Ile Ser
1               5
```

<210> SEQ ID NO 182
<211> LENGTH: 17
<212> TYPE: PRT
<213> ORGANISM: Artificial Sequence
<220> FEATURE:
<223> OTHER INFORMATION: VH ABR2

<400> SEQUENCE: 182

```
Gly Ile Ile Pro Ser Phe Gly Thr Ala Arg Tyr Ala Gln Lys Phe Gln
1               5                   10                  15

Gly
```

<210> SEQ ID NO 183
<211> LENGTH: 14
<212> TYPE: PRT
<213> ORGANISM: Artificial Sequence
<220> FEATURE:
<223> OTHER INFORMATION: VH ABR3

<400> SEQUENCE: 183

```
Ala Arg Thr Pro Tyr Tyr Asp Ser Ser Gly Tyr Leu Asp Val
1               5                   10
```

<210> SEQ ID NO 184
<211> LENGTH: 11
<212> TYPE: PRT
<213> ORGANISM: Artificial Sequence
<220> FEATURE:
<223> OTHER INFORMATION: VH ABR1

<400> SEQUENCE: 184

```
Gly Ser Ile Ser Ser Ser Ala Tyr Tyr Trp Ala
1               5                   10
```

<210> SEQ ID NO 185
<211> LENGTH: 16
<212> TYPE: PRT
<213> ORGANISM: Artificial Sequence
<220> FEATURE:
<223> OTHER INFORMATION: VH ABR2

<400> SEQUENCE: 185

```
Ser Ile Tyr Leu Ser Gly Ser Thr Thr Tyr Asn Pro Ser Leu Lys Ser
1               5                   10                  15
```

<210> SEQ ID NO 186
<211> LENGTH: 19
<212> TYPE: PRT
<213> ORGANISM: Artificial Sequence
<220> FEATURE:
<223> OTHER INFORMATION: VH ABR3

```
<400> SEQUENCE: 186

Ala Arg Asp Gly Arg Tyr Gln Ser Ala Thr Ala Asp Tyr Tyr Gly
1               5                   10                  15

Met Asp Val

<210> SEQ ID NO 187
<211> LENGTH: 9
<212> TYPE: PRT
<213> ORGANISM: Artificial Sequence
<220> FEATURE:
<223> OTHER INFORMATION: VH ABR1

<400> SEQUENCE: 187

Tyr Thr Phe Ala Gly Tyr Asn Met His
1               5

<210> SEQ ID NO 188
<211> LENGTH: 17
<212> TYPE: PRT
<213> ORGANISM: Artificial Sequence
<220> FEATURE:
<223> OTHER INFORMATION: VH ABR2

<400> SEQUENCE: 188

Ile Ile Asn Pro Asn Ser Gly Trp Thr Asn Tyr Ala Gln Lys Phe Gln
1               5                   10                  15

Gly

<210> SEQ ID NO 189
<211> LENGTH: 14
<212> TYPE: PRT
<213> ORGANISM: Artificial Sequence
<220> FEATURE:
<223> OTHER INFORMATION: VH ABR3

<400> SEQUENCE: 189

Ala Arg Asp Pro Val Gly Ala Arg Tyr Glu Val Phe Asp Tyr
1               5                   10
```